United States Patent
Cooper et al.

(10) Patent No.: US 10,550,092 B2
(45) Date of Patent: Feb. 4, 2020

(54) SUBSTITUTED PHENYLOXAZOLIDINONES FOR ANTIMICROBIAL THERAPY

(71) Applicant: The Global Alliance for TB Drug Development, Inc., New York, NY (US)

(72) Inventors: Christopher B. Cooper, New York, NY (US); Haihong Huang, New York, NY (US); Dongfeng Zhang, New York, NY (US); Nader Fotouhi, New York, NY (US); Takushi Kaneko, New York, NY (US)

(73) Assignee: The Global Alliance for TB Drug Development, Inc., New York, NY (US)

( * ) Notice: Subject to any disclaimer, the term of this patent is extended or adjusted under 35 U.S.C. 154(b) by 0 days.

(21) Appl. No.: 15/738,503

(22) PCT Filed: Jul. 15, 2016

(86) PCT No.: PCT/US2016/042486
§ 371 (c)(1),
(2) Date: Dec. 20, 2017

(87) PCT Pub. No.: WO2017/015106
PCT Pub. Date: Jan. 26, 2017

(65) Prior Publication Data
US 2018/0179168 A1    Jun. 28, 2018

Related U.S. Application Data

(60) Provisional application No. 62/193,963, filed on Jul. 17, 2015.

(51) Int. Cl.
| | |
|---|---|
| C07D 263/20 | (2006.01) |
| C07D 263/24 | (2006.01) |
| A61K 31/422 | (2006.01) |
| A61K 45/06 | (2006.01) |
| A61K 31/554 | (2006.01) |
| C07D 491/107 | (2006.01) |
| C07D 495/10 | (2006.01) |
| C07D 498/08 | (2006.01) |
| A61P 31/06 | (2006.01) |
| A61K 31/5386 | (2006.01) |
| C07D 413/06 | (2006.01) |
| C07D 413/12 | (2006.01) |
| C07D 491/08 | (2006.01) |
| C07D 495/08 | (2006.01) |

(52) U.S. Cl.
CPC .......... *C07D 263/20* (2013.01); *A61K 31/422* (2013.01); *A61K 31/5386* (2013.01); *A61K 31/554* (2013.01); *A61K 45/06* (2013.01); *A61P 31/06* (2018.01); *C07D 263/24* (2013.01); *C07D 413/06* (2013.01); *C07D 413/12* (2013.01); *C07D 491/08* (2013.01); *C07D 491/107* (2013.01); *C07D 495/08* (2013.01); *C07D 495/10* (2013.01); *C07D 498/08* (2013.01)

(58) Field of Classification Search
CPC ........................... C07D 263/20; C07D 263/24
See application file for complete search history.

(56) References Cited

U.S. PATENT DOCUMENTS

| | | |
|---|---|---|
| 6,090,820 A | 7/2000 | Barbachyn et al. |
| 2004/0077626 A1 | 4/2004 | Hester et al. |
| 2008/0119533 A1 | 5/2008 | Turos et al. |
| 2009/0281088 A1 | 11/2009 | Ding et al. |
| 2010/0069449 A1 | 3/2010 | Oh et al. |
| 2011/0053916 A1 | 3/2011 | Wang et al. |

FOREIGN PATENT DOCUMENTS

| | | | |
|---|---|---|---|
| WO | 9507271 A1 | 3/1995 | |
| WO | 9615130 A1 | 5/1996 | |
| WO | WO 00/32599 * | 6/2000 | ........... C07D 417/10 |
| WO | 03006440 A2 | 1/2003 | |
| WO | 2004033451 A1 | 4/2004 | |
| WO | 2007000644 A1 | 1/2007 | |

OTHER PUBLICATIONS

Lafond. Clinical Microbiology Reviews, 2006, 29-49 (Year: 2006).*
Syphilis-prevention, http://www.webmd.com/sexual-conditions/tc/syphilis-prevention?print=true, updated Oct. 2, 2007, accessed Apr. 9, 2010 (Year: 2007).*
Kim. Bioorganic and Medicinal Chemistry Letters, 2009, 19, 550-3 (Year: 2009).*
The International Search Report and Written Opinion, dated Sep. 19, 2016, in the related PCT Appl. No. PCT/US16/42486.

(Continued)

*Primary Examiner* — Noble E Jarrell

(57) ABSTRACT

The present invention relates to novel oxazolidinones (Formula I): or a pharmaceutically acceptable salt having ring A characterized by N-containing monocyclic, bicyclic or spirocyclic substituents, to their preparation, and to their use as drugs for treating *Mycobacterium tuberculosis* and other microbial infections, either alone or in combination with other anti-infective treatments.

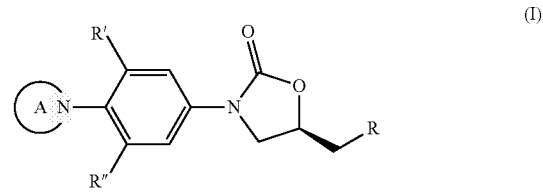

(I)

17 Claims, No Drawings

(56) References Cited

OTHER PUBLICATIONS

Gadekar et al., "Design, synthesis and biological evaluation of novel azaspiro analogs of linezolid as antibacterial and antitubercular agents," Eur J Med Chem. Oct. 21, 2016;122, pp. 475-487.
The extended European search report, dated Dec. 6, 2018, in the related European Appl. No. 16828300.0.
The partial supplementary European search report, dated Oct. 5, 2018, in the related European Appl. No. 16828300.0.
The English translation of the Eurasian Office Action, dated Feb. 25, 2019, in the related Eurasian Patent Application No. 201792566.

* cited by examiner

SUBSTITUTED PHENYLOXAZOLIDINONES FOR ANTIMICROBIAL THERAPY

CROSS-REFERENCE TO RELATED APPLICATIONS

This application is a National Stage Application of PCT/US2016/042486 filed Jul. 15, 2016, claims priority from U.S. Provisional Patent Application No. 62/193,963, filed on Jul. 17, 2015. The priority of both said PCT and U.S. Provisional Patent Application are claimed. Each of prior mentioned applications is hereby incorporated by reference herein in its entirety.

FIELD OF THE INVENTION

The invention relates generally to compounds with antibacterial activity and, more specifically, with anti-tuberculosis properties. In particular, it relates to substituted phenyloxazolidinone compounds useful for the treatment of tuberculosis in patients in need thereof.

All documents cited to or relied upon below are expressly incorporated herein by reference.

BACKGROUND OF THE INVENTION

Linezolid is the first-in-class drug and was approved in 2000 for a number of clinical applications including the treatment of nosocomial and community-acquired pneumonia and skin infections caused by *Staphylococcus aureus*/Methicillin-resistant *S. aureus*, Vancomycin-resistant *Enterococci*, and *Streptococcus pneumoniae* (Pen-S). Linezolid exhibits in vitro bacteriostatic activity against *Mycobacterium tuberculosis*, including multidrug-resistant (MDR) and extensively drug resistant (XDR) strains, with a minimum inhibitory concentration (MIC) of less than 1 μg/ml. However, it has demonstrated only modest activity in murine models of tuberculosis. Nonetheless, Linezolid has been used off-label in combination regimens to treat multi-drug-resistant tuberculosis.

Oxazolidinones currently in clinical development show bone marrow toxicity in animals after long term administration (i.e., greater than one month) that is believed to be related to mitochondrial protein synthesis (MPS) inhibition, with very narrow safety margins or no safety margins. Since the antimicrobial mode of action of this class of compounds is inhibition of microbial protein synthesis, the MPS inhibition and consequent bone marrow toxicity exhibited by these compounds is considered mechanism specific. These oxazolidinones generally show high clearance and so require administration of high doses in clinical treatment of TB or the other indications for which they are being developed (e.g., 500 mg to 1600 mg daily) to achieve efficacious exposures. Therefore, it would be highly desirable to identify a new generation of oxazolidinones for TB treatment that would demonstrate improved potency and efficacy against TB, reduced systemic clearance to reduce the daily dose below 500 mg, and diminished MPS inhibition and related bone marrow toxicity, resulting in an improved safety margin for long term administration.

SUMMARY OF THE INVENTION

The present invention relates to novel oxazolidinones of Formula I, or a pharmaceutically acceptable salt, hydrate, or solvate thereof:

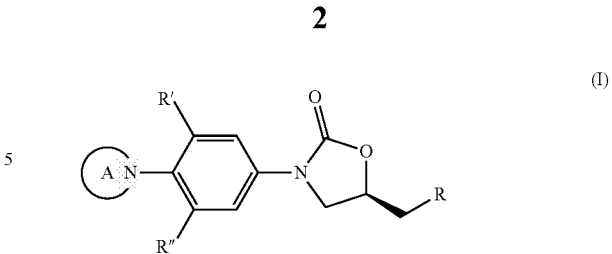

wherein,

R is independently $OR_1$, $OC(O)R_2$, $OC(O)NHR_2$, $OS(O_2)R_2$, $NHS(O)_2R_2$, $NR_3R_4$, $NHC(O)R_5$;

R' and R" are independently H, F, Cl or OMe;

each $R_1$ is independently H, $C_1$-$C_6$ alkyl, $C_3$-$C_8$ cycloalkyl, wherein said alkyl, cycloalkyl are optionally substituted with 1 to 4 groups selected from halo, hydroxy, $C_1$-$C_6$ alkyl, $C_1$-$C_6$ alkyloxy;

each $R_2$ is independently $C_1$-$C_6$ alkyl, $C_3$-$C_8$ cycloalkyl, heterocyclyl, heteroaryl or aryl, wherein said alkyl, cycloalkyl, heterocyclyl, heteroaryl, or aryl are optionally substituted with 1 to 4 groups selected from halo, hydroxyl, $C_1$-$C_6$ alkyl, $C_1$-$C_6$ alkoxy, $C_1$-$C_6$ acyloxy, $CF_3$, $NO_2$, CN and $NH_2$;

each $R_3$ and $R_4$ is independently H, $C_1$-$C_6$ alkyl, $C_3$-$C_8$ cycloalkyl, heterocyclyl heteroaryl, aryl; or $R_3$ and $R_4$ taken together with the nitrogen to which they are attached, form a 4- to 8-membered heterocyclyl or heteroaryl with 1 to 3 additional heteroatoms selected from O, S, or N, wherein said alkyl, cycloalkyl, heterocyclyl, heteroaryl, or aryl are optionally substituted with 1 to 4 groups selected from halo, $C_1$-$C_6$ alkyl, $C_1$-$C_6$ alkoxy, $CF_3$, $NO_2$, CN;

each $R_5$ is independently $C_1$-$C_6$ alkyl, $C_3$-$C_8$ cycloalkyl, $C_1$-$C_6$ alkoxy, heteroaryl, aryl, wherein said alkyl, cycloalkyl, heterocyclyl, heteroaryl, or aryl are optionally substituted with 1 to 4 groups selected from halo, hydroxyl, $C_1$-$C_6$ alkyl, $C_1$-$C_6$ alkoxy, $C_1$-$C_6$ acyloxy, $CF_3$, $NO_2$, CN and $NH_2$;

Ring A is selected from:

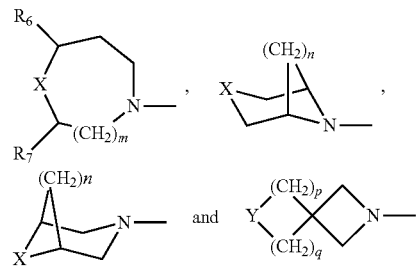

wherein, each $R_6$ and $R_7$ is independently H, F, $CH_3$, $CH_2CH_3$, $CF_3$, phenyl;

X=O, S, SO, $SO_2$;

Y=O, S, SO, $SO_2$, and $NR_8$;

m is 1, or 2;

n is 1, or 2;

p is 1, or 2;

q is 1, or 2;

$R_8$ in independently H, $C_1$-$C_4$ alkyl, $C_3$-$C_6$ cycloalkyl, $COCH_3$, and p-toluenesulfonyl, wherein said alkyl, cycloalkyl are optionally substituted with 1 to 4 groups selected from halo, hydroxyl, $C_1$-$C_6$ alkyl, $C_1$-$C_6$ alkoxy, $C_1$-$C_6$ acyloxy, $CF_3$, $NO_2$, CN and $NH_2$.

In a further aspect, the present invention provides pharmaceutical compositions comprising at least one compound of Formula I, or a salt, hydrate, or solvate thereof, and one or more pharmaceutically acceptable carriers and/or additives.

In a further aspect, the present invention provides a method for treating microbial infections in humans by administering a therapeutically effective amount of a compound of Formula I, or a salt, hydrate, or solvate thereof to a patient in need thereof.

In a further aspect, the present invention includes pharmaceutical compositions of Formula I, or a salt, hydrate, or solvate thereof, further comprising one or more additional anti-infective treatments.

In still a further aspect, the present invention relates to a compound in accordance with Formula I or a pharmaceutically acceptable salt, hydrate, or solvate thereof for use as an anti-tuberculosis (TB) agent in a human.

DETAILED DESCRIPTION OF THE INVENTION

One aspect of the present invention is to provide novel compounds according to Formula I shown and described above. Specifically, the compounds of the invention are useful antimicrobial agents, effective against a number of human and veterinary pathogens, including gram-positive aerobic bacteria, *Mycobacterium tuberculosis*, *Mycobacterium avium*, and the like. As a result, this invention provides novel compounds according to Formula I, as well as pharmaceutically acceptable salts, hydrates, or solvates thereof. Values for the variables in Formula I are provided in the following paragraphs.

Table 1 below shows some specific examples of the compounds of the invention, by indicating their structures as well as their in vitro activity against *Mycobacterium tuberculosis* H37Rv strains, and in vitro MPS inhibition activity when tested as described in Example 9 and 10 below, respectively. As shown in Table 1 below, potent anti-tubercular agents demonstrate low MIC values (particular compounds with MIC's below 1 μg/mL). Conversely, high MPS inhibition $IC_{50}$'s indicate diminished mitochondrial protein synthesis activity in vitro, and are indicative of reduced myelosuppression toxicity in vivo. In certain embodiments of the invention, compounds having the best therapeutic index are those demonstrating a relatively lower MIC value combined a relatively higher MPS inhibition $IC_{50}$. Representative compounds of the invention are provided in Table 1 (wherein the entry "NA" (i.e., "not available") indicates that a particular value was not measured):

TABLE 1

| Compound | Structure | HRMS [M + H]⁺ | MIC (μg/mL) against H₃₇Rv | $IC_{50}$ (μM) MPS inhibition |
|---|---|---|---|---|
| OTB-107 | 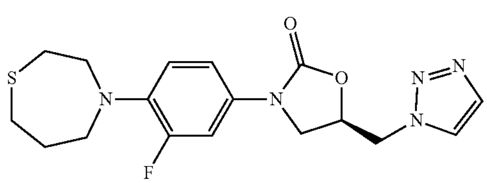 [SMILES: O=C1O[C@@H](Cn2ccnn2)CN1c1ccc(N2CCCSCC2)c(F)c1] | 378.1396 | 0.03 | 84.85 |
| OTB-106 | 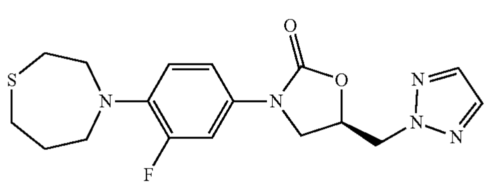 [SMILES: O=C1O[C@@H](Cn2nccn2)CN1c1ccc(N2CCCSCC2)c(F)c1] | 378.1403 | 2 | >100 |
| OTB-109 | 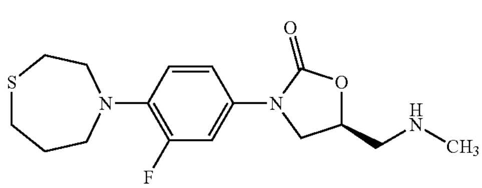 [SMILES: CNC[C@H]1CN(c2ccc(N3CCCSCC3)c(F)c2)C(=O)O1] | 340.1484 | 32 | NA |
| OTB-108 | 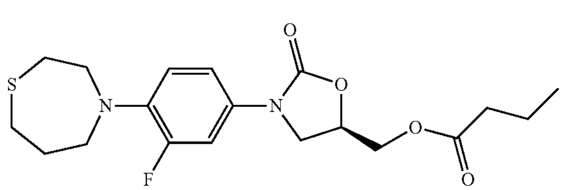 [SMILES: CCCC(=O)OC[C@H]1CN(c2ccc(N3CCCSCC3)c(F)c2)C(=O)O1] | 397.1613 | 0.125 | >100 |

TABLE 1-continued
| Compound | Structure | HRMS [M + H]+ | MIC (μg/mL) against H37Rv | IC50 (μM) MPS inhibition |
|---|---|---|---|---|
| OTB-111 | 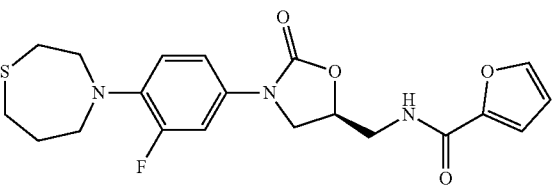 [SMILES: O=C(NC[C@H]1CN(c2ccc(N3CCCSCC3)c(F)c2)C(=O)O1)c1cccs1] | 420.1400 | 0.125 | 60.32 |
| OTB-112 | 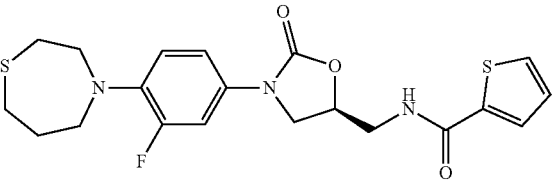 | 382.1620 | 0.5 | >100 |
| OTB-115 | 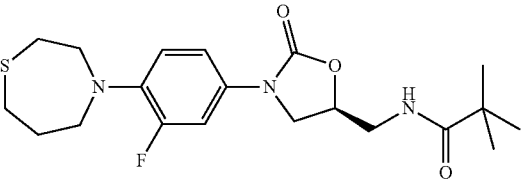 [SMILES: CC(C)(C)C(=O)NC[C@H]1CN(c2ccc(N3CCCSCC3)c(F)c2)C(=O)O1] | 410.1942 | 3.733 | >100 |
| OBD-005 | 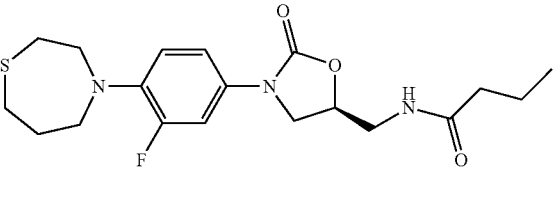 [SMILES: CCCC(=O)NC[C@H]1CN(c2ccc(N3CCCSCC3)c(F)c2)C(=O)O1] | 395.1679 | 0.055 | 15.63 |
| OTB-116 | 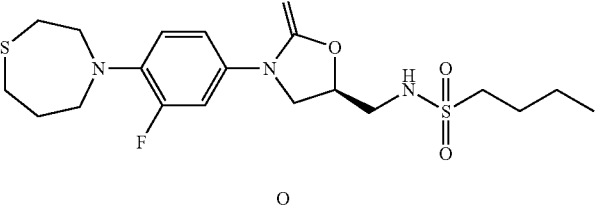 | 446.1623 | 3.812 | >100 |
| OTB-119 | 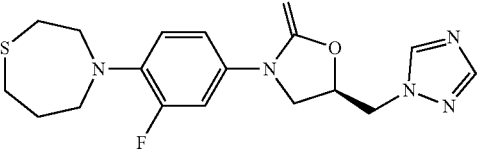 | 378.1421 | 0.456 | >100 |
| OTB-412 | 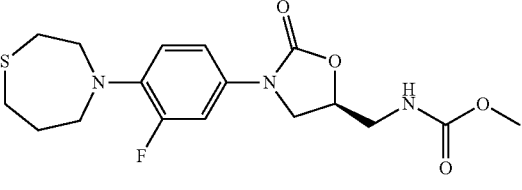 [SMILES: COC(=O)NC[C@H]1CN(c2ccc(N3CCCSCC3)c(F)c2)C(=O)O1] | 384.1371 | 0.199 | 10 |
| OTB-413 | 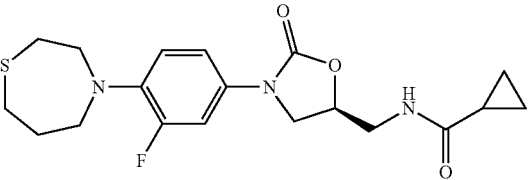 [SMILES: O=C(NC[C@H]1CN(c2ccc(N3CCCSCC3)c(F)c2)C(=O)O1)C1CC1] | 394.1580 | 0.108 | 9.13 |

TABLE 1-continued

| Compound | Structure | HRMS [M + H]+ | MIC (μg/mL) against $H_{37}Rv$ | $IC_{50}$ (μM) MPS inhibition |
|---|---|---|---|---|
| OTB-414 | 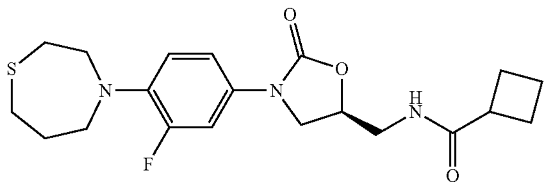 [SMILES: O=C(NC[C@H]1CN(c2ccc(N3CCCSCC3)c(F)c2)C(=O)O1)C1CCC1] | 408.1736 | 0.171 | NA |
| OTB-407 | 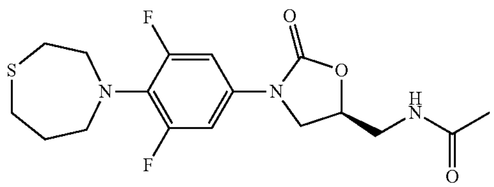 [SMILES: CC(=O)NC[C@H]1CN(c2cc(F)c(N3CCCSCC3)c(F)c2)C(=O)O1] | 386.1330 | 0.097 | 3.079 |
| OTB-410 | 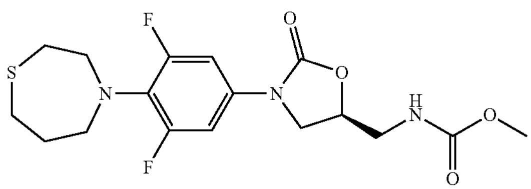 [SMILES: COC(=O)NC[C@H]1CN(c2cc(F)c(N3CCCSCC3)c(F)c2)C(=O)O1] | 402.1287 | 0.125 | >100 |
| OTB-408 | 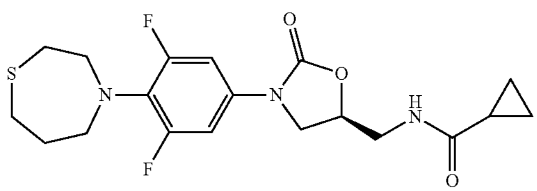 [SMILES: O=C(NC[C@H]1CN(c2cc(F)c(N3CCCSCC3)c(F)c2)C(=O)O1)C1CC1] | 412.1485 | 0.342 | 3.608 |
| OTB-409 | 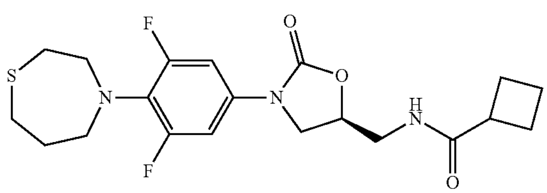 [SMILES: O=C(NC[C@H]1CN(c2cc(F)c(N3CCCSCC3)c(F)c2)C(=O)O1)C1CCC1] | 426.1643 | 0.477 | 8.51 |
| OTB-411 | 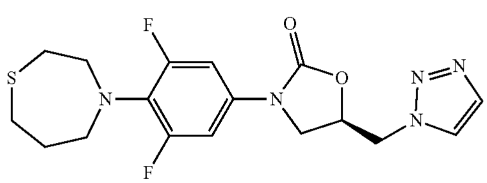 [SMILES: O=C1O[C@@H](Cn2ccnn2)CN1c1cc(F)c(N2CCCSCC2)c(F)c1] | 396.1296 | 0.124 | 8.73 |
| OTB-126 | 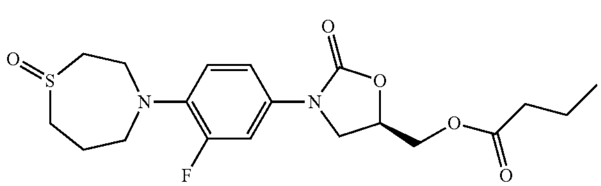 [SMILES: CCCC(=O)OC[C@H]1CN(c2ccc(N3CCCS(=O)CC3)c(F)c2)C(=O)O1] | 413.1573 | 0.847 | 35.60 |

TABLE 1-continued

| Compound | Structure | HRMS [M + H]+ | MIC (μg/mL) against H37Rv | IC50 (μM) MPS inhibition |
|---|---|---|---|---|
| OTB-127 | 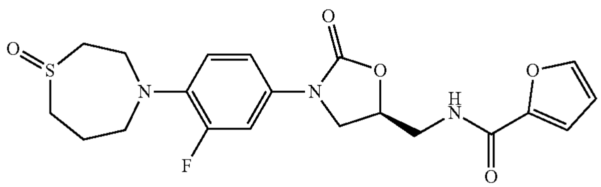 [SMILES: O=C(NC[C@H]1CN(c2ccc(N3CCCS(=O)CC3)c(F)c2)C(=O)O1)c1ccco1] | 436.1371 | 1.234 | 10.15 |
| OTB-137 | 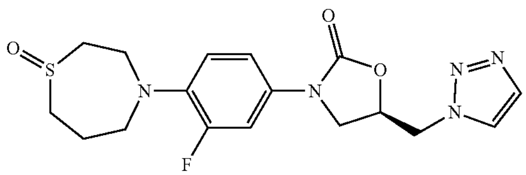 [SMILES: O=C1O[C@@H](Cn2ccnn2)CN1c1ccc(N2CCCS(=O)CC2)c(F)c1] | 394.1328 | 0.277 | 7.64 |
| OTB-138 | 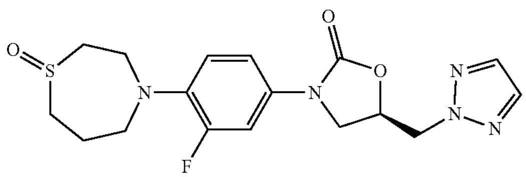 [SMILES: O=C1O[C@@H](Cn2nccn2)CN1c1ccc(N2CCCS(=O)CC2)c(F)c1] | 394.1338 | 7.565 | >100 |
| OTB-140 | 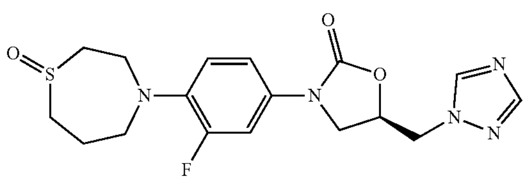 [SMILES: O=C1O[C@@H](Cn2cncn2)CN1c1ccc(N2CCCS(=O)CC2)c(F)c1] | 394.1339 | 3.695 | >100 |
| OBD-006 | 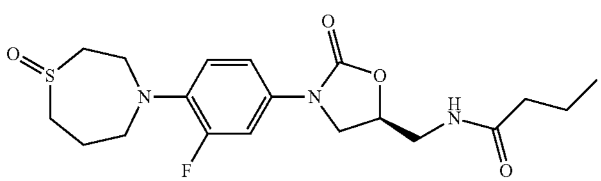 [SMILES: CCCC(=O)NC[C@H]1CN(c2ccc(N3CCCS(=O)CC3)c(F)c2)C(=O)O1] | 411.1628 | 0.49 | 7.485 |
| OBD-007 | 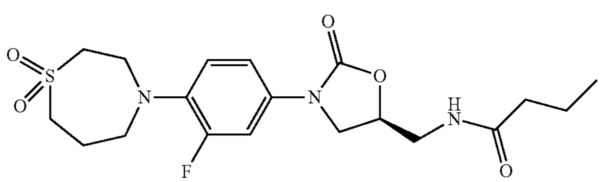 [SMILES: CCCC(=O)NC[C@H]1CN(c2ccc(N3CCCS(=O)(=O)CC3)c(F)c2)C(=O)O1] | 427.1577 | 0.46 | 19.81 |
| OTB-110 | 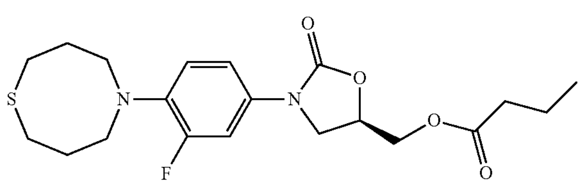 | 411.1786 | 0.125 | >100 |
| OTB-113 | 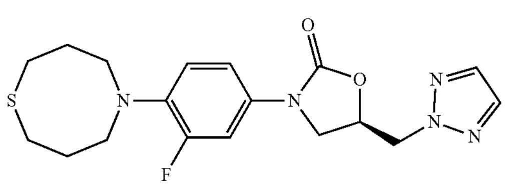 [SMILES: O=C1O[C@@H](Cn2nccn2)CN1c1ccc(N2CCCSCCC2)c(F)c1] | 392.1590 | 2 | >100 |

TABLE 1-continued

| Compound | Structure | HRMS [M + H]+ | MIC (μg/mL) against H37Rv | IC50 (μM) MPS inhibition |
|---|---|---|---|---|
| OTB-114 | 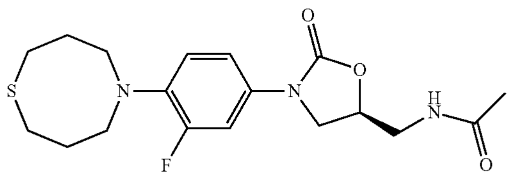 [SMILES: CC(=O)NC[C@H]1CN(c2ccc(N3CCCSCCC3)c(F)c2)C(=O)O1] | 382.1620 | 0.05-0.11 | 28-29 |
| OTB-124 | 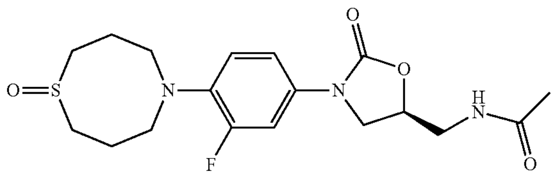 [SMILES: CC(=O)NC[C@H]1CN(c2ccc(N3CCCS(=O)CCC3)c(F)c2)C(=O)O1] | 398.1540 | 0.26-1.4 | 94->100 |
| OTB-117 | 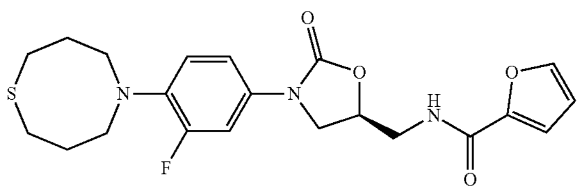 | 434.1581 | 0.665 | 56.32 |
| OTB-118 | 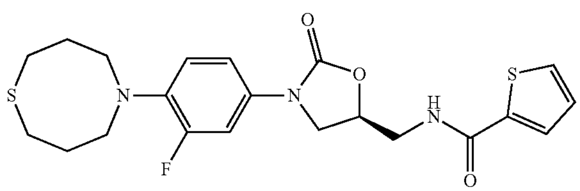 [SMILES: O=C(NC[C@H]1CN(c2ccc(N3CCCSCCC3)c(F)c2)C(=O)O1)c1ccco1] | 450.1356 | 1.548 | NA |
| OTB-120 | 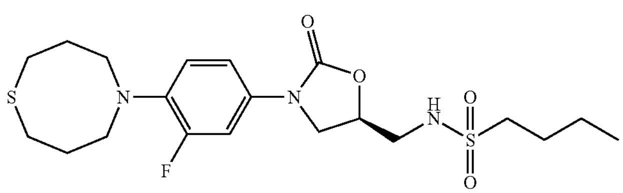 [SMILES: CCCCS(=O)(=O)NC[C@H]1CN(c2ccc(N3CCCSCCC3)c(F)c2)C(=O)O1] | 460.1778 | 3.877 | 7.27 |
| OTB-121 | 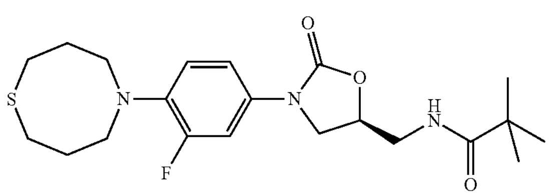 [SMILES: CC(C)(C)C(=O)NC[C@H]1CN(c2ccc(N3CCCSCCC3)c(F)c2)C(=O)O1] | 424.2096 | 2.785 | 17.63 |
| OBD-001 | 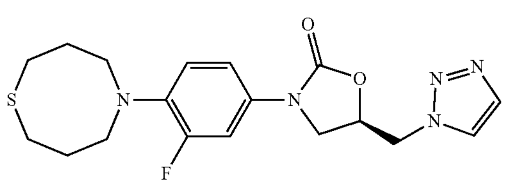 [SMILES: O=C1O[C@@H](Cn2ccnn2)CN1c1ccc(N2CCCSCCC2)c(F)c1] | 391.1478 | 0.3 | 12 |
| OBD-002 | 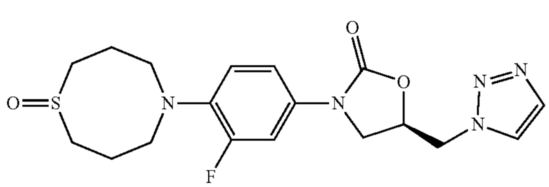 [SMILES: O=C1O[C@@H](Cn2ccnn2)CN1c1ccc(N2CCCS(=O)CCC2)c(F)c1] | 407.1427 | 1.6 | 29 |

TABLE 1-continued

| Compound | Structure | HRMS [M + H]+ | MIC (μg/mL) against H₃₇Rv | IC₅₀ (μM) MPS inhibition |
|---|---|---|---|---|
| OBD-003 | 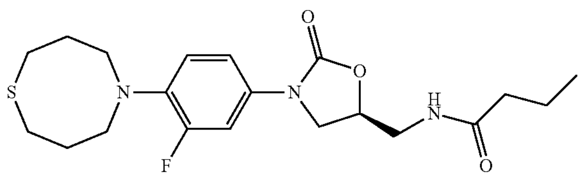 [SMILES: CCCC(=O)NC[C@H]1CN(c2ccc(N3CCCSCCC3)c(F)c2)C(=O)O1] | 409.1835 | 0.33 | >100 |
| OBD-004 | 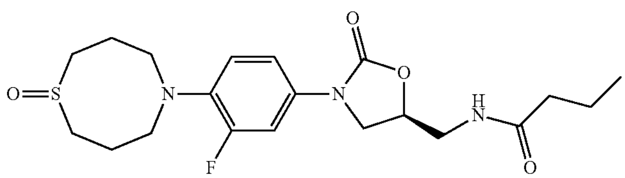 [SMILES: CCCC(=O)NC[C@H]1CN(c2ccc(N3CCCS(=O)CCC3)c(F)c2)C(=O)O1] | 425.1785 | 3.338 | 15.76 |
| OBD-008 | 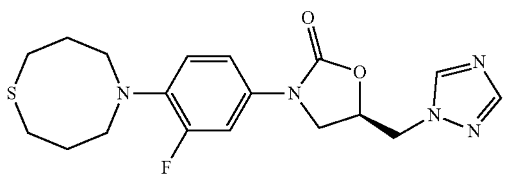 [SMILES: O=C1O[C@@H](Cn2cncn2)CN1c1ccc(N2CCCSCCC2)c(F)c1] | 391.1478 | 3.513 | 29.89 |
| OBD-009 | 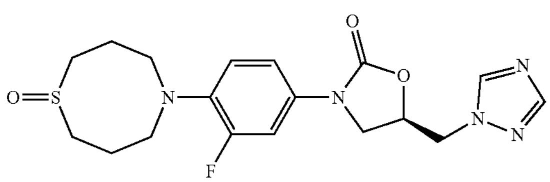 [SMILES: O=C1O[C@@H](Cn2cncn2)CN1c1ccc(N2CCCS(=O)CCC2)c(F)c1] | 407.1427 | 21.052 | >100 |
| OBD-027 | 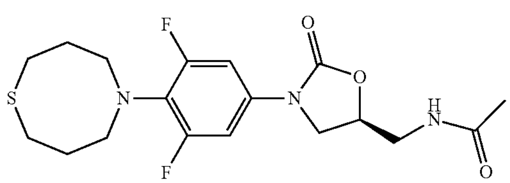 [SMILES: CC(=O)NC[C@H]1CN(c2cc(F)c(N3CCCSCCC3)c(F)c2)C(=O)O1] | | 0.3 | NA |
| OBD-240 | 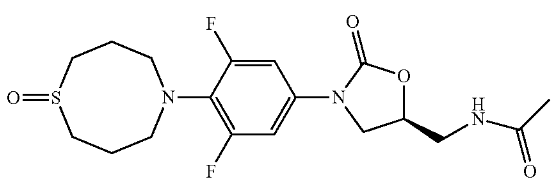 [SMILES: CC(=O)NC[C@H]1CN(c2cc(F)c(N3CCCS(=O)CCC3)c(F)c2)C(=O)O1] | | NA | NA |
| OBD-026 | 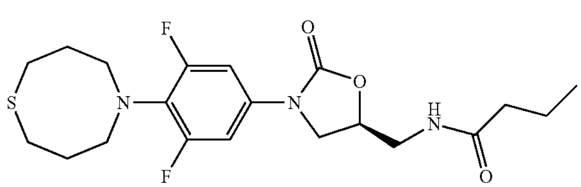 [SMILES: CCCC(=O)NC[C@H]1CN(c2cc(F)c(N3CCCSCCC3)c(F)c2)C(=O)O1] | | 0.4 | NA |
| OBD-241 | 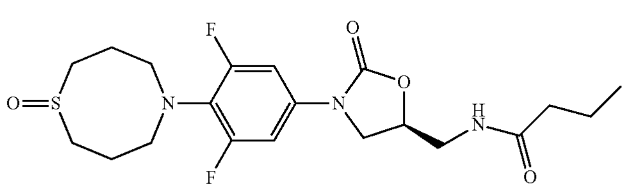 [SMILES: CCCC(=O)NC[C@H]1CN(c2cc(F)c(N3CCCS(=O)CCC3)c(F)c2)C(=O)O1] | | NA | NA |

TABLE 1-continued

| Compound | Structure | HRMS [M + H]+ | MIC (μg/mL) against H37Rv | IC50 (μM) MPS inhibition |
|---|---|---|---|---|
| OTB-227 | 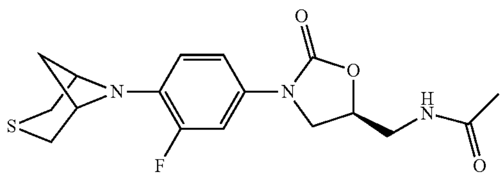 [SMILES: CC(=O)NC[C@H]1CN(c2ccc(N3C4CSCC3C4)c(F)c2)C(=O)O1] | 366.1277 | 0.889 | 15.22 |
| OTB-501 | 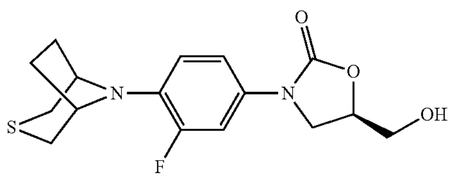 [SMILES: O=C1O[C@@H](CO)CN1c1ccc(N2C3CCC2CSC3)c(F)c1] | 339.1169 | 4.5 | NA |
| OBD-081 | 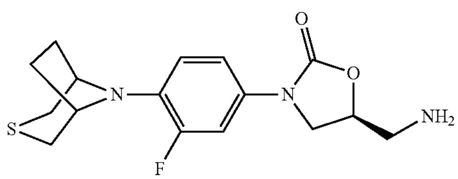 [SMILES: NC[C@H]1CN(c2ccc(N3C4CCC3CSC4)c(F)c2)C(=O)O1] | 407.9 | 0.47 | 77 |
| OBD-085 | 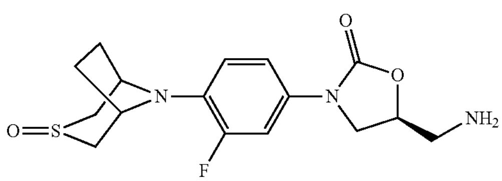 [SMILES: NC[C@H]1CN(c2ccc(N3C4CCC3CS(=O)C4)c(F)c2)C(=O)O1] | | 1.1 | >100 |
| OTB-502 | 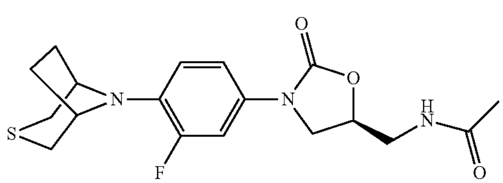 [SMILES: CC(=O)NC[C@H]1CN(c2ccc(N3C4CCC3CSC4)c(F)c2)C(=O)O1] | 380.1435 | 0.246 | 13.55 |
| OTB-503 | 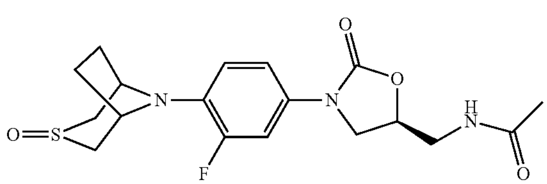 [SMILES: CC(=O)NC[C@H]1CN(c2ccc(N3C4CCC3CS(=O)C4)c(F)c2)C(=O)O1] | 396.1379 | 0.2-1.3 | 78->100 |
| OTB-504 | 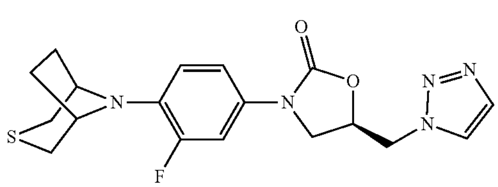 [SMILES: O=C1O[C@@H](Cn2ccnn2)CN1c1ccc(N2C3CCC2CSC3)c(F)c1] | 390.1385 | 0.5-0.7 | 17->100 |
| OTB-505 | 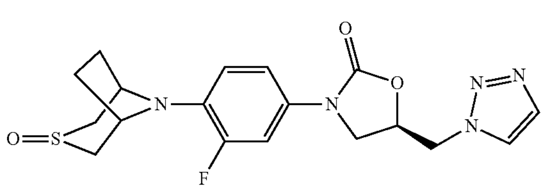 [SMILES: O=C1O[C@@H](Cn2ccnn2)CN1c1ccc(N2C3CCC2CS(=O)C3)c(F)c1] | 406.1339 | 1.8-3.5 | 57->100 |

TABLE 1-continued

| Compound | Structure | HRMS [M + H]+ | MIC (μg/mL) against H37Rv | IC50 (μM) MPS inhibition |
|---|---|---|---|---|
| OTB-236 | 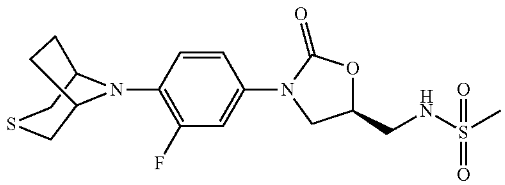 [SMILES: CS(=O)(=O)NC[C@H]1CN(c2ccc(N3C4CCC3CSC4)c(F)c2)C(=O)O1] | 416.1097 | 14.256 | NA |
| OTB-237 | 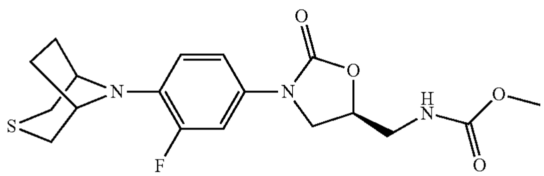 [SMILES: COC(=O)NC[C@H]1CN(c2ccc(N3C4CCC3CSC4)c(F)c2)C(=O)O1] | 396.1388 | 0.03-0.11 | 15-23 |
| OTB-518 | 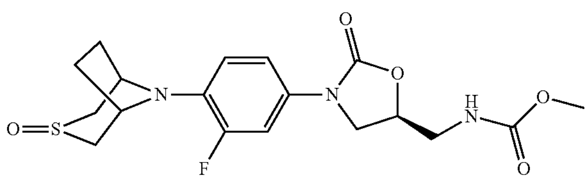 [SMILES: COC(=O)NC[C@H]1CN(c2ccc(N3C4CCC3CS(=O)C4)c(F)c2)C(=O)O1] | | 3.5 | 73 |
| OBD-016 | 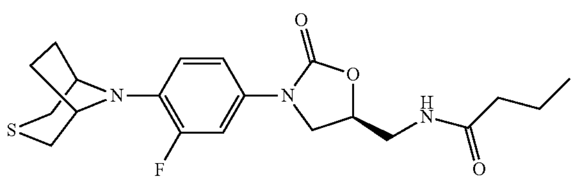 [SMILES: CCCC(=O)NC[C@H]1CN(c2ccc(N3C4CCC3CSC4)c(F)c2)C(=O)O1] | 407.1679 | 0.486 | 13 |
| OBD-017 | 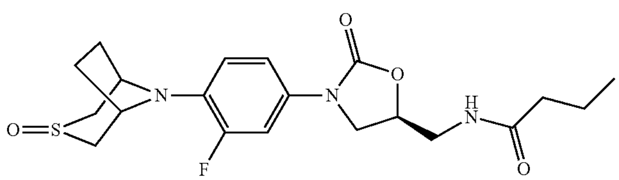 [SMILES: CCCC(=O)NC[C@H]1CN(c2ccc(N3C4CCC3CS(=O)C4)c(F)c2)C(=O)O1] | 423.8 | 5.8-6.3 | 41 |
| OBD-021 | 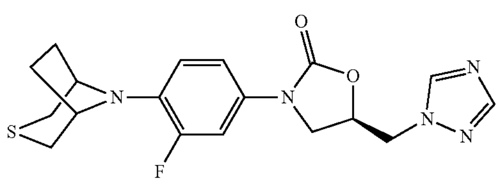 [SMILES: O=C1O[C@@H](Cn2cncn2)CN1c1ccc(N2C3CCC2CSC3)c(F)c1] | 389.1322 | 27.456 | NA |
| OBD-018 | 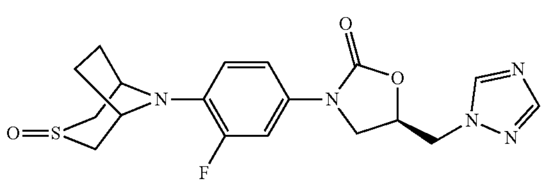 [SMILES: O=C1O[C@@H](Cn2cncn2)CN1c1ccc(N2C3CCC2CS(=O)C3)c(F)c1] | 405.1271 | >32 | NA |
| OTB-506 | 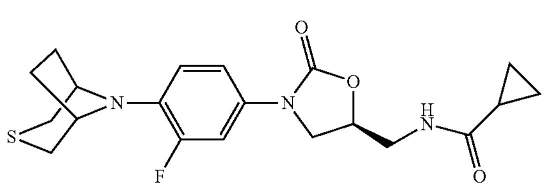 [SMILES: O=C(NC[C@H]1CN(c2ccc(N3C4CCC3CSC4)c(F)c2)C(=O)O1)C1CC1] | 406.1527 | 1 | 8 |

TABLE 1-continued

| Compound | Structure | HRMS [M + H]+ | MIC (μg/mL) against H37Rv | IC50 (μM) MPS inhibition |
|---|---|---|---|---|
| OTB-507 | 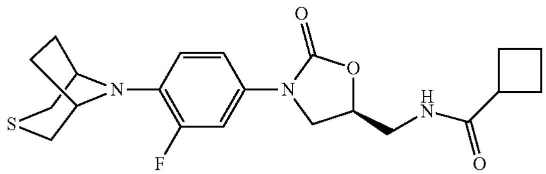 [SMILES: O=C(NC[C@H]1CN(c2ccc(N3C4CCC3CSC4)c(F)c2)C(=O)O1)C1CCC1] | 420.1736 | 0.7 | 10 |
| OTB-510 | 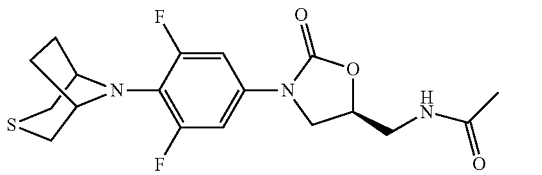 [SMILES: CC(=O)NC[C@H]1CN(c2cc(F)c(N3C4CCC3CSC4)c(F)c2)C(=O)O1] | 398.1329 | 0.03-0.22 | 3-7 |
| OTB-514 | 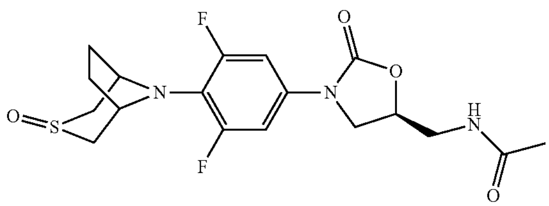 [SMILES: CC(=O)NC[C@H]1CN(c2cc(F)c(N3C4CCC3CS(=O)C4)c(F)c2)C(=O)O1] | 414.1275 | 0.5 | 25 |
| OTB-512 | 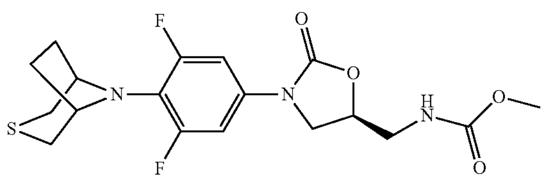 [SMILES: COC(=O)NC[C@H]1CN(c2cc(F)c(N3C4CCC3CSC4)c(F)c2)C(=O)O1] | 414.1278 | 0.063 | 42.47 |
| OTB-519 | 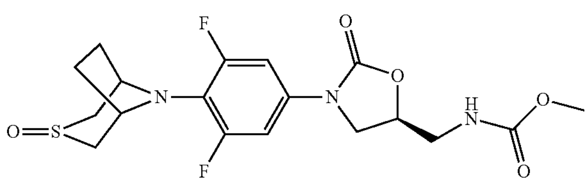 [SMILES: COC(=O)NC[C@H]1CN(c2cc(F)c(N3C4CCC3CS(=O)C4)c(F)c2)C(=O)O1] | | 0.9 | 51 |
| OTB-511 | 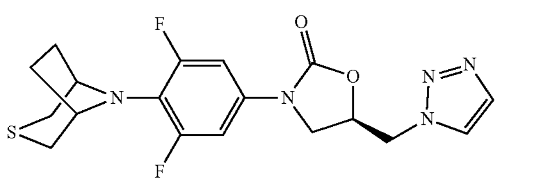 [SMILES: O=C1O[C@@H](Cn2ccnn2)CN1c1cc(F)c(N2C3CCC2CSC3)c(F)c1] | 408.1295 | 0.06-0.2 | 9->100 |
| OTB-517 | 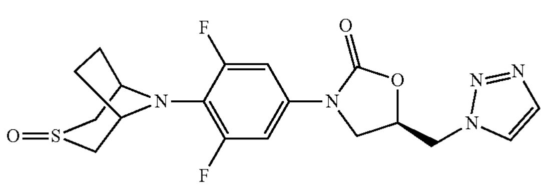 [SMILES: O=C1O[C@@H](Cn2ccnn2)CN1c1cc(F)c(N2C3CCC2CS(=O)C3)c(F)c1] | | 1.3-2 | 30-55 |
| OTB-508 | 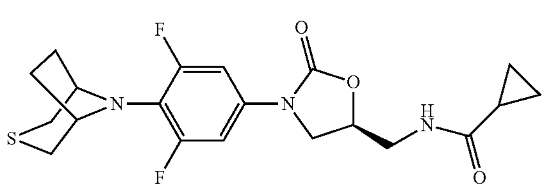 [SMILES: O=C(NC[C@H]1CN(c2cc(F)c(N3C4CCC3CSC4)c(F)c2)C(=O)O1)C1CC1] | 424.1484 | 0.2 | 8 |

TABLE 1-continued

| Compound | Structure | HRMS [M + H]+ | MIC (μg/mL) against H37Rv | IC50 (μM) MPS inhibition |
|---|---|---|---|---|
| OTB-509 | 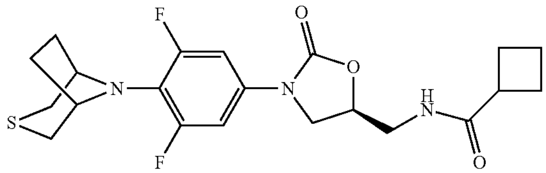 [SMILES: O=C(NC[C@H]1CN(c2cc(F)c(N3C4CCC3CSC4)c(F)c2)C(=O)O1)C1CCC1] | 438.1642 | 0.04 | 5 |
| OTB-513 | 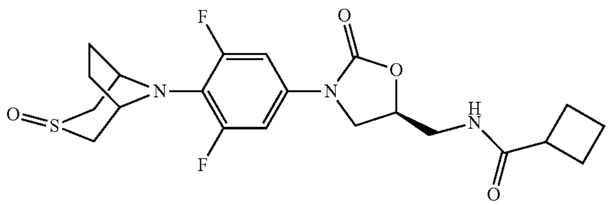 [SMILES: O=C(NC[C@H]1CN(c2cc(F)c(N3C4CCC3CS(=O)C4)c(F)c2)C(=O)O1)C1CCC1] | 454.1588 | 1.664 | 12.96 |
| OBD-083 | 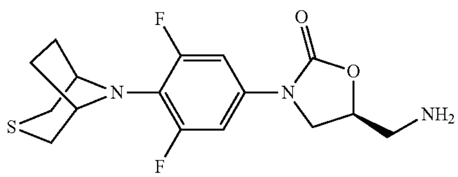 [SMILES: NC[C@H]1CN(c2cc(F)c(N3C4CCC3CSC4)c(F)c2)C(=O)O1] | | 0.05 | 20 |
| OBD-087 | 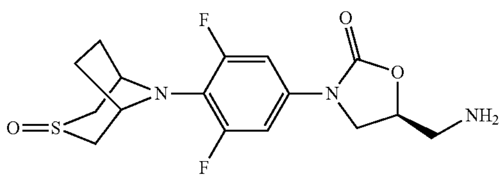 | | 0.86 | >100 |
| OBD-029 | 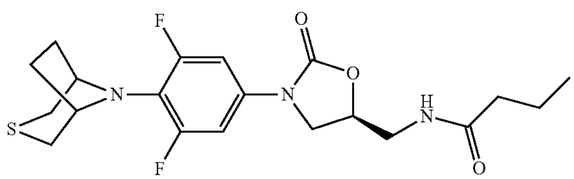 [SMILES: CCCC(=O)NC[C@H]1CN(c2cc(F)c(N3C4CCC3CSC4)c(F)c2)C(=O)O1] | | 0.11 | >100 |
| OBD-242 | 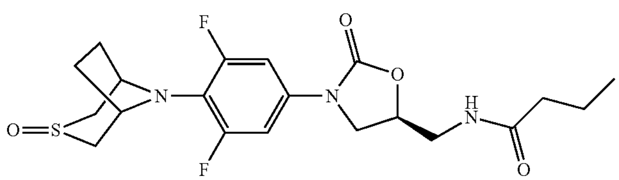 [SMILES: CCCC(=O)NC[C@H]1CN(c2cc(F)c(N3C4CCC3CS(=O)C4)c(F)c2)C(=O)O1] | | 0.61 | >100 |
| OTB-260 | 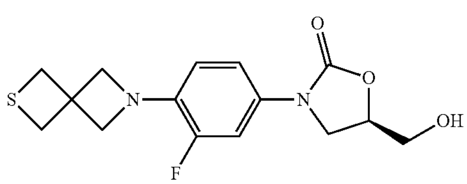 [SMILES: O=C1O[C@@H](CO)CN1c1ccc(N2CC3(CSC3)C2)c(F)c1] | 325.1010 | 1.49 | 30.03 |
| OTB-261 | 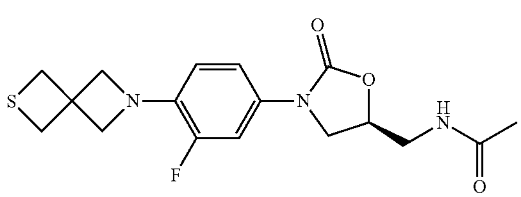 [SMILES: CC(=O)NC[C@H]1CN(c2ccc(N3CC4(CSC4)C3)c(F)c2)C(=O)O1] | 366.1274 | 0.12 | 2 |

TABLE 1-continued

| Compound | Structure | HRMS [M + H]+ | MIC (μg/mL) against H37Rv | IC50 (μM) MPS inhibition |
|---|---|---|---|---|
| OTB-523 | 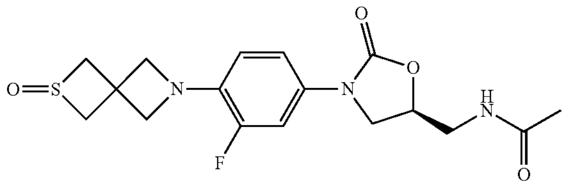 [SMILES: CC(=O)NC[C@H]1CN(c2ccc(N3CC4(C3)CS(=O)C4)c(F)c2)C(=O)O1] | | 0.5 | 4 |
| OTB-515 | 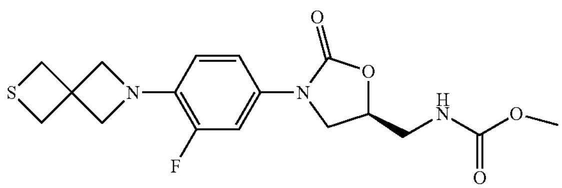 [SMILES: COC(=O)NC[C@H]1CN(c2ccc(N3CC4(CSC4)C3)c(F)c2)C(=O)O1] | NA | 0.03-0.06 | 23-71 |
| OTB-256 | 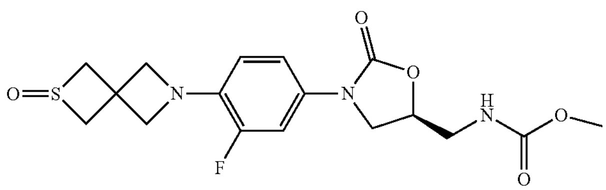 [SMILES: COC(=O)NC[C@H]1CN(c2ccc(N3CC4(C3)CS(=O)C4)c(F)c2)C(=O)O1] | | 4 | 46 |
| OTB-241 | 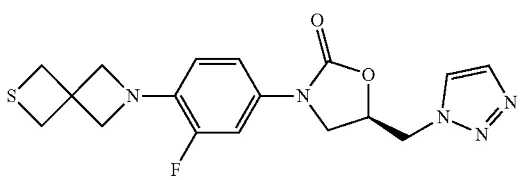 [SMILES: O=C1O[C@@H](Cn2ccnn2)CN1c1ccc(N2CC3(CSC3)C2)c(F)c1] | 376.1231 | 0.116 | 19.81 |
| OTB-247 | 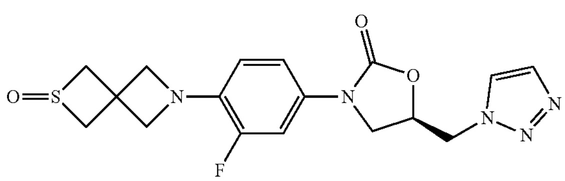 [SMILES: O=C1O[C@@H](Cn2ccnn2)CN1c1ccc(N2CC3(C2)CS(=O)C3)c(F)c1] | 392.0 | 1.2-1.4 | 10 |
| OTB-249 | 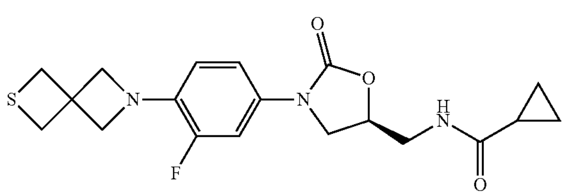 [SMILES: O=C(NC[C@H]1CN(c2ccc(N3CC4(CSC4)C3)c(F)c2)C(=O)O1)C1CC1] | 392.1426 | 0.06-0.15 | 7->100 |
| OTB-255 | 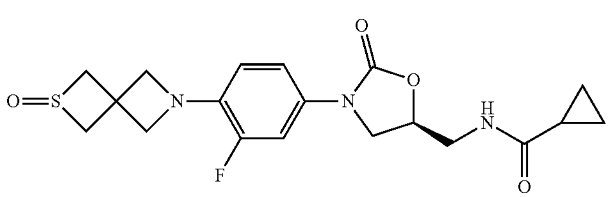 [SMILES: O=C(NC[C@H]1CN(c2ccc(N3CC4(C3)CS(=O)C4)c(F)c2)C(=O)O1)C1CC1] | 408.1378 | 1.9 | 10 |
| OTB-250 | 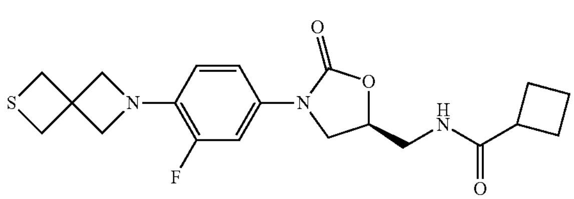 [SMILES: O=C(NC[C@H]1CN(c2ccc(N3CC4(CSC4)C3)c(F)c2)C(=O)O1)C1CCC1] | 428.2 | 0.06 | 10->100 |

TABLE 1-continued
| Compound | Structure | HRMS [M + H]+ | MIC (μg/mL) against H37Rv | IC50 (μM) MPS inhibition |
|---|---|---|---|---|
| OTB-254 | 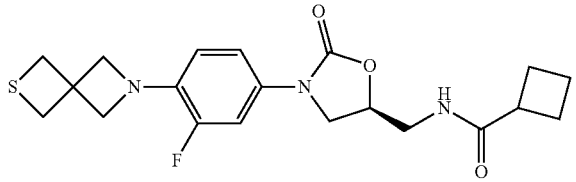 [SMILES: O=C(NC[C@H]1CN(c2ccc(N3CC4(CSC4)C3)c(F)c2)C(=O)O1)C1CCC1] | 422.1531 | 1.8 | 23 |
| OTB-260-2A | 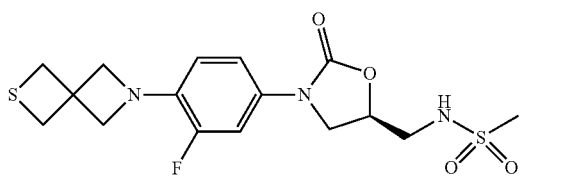 [SMILES: CS(=O)(=O)NC[C@H]1CN(c2ccc(N3CC4(CSC4)C3)c(F)c2)C(=O)O1] | 402.1 | 0.82 | >100 |
| OTB-260-2B | 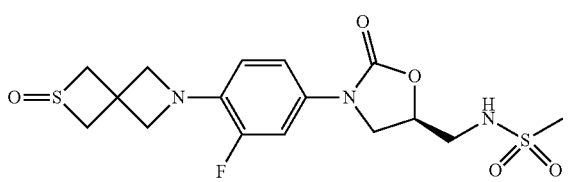 [SMILES: CS(=O)(=O)NC[C@H]1CN(c2ccc(N3CC4(C3)CS(=O)C4)c(F)c2)C(=O)O1] | 418.0 | 0.49 | >100 |
| OTB-260-5A | 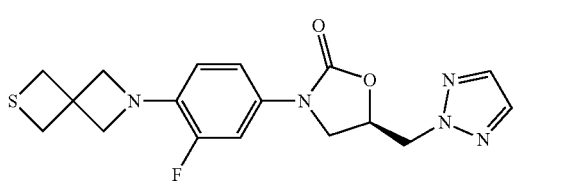 [SMILES: O=C1O[C@@H](Cn2nccn2)CN1c1ccc(N2CC3(CSC3)C2)c(F)c1] | 376.1 | 0.44 | >100 |
| OTB-260-5B | 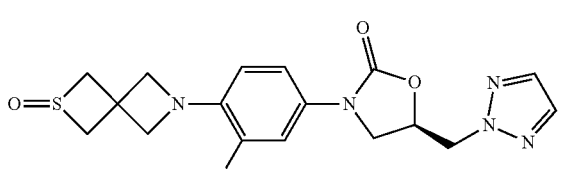 | 392.1 | >32 | >100 |
| OTB-260-4A | 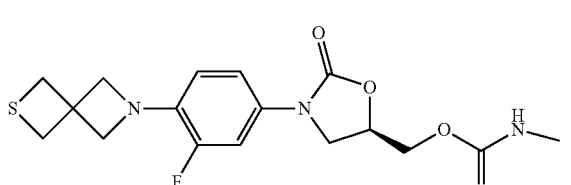 | 382.0 | 0.39 | >100 |
| OTB-260-4B | 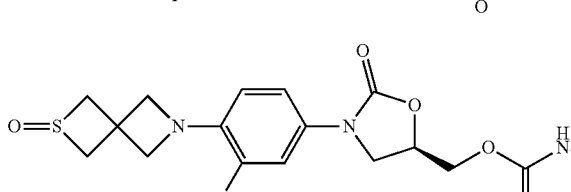 | 398.0 | 20 | >100 |
| OTB-516 | 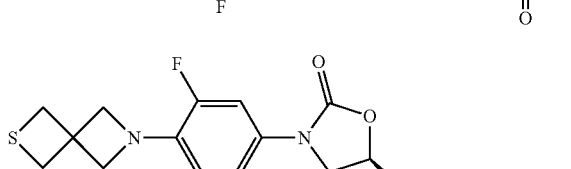 | 343.0912 | 0.465 | 15.33 |

TABLE 1-continued

| Compound | Structure | HRMS [M + H]+ | MIC (μg/mL) against H37Rv | IC50 (μM) MPS inhibition |
|---|---|---|---|---|
| OTB-515 | 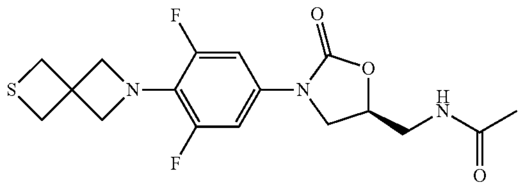 [SMILES: CC(=O)NC[C@H]1CN(c2cc(F)c(N3CC4(CSC4)C3)c(F)c2)C(=O)O1] | 384.1168 | 0.03-0.57 | 14-21 |
| OTB-520 | 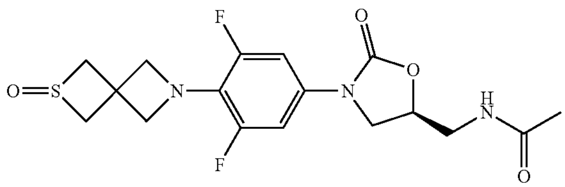 [SMILES: CC(=O)NC[C@H]1CN(c2cc(F)c(N3CC4(C3)CS(=O)C4)c(F)c2)C(=O)O1] | 400.1158 | 0.4 | 17 |
| OTB-242 | 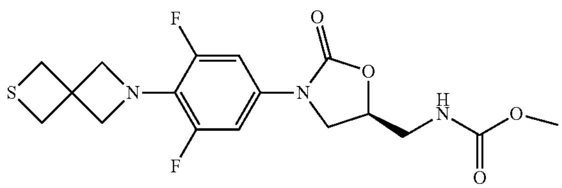 [SMILES: COC(=O)NC[C@H]1CN(c2cc(F)c(N3CC4(CSC4)C3)c(F)c2)C(=O)O1] | 400.1125 | 0.02-0.06 | 23-71 |
| OTB-253 | 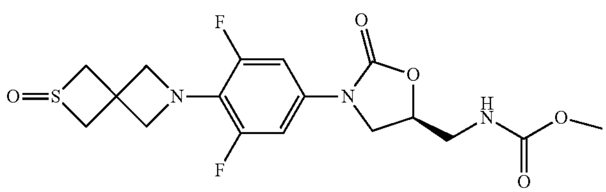 [SMILES: COC(=O)NC[C@H]1CN(c2cc(F)c(N3CC4(C3)CS(=O)C4)c(F)c2)C(=O)O1] | 416.1073 | 0.7 | 10 |
| OTB-245 | 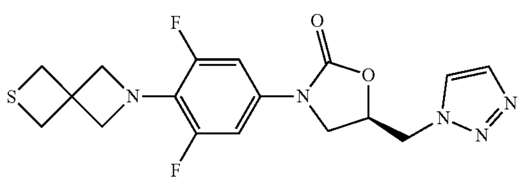 [SMILES: O=C1O[C@@H](Cn2ccnn2)CN1c1cc(F)c(N2CC3(CSC3)C2)c(F)c1] | 394.1129 | 0.03-0.5 | 25-35 |
| OTB-522 | 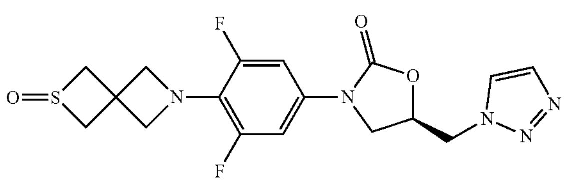 [SMILES: O=C1O[C@@H](Cn2ccnn2)CN1c1cc(F)c(N2CC3(C2)CS(=O)C3)c(F)c1] | 410.1 | 1 | 38 |
| OTB-243 | 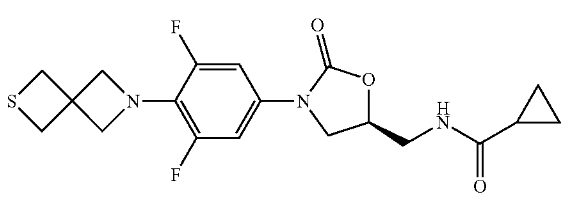 [SMILES: O=C(NC[C@H]1CN(c2cc(F)c(N3CC4(CSC4)C3)c(F)c2)C(=O)O1)C1CC1] | 410.1331 | 0.03 | 14 |
| OTB-252 | 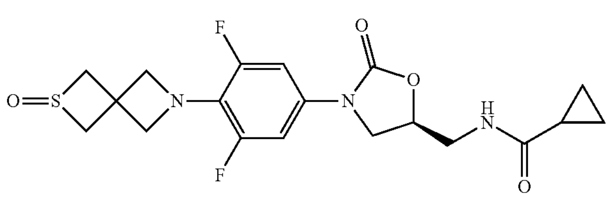 [SMILES: O=C(NC[C@H]1CN(c2cc(F)c(N3CC4(C3)CS(=O)C4)c(F)c2)C(=O)O1)C1CC1] | 426.1278 | 0.7 | 52 |

TABLE 1-continued

| Compound | Structure | HRMS [M + H]+ | MIC (μg/mL) against H$_{37}$Rv | IC$_{50}$ (μM) MPS inhibition |
|---|---|---|---|---|
| OTB-244 | 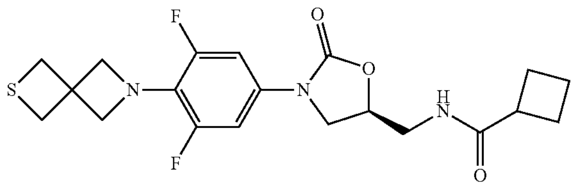 [SMILES: O=C(NC[C@H]1CN(c2cc(F)c(N3CC4(CSC4)C3)c(F)c2)C(=O)O1)C1CCC1] | 424.1483 | 0.02-0.6 | 6->22 |
| OTB-251 | 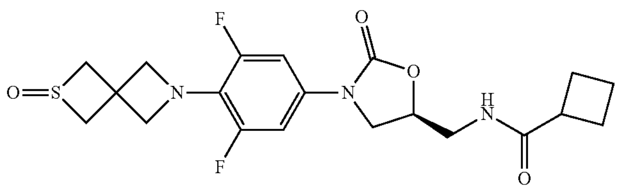 [SMILES: O=C(NC[C@H]1CN(c2cc(F)c(N3CC4(C3)CS(=O)C4)c(F)c2)C(=O)O1)C1CCC1] | 440.1441 | 0.9 | 24 |
| OTB-516-2A | 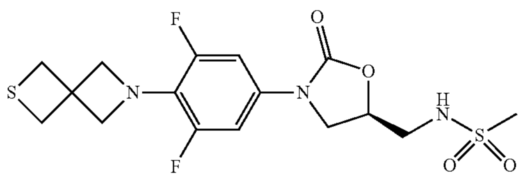 [SMILES: CS(=O)(=O)NC[C@H]1CN(c2cc(F)c(N3CC4(CSC4)C3)c(F)c2)C(=O)O1] | 420.1 | 0.05 | >100 |
| OTB-516-2B | 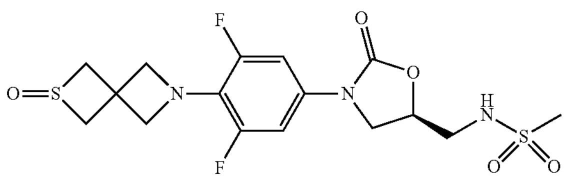 [SMILES: CS(=O)(=O)NC[C@H]1CN(c2cc(F)c(N3CC4(C3)CS(=O)C4)c(F)c2)C(=O)O1] | 436.0 | 3 | >100 |
| OTB-516-4A | 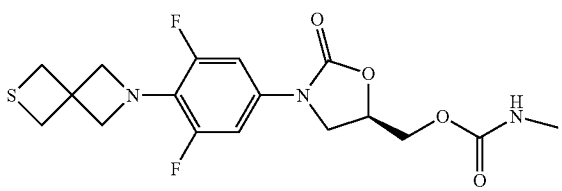 [SMILES: CNC(=O)OC[C@H]1CN(c2cc(F)c(N3CC4(CSC4)C3)c(F)c2)C(=O)O1] | 400.1 | 0.03 | >100 |
| OTB-516-4B | 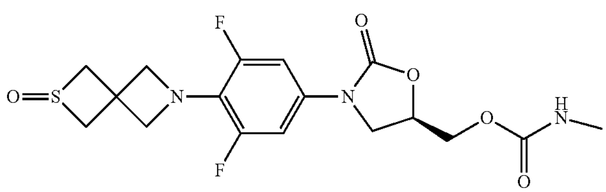 [SMILES: CNC(=O)OC[C@H]1CN(c2cc(F)c(N3CC4(C3)CS(=O)C4)c(F)c2)C(=O)O1] | 416.0 | 4.7 | >100 |
| OTB-201 | 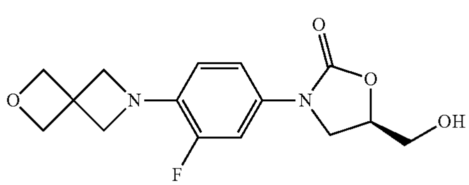 [SMILES: O=C1O[C@@H](CO)CN1c1ccc(N2CC3(COC3)C2)c(F)c1] | 309.1269 | 16 | NA |
| OBD-057 | 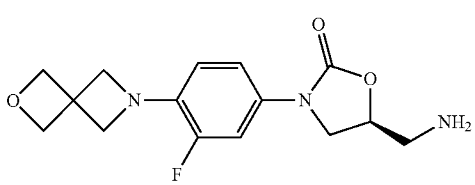 [SMILES: NC[C@H]1CN(c2ccc(N3CC4(COC4)C3)c(F)c2)C(=O)O1] | | 0.4 | 67 |

TABLE 1-continued

| Compound | Structure | HRMS [M + H]+ | MIC (μg/mL) against H37Rv | IC50 (μM) MPS inhibition |
|---|---|---|---|---|
| OTB-202 | 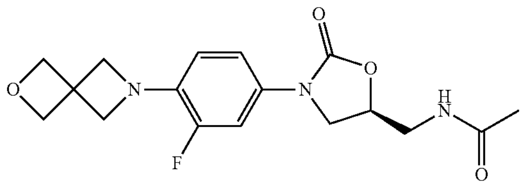 [SMILES: CC(=O)NC[C@H]1CN(c2ccc(N3CC4(COC4)C3)c(F)c2)C(=O)O1] | 350.1497 | 0.6-1.2 | 17-29 |
| OTB-203 | 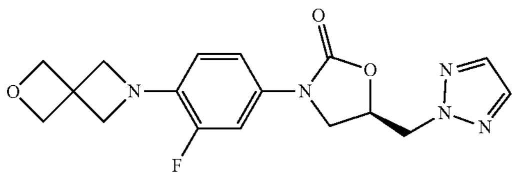 [SMILES: O=C1O[C@@H](Cn2nccn2)CN1c1ccc(N2CC3(COC3)C2)c(F)c1] | 360.1451 | >32 | NA |
| OTB-204 | 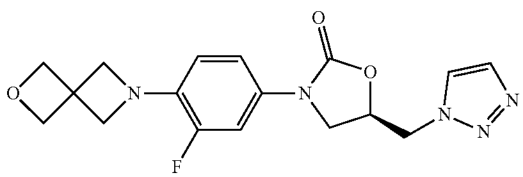 | 360.1451 | 3.2-3.7 | >100 |
| OTB-205 | 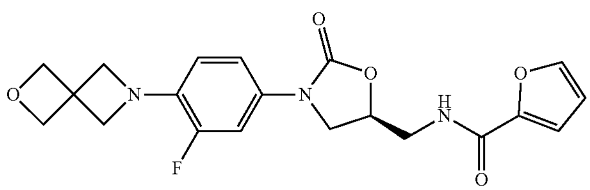 | 402.1561 | 3.9 | NA |
| OTB-206 | 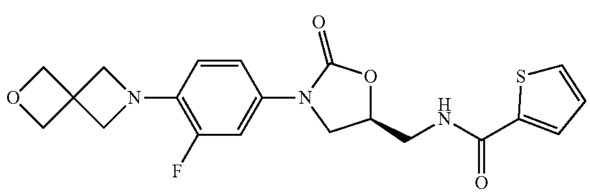 [SMILES: O=C(NC[C@H]1CN(c2ccc(N3CC4(COC4)C3)c(F)c2)C(=O)O1)c1ccco1] | 418.1331 | 2.8 | NA |
| OBD-056 | 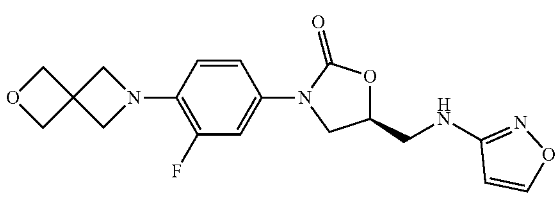 [SMILES: O=C1O[C@@H](CNc2ccon2)CN1c1ccc(N2CC3(COC3)C2)c(F)c1] | | 1.9 | 17 |
| OTB-222 | 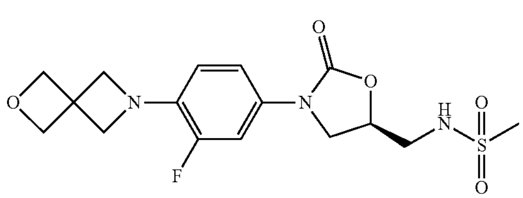 [SMILES: CS(=O)(=O)NC[C@H]1CN(c2ccc(N3CC4(COC4)C3)c(F)c2)C(=O)O1] | 386.1185 | 7.4 | NA |
| OTB-223 | 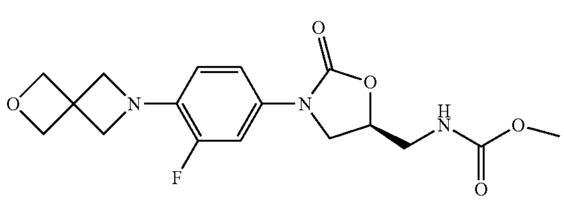 [SMILES: COC(=O)NC[C@H]1CN(c2ccc(N3CC4(COC4)C3)c(F)c2)C(=O)O1] | 366.1466 | 0.8-2.6 | 38->100 |

TABLE 1-continued

| Compound | Structure | HRMS [M + H]+ | MIC (μg/mL) against H37Rv | IC50 (μM) MPS inhibition |
|---|---|---|---|---|
| OTB-238 | 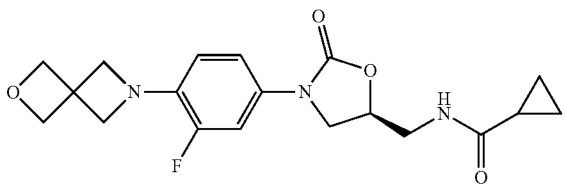 [SMILES: O=C(NC[C@H]1CN(c2ccc(N3CC4(COC4)C3)c(F)c2)C(=O)O1)C1CC1] | 376.1652 | 2-4 | 20 |
| OTB-239 | 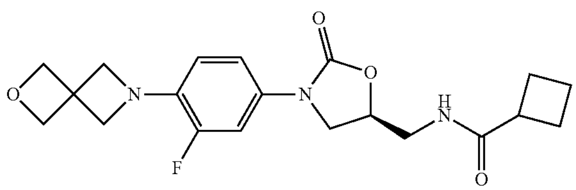 | 390.1808 | 2.1-3.8 | 19-67 |
| OTB-229 | 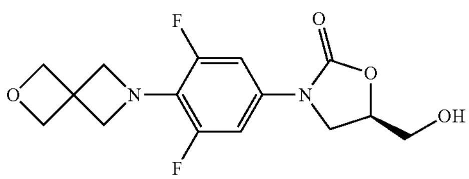 | 327.1135 | 1.9-7.4 | >100 |
| OBD-062 | 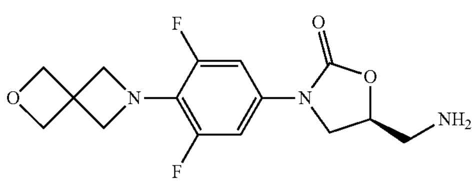 [SMILES: NC[C@H]1CN(c2cc(F)c(N3CC4(COC4)C3)c(F)c2)C(=O)O1] | | 0.1-0.25 | 21->100 |
| OTB-230 | 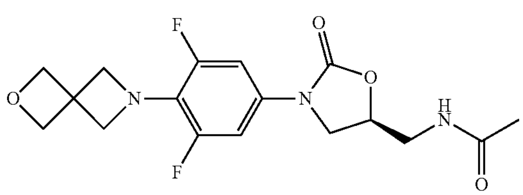 [SMILES: CC(=O)NC[C@H]1CN(c2cc(F)c(N3CC4(COC4)C3)c(F)c2)C(=O)O1] | 368.1418 | 0.2 | 13 |
| OTB-231 | 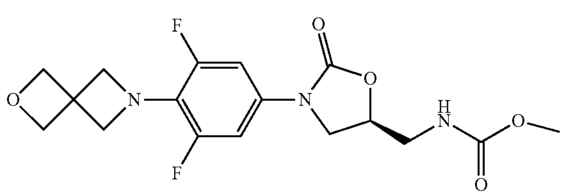 [SMILES: COC(=O)NC[C@H]1CN(c2cc(F)c(N3CC4(COC4)C3)c(F)c2)C(=O)O1] | 384.1367 | 0.24-0.7 | 37-63 |
| OTB-232 | 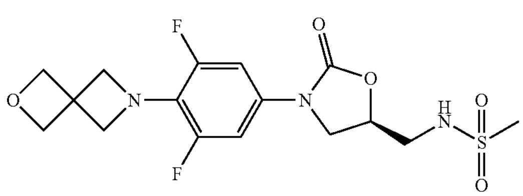 | 404.1087 | 1.5-4 | >100 |
| OTB-233 | 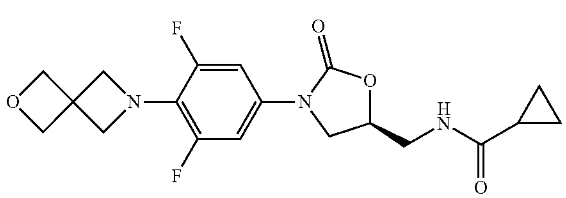 | 394.1575 | 0.36-1 | 8.4-50 |

TABLE 1-continued

| Compound | Structure | HRMS [M + H]+ | MIC (μg/mL) against H37Rv | IC50 (μM) MPS inhibition |
|---|---|---|---|---|
| OTB-234 | 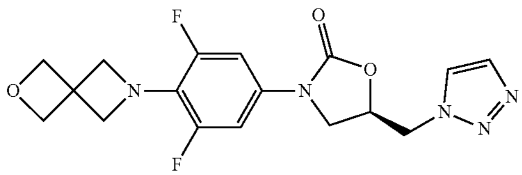 [SMILES: O=C1O[C@@H](Cn2ccnn2)CN1c1cc(F)c(N2CC3(COC3)C2)c(F)c1] | 378.1365 | 0.39-4 | 43->100 |
| OBD-061 | 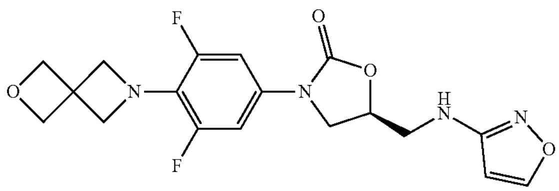 [SMILES: O=C1O[C@@H](CNc2ccon2)CN1c1cc(F)c(N2CC3(COC3)C2)c(F)c1] | | 0.8 | 29 |
| OTB-240 | 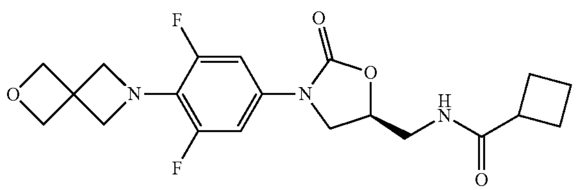 [SMILES: O=C(NC[C@H]1CN(c2cc(F)c(N3CC4(COC4)C3)c(F)c2)C(=O)O1)C1CCC1] | 408.1716 | 0.24-0.6 | 19-67 |
| OBD-051 | 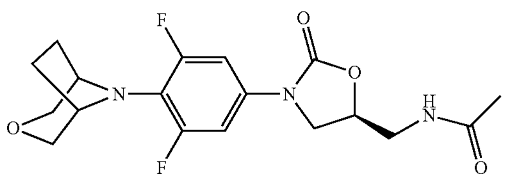 [SMILES: CC(=O)NC[C@H]1CN(c2cc(F)c(N3C4CCC3COC4)c(F)c2)C(=O)O1] | 381.9 | 0.6 | 6 |
| OBD-052 | 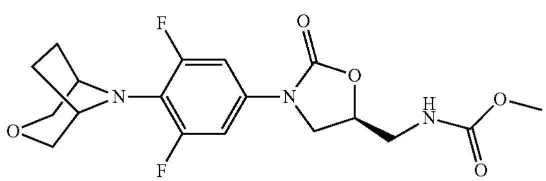 [SMILES: COC(=O)NC[C@H]1CN(c2cc(F)c(N3C4CCC3COC4)c(F)c2)C(=O)O1] | 398.0 | 0.95 | 13 |
| OBD-055 | 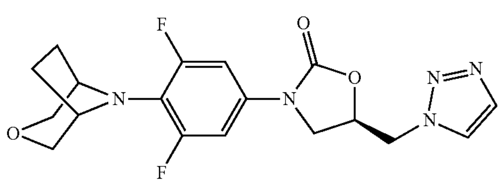 [SMILES: O=C1O[C@@H](Cn2ccnn2)CN1c1cc(F)c(N2C3CCC2COC3)c(F)c1] | 391.8 | 1.3 | 15 |
| OBD-112 | 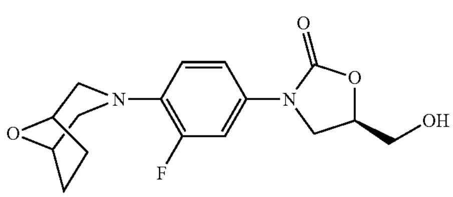 [SMILES: O=C1O[C@@H](CO)CN1c1ccc(N2CC3CCC(C2)O3)c(F)c1] | | 3.5 | >100 |
| OBD-113 | 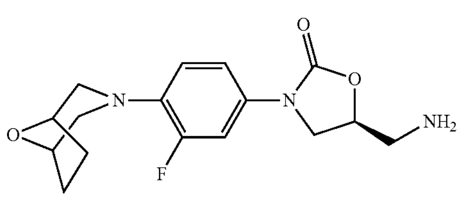 [SMILES: NC[C@H]1CN(c2ccc(N3CC4CCC(C3)O4)c(F)c2)C(=O)O1] | | 0.39 | >100 |

TABLE 1-continued

| Compound | Structure | HRMS [M + H]+ | MIC (μg/mL) against H₃₇Rv | IC₅₀ (μM) MPS inhibition |
|---|---|---|---|---|
| OBD-110 | 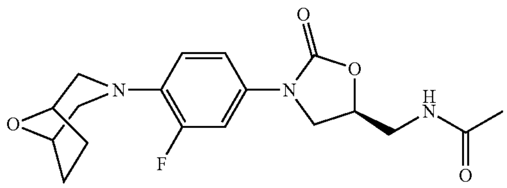 [SMILES: CC(=O)NC[C@H]1CN(c2ccc(N3CC4CCC(C3)O4)c(F)c2)C(=O)O1] | | 0.45 | 7 |
| OBD-111 | 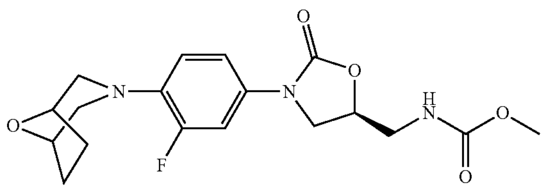 [SMILES: COC(=O)NC[C@H]1CN(c2ccc(N3CC4CCC(C3)O4)c(F)c2)C(=O)O1] | | 0.49 | 7 |
| OBD-114 | 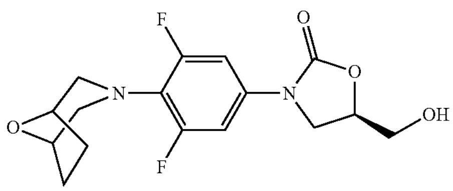 [SMILES: O=C1O[C@@H](CO)CN1c1cc(F)c(N2CC3CCC(C2)O3)c(F)c1] | | 1.7 | >100 |
| OBD-115 | 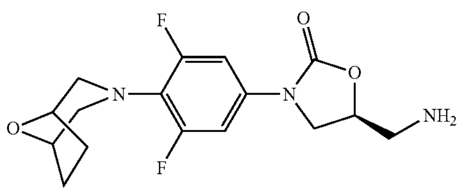 [SMILES: NC[C@H]1CN(c2cc(F)c(N3CC4CCC(C3)O4)c(F)c2)C(=O)O1] | | 0.2 = 0.3 | 87->100 |
| OBD-048 | 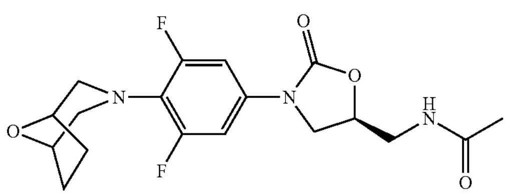 [SMILES: CC(=O)NC[C@H]1CN(c2cc(F)c(N3CC4CCC(C3)O4)c(F)c2)C(=O)O1] | | 0.39 | 5 |
| OBD-049 | 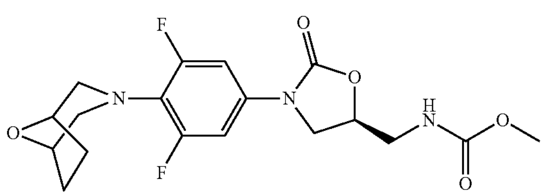 [SMILES: COC(=O)NC[C@H]1CN(c2cc(F)c(N3CC4CCC(C3)O4)c(F)c2)C(=O)O1] | | 0.25-1 | 6->100 |
| OBD-252 | 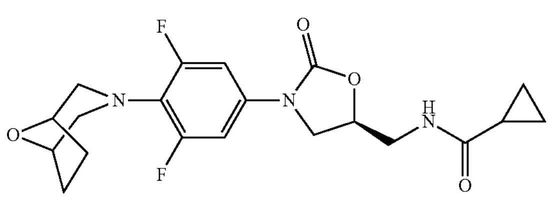 [SMILES: O=C(NC[C@H]1CN(c2cc(F)c(N3CC4CCC(C3)O4)c(F)c2)C(=O)O1)C1CC1] | | 0.47 | 32.3 |

TABLE 1-continued

| Compound | Structure | HRMS [M + H]+ | MIC (µg/mL) against H37Rv | IC50 (µM) MPS inhibition |
|---|---|---|---|---|
| OBD-253 | 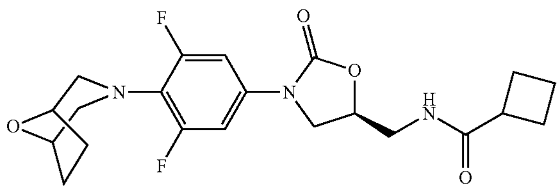 [SMILES: O=C(NC[C@H]1CN(c2cc(F)c(N3CC4CCC(C3)O4)c(F)c2)C(=O)O1)C1CCC1] | | 0.53 | 65 |
| OBD-054 | 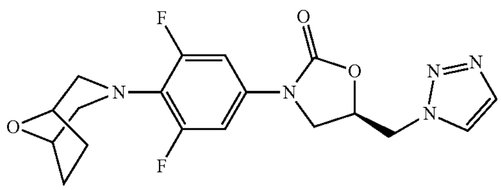 [SMILES: O=C1O[C@@H](Cn2ccnn2)CN1c1cc(F)c(N2CC3CCC(C2)O3)c(F)c1] | | 0.5 | 6-31 |
| OBD-254 | 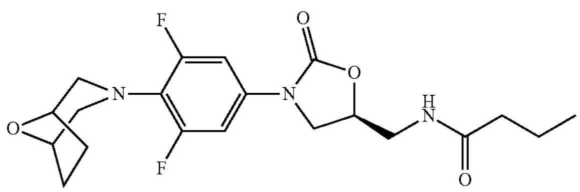 [SMILES: CCCC(=O)NC[C@H]1CN(c2cc(F)c(N3CC4CCC(C3)O4)c(F)c2)C(=O)O1] | | 0.73 | 36 |

Definitions

As used herein unless otherwise indicated, "alkyl" includes branched- and straight-chain saturated aliphatic hydrocarbon groups having the specified carbon atom numbers. Commonly used abbreviations for alkyl groups are used throughout the application, e.g. methyl may be represented by conventional abbreviations including "Me" or $CH_3$ or a symbol that is an extended bond without defined terminal group, e.g. $\xi$—, ethyl is represented by "Et" or $CH_2CH_3$, propyl is represented by "Pr" or $CH_2CH_2CH_3$, butyl can be represented by "Bu" or $CH_2CH_2CH_2CH_3$, etc. "$C_{1-6}$ alkyl" (or "$C_1$-$C_6$ alkyl") means branched or linear chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. If no number is provided, 1-10 carbon atoms are intended for linear or branched alkyl groups. $C_{1-6}$ alkyl may be unsubstituted or substituted with 1-3 fluorine or 1-3 chlorine atoms.

"Cycloalkyl" means $C_{3-10}$ carbocycles not containing heteroatoms. For example, cycloalkyl includes cyclopropyl, cyclobutyl, cyclopentyl, cyclohexyl, cycloheptyl, decahydronaphthyl, and the like.

"Aryl" means mono- and bicyclic aromatic rings containing 6-12 carbon atoms. Examples of aryl include, but are not limited to, phenyl, naphthyl, indenyl and so on. Aryl also includes monocyclic rings fused to an aryl group. Examples include tetrahydronaphthyl, indanyl and the like.

"Heterocyclyl," unless otherwise indicated, means a 4-, 5-, 6-, 7- or 8-membered monocyclic saturated ring containing 1-2 heteroatoms selected from N, O and S, in which the point of attachment may be carbon or nitrogen. Examples of "heterocyclyl" include, but are not limited to, piperidinyl, piperazinyl, morpholinyl, pyrrolidinyl, oxazolidinyl, imidazolidinyl, and so on. The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl may also include such moieties in charged form, e.g., piperidinium.

"Heteroaryl" means a mono- or bicyclic aromatic ring or ring system having 5 to 10 atoms and containing 1-3 heteroatoms selected from N, O, and S. Examples include, but are not limited to, oxadiazolyl, thiadiazolyl, pyrrolyl, furanyl, triazinyl, thienyl, pyrimidyl, pyrimidinyl, pyridazinyl, pyrazinyl, isoxazolyl, triazolyl, isothiazolyl, pyrazolyl, imidazolyl, pyridyl, pyridinyl, oxazolyl, thiazolyl, tetrazolyl, and the like. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, imidazopyridinyl, imidazopyridazinyl, pyrazolopyrazolyl, indazolyl, thienopyrazolyl, pyrazolopyridinyl, and imidazothiazolyl. Heteroaryl also includes such groups in charged form, such as pyridinium. In an embodiment, heteroaryl is triazolyl, imidazolyl, oxadiazolyl, pyrazolyl, oxazolyl, and pyridinyl.

"Heterocyclic alkyl," unless otherwise indicated, includes both branched- and straight-chain saturated aliphatic hydrocarbon groups which is bonded to a carbon or nitrogen atom of a heterocyclyl, as described above.

"Halogen (or halo)" includes fluorine (fluoro), chlorine (chloro), bromine (bromo) and iodine (iodo). In one embodiment, halogen is chlorine or fluorine.

Substitution by a named substituent is permitted on any atom in a ring (e.g., aryl, a heteroaryl ring, or a saturated heterocyclic ring) provided such ring substitution is chemically allowed and results in a stable compound. A "stable" compound can be prepared and isolated, and whose structure and properties remain or can be caused to remain essentially unchanged for a period of time that allows use of the compound for the described purposes.

Under standard nomenclature used throughout this disclosure, the terminal portion of the designated side chain is described first, followed by the adjacent functionality toward the point of attachment. For example, a $C_{1-5}$ alkyl COOR is equivalent to

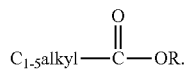

When a variable (e.g., R, $R_x$, etc.) occurs more than once in any constituent or formula, its definition on each occurrence is independent of its definition at every other occurrence. In addition, combinations of substituents and/or variables are allowed only if such combinations lead to stable compounds.

In choosing compounds of the present disclosure, one of ordinary skill in the art will recognize that the various substituents, i.e. $R^1$, $R^2$, R, etc., are to be chosen in conformity with common principles of chemical structure connectivity and stability.

The term "substituted" is used to include multiple degrees of substitution by a named substituent. Where multiple substituents are claimed, the substituted compound can be independently substituted by one or more of the disclosed substituents. By independently substituted, it is meant that the (two or more) substituents can be the identical or different.

Where a substituent or variable has multiple definitions, the substituent or variable is defined as being selected from the group consisting of the indicated definitions.

Salts:

Compounds of structural Formula I also cover the pharmaceutically acceptable salts. The compounds of the present invention may be administered in the form of a pharmaceutically acceptable salt. The term "pharmaceutically acceptable salt" means salts prepared from pharmaceutically acceptable bases or acids including inorganic or organic bases or acids. Pharmaceutically acceptable salts of basic compounds refer to non-toxic salts of the compounds of this invention which are generally prepared by mixing the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, butyrate, camphorate, camphorsulfonate, camsylate, carbonate, clavulanate, citrate, edetate, edisylate, estolate, esylate, fumarate, gluceptate, gluconate, glutamate, hydrobromide, hydrochloride, lactobionate, laurate, malate, maleate, mandelate, mesylate, methylbromide, methylnitrate, methyl sulfate, methanesulfonate, phosphate/diphosphate, polygalacturonate, propionate, salicylate, stearate, sulfate, subacetate, succinate, tannate, tartrate, teoclate, thiocyanate, tosylate, triethiodide, valerate and the like. Suitable pharmaceutically acceptable salts of acids covered by Formula I include, but are not limited to, salts generated from inorganic bases including aluminum, ammonium, calcium, copper, ferric, ferrous, lithium, magnesium, manganic, mangamous, potassium, sodium, zinc, and the like. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and so on.

Solvates and hydrates of the compounds of Formula I are also included in the present invention.

The present invention also discloses processes to synthesize the compounds of Formula I, as described below.

One aspect of the invention that is of interest relates to a compound in accordance with Formula I, or a pharmaceutically acceptable salt, hydrate, or solvate thereof, for use in a method of treatment of microbial infections in humans.

Another aspect of the invention that is of interest is a method of treating microbial infections in a human patient in need of such treatment, comprising administering a therapeutically effective amount of a compound of Formula I or a pharmaceutically acceptable salt, hydrate, or solvate thereof to said patient.

In a further aspect, the present invention provides pharmaceutical compositions of Formula I, or a salt, hydrate, or solvate thereof, further comprising one or more additional anti-infective agents.

In still a further aspect, the present invention relates to a compound in accordance with Formula I or a pharmaceutically acceptable salt, hydrate, or solvate thereof for use as an anti-tuberculosis (TB) agent in a human.

While it may be possible for the compounds of the invention to be administered as the raw chemical, it is preferable to present these as a pharmaceutical composition. Thus, according to a further aspect, the present invention provides a pharmaceutical composition comprising a compound of Formula (I) or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. Tablets, capsules, intraocular topical formulations and parenteral solutions are common among aminoglycosides. The formulations may conveniently be presented in unit dosage form and may be prepared by any of the methods well known in the art of pharmacy. All methods include the step of bringing into association a compound of Formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

ABBREVIATIONS

Throughout the synthetic schemes and examples below, abbreviations are used with the following meanings unless otherwise indicated:

Ac is acetate, or acetyl;
aq. is aqueous;
Ar is Aryl;
Bn is benzyl;
BnNH$_2$ is benzylamine;
Boc is tert-butylcarbamoyl;
br is broad;
Bu is butyl;
$^t$Bu is tert-butyl;
n-BuLi is n-butyllithium;
CbzCl is benzyl chloroformate;
CFU is colony forming units
CO$_2$ is carbon dioxide
COX-1 is cyclooxygenase I
$^c$Pr is cyclopropyl;
DCM is dichloromethane;
DIPEA is N,N-diisopropylethylamine;
DMAP is 4-dimethylaminopyridine
DMEM is Dulbecco's Modified Eagle Medium
DMF is N,N-dimethylformamide;
DMSO is dimethyl sulfoxide;
ELISA is enzyme-linked immunosorbent assay
ESI is electrospray ionization;
Et is ethyl;
Et$_3$N is triethylaimne;
Et$_2$O is diethyl ether;
EtOH is ethanol,
EtOAc is ethyl acetate;
FBS is Fetal Bovine Serum
Halo is a halogen (e.g., fluorine or chlorine);
$^1$H-NMR is proton nuclear magnetic resonance;
$^{13}$C-NMR is carbon nuclear magnetic resonance;
H9C2 is a cell line from rat heart myoblasts
HPLC is high performance liquid chromatography;
HRMS is high-resolution mass spectrometry;
Hz is hertz;
i is Iso;
IC$_{50}$ is half-maximum inhibitory concentration;
Kg is kilogram;
M is molar;
Me is methyl;
μg is microgram;
MeCN is acetonitrile;
MeOH is methanol;
MsCl is methanesulfonyl chloride;
MHz is megahertz;
mm is millimeter;
μL is microliter;
mM is milimolar;
μM is micromolar;
mmol is milimoles;
MABA is microplate alamar blue assay;
MIC is minimum inhibitory concentration;
MPS is mitochondrial protein synthesis;
m/z is mass to charge ratio;
n is normal;
NEAA is non-essential amino acids
nm is nanometer;
nPr is n-propyl;
p is para;
PE is petroleum ether;
Ph is phenyl;
Pr is propyl;
rt is room temperature;
sec is secondary;
SDH-A is succinate dehydrogenase-A
tert is tertiary;
TFA is trifluoroacetic acid;
TsCl is p-toluene sulfonyl chloride;
TMSI is trimethylsilyl iodide;
TPP is triphenylphosphine;
TsNH$_2$ is p-toluenesulfonamide;
Tosyl is p-toluenesulfonyl;
THF is tetrahydrofuran;
TLC is thin layer chromatography.

EXAMPLES

Synthetic methods for preparing the representative compounds of the present invention are illustrated in the following Examples. Starting materials are commercially available or may be made according to procedures known in the art or as illustrated herein. The following Examples are intended to help illustrate the invention, and are not intended to, nor should they be constructed to limit its scope.

Example 1

Preparation of [1,4]Thiazepane (1a)

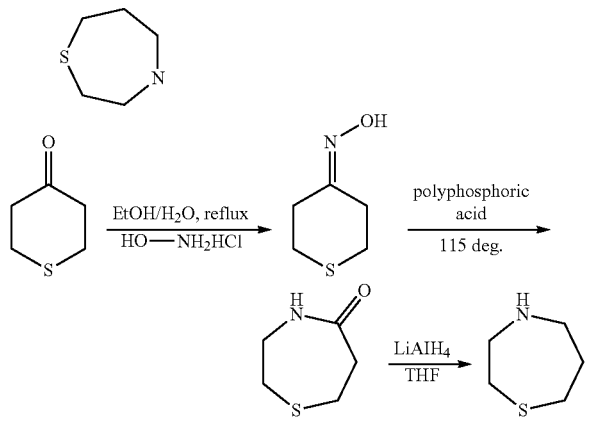

Step 1: Synthesis of Dihydro-2H-thiopyran-4(3H)-one oxime (1a-1)

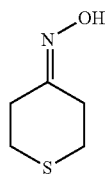

To a solution of dihydro-2H-thiopyran-4(3H)-one (10 g, 0.086 mol) and hydroxylamine hydrochloride (10.4 g, 0.15 mol) in H$_2$O (100 mL) and ethanol (40 mL) was added sodium acetate (13.1 g, 0.16 mol). The mixture was refluxed for 4 h, the organic solvent was removed in vacuum and the residue was cooled in an ice bath, 8.92 g solid was obtained in 79% yield by filtration. $^1$H-NMR (400 MHz, CDCl$_3$) δ: 2.88 (m, 2H), 2.80 (m, 2H), 2.74 (m, 2H), 2.57 (m, 2H).

Step 2: Synthesis of 1,4-Thiazepan-5-one (1a-2)

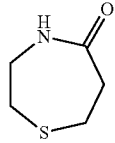

The mixture of dihydro-2H-thiopyran-4(3H)-one oxime (4.01 g, 0.03 mol) in polyphosphoric acid was heated at 115□ for 15 min, and cooled to rt, ice-water was added, then the mixture was extracted with EtOAc 5 times. The combined organic layer was dried over Na$_2$SO$_4$ and concentrated under vacuum to give 2.4 g product as brown solid in 60% yield. $^1$H-NMR (400 MHz, CDCl$_3$) δ: 6.79 (brs, 1H), 3.63 (m, 2H), 2.94 (m, 2H), 2.74 (m, 4H).

Step 3: Synthesis of 1,4-Thiazepane (1a)

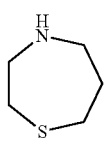

To a solution of 1,4-thiazepan-5-one (2.07 g, 15.7 mmol) in dry THF was added LiAlH$_4$ (0.66 g, 17.3 mmol) at 0□, then the mixture was stirred at rt for 4 h. H$_2$O (0.7 mL), 15% NaOH (0.7 mL) and H$_2$O (2.1 mL) were added to the reaction in successively. The mixture was filtrated to give 1.77 g product in 96% yield. $^1$H-NMR (400 MHz, CDCl$_3$) δ: 3.07 (m, 2H), 2.98 (m, 2H), 2.75 (m, 4H), 1.93 (m, 2H).

Example 2

Preparation of 1,5-Thiazocane Hydrochloride (1b)

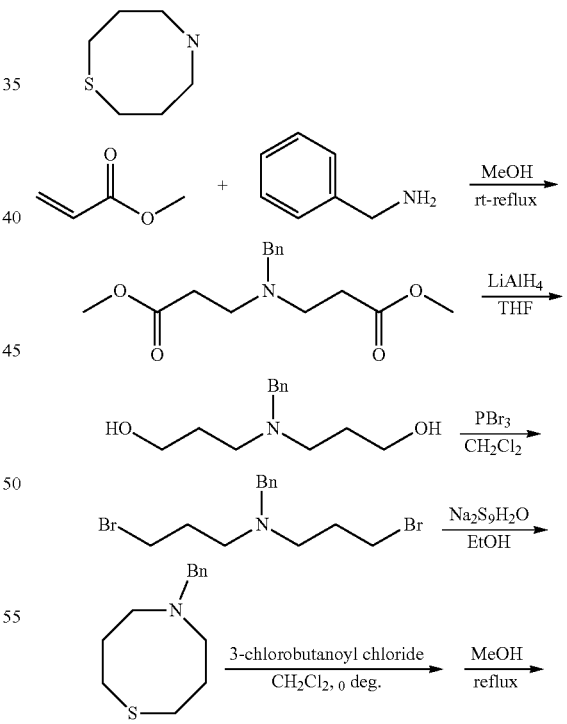

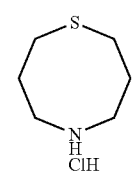

Step 1: Synthesis of Dimethyl 3,3'-(benzylazanediyl)dipropanoate (1b-1)

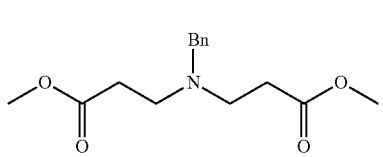

A solution of benzylamine (10.7 g, 0.1 mol) in MeOH (50 mL) was added in dropwise to a solution of methyl acrylate (18.9 g, 0.022 mol) in MeOH (100 mL) at rt. The result mixture was refluxed for 8 h, and evaporated in vacuum to give 27.9 g product in quantitative yield. $^1$H-NMR (400 MHz, CDCl$_3$) δ: 7.28 (m., 5H), 3.64 (s, 2H), 3.59 (s, 6H), 2.80 (m, 4H), 2.47 (m, 4H).

Step 2: Synthesis of 3,3'-(Benzylazanediyl)bis(propan-1-ol) (1b-2)

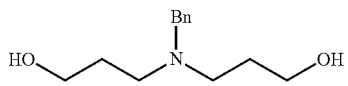

To a solution of dimethyl 3,3'-(benzylazanediyl)dipropanoate (4.47 g, 16.0 mmol) in dry THF was added LiAlH$_4$ (0.77 g, 20.2 mmol) at 0□, then the mixture was stirred at rt for 24 h. MeOH (1.5 mL), 15% NaOH (1.0 mL) and H$_2$O (1.0 mL) were added to the reaction in successively. The mixture was filtrated to give 3.4 g product in 91% yield. $^1$H-NMR (400 MHz, CDCl$_3$) δ: 7.31 (m, 5H), 3.68 (t, J=5.6 Hz, 5.6 Hz, 4H), 3.57 (s, 2H), 2.63 (t, J=6.4 Hz, 6.0 Hz, 4H), 1.76 (m, 4H).

Step 3: Synthesis of N-Benzyl-3-bromo-N-(3-bromopropyl)propan-1-amine (1b-3)

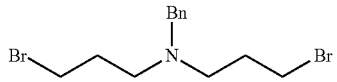 [SMILES: BrCCCN(CCCBr)Cc1ccccc1]

To a solution of 3,3'-(benzylazanediyl)bis(propan-1-ol) (447 mg, 2.0 mmol) in dry CH$_2$Cl$_2$ was added PBr3 in dropwise at 0□, then the mixture was stirred at rt for 12 h. The reaction mixture was diluted with water and extracted with CH$_2$Cl$_2$. The combined organic layer was washed with sat. NaHCO$_3$ and brine, dried over Na$_2$SO$_4$, and concentrated. The 0.43 g product was obtained as yellow oil in 61% yield. $^1$H-NMR (400 MHz, CDCl$_3$) δ: 7.27 (m, 5H), 3.56 (s, 2H), 3.44 (t, J=6.8 Hz, 6.4 Hz, 4H), 2.58 (t, J=6.4 Hz, 6.4 Hz, 4H), 2.02 (m, 4H).

Step 4: Synthesis of 5-Benzyl-1,5-thiazocane (1b-4)

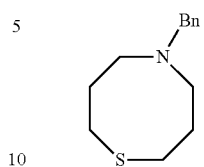

To a solution of N-benzyl-3-bromo-N-(3-bromopropyl)propan-1-amine (1.0 g, 2.9 mmol) in ethanol was added Na$_2$S.9H$_2$O (697 mg, 2.9 mmol). The mixture was refluxed for 18 h. The mixture was then cooled to r.t., and the solvent was removed in vacuum. To the residue was added H$_2$O and Et$_2$O. The aqueous layer was extracted with Et$_2$O, and the combined organic layer was washed with brine, dried over Na$_2$SO$_4$ and concentrated under vacuum. The crude product was used without purification.

Step 5: Synthesis of 1,5-Thiazocane hydrochloride (1b)

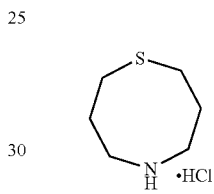

To a solution of 5-benzyl-1,5-thiazocane (8.6 g, 39 mmol) in CH$_2$Cl$_2$ was added (6.15 g, 43 mmol) at 0□. The mixture was stirred at rt for 6 h. the solvent was evaporated in vacuum and the residue was refluxed in MeOH for 3 h. The mixture was concentrated and washed with Et$_2$O. The crude product was used without purification.

Example 3

Preparation of (1R,5S)-3-thia-6-azabicyclo[3.1.1]heptane (1c)

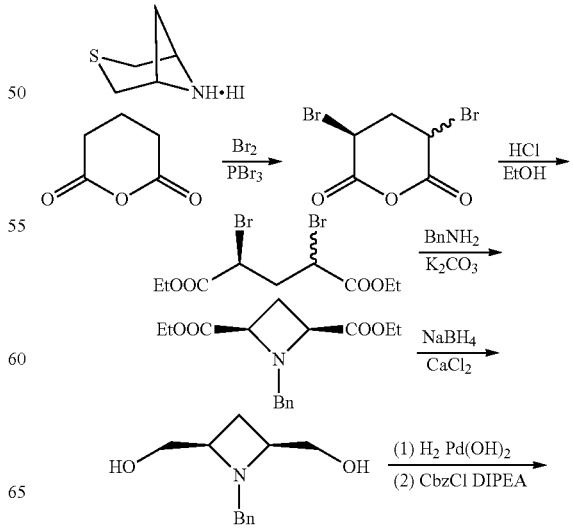

-continued

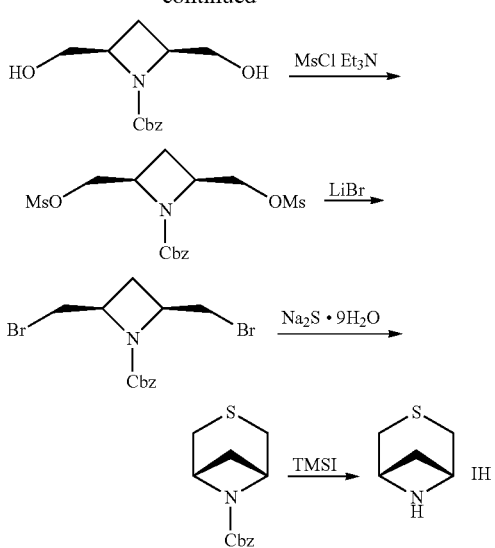

Step 1: Synthesis of diethyl
2,4-dibromopentanedioate (1c-1)

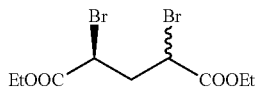 [SMILES: CCOC(=O)C(Br)C[C@H](Br)C(=O)OCC]

To a solution of dihydro-2H-pyran-2,6(3H)-dione (11.4 g, 0.1 mol) and PBr$_3$ (0.1 mL) was added Br$_2$ (32 g, 0.2 mol) dropwise at 100° C., the mixture was stirred at 100° C. for 7 h and cooled to rt. HCl/EtOH (10 mL) was added to the reaction mixture and stirred overnight at rt. After EtOH was evaporated, Et$_2$O was added to the residue and washed with sat. NaHCO$_3$ and brine, dried over Na$_2$SO$_4$, concentrated to give 32 g product was used for next step without purification.

Step 2: Synthesis of (2R,4S)-diethyl
1-benzylazetidine-2,4-dicarboxylate (1c-2)

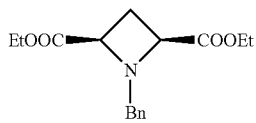

A mixture of (2R,4S)-diethyl 2,4-dibromopentanedioate (54 g, 156 mmol), benzylamine (17 g, 159 mmol) and K$_2$CO$_3$ (25.9 g, 187.2 mmol) in toluene was refluxed for 24 h. the mixture was washed with brine, dried over and concentrated. The crude product was purified by chromatography on silica gel to give 18.39 g product in 41% yield. HRMS (ESI): m/z [M+H]$^+$ calcd for C$_{16}$H$_{22}$NO$_4$: 292.1549; found: 292.1542.

Step 3: Synthesis of ((2R,4S)-1-benzylazetidine-2,4-diyl)dimethanol (1c-3)

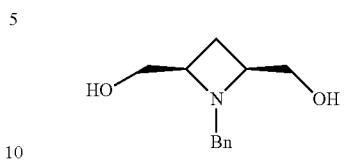

To a solution of (2R,4S)-diethyl 1-benzylazetidine-2,4-dicarboxylate (0.8 g, 2.75 mmol) in EtOH/MeOH (9:1; 10 mL) was added CaCl$_2$ (0.92 g, 8.25 mmol) at r.t. To the resulting stirred mixture was then added NaBH$_4$ (0.63 g, 16.5 mmol) in portions. The reaction mixture was stirred for overnight at r.t. Subsequently H$_2$O (5 mL) was added, and the mixture was stirred for 30 min. The mixture was then concentrated in vacuum, and partitioned between H$_2$O (10 mL) and CH$_2$Cl$_2$ (10 mL). The aqueous layer was extracted with CH$_2$Cl$_2$ (2×10 mL), and the organic layers were combined, washed with brine (10 mL), dried over Na$_2$SO$_4$, and concentrated in vacuo to give 0.25 g product as yellow oil. This product was used in the next step without further purification. MS (ESI): m/z [M+H]$^+$: 208.1477.

Step 4: Synthesis of (2R,4S)-benzyl 2,4-bis(hydroxymethyl)azetidine-1-carboxylate (1c-4)

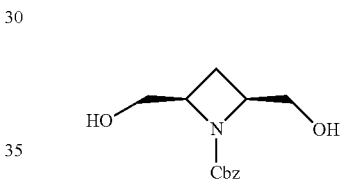

To a solution of ((2R,4S)-1-benzylazetidine-2,4-diyl)dimethanol (0.52 g, 2.9 mmol) in MeOH (10 mL) was added Pd(OH)$_2$ (0.13 g), and the mixture was stirred for 2 h under H$_2$ at r.t. The suspension was filtered through a short pad of Celite and eluted with additional MeOH. The solvent was removed in vacuo. The residue was dissolved in anhydrous CH$_2$Cl$_2$ (30 mL). To the resulting solution was added DIPEA (0.37 g, 2.9 mmol), and then CbzCl (0.44 g, 2.56 mmol) dropwise. The mixture was stirred for 2 h at r.t., and then quenched with H$_2$O (50 mL). The organic layer was washed with brine, dried over Na$_2$SO$_4$, and concentrated. The crude product was purified by chromatography on silica gel (5% MeOH in CH$_2$Cl$_2$) to afford 0.33 g product as a yellow oil in 45% yield.

Step 5: Synthesis of (2R,4S)-benzyl-2,4-bis(((methylsulfonyl)oxy)methyl)azetidine-1-carboxylate (1c-5)

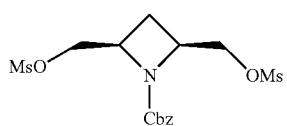 [SMILES: CS(=O)(=O)OC[C@@H]1C[C@H](COS(C)(=O)=O)N1C(=O)OCc1ccccc1]

To a solution of (2R,4S)-benzyl 2,4-bis(hydroxymethyl) azetidine-1-carboxylate (51 mg, 0.2 mmol) in CH$_2$Cl$_2$ (15 mL) was added Et$_3$N (61 mg, 0.6 mmol), and then MSCl (70 mg, 0.6 mmol) dropwise. The mixture was stirred for 5 h at r.t., and the reaction mixture was washed with 1N HCl and brine, dried over Na$_2$SO$_4$, and concentrated. The crude product was purified by chromatography on silica gel (5% MeOH in CH$_2$Cl$_2$) to afford 65 mg product as a yellow oil in 80% yield.

HRMS (ESI): m/z [M+H]$^+$ calcd for C$_{15}$H$_{22}$NO$_8$S$_2$: 408.0787; found: 408.0780.

Step 6: Synthesis of (2R,4S)-benzyl-2,4-bis(bromomethyl)azetidine-1-carboxylate (1c-6)

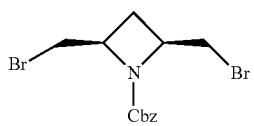 [SMILES: O=C(OCc1ccccc1)N1[C@H](CBr)C[C@@H]1CBr]

A mixture of (2R,4S)-benzyl-2,4-bis(((methylsulfonyl)oxy)methyl)azetidine-1-carboxylate (65 mg, 0.16 mmol) and LiBr (139 mg, 1.6 mmol) in acetone (15 mL) was refluxed for 10 h. The reaction mixture was evaporated, the residue was added H$_2$O (20 mL) and Et$_2$O (20 mL). The aqueous layer was extracted with Et$_2$O (2×20 mL), and the combined organic layer was washed with brine (10 mL), dried over Na$_2$SO$_4$ and concentrated under vacuum to give 51 mg product as yellow oil in 85% yield. HRMS (ESI): m/z [M+H]$^+$ calcd for C$_{13}$H$_{15}$Br$_2$NO$_2$: 375.9548; found: 375.9558.

Step 7: Synthesis of (1R,5S)-benzyl 3-thia-6-azabicyclo[3.1.1]heptane-6-carboxylate (1c-7)

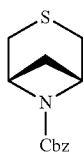

To a solution of (2R,4S)-benzyl 2,4-bis(bromomethyl)azetidine-1-carboxylate (0.77 g, 2.05 mmol) in DMF (5 mL) was added Na$_2$S.9H$_2$O (0.59 g, 2.46 mmol). The mixture was stirred at rt for 45 min. To the solution was added H$_2$O (20 mL) and EtOAc (25 mL). The aqueous layer was extracted with EtOAc (2×20 mL), and the combined organic layer was washed with brine (10 mL), dried over Na$_2$SO$_4$ and concentrated under vacuum. The crude product was purified by chromatography on silica gel (20-30% EtOAc in PE) to give 0.15 g product as a colorless oil in 28.7% yield. HRMS (ESI): m/z [M+H]$^+$ calcd for C$_{13}$H$_{17}$NO$_2$S: 250.0902; found: 250.0900.

Step 8: Synthesis of (1R,5S)-3-thia-6-azabicyclo[3.1.1]heptane iodate (1c)

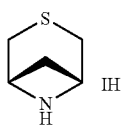

To a solution of (1R,5S)-benzyl-3-thia-6-azabicyclo[3.1.1]heptane-6-carboxylate (0.19 g, 0.8 mmol) in anhydrous CH$_2$Cl$_2$ (20 mL) was added TMSI (0.39 g, 1.9 mmol) under Ar at 0° C. The resulting mixture was stirred at rt for 2 h, and MeOH (5 mL) was added to the reaction dropwise. The result solution was stirred for additional 0.5 h, and then evaporated to remove the solvent. The residue was washed with PE/EtOAc (2:1) to give 0.24 g crude product as a brown solid and was used without purification.

Example 4

Preparation of (1R,5S)-3-Thia-8-azabicyclo[3.2.1]octane iodate (1d)

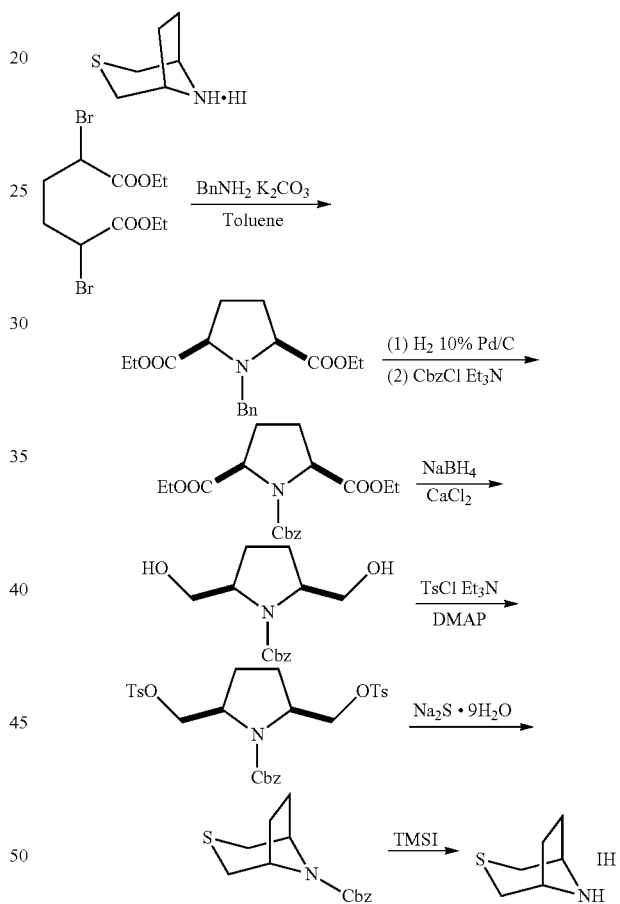

Step 1: Synthesis of cis-Diethyl 1-benzylpyrrolidine-2,5-dicarboxylate (1d-1)

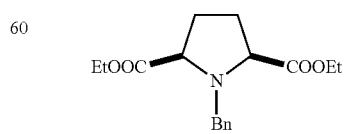

To a stirred solution of diethyl 2,5-dibromohexanedioate (10.8 g, 30 mmol) and benzylamine (3.2 g, 30 mmol) in toluene (45 mL) and H$_2$O (9 mL) was added K$_2$CO$_3$ (5 g, 36 mmol) at r.t. The mixture was refluxed for 20 h under Ar, and then poured into H$_2$O (30 mL). The aqueous layer was extracted with EtOAc (2×20 mL), the combined organic layers were washed with brine (20 mL), dried over Na$_2$SO$_4$, and purified by chromatography on silica gel (10-20% EtOAc in PE) to afford 6.1 g product as a yellow oil in 67% yield.

$^1$H-NMR (400 MHz, CDCl$_3$) δ: 7.35-7.22 (m, 5H), 4.06-4.00 (m, 4H), 3.97 (s, 2H), 3.46 (brs, 2H), 2.08-2.04 (m, 4H), 1.19 (t, J=7.1 Hz, 6H). HRMS (ESI): m/z [M+H]$^+$ calcd for C$_{17}$H$_{24}$NO$_4$: 306.1705; found: 306.1695.

Step 2: Synthesis of cis-1-Benzyl 2,5-diethyl pyrrolidine-1,2,5-tricarboxylate (1d-2)

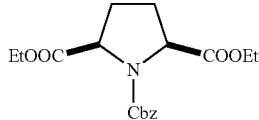 [SMILES: CCOC(=O)[C@H]1CC[C@@H](C(=O)OCC)N1C(=O)OCc1ccccc1]

To a solution of cis-diethyl 1-benzylpyrrolidine-2,5-dicarboxylate (5.4 g, 17.7 mmol) in MeOH (100 mL) was added 10% Pd/C (0.54 g), and the mixture was shaken in a Parr Shaker for 4 h at 50 psi under H$_2$ at r.t. The suspension was filtered through a short pad of Celite and eluted with additional MeOH. The solvent was removed in vacuo. The residue was dissolved in anhydrous CH$_2$Cl$_2$ (50 mL), and cooled to 0° C. To the resulting solution was added Et$_3$N (2.2 g, 21.6 mmol), and then CbzCl (3.7 g, 21.6 mmol) dropwise. The mixture was stirred overnight at r.t., and then quenched with H$_2$O (50 mL). The organic layer was washed with brine, dried over Na$_2$SO$_4$, and concentrated. The crude product was purified by chromatography on silica gel (5-20% EtOAc in PE) to afford 5.22 g product as a yellow oil in 84% yield. $^1$H-NMR (400 MHz, CDCl$_3$) δ: 7.33-7.29 (m, 5H), 5.19-5.10 (m, 2H), 4.47 (m, 1H), 4.40 (m, 1H), 4.22 (q, J=7.2 Hz, 2H), 4.09 (q, J=6.8 Hz, 2H), 2.25-2.14 (m, 4H), 1.28 (t, J=6.8 Hz, 3H), 1.17 (t, J=6.8 Hz, 3H). HRMS (ESI): m/z [M+H]$^+$ calcd for C$_{18}$H$_{24}$NO$_6$: 350.1604; found: 350.1649.

Step 3: Synthesis of cis-Benzyl 2,5-bis(hydroxymethyl)pyrrolidine-1-carboxylate (1d-3)

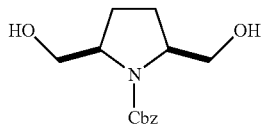 [SMILES: O=C(OCc1ccccc1)N1[C@H](CO)CC[C@@H]1CO]

To a solution of cis-1-benzyl 2,5-diethyl pyrrolidine-1,2,5-tricarboxylate (5.75 g, 16.4 mmol) in EtOH/MeOH (10:1; 300 mL) was added CaCl$_2$ (5.5 g, 49.2 mmol) at r.t. To the resulting stirred mixture was then added NaBH$_4$ (3.75 g, 98.4 mmol) in portions. The reaction mixture was stirred for overnight at r.t. Subsequently H$_2$O (50 mL) was added, and the mixture was stirred for 30 min. The mixture was then concentrated in vacuo, and partitioned between H$_2$O (100 mL) and EtOAc (100 mL). The aqueous layer was extracted with EtOAc (2×50 mL), and the organic layers were combined, washed with brine (10 mL), dried over Na$_2$SO$_4$, and concentrated in vacuo to give 4.57 g product as colorless oil. This product was used in the next step without further purification.

$^1$H-NMR (400 MHz, CDCl$_3$) δ: 7.39-7.33 (m, 5H), 5.16 (s, 2H), 4.09-3.82 (m, 4H), 3.56 (d, J=8.1 Hz, 2H), 2.91 (brs, 2H), 2.04-1.97 (m, 4H). HRMS (ESI): m/z [M+Na]$^-$ calcd for C$_{14}$H$_{19}$NNaO$_4$: 288.1206; found: 288.1196.

Step 4: Synthesis of cis-Benzyl 2,5-bis(tosyloxymethyl)pyrrolidine-1-carboxylate (1d-4)

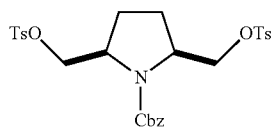 [SMILES: Cc1ccc(S(=O)(=O)OC[C@H]2CC[C@@H](COS(=O)(=O)c3ccc(C)cc3)N2C(=O)OCc2ccccc2)cc1]

A solution of compound cis-benzyl 2,5-bis(hydroxymethyl)pyrrolidine-1-carboxylate (4.35 g, 16.4 mmol), Et$_3$N (3.65 g, 36.1 mmol), and DMAP (4.01 g, 32.8 mmol) in CH$_2$Cl$_2$ (50 mL) was cooled to 0° C. To this mixture was added p-toluenesulfonyl chloride (6.88 g, 36.1 mmol) in one portion and the resulting mixture was stirred overnight at r.t. The mixture was then washed with water and brine, dried over Na$_2$SO$_4$ and concentrated under vacuum. The residue was purified by flash column chromatography (30-40% EtOAc in PE) to give 8.97 g product as a semi-solid in 95% yield.

$^1$H-NMR (400 MHz, CDCl$_3$) δ: 7.73 (brs, 4H), 7.36-7.29 (m, 9H), 5.03-4.96 (m, 2H), 4.15-3.89 (m, 6H), 2.44 (s, 6H), 1.87-1.83 (m, 4H). $^{13}$C-NMR (100 MHz, CDCl$_3$) δ (rotamers): 165.30, 154.49, 144.90, 135.88, 132.61, 129.90, 128.55, 128.19, 127.89, 69.16, 68.87, 67.28, 57.30, 56.56, 26.61, 25.44, 21.63. HRMS (ESI): m/z [M+H]$^+$ calcd for C$_{28}$H$_{32}$NO$_8$S$_2$: 574.1564; found: 574.1547.

Step 5: Synthesis of (1R,5S)-Benzyl-3-thia-8-azabicyclo[3.2.1]octane-8-carboxylate (1d-5)

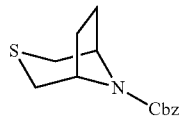 [SMILES: O=C(OCc1ccccc1)N1C2CCC1CSC2]

To a solution of cis-benzyl 2,5-bis(tosyloxymethyl)pyrrolidine-1-carboxylate (4.1 g, 7.1 mmol) in ethanol (25 mL) and H$_2$O (25 mL) was added Na$_2$S.9H$_2$O (5.12 g, 21.3 mmol). The mixture was refluxed for 5 h. The mixture was then cooled to r.t., and the solvent was removed in vacuo. To the residue was added H$_2$O (20 mL) and EtOAc (25 mL). The aqueous layer was extracted with EtOAc (2×20 mL), and the combined organic layer was washed with brine (10 mL), dried over Na$_2$SO$_4$ and concentrated under vacuum. The crude product was purified by chromatography on silica gel (20-30% EtOAc in PE) to give 1.38 g product as a colorless oil in 73% yield.

$^1$H-NMR (400 MHz, CDCl$_3$) δ: 7.37-7.30 (m, 5H), 5.16 (s, 2H), 4.52-4.47 (m, 2H), 3.22 (d, J=11.6 Hz, 1H), 3.11 (d, J=10.8 Hz, 1H), 2.12 (d, J=12.8 Hz, 2H), 2.06 (d, J=1.2 Hz, 4H). $^{13}$C-NMR (100 MHz, CDCl$_3$) δ: 152.95, 136.59, 128.40, 127.93, 127.80, 66.73, 53.94, 32.72, 32.08, 28.82, 27.99. HRMS (ESI): m/z [M+H]$^+$ calcd for $C_{14}H_{18}NO_2S$: 264.1058; found: 264.1113.

Step 6: Synthesis of (1R,5S)-3-Thia-8-azabicyclo[3.2.1]octane iodate (1d)

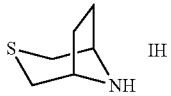

To a solution of (1R,5S)-benzyl-3-thia-8-azabicyclo[3.2.1]octane-8-carboxylate (0.24 g, 0.91 mmol) in anhydrous $CH_2Cl_2$ (20 mL) was added TMSI (0.44 g, 2.18 mmol) under Ar at 0° C. The resulting mixture was stirred at rt for 0.5 h, and MeOH (0.26 mL) was added to the reaction dropwise. The result solution was stirred for additional 0.5 h, and then evaporated to remove the solvent. The residue was washed with PE/EtOAc (1:2) to give 0.21 g product as a yellow solid in 91% yield. Mp: 208-210□. $^1$H-NMR (400 MHz, CDCl$_3$) δ: 8.92 (brs, 1H), 8.72 (brs, 1H), 4.38 (s, 2H), 3.78 (d, J=14.0 Hz, 2H), 2.41-2.35 (m, 4H), 2.24-2.22 (d, J=7.6 Hz, 2H). $^{13}$C-NMR (100 MHz, CDCl$_3$) δ: 55.67, 31.42, 27.23. HRMS (ESI): m/z [M+H]$^+$ calcd for $C_6H_{12}NS$: 130.0685; found: 130.0686.

Example 5

Preparation of 2-Thia-6-aza-spiro[3.3]heptane (1e)

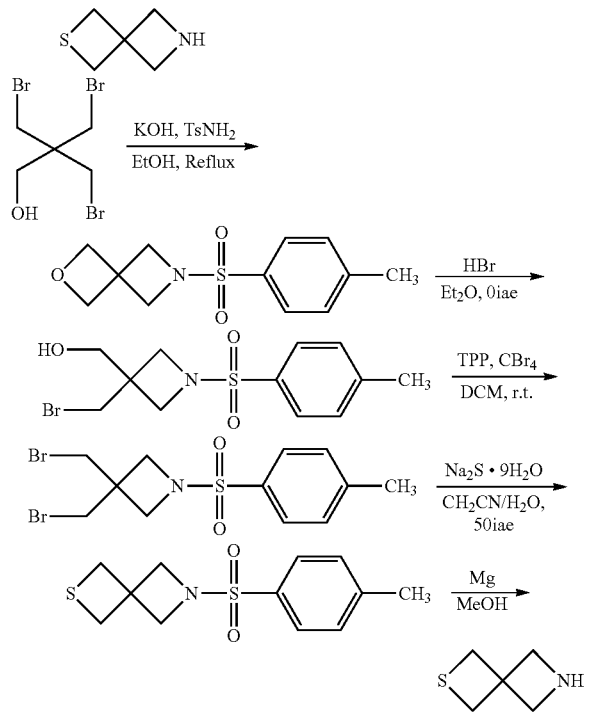

Step 1: Synthesis of 6-Tosyl-2-oxa-6-azaspiro[3.3]heptane (1e-1)

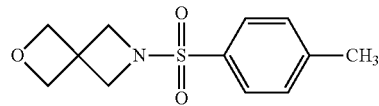 [SMILES: Cc1ccc(S(=O)(=O)N2CC3(COC3)C2)cc1]

To a solution of KOH (9.04 g, 161 mmol) and 3-bromo-2,2-bis(bromomethyl)propan-1-ol (15.3 g, 47.0 mmol) in 500 mL ethanol was added p-tosylamide (17.9 g, 104 mmol) at room temperature and the reaction mixture was refluxed for 20 h. The solvent was removed by evaporation, 100 mL 8% NaOH solution was added and the suspension was stirred for another 2 h. The mixture was filtered and the white filter cake was rinsed with water until the washing water was neutral. The filter cake was dried to give the title product. Yield: 6.1 g (40.2%). $^1$H-NMR (400 MHz, CDCl$_3$) δ: 7.71 (d, J=8.0 Hz, 2H), 7.37 (d, J=8.0 Hz, 2H), 4.59 (s, 4H), 3.91 (s, 4H), 2.46 (s, 3H). HRMS (ESI-TOF$^+$): m/z [M+H]$^+$ calcd for $C_{12}H_{16}NO_3S$: 254.0825; found: 254.0851.

Step 2: Synthesis of (3-(bromomethyl)-1-tosylazetidin-3-yl)methanol (1e-2)

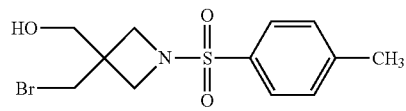 [SMILES: Cc1ccc(S(=O)(=O)N2CC(CO)(CBr)C2)cc1]

To a suspension of 6-(p-toluenesulfonyl)-2-oxa-6-azaspiro[3.3]heptane (1e-1) (9.79 g, 38.7 mmol) in Et$_2$O (200 mL) at 0° C. was added a solution of hydrobromic acid (ca. 33% in AcOH) in dropwise. The resulting solution was stirred at room temperature for 30 min, it was adjusted to pH=8 with 1 mol/L NaOH. The phases were separated and the aqueous phase was extracted with Et$_2$O (3×100 mL). The combined organic layers were dried (Na$_2$SO$_4$), filtered, and concentrated in vacuo to afford the title compound as a colorless solid. Yield: 10.0 g (77.4%). $^1$H-NMR (400 MHz, CDCl$_3$) δ: 7.74 (d, J=8.0 Hz, 2H), 7.39 (d, J=8.0 Hz, 2H), 3.68 (s, 2H), 3.68 (s, 2H), 3.62 (d, J=8.4 Hz, 2H), 3.55 (d, J=8.4 Hz, 2H), 3.45 (s, 2H), 2.47 (s, 3H).

Step 3: Synthesis of 3,3-bis(bromomethyl)-1-tosylazetidine (1e-3)

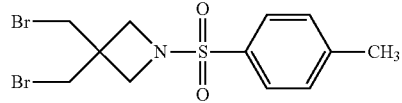

(3-(Bromomethyl)-1-tosylazetidin-3-yl)methanol (1e-2) (10.0 g, 30.0 mmol) was dissolved in CH$_2$Cl$_2$ and CBr$_4$ (16.4 g, 49.4 mmol) was added. The resulting solution was cooled to 0° C. and PPh$_3$ (17.9 g, 104 mmol) was added. The reaction mixture was stirred at room temperature overnight. The mixture was concentrated under reduced pressure and the residue was purified by chromatography on silica gel (5-10% EtOAc in PE) to give the pure title compound. Yield:

8.85 g (74.8%). $^1$H-NMR (400 MHz, CDCl$_3$) δ: 7.73 (d, J=8.0 Hz, 2H), 7.39 (d, J=8.0 Hz, 2H), 3.59 (s, 4H), 3.53 (s, 4H), 2.47 (s, 3H).

Step 4: Synthesis of
6-tosyl-2-thia-6-azaspiro[3.3]heptane (1e-4)

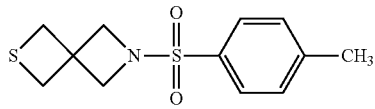 [SMILES: Cc1ccc(S(=O)(=O)N2CC3(CSC3)C2)cc1]

To a solution of 3,3-bis(bromomethyl)-1-tosylazetidine (1e-3) (8.82 g, 7.9 mmol) in a mixture of CH$_3$CN (90 mL) and H$_2$O (9 mL) was added Na$_2$S.9H$_2$O (10.7 g, 44.7 mmol) and the reaction mixture was stirred at 50° C. for 4 h, then it was concentrated to dryness. EtOAc (100 mL) and NaHCO$_3$ solution (100 mL) were added, and the phases were separated. The aqueous phase was extracted with EtOAc (2×100 mL). The organic phase was washed with brine, dried (Na$_2$SO$_4$), filtered, and concentrated in vacuo to give the title compound. Yield: 5.46 g (90.1%). $^1$H-NMR (400 MHz, CDCl$_3$) δ: 7.71 (d J=8.0 Hz, 2H), 7.37 (d J=8.0 Hz, 2H), 3.78 (s, 4H), 3.14 (s, 4H), 2.46 (s, 3H). HRMS (ESI-TOF$^+$): m/z [M+H]$^+$ calcd for C$_{12}$H$_{16}$NO$_2$S$_2$: 270.0622; found: 270.0621.

Step 5: Synthesis of 2-thia-6-azaspiro[3.3]heptane (1e)

6-Tosyl-2-thia-6-azaspiro[3.3]heptane (1e-4) (2.0 g, 7.9 mmol) was dissolved in MeOH (40 mL). To the resulting solution was added magnesium powder (1.0 g), and the reaction mixture was sonicated at RT for about 3 hrs. The reaction mixture was concentrated in vacuo, the crude product was used in next step without purification.

Example 6

Preparation of 2-Oxa-6-aza-spiro[3.3]heptane (1f)

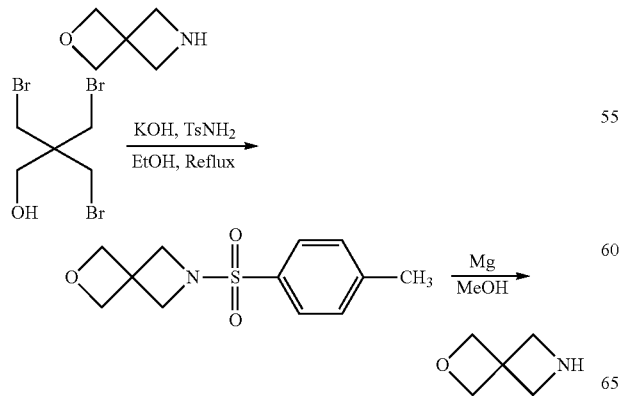

Step 1: Synthesis of
6-Tosyl-2-oxa-6-azaspiro[3.3]heptane

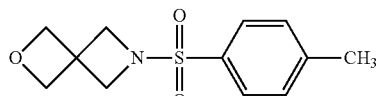

This product was synthesized as described in Example 5, Step 1.

Step 2: Synthesis of 2-oxa-6-azaspiro[3.3]heptane (1f)

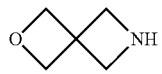

6-Tosyl-2-oxa-6-azaspiro[3.3]heptane (6.3 g, 25.0 mmol) was dissolved in MeOH (50 mL). To the resulting solution was added magnesium powder (6.0 g), and the reaction mixture was sonicated at RT for about 3 hrs. The reaction mixture was concentrated in vacuo, the crude product was used in next step without purification.

Example 7

Preparation of N-Boc Protected
2,6-Diaza-spiro[3.3]heptane (1 g)

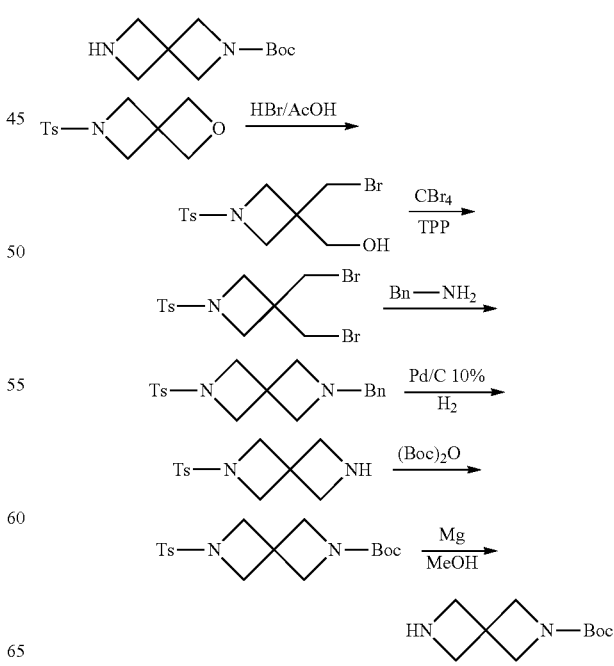

Step 1: Synthesis of (3-(Bromomethyl)-1-(p-toluenesulfonyl)azetidin-3-yl)methanol (1g-1)

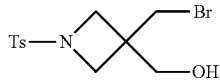

To a suspension of 6-(p-toluenesulfonyl)-2-oxa-6-azaspiro[3.3]heptane (6.25 g, 24.7 mmol) (obtained according to Example 5 step 1) in Et$_2$O (100 mL) at 0° C. was dropwise added over a period of 15 min a solution of hydrobromic acid (ca. 33% in AcOH; 4.1 mL, 24.7 mmol) in Et$_2$O (5 mL). The resulting mixture was warmed to room temperature and stirred for 45 min. The resulting colorless solution was poured into a saturated aqueous solution of NaHCO$_3$ (100 mL). The organic phase was separated and the aqueous phase was extracted with Et$_2$O (100 mL). The combined organic layers were dried (MgSO$_4$), filtered, and concentrated in vacuo to afford the title compound 7.74 g as a colorless solid. The crude product was pure enough for further transformations.

Step 2: Synthesis of 3,3-Bis(bromomethyl)-1-(p-toluenesulfonyl)azetidine (1g-2)

The above crude product 1g-1 (7.74 g, 23.1 mmol) was dissolved in CH$_2$Cl$_2$ (100 mL) and CBr$_4$ (13.7 g, 41.2 mmol) was added in one portion. The resulting solution was cooled to 0° C. and PPh$_3$ (26.26 g, 41.2 mmol) was added in one portion. The reaction mixture turned to a dark orange solution, which was stirred at 0° C. for 1.5 h, then warmed to room temperature and stirred for further 8 h. The mixture was concentrated under reduced pressure to afford a dark orange oil, which was purified by chromatography (hexanes:EtOAc 4:1) to give the title compound 7.61 g. $^1$H-NMR (400 MHz, CDCl$_3$) δ: 7.73 (d, J=8.4 Hz, 2H), 7.40 (d, J=7.6 Hz, 2H), 3.60 (s, 4H), 3.53 (s, 4H), 2.48 (s, 3H).

Step 3: Synthesis of 2-Benzyl-6-(p-toluenesulfonyl)-2,6-diazaspiro[3.3]heptane (1g-3)

Dibromide 1g-2 (7.61 g, 19.1 mmol) was dissolved in CH$_3$CN (100 mL). Benzylamine (4.1 g, 38.3 mmol) and DIPEA (12.4 g, 95.5 mmol) were added to the above mixture and the reaction mixture was heated to reflux for 3 d. Then the yellowish solution was cooled to room temperature and concentrated to about ⅙ of the initial volume. The residue was partitioned between CH$_2$Cl$_2$ (100 mL) and 1 mol/L NaOH (100 mL). The organic phase was separated and the aqueous layer was extracted with CH$_2$Cl$_2$ (50 mL). The combined organic layers were dried (MgSO$_4$), filtered, and concentrated in vacuo. The residue was purified by chromatography (hexanes:EtOAc:Et3N 1:1:1% to 1:2:1% gradient) to afford the title compound 4.0 g. $^1$H-NMR (400 MHz, CDCl$_3$) δ: 7.69 (d, J=8.2 Hz, 2H), 7.34 (d, J=8.2 Hz, 2H), 7.32-7.11 (m, 5H), 3.82 (s, 4H), 3.47 (s, 2H), 3.13 (s, 4H), 2.44 (s, 3H).

Step 4: Synthesis of tert-Butyl 6-(p-toluenesulfonyl)-2,6-diazaspiro[3.3]heptane-2-carboxylate (1g-5)

Benzyl azetidine 1g-3 (2.70 g, 7.88 mmol) was dissolved in MeOH (40 mL), and Pd/C (10% on charcoal; 0.54 g) was added to the above mixture. A hydrogen atmosphere (50 PSI) was built up and the mixture was heated to 45° C. and stirred at this temperature for 48 h. Then the reaction mixture was cooled to room temperature and filtered over celite. The filter cake was washed thoroughly with MeOH (2×20 mL). To the above solution of the intermediate Ts-protected azetidine (1g-4) in MeOH (ca. 80 mL) was added Boc$_2$O (1.77 g, 7.88 mmol). The resulting solution was stirred at room temperature for 1 h and concentrated in vacuo. The residue was purified by chromatography (hexanes:EtOAc 1:1 to 1:2 gradient) to furnish the pure title compound. $^1$H-NMR (400 MHz, CDCl$_3$) δ: 7.71 (d, J=7.6 Hz, 2H), 7.37 (d, J=8.0 Hz, 2H), 3.85 (s, 4H), 3.84 (s, 4H), 2.46 (s, 3H), 1.39 (s, 9H).

Step 5: Synthesis of tert-Butyl 2,6-diazaspiro[3.3]heptane-2-carboxylate (1g)

The above product 1g-5 (3.50 g, 10.0 mmol) was dissolved in MeOH (30 mL). Mg powder (1.92 g, 80.0 mmol) was added, and the mixture was sonicated for 6 h. The reaction mixture was concentrated in vacuo to afford a dark gray solid, which can be used for the further reaction without purification.

Example 8

General Synthetic Methods: Preparation of Oxazolidinone Compounds

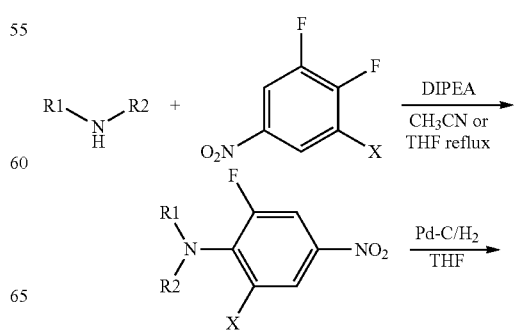

-continued

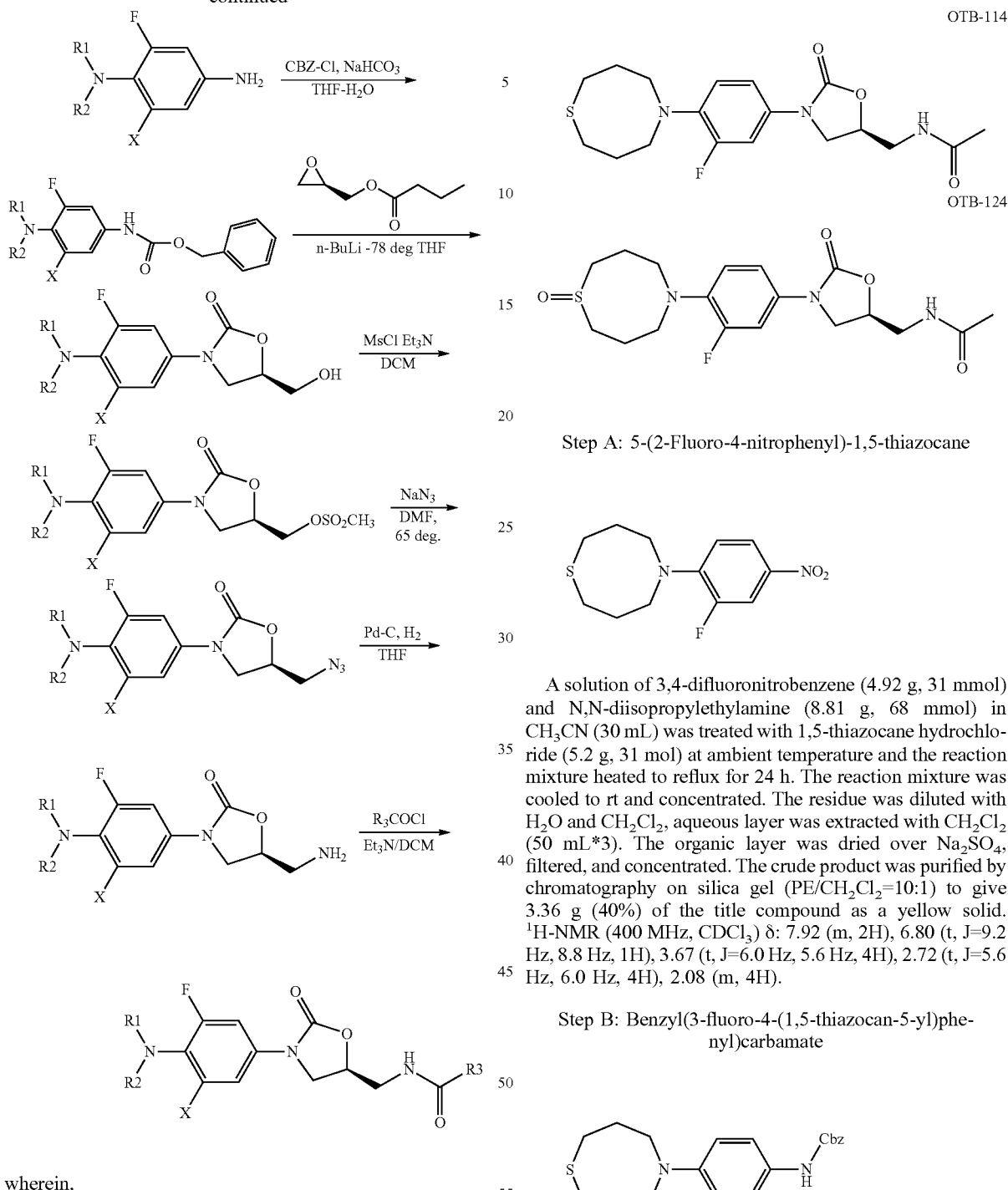

wherein,

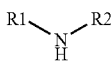

represents ring A as previously defined in Formula I; X=H, or F.

General procedures for the preparation of (S)—N-((3-(3-fluoro-4-(1,5-thiazocan-5-yl) phenyl)-2-oxooxazolidin-5-yl) methyl)acetamide (OTB-114) and its sulfoxide (OTB-124), are provided below.

Step A: 5-(2-Fluoro-4-nitrophenyl)-1,5-thiazocane

A solution of 3,4-difluoronitrobenzene (4.92 g, 31 mmol) and N,N-diisopropylethylamine (8.81 g, 68 mmol) in $CH_3CN$ (30 mL) was treated with 1,5-thiazocane hydrochloride (5.2 g, 31 mol) at ambient temperature and the reaction mixture heated to reflux for 24 h. The reaction mixture was cooled to rt and concentrated. The residue was diluted with $H_2O$ and $CH_2Cl_2$, aqueous layer was extracted with $CH_2Cl_2$ (50 mL*3). The organic layer was dried over $Na_2SO_4$, filtered, and concentrated. The crude product was purified by chromatography on silica gel ($PE/CH_2Cl_2$=10:1) to give 3.36 g (40%) of the title compound as a yellow solid. $^1$H-NMR (400 MHz, $CDCl_3$) δ: 7.92 (m, 2H), 6.80 (t, J=9.2 Hz, 8.8 Hz, 1H), 3.67 (t, J=6.0 Hz, 5.6 Hz, 4H), 2.72 (t, J=5.6 Hz, 6.0 Hz, 4H), 2.08 (m, 4H).

Step B: Benzyl(3-fluoro-4-(1,5-thiazocan-5-yl)phenyl)carbamate

To a solution of 5-(2-fluoro-4-nitrophenyl)-1,5-thiazocane (3.0 g, 12.5 mmol) in MeOH/THF was added 10% Pd/C (0.3 g), and the mixture was shaken 4 h under $H_2$ at r.t. The suspension was filtered through a short pad of Celite and eluted with additional MeOH. The solvent was removed in vacuo. The residue was dissolved in $THF/H_2O$ (50 mL). To the resulting solution was added $NaHCO_3$ (2.12 g, 25.2 mmol), and then CbzCl (2.58 g, 15.1 mmol) dropwise. The mixture was stirred overnight at r.t., and concentrated. The residue was added H₂O (50 mL) and extracted with CH₂Cl₂. The organic layer was washed with brine, dried over Na₂SO₄, and concentrated. The crude product was purified by chromatography on silica gel (PE/EtOAc=5:1) to afford 4.6 g product as a colorless solid in 98% yield. $^1$H-NMR (400 MHz, CDCl₃) δ: 7.30 (m, 5H), 6.96 (m, 2H), 6.76 (s, 1H), 4.11 (m, 2H), 3.30 (m, 4H), 2.74 (m, 4H), 1.93 (m, 4H).

Step C (R)-[3-[3-Fluoro-4-(1,5-thiazocane-5-yl)phenyl]-2-oxo-5-oxazolidinyl]methanol

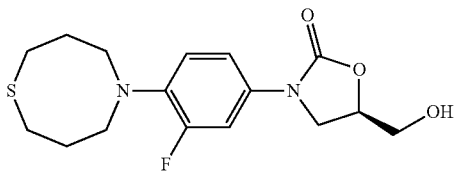 [SMILES: O=C1O[C@@H](CO)CN1c1ccc(N2CCCSCCC2)c(F)c1]

A solution of benzyl(3-fluoro-4-(1,5-thiazocan-5-yl)phenyl)carbamate (2.44 g, 6.5 mmol) in dry THF (20 mL) was cooled to −78° C. (dry ice/acetone bath) under N₂. n-Butyllithium (2.5 M solution in hexanes, 2.9 mL, 7.2 mmol) was added to the reaction mixture over 10 min. The resultant light yellow solution was stirred at −78° C. for 50 min and then treated with (R)-(−)-glycidyl butyrate (0.95 mL, 6.9 mmol) dropwise. The reaction mixture was stirred for an additional 30 min at −78° C., and then the cooling bath was removed. The reaction mixture was allowed to warm to ambient temperature overnight. Saturated aqueous NH₄Cl (50 mL) was added to the reaction mixture. The reaction mixture was extracted with EtOAc. The combined organic extracts were washed with brine, dried over Na₂SO₄, filtered, and concentrated. The residue was purified by by chromatography on silica gel (PE/EtOAc=1:2) to afford 1.33 g product as a colorless solid in 59% yield. $^1$H-NMR (400 MHz, CDCl₃) δ: 7.37 (dd, J=14.8 Hz, 2.4 Hz, 1H), 7.09 (dd, J=8.8 Hz, 2.4 Hz, 1H), 7.00 (m, 1H), 4.73 (m, 1H), 3.95 (m, 3H), 3.76 (m, 1H), 3.35 (m, 4H), 2.74 (m, 4H), 1.97 (m, 4H).

Step D: (R)-[3-[3-Fluoro-4-(1,5-thiazocane-5-yl)phenyl]-2-oxo-5-oxazolidinyl]methyl methanesulfonate

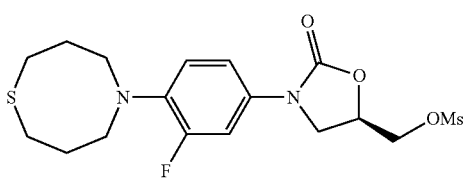 [SMILES: CS(=O)(=O)OC[C@H]1CN(c2ccc(N3CCCSCCC3)c(F)c2)C(=O)O1]

A solution of (R)-[3-[3-Fluoro-4-(1,5-thiazocane-5-yl)phenyl]-2-oxo-5-oxazolidinyl] methanol (1.0 g, 2.94 mmol) in dry CH₂Cl₂ was cooled with an ice bath and treated with Et₃N (446 mg, 4.41 mmol) and methanesulfonyl chloride (404 mg, 3.53 mmol). The mixture was stirred for 2 h at rt, and was washed with H₂O, saturated aqueous NaHCO₃, and brine. The organic layer was then dried over Na₂SO₄, filtered, and concentrated. The product was used in next step without purification.

Step E: (R)-[3-[3-Fluoro-4-(1,5-thiazocane-5-yl)phenyl]-2-oxo-5-oxazolidinyl]methyl azide

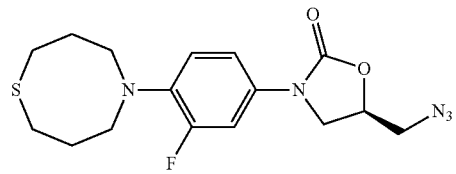 [SMILES: [N-]=[N+]=NC[C@H]1CN(c2ccc(N3CCCSCCC3)c(F)c2)C(=O)O1]

A solution of (R)-[3-[3-Fluoro-4-(1,5-thiazocane-5-yl)phenyl]-2-oxo-5-oxazolidinyl] methyl methanesulfonate (859 mg, 2.1 mmol) in dry DMF was treated with solid NaN₃ (683 mg, 10.5 mmol) at rt. The mixture was then heated to 65° C. for 8 h, after cooling to rt; the reaction mixture was quenched with H₂O and was extracted with EtOAc. The combined organic layer was washed with H₂O and brine, dried over Na₂SO₄, filtered, and concentrated. The product was used in next step without purification.

Step F: (S)—N-((3-(3-fluoro-4-(1,5-thiazocan-5-yl)phenyl)-2-oxooxazolidin-5-yl)methyl)acetamide

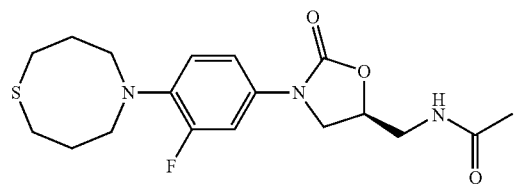 [SMILES: CC(=O)NC[C@H]1CN(c2ccc(N3CCCSCCC3)c(F)c2)C(=O)O1]

To a solution of (R)-[3-[3-fluoro-4-(1,5-thiazocane-5-yl)phenyl]-2-oxo-5-oxazolidinyl]methyl azide (216 mg, 0.59 mmol) in MeOH/THF was added 10% Pd/C (22 mg), and the mixture was shaken 4 h under H₂ at r.t. The suspension was filtered through a short pad of Celite and eluted with additional MeOH. The solvent was removed in vacuo. The residue was dissolved in CH₂Cl₂ and was treated with Et₃N (121 mg, 1.2 mmol) and AcCl (56 mg, 1.2 mmol). The reaction mixture was quenched with H₂O and extracted with CH₂Cl₂. The combined organic extracts were washed with brine, dried over Na₂SO₄, filtered, and concentrated. The residue was purified by chromatography on silica gel (CH₂Cl₂/MeOH=100:1) to afford 0.1 g product as a colorless solid in 44% yield. mp 78-80° C. $[\alpha]_D^{20}$ −15.4 (c 0.25, CHCl₃). $^1$H-NMR (400 MHz, CDCl₃) δ: 7.34 (m, 1H), 7.02 (m, 2H), 6.23 (m, 1H), 4.75 (m, 1H), 4.00 (t, J=8.8 Hz, 8.8 Hz, 1H), 3.73 (m, 2H), 3.64 (m, 1H), 3.36 (t, J=6.4 Hz, 6.0 Hz, 4H), 2.73 (m, 4H), 2.04 (s, 3H), 1.97 (m, 4H). $^{13}$C-NMR (125 MHz, CDCl₃) δ: 171.4, 155.2 (d, J=243.5 Hz), 154.4, 134.5, 130.2, 119.9, 114.3, 108.3 (d, J=26.8 Hz), 71.9, 48.1, 47.8, 42.0, 31.9, 29.7, 23.1. HR-MS (ESI-TOF): m/z [M+H]⁺ calcd for C₁₈H₂₅O₃N₃FS: 382.1595; found: 382.1620.

Step G: (S)—N-[[3-(3-fluoro-4-(1-oxido-1,5-thiazo-can-5-yl)phenyl)-2-oxo-oxazolidin-5-yl]methyl]acetamide

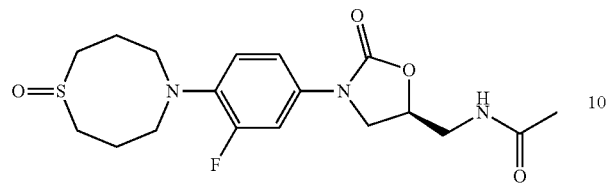

A solution of sodium metaperiodate (30 mg, 0.14 mmol) in H$_2$O (2 mL) was cooled to 0° C. (S)—N-((3-(3-fluoro-4-(1,5-thiazocan-5-yl)phenyl)-2-oxooxazolidin-5-yl)methyl)acetamide (50 mg, 0.13 mmol) was added and then MeOH (3 mL). The reaction mixture was stirred at 0° C. for 2 h, and was concentrated. H$_2$O was added to the residue and then extracted with CH$_2$Cl$_2$ The combined organic layer was washed with brine, dried over anhydrous Na$_2$SO$_4$, filtered, and concentrated. The residue was purified by chromatography on silica gel (CH$_2$Cl$_2$/MeOH=100:1) to afford 39 mg product as a colorless solid in 75% yield. mp 69-70° C. $^1$H-NMR (400 MHz, CDCl$_3$) δ: 7.46 (dd, J=2.8 Hz, 14.8 Hz, 1H), 7.14 (t, J=9.2 Hz, 8.8 Hz, 1H), 7.07 (m, 1H), 6.15 (m, 1H), 4.78 (m, 1H), 4.03 (t, J=9.2 Hz, 8.8 Hz, 1H), 3.74 (m, 3H), 3.31 (m, 1H), 3.18 (m, 4H), 2.98 (m, 2H), 2.17 (m, 4H), 2.03 (s, 3H). $^{13}$C-NMR (125 MHz, CDCl$_3$) δ: 171.0, 154.2, 134.0, 128.5, 127.3, 122.6, 113.9, 108.1 (d, J=26.9 Hz), 71.9, 53.1, 51.7, 47.7, 42.0, 29.7, 25.0, 23.2. HR-MS (ESI): m/z [M+H]$^+$ calcd for C$_{18}$H$_{25}$O$_4$N$_3$FS: 398.1544; found: 398.1540.

Example 9

In Vitro Assay for Antimicrobial Susceptibility

Antimicrobial susceptibility testing was performed in 96-well microplates. Initial drug dilutions (6.4 mg/ml) were prepared in dimethyl sulfoxide, and subsequent two-fold dilutions were performed in 0.1 ml of 7H9 broth media (BD) in the microplates. The final drug concentrations were about 0.008 μg/ml. Every concentration of test compounds was added to two wells. Control wells consisted of bacteria and positive drug (Linezolid). Plates were incubated at 37° C. The final bacterial titers were 1×10$^6$ CFU/ml for H$_{37}$Rv. Starting at day 7 of incubation, 20 μl of 10× Alamar blue solution (Life Technologies) and 12.5 μl of 20% Tween 80 (Sigma-Aldrich) were added to each well and the plates were reincubated at 37° C. Wells were observed at 24 h and the colors of all were recorded. Visual MICs were defined as the lowest amount of drug that prevented a color change from blue to pink. Fluorescence was measured in a microplate fluorometer in bottom-reading mode with excitation at 530 nm and emission at 590 nm. For fluorometric MICs, the lowest drug concentration effecting an inhibition of ≥90% was considered the MIC. The MIC results are provided in Table 1 above.

Example 10

In Vitro Assay for MPS Inhibition

H9C2 cells were incubated in DMEM (Hyclone, GE LifeSciences) with 10% FBS (Gibco, Life Technologies) and 1× Glutamine (Gibco, Life Technologies) and NEAA (Gibco, Life Technologies) at 37° C., 5% CO2 at 1500 cells/well in a 384-well plate. Test compound was added after 18 hr incubation, and then incubated for 5 days. COX-1 protein (cyclooxygenase I) and SDH-A (succinate dehydrogenase-A) formation reduction were measured by ELISA assay (MitoBiogenesis™ In-Cell ELISA Kit (Colorimetric, Abcam). MPS assay results are provided in Table 1 above.

Example 11

Specific Compounds Synthesized According to General Methods

OTB-107

(R)-5-[(1H-1,2,3-Triazol-1-yl)methyl]-3-[3-fluoro-4-(1,4-thiazepan-4-yl)phenyl]oxazolidin-2-one

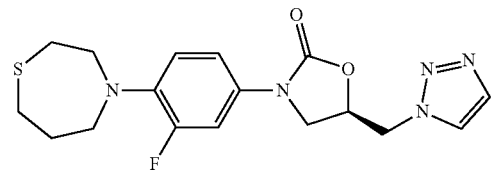 [SMILES: O=C1O[C@@H](Cn2ccnn2)CN1c1ccc(N2CCCSCC2)c(F)c1]

$^1$H-NMR (400 MHz, CDCl$_3$) δ: 7.94 (s, 1H), 7.75 (s, 1H), 7.17 (dd, J=15.2 Hz, 1.2 Hz, 1H), 6.89 (dd, J=8.8 Hz, 1.6 Hz, 1H), 6.82 (t, J=9.6 Hz, 8.8 Hz, 1H), 5.03 (m, 1H), 4.78 (s, 2H), 4.10 (t, J=9.2 Hz, 8.8 Hz, 1H), 3.87 (m, 1H), 3.68 (m, 4H), 2.87 (m, 2H), 2.68 (t, J=6.4 Hz, 6.0 Hz, 2H), 2.06 (m, 2H). $^{13}$C-NMR (100 MHz, CDCl$_3$) δ: 153.4, 151.0, 134.3, 124.9, 116.8, 115.1, 108.7 (d, J=27.3 Hz), 70.2, 56.1, 51.9, 51.3, 47.4, 34.0, 31.5, 30.3. HR-MS (ESI): m/z [M+H]$^+$ calcd for C$_{17}$H$_{21}$O$_2$N$_5$FS: 378.1395; found: 378.1396.

OTB-106

(R)-5-[(2H-1,2,3-Triazol-2-yl)methyl]-3-[3-fluoro-4-(1,4-thiazepan-4-yl)phenyl]oxazolidin-2-one

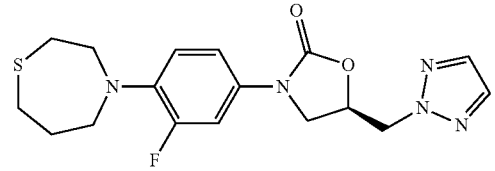 [SMILES: O=C1O[C@@H](Cn2nccn2)CN1c1ccc(N2CCCSCC2)c(F)c1]

$^1$H-NMR (400 MHz, CDCl$_3$) δ: 7.65 (s, 2H), 7.27 (m, 1H), 7.01 (dd, J=8.8 Hz, 1.6 Hz, 1H), 6.84 (t, J=9.2 Hz, 9.2 Hz, 1H), 5.11 (m. 1H), 4.85 (dd, J=14 Hz, 4.8 Hz, 1H), 4.74 (dd, J=14 Hz, 6.8 Hz, 1H), 4.05 (t, J=9.2 Hz, 8.8 Hz, 1H), 3.95 (m, 1H), 3.67 (m, 4H), 2.87 (m, 2H), 2.69 (t, J=6.4 Hz, 6.0 Hz, 2H), 2.06 (m, 2H). $^{13}$C-NMR (125 MHz, CDCl$_3$) δ: 153.7, 152.4 (d, J=241.8 Hz), 135.0, 134.7, 129.1, 116.9 (d, J=5.1 Hz), 114.7 (d, J=2.9 Hz), 108.4 (d, J=27.4 Hz), 69.9, 56.2, 56.1, 51.4, 48.2, 34.1, 31.6, 30.4. HR-MS (ESI): m/z [M+H]$^+$ calcd for C$_{17}$H$_{21}$O$_2$N$_5$FS: 378.1395; found: 378.1403.

OTB-109

(S)-3-[3-Fluoro-4-(1,4-thiazepan-4-yl)phenyl]-5-[(methylamino)methyl]oxazolidin-2-one

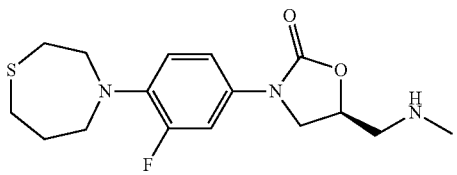 [SMILES: CNC[C@H]1CN(c2ccc(N3CCCSCC3)c(F)c2)C(=O)O1]

¹H-NMR (400 MHz, CDCl₃) δ: 7.30 (dd, J=15.6 Hz, 2.4 Hz, 1H), 7.06 (d, J=8.8 Hz, 1H), 6.82 (t, J=9.6 Hz, 9.6 Hz, 1H), 4.83 (m, 1H), 4.02 (t, J=8.8 Hz, 8.4 Hz, 1H), 3.79 (t, J=8.0 Hz, 7.2 Hz, 1H), 3.67 (m, 4H), 2.97 (m, 2H), 2.87 (m, 2H), 2.68 (m, 2H), 2.54 (s, 3H), 2.05 (m, 2H). HR-MS (ESI): m/z [M+H]⁺ calcd for $C_{16}H_{23}O_2N_3FS$: 340.1490; found: 340.1484.

OTB-108

(R)-[3-[3-Fluoro-4-(1,4-thiazepan-4-yl)phenyl]-2-oxo-5-oxazolidinyl]methylbutyrate

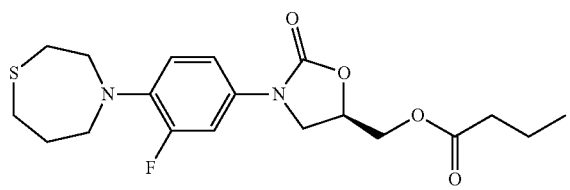 [SMILES: CCCC(=O)OC[C@H]1CN(c2ccc(N3CCCSCC3)c(F)c2)C(=O)O1]

¹H-NMR (400 MHz, CDCl₃) δ: 7.34 (dd, J=15.6 Hz, 2.4 Hz, 1H), 7.05 (dd, J=9.2 Hz, 2.0 Hz, 1H), 6.89 (m, 1H), 4.84 (m, 1H), 4.37 (dd, J=16.0 Hz, 4.0 Hz, 1H), 4.31 (dd, J=12.0 Hz, 4.8 Hz, 1H), 4.06 (t, J=9.2 Hz, 8.8 Hz, 1H), 3.76 (m, 1H), 3.68 (m, 4H), 2.89 (m, 2H), 2.70 (t, J=6.4 Hz, 6.0 Hz, 2H), 2.34 (t, J=7.6 Hz, 7.2 Hz, 2H), 2.08 (m, 2H), 1.65 (m, 2H), 0.94 (t, J=7.6 Hz, 7.2 Hz, 3H). ¹³C-NMR (125 MHz, CDCl₃) δ: 173.3, 154.4, 152.7 (d, J=241.6 Hz), 134.9 (d, J=8.3 Hz), 129.5 (d, J=10.1 Hz), 117.2 (d, J=5.4 Hz), 114.7 (d, J=2.9 Hz), 108.5 (d, J=27.5 Hz), 70.2, 64.1, 56.3, 51.7, 47.5, 36.0, 34.4, 31.9, 30.7, 18.4, 13.7. HR-MS (ESI-TOF): m/z [M+H]⁺ calcd for $C_{19}H_{26}O_4N_2FS$: 397.1592; found: 397.1613.

OTB-111

(S)—N-[(3-[3-Fluoro-4-(1,4-thiazepan-4-yl)phenyl]-2-oxo-oxazolidin-5-yl)methyl]furan-2-carboxamide

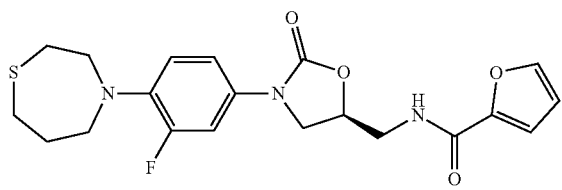

¹H-NMR (400 MHz, CDCl₃) δ: 7.47 (s, 1H), 7.32 (dd, J=16.0 Hz, 2.0 Hz, 1H), 7.14 (d, J=3.2 Hz, 1H), 7.01 (dd, J=8.8 Hz, 1.6 Hz, 1H), 6.87 (m, 1H), 6.81 (m, 1H), 6.52 (s, 1H), 4.82 (m, 1H), 4.04 (t, J=9.2 Hz, 8.8 Hz, 1H), 3.89 (m, 1H), 3.76 (m, 2H), 3.67 (m, 4H), 2.88 (m, 2H), 2.69 (t, J=6.4 Hz, 6.0 Hz, 2H), 2.07 (m, 2H). ¹³C-NMR (125 MHz, CDCl₃) δ: 159.0, 154.4, 152.6 (d, J=241.9 Hz), 147.1, 144.5, 134.5, 129.3, 117.2, 115.1, 114.7, 112.3, 108.5 (d, J=27.4 Hz), 71.9, 56.3, 51.7, 47.9, 41.6, 34.1, 31.7, 30.5. HR-MS (ESI-TOF): m/z [M+H]⁺ calcd for $C_{20}H_{23}O_4N_3FS$: 420.1388; found: 420.1400.

OTB-112

(S)—N-[(3-[3-Fluoro-4-(1,4-thiazepan-4-yl)phenyl]-2-oxo-oxazolidin-5-yl)methyl]thiophene-2-carboxamide

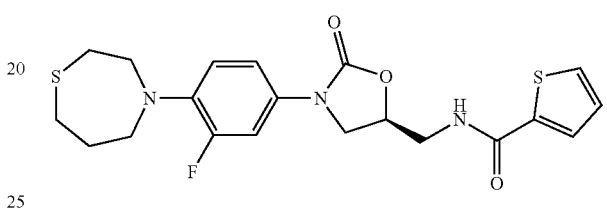

¹H-NMR (400 MHz, CDCl₃) δ: 7.34 (m, 1H), 7.02 (m, 2H), 6.23 (m, 1H), 4.75 (m, 1H), 4.00 (t, J=8.8 Hz, 8.8 Hz, 1H), 3.73 (m, 2H), 3.64 (m, 1H), 3.36 (t, J=6.4 Hz, 6.0 Hz, 4H), 2.73 (m, 4H), 2.04 (s, 3H), 1.97 (m, 4H). ¹³C-NMR (125 MHz, CDCl₃) δ: 171.4, 155.2 (d, J=243.5 Hz), 154.4, 134.5, 130.2, 119.9, 114.3, 108.3 (d, J=26.8 Hz), 71.9, 48.1, 47.8, 42.0, 31.9, 29.7, 23.1. HR-MS (ESI-TOF): m/z [M+H]⁺ calcd for $C_{18}H_{25}O_3N_3FS$: 382.1595; found: 382.1620.

OTB-115

(S)—N-[[3-(3-Fluoro-4-(1,4-thiazepan-4-yl)phenyl)-2-oxo-oxazolidin-5-yl]methyl]pivalamide

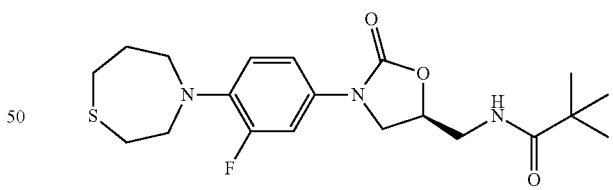

¹H-NMR (400 MHz, CDCl₃) δ: 7.34 (dd, J=15.6 Hz, 2.0 Hz, 1H), 7.01 (dd, J=8.8 Hz, 2.4 Hz, 1H), 6.89 (m, 1H), 6.12 (m, 1H), 4.74 (m, 1H), 3.99 (t, J=9.2 Hz, 8.8 Hz, 1H), 3.74 (m, 1H), 3.67 (m, 6H), 2.89 (t, J=5.6 Hz, 5.2 Hz, 2H), 2.70 (t, J=6.4 Hz, 6.4 Hz, 2H), 2.08 (m, 2H), 1.17 (s, 9H). ¹³C-NMR (125 MHz, CDCl₃) δ: 179.7, 154.6, 152.7 (d, J=241.6 Hz), 134.8, 129.5, 117.2 (d, J=5.4 Hz), 114.7 (d, J=2.9 Hz), 108.5 (d, J=27.6 Hz), 72.1, 56.3, 51.7, 48.0, 42.4, 39.0, 34.4, 31.9, 30.7, 27.7. HR-MS (ESI-TOF): m/z [M+H]⁺ calcd for $C_{20}H_{29}O_3N_3FS$: 410.1908; found: 410.1942.

OBD-005

(S)—N-((3(3-Fluoro-4-(1,4-thiazepan-4-yl)phenyl)-2-oxooxazolidin-5-yl)methyl)butyramide

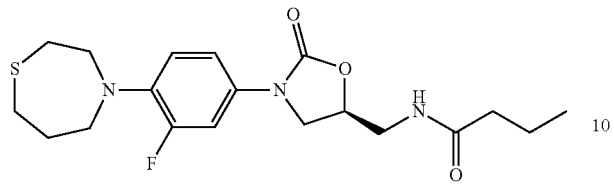

¹H-NMR (300 MHz, CDCl₃) δ: 7.42-7.23 (m, 2H), 7.01 (dd, J=8.9, 2.3 Hz, 1H), 6.04 (s, 1H), 4.75 (ddd, J=9.0, 7.9, 4.6 Hz, 1H), 4.00 (t, J=9.0 Hz, 1H), 3.79-3.05 (m, 7H), 2.91 (dd, J=16.2, 10.1 Hz, 2H), 2.70 (t, J=6.3 Hz, 2H), 2.28-2.13 (m, 2H), 2.13-1.97 (m, 2H), 1.82-1.25 (m, 3H), 0.92 (t, J=7.4 Hz, 3H), 0.01 (s, 1H).

LC-MS (ESI): m/z=395.9 [M+H]⁺.

OTB-116

(R)—N-[[3-(3-Fluoro-4-(1,4-thiazepan-4-yl)phenyl)-2-oxo-oxazolidin-5-yl]methyl]butane-1-sulfonamide

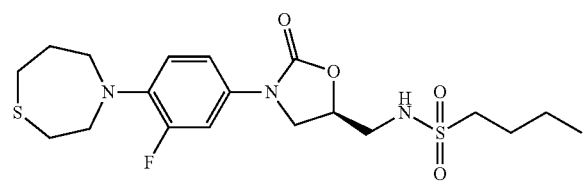 [SMILES: CCCCS(=O)(=O)NC[C@H]1CN(c2ccc(N3CCCSCC3)c(F)c2)C(=O)O1]

¹H-NMR (400 MHz, CDCl₃) δ: 7.33 (d, J=15.6 Hz, 1H), 7.05 (d, J=8.8 Hz, 1H), 6.88 (m, 1H), 4.92 (t, J=6.8 Hz, 6.4 Hz, 1H), 4.78 (m, 1H), 4.02 (t, J=9.2 Hz, 8.8 Hz, 1H), 3.90 (m, 1H), 3.69 (m, 4H), 3.54 (m, 1H), 3.43 (m, 1H), 3.07 (m, 2H), 2.94 (m, 2H), 2.69 (m, 2H), 2.08 (m, 2H), 1.79 (m, 2H), 1.46 (m, 2H), 0.95 (t, J=7.2 Hz, 7.2 Hz, 3H). ¹³C-NMR (125 MHz, CDCl₃) δ: 154.2, 152.5 (d, J=241.8 Hz), 134.8 (d, J=8.3 Hz), 129.2 (d, J=10.5 Hz), 117.2, 115.0, 108.6 (d, J=27.5 Hz), 71.5, 56.3, 53.2, 51.6, 47.5, 45.5, 34.1, 31.7, 30.5, 25.6, 21.5, 13.5. HR-MS (ESI-TOF): m/z [M+H]⁺ calcd for $C_{19}H_{29}O_4N_3FS_2$: 446.1578; found: 446.1623.

OTB-119

(R)-5-[(1H-1,2,4-Triazol-1-yl)methyl]-3-[3-fluoro-4-(1,4-thiazepan-4-yl)phenyl]oxazolidin-2-one

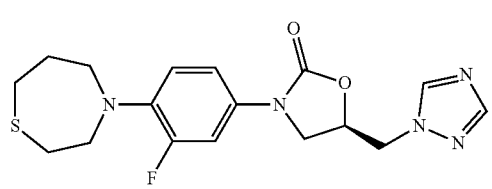 [SMILES: O=C1O[C@@H](Cn2cncn2)CN1c1ccc(N2CCCSCC2)c(F)c1]

¹H-NMR (400 MHz, CDCl₃) δ: 8.24 (s, 1H), 7.96 (s, 1H), 7.22 (m, 1H), 6.97 (m, 1H), 6.89 (m, 1H), 5.02 (m, 1H), 4.54 (d, J=4.8 Hz, 2H), 4.10 (t, J=9.2 Hz, 9.2 Hz, 1H), 3.94 (m, 1H), 3.68 (m, 4H), 2.89 (m, 2H), 2.70 (m, 2H), 2.08 (m, 2H). HR-MS (ESI-TOF): m/z [M+H]⁺ calcd for $C_{17}H_{21}O_2N_5FS$: 378.1395; found: 378.1421.

OTB-412

Methyl (S)-((3-(3-fluoro-4-(1,4-thiazepan-4-yl)phenyl)-2-oxo-oxazolidin-5-yl)methyl)carbamate

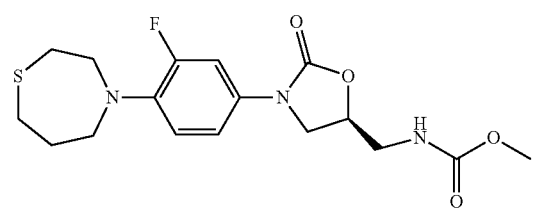 [SMILES: COC(=O)NC[C@H]1CN(c2ccc(N3CCCSCC3)c(F)c2)C(=O)O1]

¹H-NMR (400 MHz, CDCl₃) δ: 7.29-7.33 (m, 1H), 7.03-7.05 (m, 1H), 6.82 (t, J=8.8 Hz, 1H), 5.10 (m, 1H), 4.73 (m, 1H), 3.99 (t, J=9.9 Hz, 1H), 3.69-3.74 (m, 1H), 3.67 (s, 3H), 3.66-3.67 (m, 4H), 3.61 (m, 1H), 3.50-3.55 (m, 1H), 2.87 (m, 1H), 2.68 (m, 2H), 2.04-2.07 (m, 2H). ¹³C-NMR (150 MHz, CDCl₃) δ: 157.5, 154.3, 153.3, 151.7, 134.8, 134.7, 129.3, 129.2, 117.0, 117.0, 114.7, 114.7, 108.5, 108.4, 71.7, 56.2, 56.2, 51.5, 47.7, 43.7, 34.3, 31.8, 30.6. HR-MS (ESI-TOF): m/z [M+H]⁺ calcd for $C_{17}H_{23}O_4N_3FS$: 384.1388; found: 384.1371.

OTB-413

(S)—N-((3-(3-Fluoro-4-(1,4-thiazepan-4-yl)phenyl)-2-oxo-oxazolidin-5-yl)methyl)cyclopropanecarboxamide

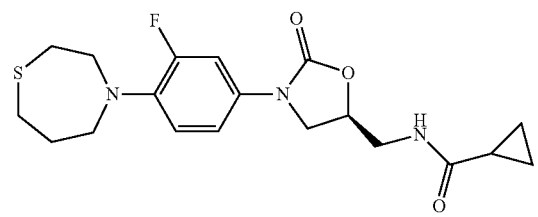 [SMILES: O=C(NC[C@H]1CN(c2ccc(N3CCCSCC3)c(F)c2)C(=O)O1)C1CC1]

¹H-NMR (400 MHz, CDCl₃) δ: 7.29-7.33 (m, 1H), 7.03-7.00 (m, 1H), 6.81 (t, J=9.6 Hz, 1H), 6.09 (m, 1H), 4.74 (m, 1H), 3.98 (t, J=8.8 Hz, 1H), 3.73-3.74 (m, 1H), 3.67-3.71 (m, 4H), 3.62-3.66 (m, 1H), 2.87 (t, J=4.8 Hz, 2H), 2.68 (t, J=10.0 Hz, 2H), 2.04-2.07 (m, 2H), 1.36-1.43 (m, 1H), 1.05-1.07 (m, 1H), 0.93-0.97 (m, 2H), 0.77-0.78 (m, 1H). ¹³C-NMR (150 MHz, CDCl₃) δ: 174.5, 154.5, 153.3, 151.7, 134.8, 134.7, 129.2, 129.2, 117.0, 114.7, 108.6, 108.4, 72.0, 56.2, 51.5, 47.8, 42.1, 34.3, 31.8, 30.6, 14.7, 7.7. HR-MS (ESI-TOF): m/z [M+H]⁺ calcd for $C_{19}H_{25}O_3N_3FS$: 394.1595; found: 394.1580.

OTB-414

(S)—N-((3-(3-Fluoro-4-(1,4-thiazepan-4-yl)phenyl)-2-oxooxazolidin-5-yl)methyl)cyclobutanecarboxamide

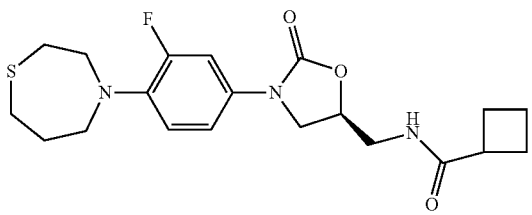 [SMILES: O=C(NC[C@H]1CN(c2ccc(N3CCCSCC3)c(F)c2)C(=O)O1)C1CCC1]

$^1$H-NMR (400 MHz, CDCl$_3$) δ: 7.29-7.34 (m, 1H), 7.03-7.00 (m, 1H), 6.82 (t, J=9.6 Hz, 1H), 5.84 (m, 1H), 4.75 (m, 1H), 3.99 (t, J=8.8 Hz, 1H), 3.72-3.76 (m, 1H), 3.67-3.71 (m, 4H), 3.63-3.66 (m, 1H), 3.14-3.23 (m, 2H), 2.68 (m, 1H), 1.89-2.35 (m, 10H). $^{13}$C-NMR (150 MHz, CDCl$_3$) δ: 180.2, 176.0, 154.5, 134.8, 134.8, 129.2, 129.1, 117.0, 117.0, 114.7, 114.7, 108.5, 108.4, 72.0, 56.2, 56.2, 51.5, 51.5, 47.9, 42.0, 39.7, 37.8, 34.3, 31.8, 30.6, 25.2, 18.4. HR-MS (ESI-TOF): m/z [M+H]$^-$ calcd for C$_{20}$H$_{27}$O$_3$N$_3$FS: 408.1752; found: 408.1736.

OTB-407

(S)—N-((3-(3,5-Difluoro-4-(1,4-thiazepan-4-yl)phenyl)-2-oxo-oxazolidin-5-yl)methyl)acetamide

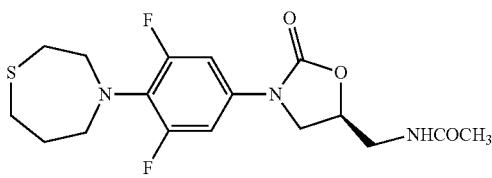

$^1$H-NMR (400 MHz, CDCl$_3$) δ: 7.07 (d, J=10.4 Hz, 2H), 6.08 (m, 1H), 4.76-4.77 (m, 1H), 3.98 (t, J=9.2 Hz, 1H), 3.59-3.70 (m, 3H), 3.45-3.48 (m, 4H), 2.89 (t, J=6.0 Hz, 2H), 2.77-2.80 (m, 2H), 2.02 (s, 3H). $^{13}$C-NMR (150 MHz, CDCl$_3$) δ: 171.1, 159.8, 159.7, 158.1, 158.1, 154.0, 133.3, 126.0, 102.5, 102.3, 71.9, 58.8, 54.1, 47.5, 41.9, 36.1, 31.8, 31.6, 23.1. HR-MS (ESI-TOF): m/z [M+H]$^+$ calcd for C$_{17}$H$_{22}$O$_3$N$_3$F$_2$S: 386.1344; found: 386.1330.

OTB-410

Methyl (S)-((3-(3,5-difluoro-4-(1,4-thiazepan-4-yl)phenyl)-2-oxo-oxazolidin-5-yl)methyl)carbamate

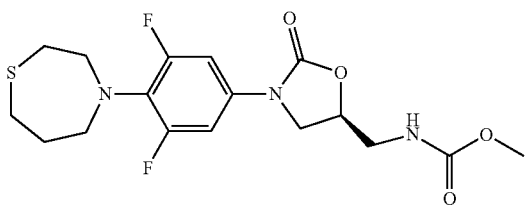 [SMILES: COC(=O)NC[C@H]1CN(c2cc(F)c(N3CCCSCC3)c(F)c2)C(=O)O1]

$^1$H-NMR (500 MHz, CDCl$_3$) δ: 7.09 (d, J=10.0 Hz, 2H), 5.09 (m, 1H), 4.76 (m, 1H), 3.99 (t, J=9.0 Hz, 1H), 3.74-3.76 (m, 1H), 3.73 (s, 3H), 3.61 (m, 1H), 3.52-3.55 (m, 1H), 3.46-3.47 (m, 4H), 2.90 (t, J=6.0 Hz, 1H), 2.78-2.80 (m, 2H), 1.94-1.98 (m, 2H). $^{13}$C-NMR (125 MHz, CDCl$_3$) δ: 157.5, 154.3, 153.3, 151.7, 134.8, 134.7, 129.3, 129.2, 117.0, 117.0, 114.7, 114.7, 108.4, 108.4, 71.3, 56.2, 56.2, 51.5, 47.8, 43.7, 34.3, 31.8, 30.6. HR-MS (ESI-TOF): m/z [M+H]$^+$ calcd for C$_{17}$H$_{22}$O$_4$N$_3$F$_2$S: 402.1297; found: 402.1287.

OTB-408

(S)-5-(((Cyclopropylamino)methyl)-3-(3,5-difluoro-4-(1,4-thiazepan-4-yl)phenyl)oxazolidin-2-one

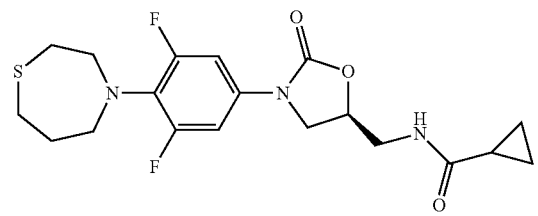 [SMILES: O=C(NC[C@H]1CN(c2cc(F)c(N3CCCSCC3)c(F)c2)C(=O)O1)C1CC1]

$^1$H-NMR (400 MHz, CDCl$_3$) δ: 7.07 (d, J=10.8 Hz, 2H), 6.06 (m, 1H), 4.76 (m, 1H), 3.96 (t, J=8.8 Hz, 1H), 3.66-3.75 (m, 3H), 3.43-3.47 (m, 3H), 2.89 (t, J=9.2 Hz, 2H), 2.78-2.80 (m, 3H), 1.94-1.97 (m, 2H), 1.37-1.39 (m, 1H), 0.97 (m, 1H), 0.93 (m, 1H), 0.77-0.79 (m, 2H). $^{13}$C-NMR (150 MHz, CDCl$_3$) δ: 174.7, 159.8, 159.7, 158.2, 158.1, 154.0, 133.4, 126.0, 102.6, 102.4, 72.0, 58.8, 54.1, 47.5, 42.0, 36.1, 31.8, 31.6, 14.7, 7.8, 7.7. HR-MS (ESI-TOF): m/z [M+H]$^+$ calcd for C$_{19}$H$_{24}$O$_3$N$_3$F$_2$S: 412.1501; found: 412.1485.

OTB-409

(S)-5-(((Cyclobutylamino)methyl)-3-(3,5-difluoro-4-(1,4-thiazepan-4-yl)phenyl)oxazolidin-2-one

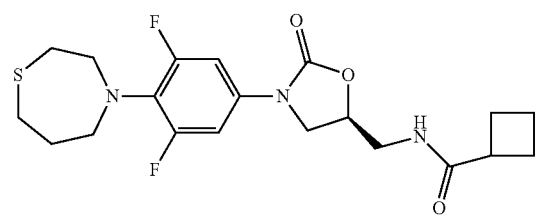 [SMILES: O=C(NC[C@H]1CN(c2cc(F)c(N3CCCSCC3)c(F)c2)C(=O)O1)C1CCC1]

$^1$H-NMR (400 MHz, CDCl$_3$) δ: 7.07 (d, J=10.8 Hz, 2H), 5.81 (m, 1H), 4.75 (m, 1H), 3.98 (t, J=8.8 Hz, 1H), 3.72-3.76 (m, 1H), 3.64-3.66 (m, 2H), 3.45-3.46 (m, 3H), 3.01 (t, J=8.8 Hz, 1H), 2.90 (t, J=6.4 Hz, 2H), 2.77-2.80 (m, 2H), 2.13-2.26 (m, 4H), 1.92-1.96 (m, 3H). $^{13}$C-NMR (150 MHz, CDCl$_3$) δ: 176.0, 159.8, 159.8, 158.2, 158.1, 154.0, 133.3, 126.0, 102.5, 102.3, 72.0, 58.8, 54.1, 47.5, 41.9, 39.7, 36.1, 31.8, 31.6, 25.4, 25.3, 18.1. HR-MS (ESI-TOF): m/z [M+H]$^+$ calcd for C$_{20}$H$_{26}$O$_3$N$_3$F$_2$S: 426.1658; found: 426.1643.

OTB-411

(R)-5-((1H-1,2,3-triazol-1-yl)methyl)-3-(3,5-difluoro-4-(1,4-thiazepan-4-yl)phenyl)oxazolidin-2-one

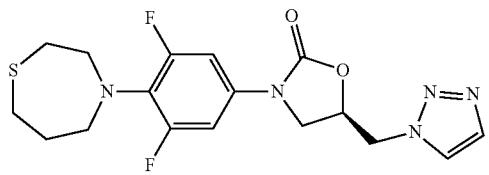 [SMILES: O=C1O[C@@H](Cn2ccnn2)CN1c1cc(F)c(N2CCCSCC2)c(F)c1]

$^1$H-NMR (400 MHz, CDCl$_3$) δ: 7.76 (d, J=11.2 Hz, 2H), 6.95 (d, J=10.4 Hz, 2H), 5.04-5.07 (m, 1H), 4.78 (d, J=4.0 Hz, 2H), 4.10 (t, J=9.2 Hz, 1H), 3.86-3.90 (m, 1H), 3.44-3.46 (m, 4H), 2.88 (t, J=6.4 Hz, 2H), 2.76-2.79 (m, 2H), 1.91-1.97 (m, 2H). $^{13}$C-NMR (125 MHz, CDCl$_3$) δ: 159.8, 159.8, 157.9, 157.8, 153.0, 134.6, 125.1, 102.8, 102.5, 70.3, 58.7, 54.0, 51.9, 47.1, 36.1, 31.8, 31.6. HR-MS (ESI-TOF): m/z [M+H]$^+$ calcd for C$_{17}$H$_{20}$O$_2$N$_5$F$_2$S: 396.1300; found: 396.1296.
OTB-126

[(5R)-3-[3-Fluoro-4-(1-oxido-1,4-thiazepan-4-yl)phenyl)-2-oxo-oxazolidin-5-yl]methyl butyrate

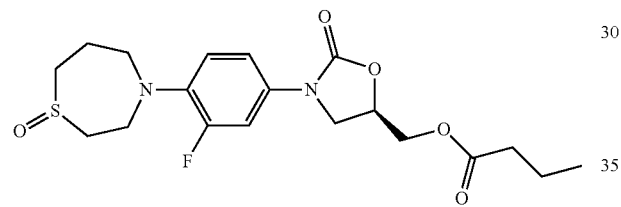

$^1$H-NMR (400 MHz, CDCl$_3$) δ: 7.45 (dd, J=14.8 Hz, 1.6 Hz, 1H), 7.07 (dd, J=8.8 Hz, 2.4 Hz, 1H), 6.96 (t, J=9.2 Hz, 9.2 Hz, 1H), 4.85 (m, 1H), 4.37 (dd, J=12.0 Hz, 4.0 Hz, 1H), 4.30 (dd, J=12.4 Hz, 4.8 Hz, 1H), 4.07 (m, 1H), 3.78 (m, 2H), 3.40 (m, 2H), 3.19 (m, 4H), 2.98 (m, 1H), 2.72 (m, 1H), 2.33 (t, J=7.6 Hz, 7.2 Hz, 2H), 2.04 (m, 1H), 1.63 (m, 2H), 0.92 (t, J=7.6 Hz, 7.2 Hz, 3H). $^{13}$C-NMR (125 MHz, CDCl$_3$) δ: 173.2, 154.1, 154.0 (d, J=241.8 Hz), 136.6, 131.4, 118.1 (d, J=4.3 Hz), 114.0, (d, J=2.9 Hz), 107.8 (d, J=26.9 Hz), 70.1, 63.9, 52.8, 49.6, 47.2, 46.4, 43.7, 35.8, 18.3, 16.2, 13.6. HR-MS (ESI-TOF): m/z [M+H]$^+$ calcd for C$_{19}$H$_{26}$O$_5$N$_2$FS: 413.1541; found: 413.1573.
OTB-127

N-[[(5S)-3-(3-Fluoro-4-(1-oxido-1,4-thiazepan-4-yl)phenyl)-2-oxo-oxazolidin-5-yl]methyl]furan-2-carboxamide

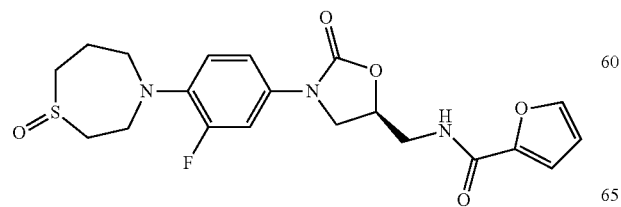

$^1$H-NMR (400 MHz, CDCl$_3$) δ: 7.47 (s, 1H), 7.42 (m, 1H), 7.14 (d, J=3.2 Hz, 1H), 7.04 (m, 1H), 6.87 (m, 2H), 6.51 (m, 1H), 4.85 (m, 1H), 4.05 (m, 1H), 3.81 (m, 4H), 3.38 (m, 2H), 3.15 (m, 2H), 3.04 (m, 3H), 2.70 (m, 1H), 2.03 (m, 1H). HR-MS (ESI-TOF): m/z [M+H]$^+$ calcd for C$_{20}$H$_{23}$O$_5$N$_3$FS: 436.1337; found: 436.1371.
OTB-137

(5R)-5-((1H-1,2,3-Triazol-1-yl)methyl)-3-(3-fluoro-4-(1-oxido-1,4-thiazepan-4-yl)phenyl)oxazolidin-2-one

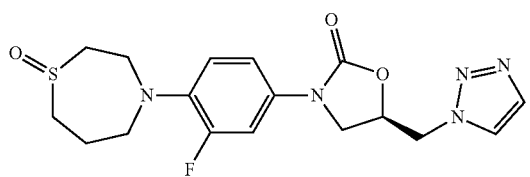 [SMILES: O=C1O[C@@H](Cn2ccnn2)CN1c1ccc(N2CCCS(=O)CC2)c(F)c1]

$^1$H-NMR (400 MHz, CDCl$_3$) δ: 7.79 (s, 1H), 7.75 (s, 1H), 7.30-7.25 (m, 1H), 6.91-6.89 (m, 2H), 5.07-5.02 (m, 1H), 4.78 (d, J=4.0 Hz, 2H), 4.11 (t, J=9.2 Hz, 1H), 3.93-3.88 (m, 1H), 3.82-3.76 (m, 1H), 3.43-3.36 (m, 2H), 3.24-2.91 (m, 4H), 2.75-2.69 (m, 1H), 2.04-2.02 (m, 2H). HR-MS (ESI): m/z [M+H]$^-$ calcd for C$_{17}$H$_{21}$O$_3$N$_5$FS: 394.1344; found: 394.1328.
OTB-138

(5R)-5-((2H-1,2,3-Triazol-2-yl)methyl)-3-(3-fluoro-4-(1-oxido-1,4-thiazepan-4-yl)phenyl)oxazolidin-2-one

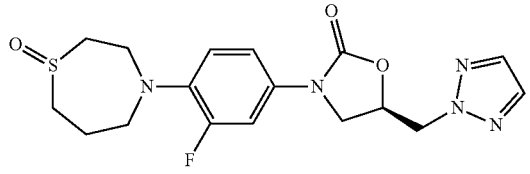 [SMILES: O=C1O[C@@H](Cn2nccn2)CN1c1ccc(N2CCCS(=O)CC2)c(F)c1]

$^1$H-NMR (400 MHz, CDCl$_3$) δ: 7.65 (s, 2H), 7.39 (d, J=14.4 Hz, 1H), 7.04-6.98 (m, 2H), 5.15-5.09 (m, 1H), 4.86 (dd, J=14.0, 4.4 Hz, 1H), 4.75 (dd, J=14.0, 6.8 Hz, 1H), 4.06 (dt, J=9.2, 2.4 Hz, 1H), 4.00-3.96 (m, 1H), 3.86-3.82 (m, 1H), 3.46-3.38 (m, 2H), 3.29-3.08 (m, 3H), 3.02-2.96 (m, 1H), 2.76-2.71 (m, 1H), 2.04-2.02 (m, 2H). HR-MS (ESI): m/z [M+H]$^+$ calcd for C$_{17}$H$_{21}$O$_3$N$_5$FS: 394.1344; found: 394.1338.
OTB-140

(5R)-5((1H-1,2,4-Triazol-1-yl)methyl)-3-(3-fluoro-4-(1-oxido-1,4-thiazepan-4-yl)phenyl)oxazolidin-2-one

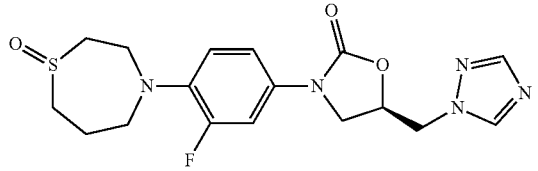 [SMILES: O=C1O[C@@H](Cn2cncn2)CN1c1ccc(N2CCCS(=O)CC2)c(F)c1]

¹H-NMR (400 MHz, CDCl₃) δ: 8.24 (s, 1H), 7.94 (s, 1H), 7.35 (d, J=14.4 Hz, 1H), 7.0-6.96 (m, 2H), 5.02-4.99 (m, 1H), 4.55 (d, J=4.4 Hz, 2H), 4.10 (dt, J=8.8, 2.0 Hz, 1H), 3.99-3.95 (m, 1H), 3.86-3.82 (m, 1H), 3.45-3.38 (m, 2H), 3.29-3.09 (m, 3H), 3.00-2.94 (m, 1H), 2.77-2.71 (m, 1H), 2.07-2.03 (m, 2H). HR-MS (ESI): m/z [M+H]⁺ calcd for $C_{17}H_{21}O_3N_5FS$: 394.1344; found: 394.1339.

OBD-006

N-(((5S)-3-(3-Fluoro-4-(1-oxido-1,4-thiazepan-4-yl)phenyl)-2-oxooxazolidin-5-yl)methyl)butyramide

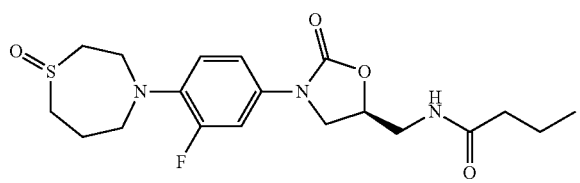 [SMILES: CCCC(=O)NC[C@H]1CN(c2ccc(N3CCCS(=O)CC3)c(F)c2)C(=O)O1]

¹H-NMR (300 MHz, CDCl₃) δ: 7.52 (d, J=15.0 Hz, 1H), 7.16 (s, 1H), 7.03 (d, J=8.7 Hz, 1H), 5.99 (s, 1H), 4.78 (s, 1H), 4.02 (t, J=8.8 Hz, 2H), 3.88-3.56 (m, 3H), 3.55-2.92 (m, 7H), 2.77 (s, 1H), 2.20 (t, J=7.1 Hz, 3H), 1.64 (dd, J=14.9, 7.4 Hz, 2H), 0.91 (t, J=7.4 Hz, 3H). LC-MS (ESI): m/z=411.8 [M+H]⁺.

OBD-007

(S)—N-((3(4-(1,1-Dioxido-1,4-thiazepan-4-yl)-3-fluorophenyl)-2-oxooxazolidin-5-yl)methyl)butyramide

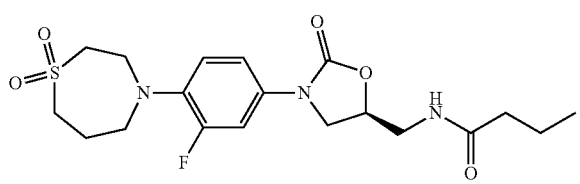 [SMILES: CCCC(=O)NC[C@H]1CN(c2ccc(N3CCCS(=O)(=O)CC3)c(F)c2)C(=O)O1]

¹-NMR (300 MHz, CDCl₃) δ: 7.51 (d, J=14.7 Hz, 1H), 7.10 (d, J=9.9 Hz, 2H), 5.92 (s, 1H), 4.78 (s, 1H), 4.03 (t, J=9.0 Hz, 1H), 3.87-3.39 (m, 7H), 3.27 (d, J=5.7 Hz, 2H), 2.39 (d, J=6.2 Hz, 2H), 2.20 (t, J=7.2 Hz, 2H), 1.64 (dd, J=14.8, 7.4 Hz, 2H), 0.92 (t, J=7.3 Hz, 3H). LC-MS (ESI): m/z=427.8 [M+H]⁺.

OTB-110

(R)-[3-[3-Fluoro-4-(1,5-thiazocan-5-yl)phenyl]-2-oxo-5-oxazolidinyl]methylbutyrate

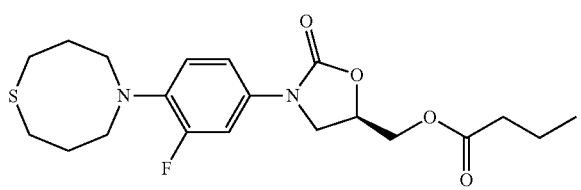 [SMILES: CCCC(=O)OC[C@H]1CN(c2ccc(N3CCCSCCC3)c(F)c2)C(=O)O1]

¹H-NMR (400 MHz, CDCl₃) δ: 7.36 (dd, J=14.8, 4.0 Hz, 1H), 7.09 (dd, J=8.8 Hz, 2.4 Hz, 1H), 7.04 (t, J=10.4 Hz, 9.2 Hz, 1H), 4.85 (m, 1H), 4.37 (m, 1H), 4.31 (m, 1H), 4.08 (m, 1H), 3.78 (m, 1H), 3.37 (m, 4H), 2.75 (m, 4H), 2.34 (t, J=7.6 Hz, 7.2 Hz, 2H), 1.97 (m, 4H), 1.64 (m, 2H), 0.93 (t, 7.6 Hz, J=7.2 Hz, 3H). ¹³C-NMR (125 MHz, CDCl₃) δ: 173.3, 155.4 (d, J=243.5 Hz), 154.3, 134.5 (d, J=8.3 Hz), 131.1 (d, J=10.1 Hz), 128.2, 127.1, 120.0 (d, J=4.9 Hz), 114.3 (d, J=3.0 Hz), 108.4 (d, J=26.8 Hz), 70.2, 64.0, 48.1, 47.4, 36.0, 32.1, 29.8, 18.4, 13.7. HR-MS (ESI-TOF): m/z [M+H]⁺ calcd for $C_{20}H_{28}O_4N_2FS$: 411.1748; found: 411.1786.

OTB-113

(R)-5-[(2H-1,2,3-triazol-2-yl)methyl]-3-[3-fluoro-4-(1,5-thiazocan-5-yl)phenyl]oxazolidin-2-one

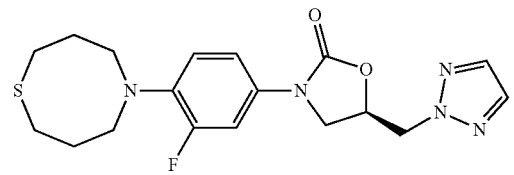

¹H-NMR (400 MHz, CDCl₃) δ: 7.65 (s, 2H), 7.30 (d, J=14.8 Hz, 1H), 7.03 (m, 2H), 5.10 (m, 1H), 4.85 (dd, J=14.0 Hz, 4.8 Hz, 1H), 4.74 (dd, J=14.0 Hz, 7.2 Hz, 1H), 4.06 (t, J=9.2 Hz, 8.8 Hz, 1H), 3.97 (m, 1H), 3.37 (t, J=6.0 Hz, 6.0 Hz, 4H), 2.73 (m, 4H), 1.97 (m, 4H). ¹³C-NMR (125 MHz, CDCl₃) δ: 155.2 (d, J=243.5 Hz), 135.2, 134.4 (d, J=8.1 Hz), 130.8 (d, J=10.3 Hz), 119.8 (d, J=4.9 Hz), 114.5 (d, J=3.1 Hz), 108.4 (d, J=26.6 Hz), 70.0, 56.3, 48.3, 47.9, 31.9, 29.6. HR-MS (ESI-TOF): m/z [M+H]⁺ calcd for $C_{18}H_{23}O_2N_5FS$: 392.1551; found: 392.1590.

OTB-114

(R)-[3-[3-Fluoro-4-(1,5-thiazocan-5-yl)phenyl]-2-oxo-5-oxazolidinyl]methylacetamide

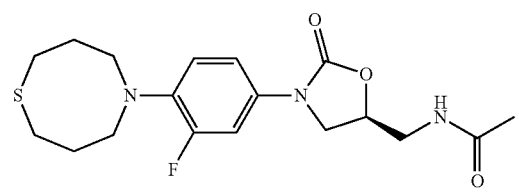 [SMILES: CC(=O)NC[C@H]1CN(c2ccc(N3CCCSCCC3)c(F)c2)C(=O)O1]

¹H-NMR (400 MHz, CDCl₃) δ: 7.34 (m, 1H), 7.02 (m, 2H), 6.23 (m, 1H), 4.75 (m, 1H), 4.00 (t, J=8.8 Hz, 8.8 Hz, 1H), 3.73 (m, 2H), 3.64 (m, 1H), 3.36 (t, J=6.4 Hz, 6.0 Hz, 4H), 2.73 (m, 4H), 2.04 (s, 3H), 1.97 (m, 4H). ¹³C-NMR (125 MHz, CDCl₃) δ: 171.4, 155.2 (d, J=243.5 Hz), 154.4, 134.5, 130.2, 119.9, 114.3, 108.3 (d, J=26.8 Hz), 71.9, 48.1, 47.8, 42.0, 31.9, 29.7, 23.1. HR-MS (ESI-TOF): m/z [M+H]⁺ calcd for $C_{18}H_{25}O_3N_3FS$: 382.1595; found: 382.1620.

OTB-117

(S)—N-[[3-(3-Fluoro-4-(1,5-thiazocan-5-yl)phenyl)-2-oxo-oxazolidin-5-yl]methyl]furan-2-carboxamide

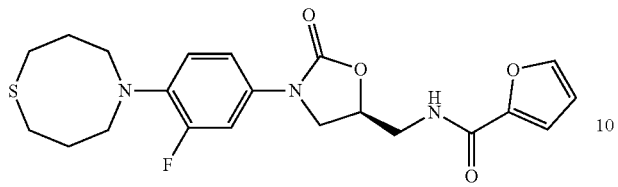

¹H-NMR (400 MHz, CDCl₃) δ: 7.47 (s, 1H), 7.36 (d, J=14.4 Hz, 1H), 7.14 (d, J=3.2 Hz, 1H), 7.01 (m, 2H), 6.78 (m, 1H), 6.51 (m, 1H), 4.84 (m, 1H), 4.05 (t, J=9.2 Hz, 8.8 Hz, 1H), 3.88 (m, 1H), 3.80 (m, 2H), 3.36 (t, J=6.0 Hz, 6.0 Hz, 4H), 2.73 (m, 4H), 1.96 (m, 4H). ¹³C-NMR (125 MHz, CDCl₃) δ: 159.0, 155.2 (d, J=243.6 Hz), 154.3, 147.1, 144.5, 134.3, 130.9, 119.8, 115.1, 114.3 (d, J=3.0 Hz), 112.3, 108.4 (d, J=26.8 Hz), 71.9, 47.9, 41.5, 31.9, 29.6. HR-MS (ESI-TOF): m/z [M+H]⁺ calcd for C₂₁H₂₅O₄N₃FS: 434.1544; found: 434.1581.
OTB-118

(S)—N-[[3-(3-Fluoro-4-(1,5-thiazocan-5-yl)phenyl)-2-oxo-oxazolidin-5-yl]methyl]thiophene-2-carboxamide

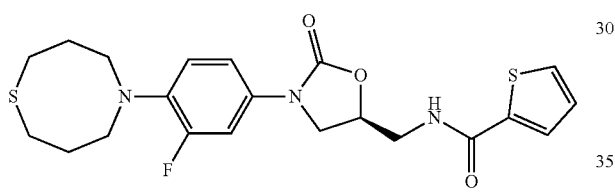

¹H-NMR (400 MHz, CDCl₃) δ: 7.54 (m, 1H), 7.52 (m, 1H), 7.34 (m, 1H), 7.10 (m, 1H), 7.04 (m, 1H), 7.00 (m, 1H), 6.57 (t, J=6.0 Hz, 6.0 Hz, 1H), 4.86 (m, 1H), 4.07 (t, J=9.2 Hz, 8.8 Hz, 1H), 4.07 (m, 1H), 3.82 (m, 2H), 3.36 (t, J=6.0 Hz, 6.0 Hz, 4H), 2.74 (m, 4H), 1.96 (m, 4H). ¹³C-NMR (125 MHz, CDCl₃) δ: 162.7, 155.2 (d, J=243.5 Hz), 154.5, 137.9, 130.8, 128.7, 127.8, 119.8, 114.5 (d, J=3.0 Hz), 108.5 (d, J=26.8 Hz), 72.1, 48.0, 42.5, 31.9, 29.6. HR-MS (ESI-TOF): m/z [M+H]⁻ calcd for C₂₁H₂₅O₄N₄FS₂: 450.1316; found: 450.1356.
OTB-120

(R)—N-[[3-(3-Fluoro-4-(1,5-thiazocan-5-yl)phenyl)-2-oxo-oxazolidin-5-yl]methyl]butane-1-sulfonamide

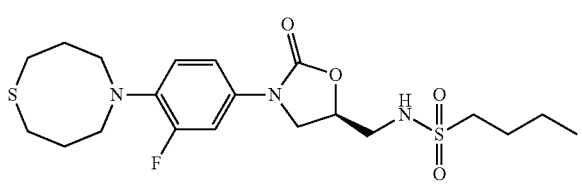 [SMILES: CCCCS(=O)(=O)NC[C@H]1CN(c2ccc(N3CCCSCCC3)c(F)c2)C(=O)O1]

¹H-NMR (400 MHz, CDCl₃) δ: 7.42 (d, J=14.4 Hz, 1H), 7.08 (m, 2H), 4.94 (m, 1H), 4.79 (m, 1H), 4.04 (t, J=8.8 Hz, 8.8 Hz, 1H), 3.93 (m, 1H), 3.55 (m, 1H), 3.43 (m, 5H), 3.07 (m, 2H), 2.76 (m, 4H), 2.01 (m, 4H), 1.80 (m, 2H), 1.45 (m, 2H), 0.95 (t, J=7.6 Hz, 7.2 Hz, 3H). ¹³C-NMR (125 MHz, CDCl₃) δ: 155.2 (d, J=243.6 Hz), 154.2, 134.5, 130.7, 119.8 (d, J=4.9 Hz), 114.5 (d, J=3.0 Hz), 108.5 (d, J=26.8 Hz), 71.5, 53.1, 47.9, 47.4, 45.5, 31.9, 29.6, 25.6, 21.5, 13.5. HR-MS (ESI-TOF): m/z [M+H]⁺ calcd for C₂₀H₃₁O₄N₃FS₂: 460.1735; found: 460.1778.
OTB-121

(S)—N-[[3-(3-Fluoro-4-(1,5-thiazocan-5-yl)phenyl)-2-oxo-oxazolidin-5-yl]methyl]pivalamide

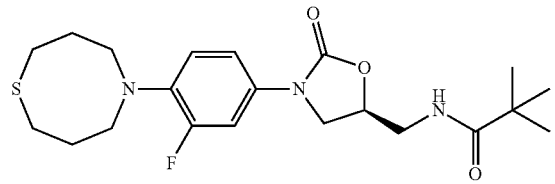 [SMILES: CC(C)(C)C(=O)NC[C@H]1CN(c2ccc(N3CCCSCCC3)c(F)c2)C(=O)O1]

¹H-NMR (400 MHz, CDCl₃) δ: 7.39 (d, J=14.4 Hz, 1H), 7.04 (m, 2H), 6.11 (m, 1H), 4.74 (m, 1H), 4.00 (t, J=9.2 Hz, 8.8 Hz, 1H), 3.76 (m, 1H), 3.67 (m, 2H), 3.39 (m, 4H), 2.74 (m, 4H), 1.98 (m, 4H), 1.17 (s, 9H). ¹³C-NMR (125 MHz, CDCl₃) δ: 179.6, 155.2 (d, J=243.6 Hz), 154.4, 134.3 (d, J=8.0 Hz), 130.9 (d, J=5.4 Hz), 128.8, 119.8 (d, J=4.9 Hz), 114.2 (d, J=2.9 Hz), 108.2 (d, J=26.9 Hz), 72.0, 47.9, 47.8, 42.2, 38.9, 31.9, 29.6, 27.5. HR-MS (ESI-TOF): m/z [M+H]⁺ calcd for C₂₁H₃₁O₃N₃FS: 424.2065; found: 424.2096.
OBD-001

(R)-5-((1H-1,2,3-Triazol-1-yl)methyl)-3-(3-fluoro-4-(1,5-thiazocan-5-yl)phenyl)oxazolidin-2-one

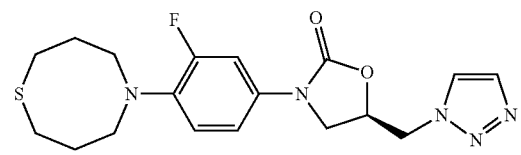 [SMILES: O=C1O[C@@H](Cn2ccnn2)CN1c1ccc(N2CCCSCCC2)c(F)c1]

¹H-NMR (300 MHz, CDCl₃) δ: 7.76 (d, J=17.6 Hz, 2H), 7.41-7.09 (m, 1H), 7.11-6.73 (m, 2H), 5.04 (d, J=3.0 Hz, 1H), 4.78 (d, J=3.4 Hz, 2H), 4.12 (t, J=9.2 Hz, 1H), 3.88 (dd, J=9.2, 6.1 Hz, 1H), 3.36 (t, J=6.0 Hz, 3H), 2.92-2.59 (m, 4H), 2.01 (dd, J=27.9, 7.3 Hz, 4H).
LC-MS (ESI): m/z=391.9 [M+H]⁺.
OBD-003

(S)—N-((3-(3-Fluoro-4-(1,5-thiazocan-5-yl)phenyl)-2-oxooxazolidin-5-yl)methyl)butyramide

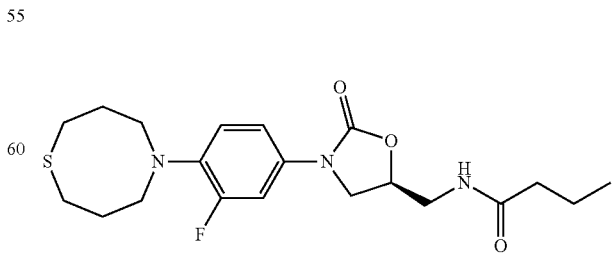

¹H-NMR (300 MHz, CDCl₃) δ: 7.50 (s, 2H), 7.03 (d, J=6.1 Hz, 1H), 5.99 (s, 1H), 4.77 (d, J=5.7 Hz, 1H), 4.02 (t,

J=9.0 Hz, 2H), 3.70 (ddd, J=20.7, 15.2, 7.7 Hz, 4H), 3.48 (s, 4H), 2.95-2.68 (m, 4H), 2.20 (t, J=7.2 Hz, 3H), 2.06 (d, J=6.1 Hz, 4H), 1.64 (dd, J=14.8, 7.4 Hz, 4H), 0.91 (t, J=7.4 Hz, 4H).

LC-MS (ESI): m/z=409.9 [M+H]$^+$.

OBD-008

(R)-5-((1H-1,2,4-Triazol-1-yl)methyl)-3-(3-fluoro-4-(1,5-thiazocan-5-yl)phenyl)oxazolidin-2-one

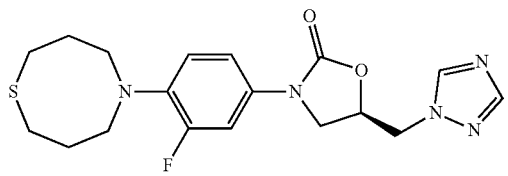 [SMILES: O=C1O[C@@H](Cn2cncn2)CN1c1ccc(N2CCCSCCC2)c(F)c1]

$^1$H-NMR (300 MHz, CDCl$_3$) δ: 8.24 (s, 1H), 7.97 (s, 1H), 7.00 (s, 2H), 5.12-4.91 (m, 1H), 4.56 (d, J=4.7 Hz, 2H), 4.24-3.83 (m, 2H), 3.38 (t, J=6.0 Hz, 4H), 2.95-2.59 (m, 4H), 1.98 (s, 5H).

LC-MS (ESI): m/z=391.9 [M+H]$^+$.

OTB-124

(S)—N-[[3-(3-Fluoro-4-(1-oxido-1,5-thiazocan-5-yl)phenyl)-2-oxo-oxazolidin-5-yl]methyl]acetamide

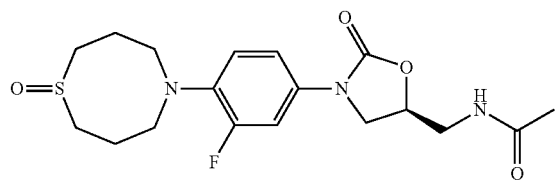 [SMILES: CC(=O)NC[C@H]1CN(c2ccc(N3CCCS(=O)CCC3)c(F)c2)C(=O)O1]

$^1$H-NMR (400 MHz, CDCl$_3$) δ: 7.46 (dd, J=2.8 Hz, 14.8 Hz, 1H), 7.14 (t, J=9.2 Hz, 8.8 Hz, 1H), 7.07 (m, 1H), 6.15 (m, 1H), 4.78 (m, 1H), 4.03 (t, J=9.2 Hz, 8.8 Hz, 1H), 3.74 (m, 3H), 3.31 (m, 1H), 3.18 (m, 4H), 2.98 (m, 2H), 2.17 (m, 4H), 2.03 (s, 3H). $^{13}$C-NMR (125 MHz, CDCl$_3$) δ: 171.0, 154.2, 134.0, 128.5, 127.3, 122.6, 113.9, 108.1 (d, J=26.9 Hz), 71.9, 53.1, 51.7, 47.7, 42.0, 29.7, 25.0, 23.2. HR-MS (ESI): m/z [M+H]$^+$ calcd for C$_{18}$H$_{25}$O$_4$N$_3$FS: 398.1544; found: 398.1540.

OBD-002

(R)-5-((1H-1,2,3-Triazol-1-yl)methyl)-3-(3-fluoro-4-(1-oxido-1,5-thiazocan-5-yl)phenyl)oxazolidin-2-one

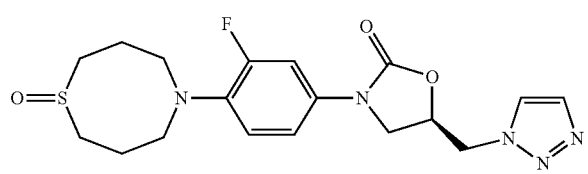 [SMILES: O=C1O[C@@H](Cn2ccnn2)CN1c1ccc(N2CCCS(=O)CCC2)c(F)c1]

$^1$H-NMR (300 MHz, CDCl$_3$) δ: 7.92-7.67 (m, 2H), 7.32 (d, J=16.8 Hz, 1H), 7.12 (t, J=9.0 Hz, 1H), 6.96 (d, J=8.1 Hz, 1H), 5.07 (s, 1H), 4.81 (d, J=4.0 Hz, 2H), 4.15 (t, J=9.0 Hz, 1H), 4.01-3.83 (m, 1H), 3.32 (d, J=14.2 Hz, 5H), 3.11-2.87 (m, 2H), 2.59 (s, 2H), 2.19 (s, 4H).

LC-MS (ESI): m/z=407.8 [M+H]$^+$.

OBD-004

(S)—N-((3-(3-Fluoro-4-(1-oxido-1,5-thiazocan-5-yl)phenyl)-2-oxooxazolidin-5-yl)methyl)butyramide

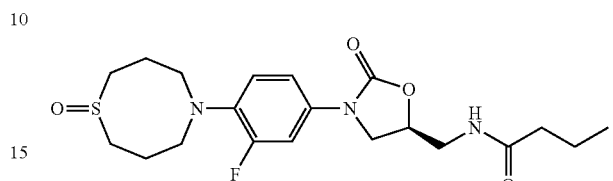

$^1$H-NMR (300 MHz, CDCl$_3$) δ: 7.44 (dd, J=14.7, 2.4 Hz, 1H), 7.19-6.99 (m, 2H), 6.44 (s, 1H), 4.84-4.71 (m, 1H), 4.02 (t, J=8.9 Hz, 1H), 3.78 (dd, J=9.0, 6.6 Hz, 1H), 3.66 (t, J=4.6 Hz, 2H), 3.38-3.09 (m, 6H), 2.99 (dd, J=12.6, 6.3 Hz, 2H), 2.20 (dd, J=9.4, 5.3 Hz, 6H), 1.71-1.56 (m, 2H), 0.91 (dd, J=9.6, 5.1 Hz, 3H).

LC-MS (ESI): m/z=425.8 [M+H]$^+$.

OBD-009

(R)-5-((1H-1,2,4-Triazol-1-yl)methyl)-3-(3-fluoro-4-(1-oxido-1,5-thiazocan-5-yl)phenyl)oxazolidin-2-one

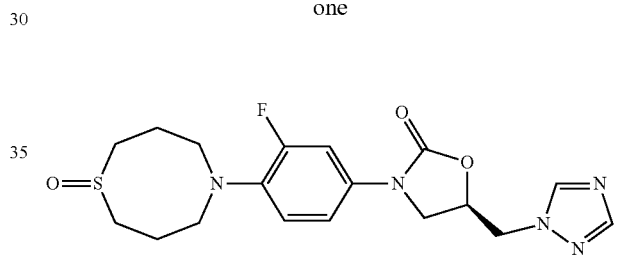

$^1$H-NMR (300 MHz, CDCl$_3$) δ: 8.24 (s, 1H), 7.93 (s, 1H), 7.41-7.20 (m, 1H), 7.19-6.92 (m, 2H), 5.10-4.92 (m, 1H), 4.56 (d, J=4.7 Hz, 2H), 4.12 (t, J=9.0 Hz, 1H), 3.97 (dd, J=9.2, 6.2 Hz, 1H), 3.28 (dd, J=13.0, 6.9 Hz, 2H), 3.12 (dd, J=12.5, 5.9 Hz, 4H), 3.02-2.83 (m, 2H), 2.22-1.99 (m, 5H), 1.26 (d, J=9.4 Hz, 4H).

LC-MS (ESI): m/z=407.8 [M+H]$^+$.

OTB-227

N-(((5S)-3-(4-(3-Thia-6-azabicyclo[3.1.1]heptan-6-yl)-3-fluorophenyl)-2-oxo-oxazolidin-5-yl)methyl)acetamide

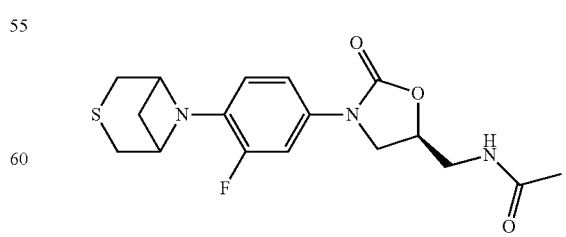

$^1$H-NMR (400 MHz, CDCl$_3$) δ: 7.36 (d, J=14.4 Hz, 1H), 7.05 (d, J=8.4 Hz, 1H), 6.60 (t, J=9.2 Hz, 1H), 6.35 (brs, 1H), 4.76-4.74 (m, 1H), 4.56-4.54 (m, 2H), 4.00 (t, J=9.2

Hz, 1H), 3.76-3.65 (m, 2H), 3.62-3.57 (m, 1H), 3.43 (d, J=12.0 Hz, 2H), 2.93-2.87 (m, 1H), 2.74 (d, J=12.0 Hz, 2H), 2.09 (s, 1H), 2.03 (s, 3H). $^{13}$C-NMR (100 MHz, CDCl$_3$) δ: 171.1, 154.5, 151.8 (d, J=238.5 Hz), 131.9 (d, J=11.8 Hz), 129.2 (d, J=9.5 Hz), 115.2 (d, J=6.2 Hz), 114.7 (d, J=2.8 Hz), 108.0 (d, J=24.9 Hz), 71.9, 60.8, 47.8, 41.9, 29.4, 25.3, 23.2. HRMS (ESI-TOF+): m/z [M+H]$^+$ calcd for C$_{17}$H$_{21}$FN$_3$O$_3$S: 366.1288; found: 366.1277.

OTB-501

(R)-3-(4-((1R,5S)-3-Thia-8-azabicyclo[3.2.1]octan-8-yl)-3-fluorophenyl)-5-(hydroxymethyl)oxazolidin-2-one

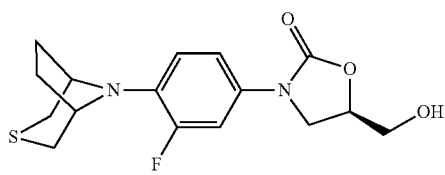 [SMILES: O=C1O[C@@H](CO)CN1c1ccc(N2C3CCC2CSC3)c(F)c1]

$^1$H-NMR (400 MHz, CDCl$_3$) δ: 7.39 (d, J=12.8 Hz, 1H), 7.16 (d, J=8.8 Hz, 1H), 6.90 (t, J=9.2 Hz, 1H), 4.74 (m, 1H), 4.43 (s, 2H), 3.99-3.96 (m, 3H), 3.79-3.75 (m, 1H), 3.48 (d, J=13.2 Hz, 2H), 2.21-2.10 (m, 6H). HRMS (ESI): m/z [M+H]$^+$ calcd for C$_{16}$H$_{20}$N$_2$O$_3$FS: 339.1179; found: 339.1169.

OTB-502

N—(((S)-3-(4-((1R,5S)-3-Thia-8-azabicyclo[3.2.1]octan-8-yl)-3-fluorophenyl)-2-oxooxazolidin-5-yl)methyl)acetamide

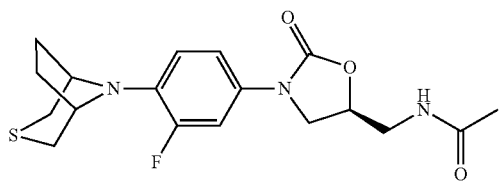 [SMILES: CC(=O)NC[C@H]1CN(c2ccc(N3C4CCC3CSC4)c(F)c2)C(=O)O1]

$^1$H-NMR (400 MHz, CDCl$_3$) δ: 7.36 (dd, J=15.2, 2.4 Hz, 1H), 7.06 (dd, J=8.8, 1.8 Hz, 1H), 6.83 (t, J=9.2 Hz, 1H), 6.18 (s, 1H), 4.77-4.75 (m, 1H), 4.40 (s, 2H), 4.00 (t, J=8.8 Hz, 1H), 3.76-3.72 (m, 2H), 3.68-3.62 (m, 1H), 3.37 (d, J=12.8 Hz, 2H), 2.26-2.04 (m, 6H), 2.02 (s, 3H). $^{13}$C-NMR (100 MHz, CDCl$_3$) δ: 171.1, 154.5, 152.8 (d, J=241.7 Hz), 132.2 (d, J=8.6 Hz), 130.2 (d, J=10.4 Hz), 118.1 (d, J=5.0 Hz), 114.7, 108.4 (d, J=27.2 Hz), 71.9, 57.4, 47.8, 42.0, 30.2, 28.4, 23.1. HR-MS (ESI-TOF): m/z [M+H]$^+$ calcd for C$_{18}$H$_{23}$N$_3$O$_3$FS: 380.1444; found: 380.1435.

OTB-504

(R)-5-((1H-1,2,3-Triazol-1-yl)methyl)-3-(4-((1R,5S)-3-thia-8-azabicyclo[3.2.1]octan-8-yl)-3-fluorophenyl)oxazolidin-2-one

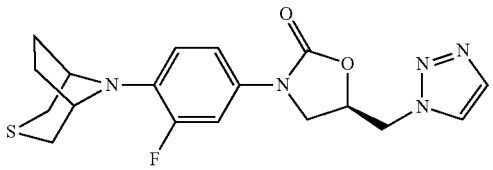 [SMILES: O=C1O[C@@H](Cn2ccnn2)CN1c1ccc(N2C3CCC2CSC3)c(F)c1]

$^1$H-NMR (400 MHz, CDCl$_3$) δ: 7.80 (s, 1H), 7.76 (s, 1H), 7.24 (m, 1H), 6.96 (d, J=8.8 Hz, 1H), 6.83 (t, J=8.8 Hz, 1H), 5.07-5.04 (m, 1H), 4.79 (s, 2H), 4.40 (s, 2H), 4.11 (t, J=8.0 Hz, 1H), 3.90-3.87 (m, 1H), 3.42 (d, J=12.8 Hz, 2H), 2.20-2.07 (m, 6H). HR-MS (ESI-TOF): m/z [M+H]$^+$ calcd for C$_{18}$H$_{21}$N$_5$O$_2$FS: 390.1400; found: 390.1385.

OTB-236

N—(((R)-3-(4-((1R,5S)-3-Thia-8-azabicyclo[3.2.1]octan-8-yl)-3-fluorophenyl)-2-oxooxazolidin-5-yl)methyl)methanesulfonamide

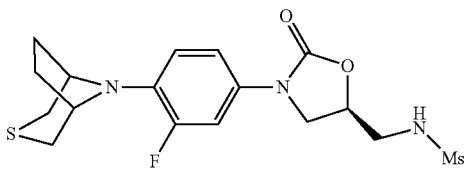 [SMILES: CS(=O)(=O)NC[C@H]1CN(c2ccc(N3C4CCC3CSC4)c(F)c2)C(=O)O1]

$^1$H-NMR (400 MHz, CDCl$_3$) δ: 7.47-7.41 (m, 1H), 7.13 (d, J=9.6 Hz, 1H), 7.02 (t, J=9.6 Hz, 1H), 4.76-4.70 (m, 1H), 4.34 (s, 2H), 4.08 (t, J=9.2 Hz, 1H), 3.76 (t, J=8.8 Hz, 1H), 3.29-3.26 (m, 2H), 3.11 (d, J=12.8 Hz, 2H), 2.93 (s, 3H), 2.11 (d, J=12.4 Hz, 2H), 2.02 (s, 4H). HR-MS (ESI-TOF): m/z [M+H]$^+$ calcd for C$_{17}$H$_{23}$N$_3$O$_4$FS$_2$: 416.1114; found: 416.1097.

OTB-237

Methyl (((S)-3-(4-((1R,5S)-3-thia-8-azabicyclo[3.2.1]octan-8-yl)-3-fluorophenyl)-2-Oxo-oxazolidin-5-yl)methyl)carbamate

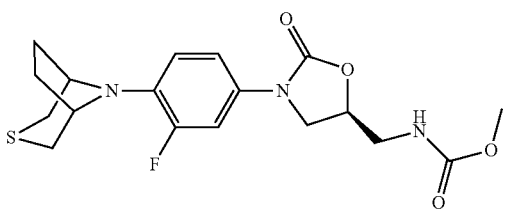 [SMILES: COC(=O)NC[C@H]1CN(c2ccc(N3C4CCC3CSC4)c(F)c2)C(=O)O1]

$^1$H-NMR (400 MHz, CDCl$_3$) δ: 7.36 (d, J=15.2 Hz, 1H), 7.07 (d, J=8.8 Hz, 1H), 6.81 (t, J=9.2 Hz, 1H), 5.18 (brs, 1H), 4.74 (brs, 1H), 4.39 (s, 2H), 4.01 (t, J=8.8 Hz, 1H), 3.76 (t, J=7.6 Hz, 1H), 3.69 (s, 3H), 3.56-3.51 (m, 1H), 3.33 (d, J=12.8 Hz, 2H), 2.18-2.07 (m, 6H). HR-MS (ESI-TOF): m/z [M+H]$^+$ calcd for C$_{18}$H$_{23}$N$_3$O$_4$FS: 396.1393; found: 396.1388.

OBD-016

N—(((S)-3-(4-((1R,5S)-3-Thia-8-azabicyclo[3.2.1]
octan-8-yl)-3-fluorophenyl)-2-oxooxazolidin-5-yl)
methyl)butyramide

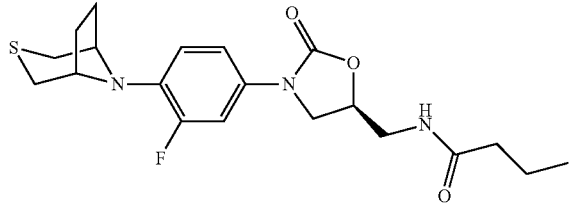 [SMILES: CCCC(=O)NC[C@H]1CN(c2ccc(N3C4CCC3CSC4)c(F)c2)C(=O)O1]

$^1$H-NMR (300 MHz, DMSO-d$_6$) δ: 8.18 (s, 1H), 7.42 (d, J=16.0 Hz, 1H), 7.35-6.88 (m, 2H), 4.71 (s, 1H), 4.35 (s, 2H), 4.07 (t, J=8.7 Hz, 1H), 3.77-3.57 (m, 1H), 3.51-3.27 (m, 2H), 3.12 (d, J=12.4 Hz, 2H), 2.09 (dd, J=20.9, 12.2 Hz, 8H), 1.47 (dd, J=14.0, 7.1 Hz, 2H), 0.80 (dd, J=8.0, 6.7 Hz, 3H). LC-MS (ESI): m/z=407.9 [M+H]$^+$.
OBD-021

(R)-5-((1H-1,2,4-Triazol-1-yl)methyl)-3-(4-((1R,
5S)-3-thia-8-azabicyclo[3.2.1]octan-8-yl)-3-fluoro-
phenyl)oxazolidin-2-one

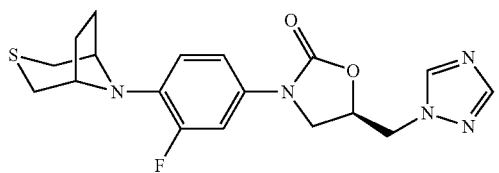 [SMILES: O=C1O[C@@H](Cn2cncn2)CN1c1ccc(N2C3CCC2CSC3)c(F)c1]

$^1$H-NMR (300 MHz, DMSO-d$_6$) δ: 8.57 (s, 1H), 8.01 (s, 1H), 7.36 (dd, J=15.8, 2.1 Hz, 1H), 7.18-6.92 (m, 2H), 5.06 (dd, J=8.9, 4.8 Hz, 1H), 4.72-4.52 (m, 2H), 4.36 (s, 2H), 4.17 (t, J=9.1 Hz, 1H), 3.84 (dt, J=49.3, 24.7 Hz, 1H), 3.12 (d, J=12.8 Hz, 2H), 2.16 (s, 1H), 2.11 (s, 1H), 2.04 (s, 4H).
LC-MS (ESI): m/z=389.9 [M+H]$^+$.
OTB-506

N—(((S)-3-(4-((1R,5S)-3-Thia-8-azabicyclo[3.2.1]
octan-8-yl)-3-fluorophenyl)-2-oxooxazolidin-5-yl)
methyl)cyclopropanecarboxamide

$^1$H-NMR (400 MHz, CDCl$_3$) δ: 7.37 (d, J=13.6 Hz, 1H), 7.07 (d, J=7.6 Hz, 1H), 6.85 (brs, 1H), 6.22 (t, J=6.0 Hz, 1H), 4.79-4.73 (m, 1H), 4.41 (brs, 2H), 3.99 (t, J=7.2 Hz, 1H), 3.77-3.64 (m, 3H), 3.39 (d, J=12.8 Hz, 2H), 2.20-2.09 (m, 6H), 1.43-1.37 (m, 1H), 0.98-0.90 (m, 2H), 0.82-0.75 (m, 2H). HR-MS (ESI-TOF): m/z [M+H]$^+$ calcd for C$_{20}$H$_{25}$N$_3$O$_3$FS: 406.1595; found: 406.1527.
OTB-507

N—(((S)-3-(4-((1R,5S)-3-Thia-8-aza-bicyclo[3.2.1]
octan-8-yl)-3-fluorophenyl)-2-oxooxazolidin-5-yl)
methyl)cyclobutanecarboxamide

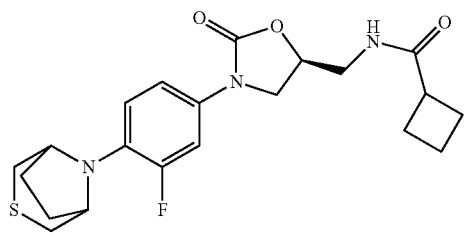 [SMILES: O=C(NC[C@H]1CN(c2ccc(N3C4CCC3CSC4)c(F)c2)C(=O)O1)C1CCC1]

$^1$H-NMR (400 MHz, CDCl$_3$) δ: 7.45 (d, J=12.4 Hz, 1H), 7.17 (d, J=8.8 Hz, 1H), 7.05 (t, J=8.8 Hz, 1H) 5.95 (m, 1H), 4.78 (m, 1H), 4.51 (brs, 2H), 4.00 (t, J=9.2 Hz, 1H), 3.84-3.74 (m, 3H), 3.66 (m, 2H), 3.02 (m, 1H), 2.28-2.15 (m, 10H), 1.95 (m, 1H), 1.85 (m, 1H). $^{13}$C-NMR (100 MHz, CDCl$_3$) δ: 175.9, 154.3, 153.0 (d, J=242.9 Hz), 131.2, 127.0, 118.6 (d, J=4.4 Hz), 114.5 (d, J=2.9 Hz), 108.3 (d, J=27.1 Hz), 71.9, 58.2, 47.7, 41.9, 39.6, 30.3, 28.3, 25.4, 25.3, 18.1. HRMS (ESI): m/z [M+H]$^+$ calcd for C$_{21}$H$_{27}$N$_3$O$_3$SF: 420.1757; found: 420.1736.
OTB-510

N—(((S)-3-(4-((1R,5S)-3-Thia-8-aza-bicyclo[3.2.1]
octan-8-yl)-3,5-difluorophenyl)-2-oxo-oxazolidin-5-
yl)methyl)acetamide

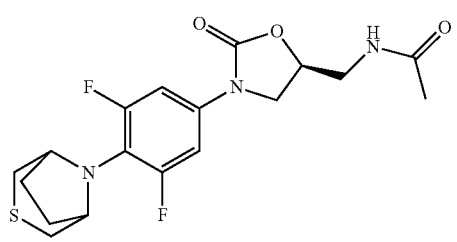 [SMILES: CC(=O)NC[C@H]1CN(c2cc(F)c(N3C4CCC3CSC4)c(F)c2)C(=O)O1]

$^1$H-NMR (400 MHz, CDCl$_3$) δ: 7.08 (m, 2H), 6.00 (m, 1H), 4.76 (m, 1H), 4.24 (brs, 2H), 3.97 (t, J=8.8 Hz, 1H), 3.75-3.60 (m, 3H), 3.38 (m, 2H), 2.21 (m, 2H), 2.14 (s, 4H), 2.03 (s, 3H). $^{13}$C-NMR (100 MHz, CDCl$_3$) δ: 171.2, 155.3 (dd, J=241.5, 9.5 Hz), 154.1, 130.6 (t, J=13.6 Hz), 122.9 (t, J=12.4 Hz), 102.9 (dd, J=20.7, 11.3 Hz), 71.9, 60.4, 47.4, 41.9, 33.7, 29.2, 23.1. HRMS (ESI): m/z [M+H]$^+$ calcd for C$_{18}$H$_{22}$N$_3$O$_3$SF$_2$: 398.1350; found: 398.1329.
OTB-512

Methyl (((S)-3-(4-((1R,5S)-3-thia-8-azabicyclo[3.2.1]octan-8-yl)-3,5-difluorophenyl)-2-oxo-oxazolidin-5-yl)methyl)carbamate

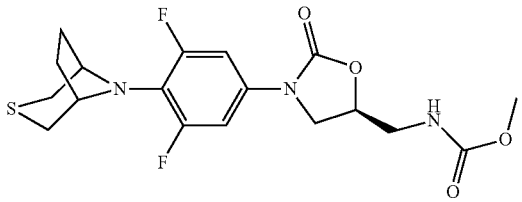 [SMILES: COC(=O)NC[C@H]1CN(c2cc(F)c(N3C4CCC3CSC4)c(F)c2)C(=O)O1]

$^1$H-NMR (400 MHz, CDCl$_3$) δ: 7.09 (m, 2H), 5.08 (m, 1H), 4.76 (m, 1H), 4.24 (brs, 2H), 3.98 (t, J=8.8 Hz, 1H), 3.75-3.50 (m, 6H), 3.38 (m, 2H), 2.20 (m, 2H), 2.14 (s, 4H). $^{13}$C-NMR (100 MHz, CDCl$_3$) δ: 157.5, 155.3 (dd, J=241.6, 9.4 Hz), 153.9, 130.7 (t, J=13.6 Hz), 122.9 (t, J=12.3 Hz), 102.9 (dd, J=20.7, 11.3 Hz), 71.8, 60.4, 52.6, 47.3, 43.6, 33.7, 29.2. HRMS (ESI): m/z [M+H]$^+$ calcd for C$_{18}$H$_{22}$N$_3$O$_4$SF$_2$: 414.1294; found: 414.1278.
OTB-511

(R)-5-((1H-1,2,3-Triazol-1-yl)methyl)-3-(4-((1R,5S)-3-thia-8-azabicyclo[3.2.1]octan-8-yl)-3,5-difluorophenyl)oxazolidin-2-one

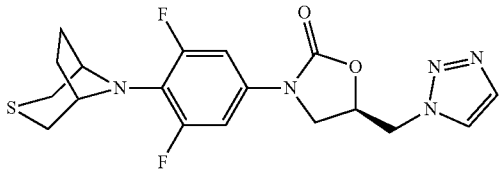 [SMILES: O=C1O[C@@H](Cn2ccnn2)CN1c1cc(F)c(N2C3CCC2CSC3)c(F)c1]

$^1$H-NMR (400 MHz, CDCl$_3$) δ: 7.78 (s, 1H), 7.76 (s, 1H), 6.94 (d, J=11.6 Hz, 2H), 5.07-5.04 (m, 1H), 4.79 (d, J=3.6 Hz, 2H), 4.20 (brs, 2H), 4.09 (t, J=8.8 Hz, 1H), 3.88-3.83 (m, 1H), 3.32 (d, J=12.8 Hz, 2H), 2.19-2.11 (m, 6H). $^{13}$C-NMR (100 MHz, CDCl$_3$) δ: 155.3 (d, J=242.1 Hz), 155.2 (d, J=242.1 Hz), 153.1, 134.5, 129.9 (t, J=13.6 Hz), 125.1, 123.3 (t, J=12.3 Hz), 103.3 (dd, J=20.7, 11.2 Hz), 70.3, 60.4, 52.0, 47.2, 33.8, 29.2. HRMS (ESI): m/z [M+H]$^+$ calcd for C$_{18}$H$_{20}$N$_5$O$_2$SF$_2$: 408.1300; found: 408.1295.
OTB-508

N—(((S)-3-(4-((1R,5S)-3-Thia-8-aza-bicyclo[3.2.1]octan-8-yl)-3,5-difluorophenyl)-2-oxo-oxazolidin-5-yl)methyl)cyclopropanecarboxamide

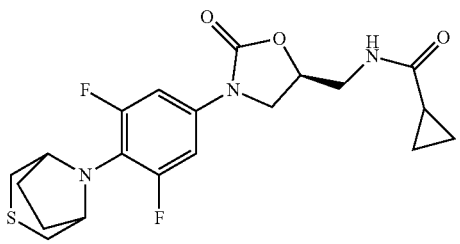 [SMILES: O=C(NC[C@H]1CN(c2cc(F)c(N3C4CCC3CSC4)c(F)c2)C(=O)O1)C1CC1]

$^1$H-NMR (400 MHz, CDCl$_3$) δ: 7.05 (m, 2H), 6.12 (m, 1H), 4.76 (m, 1H), 4.21 (brs, 2H), 3.95 (t, J=9.2 Hz, 1H), 3.72-3.65 (m, 3H), 3.34 (m, 2H), 2.21-2.12 (m, 6H), 1.37 (m, 1H), 0.99-0.75 (m, 4H). $^{13}$C-NMR (100 MHz, CDCl$_3$) δ: 174.8, 155.3 (dd, J=241.7, 9.5 Hz), 154.2, 130.5 (t, J=13.6 Hz), 123.0 (t, J=12.5 Hz), 103.0 (dd, J=20.8, 11.4 Hz), 72.1, 60.4, 47.5, 41.9, 33.8, 29.2, 14.6, 7.8, 7.7. HRMS (ESI): m/z [M+H]$^+$ calcd for C$_{20}$H$_{24}$N$_3$O$_3$SF$_2$: 420.1506; found: 424.1484.
OTB-509

N—(((S)-3-(4-((1R,5S)-3-Thia-8-aza-bicyclo[3.2.1]octan-8-yl)-3,5-difluorophenyl)-2-oxo-oxazolidin-5-yl)methyl)cyclobutanecarboxamide

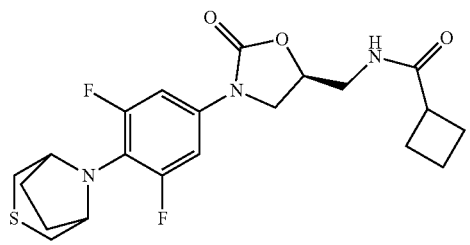 [SMILES: O=C(NC[C@H]1CN(c2cc(F)c(N3C4CCC3CSC4)c(F)c2)C(=O)O1)C1CCC1]

$^1$H-NMR (400 MHz, CDCl$_3$) δ: 7.09 (m, 2H), 5.78 (m, 1H), 4.75 (m, 1H), 4.23 (brs, 2H), 3.97 (t, J=8.8 Hz, 1H), 3.73 (m, 1H), 3.65 (m, 2H), 3.36 (m, 2H), 2.99 (m, 1H), 2.27-2.14 (m, 9H), 1.97 (m, 1H), 1.85 (m, 2H). $^{13}$C-NMR (100 MHz, CDCl$_3$) δ: 176.0, 155.3 (dd, J=243.4, 9.5 Hz), 154.1, 130.6 (t, J=13.5 Hz), 122.9 (t, J=12.2 Hz), 102.9 (dd, J=20.7, 11.4 Hz), 72.0, 60.4, 47.5, 41.8, 33.7, 29.2, 25.4, 25.3, 18.1. HRMS (ESI): m/z [M+H]$^+$ calcd for C$_{21}$H$_{26}$N$_3$O$_3$SF$_2$: 438.1663; found: 438.1642.
OTB-503

N-(((5S)-3-(3-Fluoro-4-((1R,5S)-3-oxido-3-thia-8-azabicyclo[3.2.1]octan-8-yl)phenyl)-2-oxo-oxazolidin-5-yl)methyl)acetamide

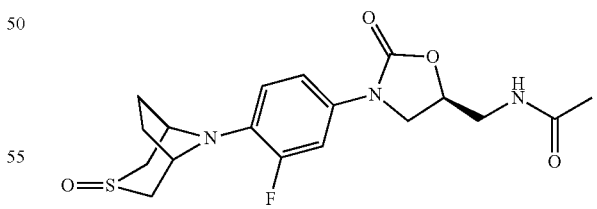

$^1$H-NMR (400 MHz, CDCl$_3$) δ: 7.45 (dd, J=16.0, 2.8 Hz, 1H), 7.12 (dd, J=8.8, 2.0 Hz, 1H), 6.83 (t, J=9.2 Hz, 1H), 6.14 (s, 1H), 4.78-4.77 (m, 1H), 4.61 (s, 2H), 4.00 (t, J=8.8 Hz, 1H), 3.77-3.64 (m, 3H), 3.45 (d, J=9.6 Hz, 2H), 2.85 (d, J=12.4 Hz, 2H), 2.22-2.20 (m, 2H), 2.03 (s, 3H), 1.92-1.88 (m, 2H). HR-MS (ESI-TOF): m/z [M+H]$^+$ calcd for C$_{18}$H$_{23}$N$_3$O$_4$FS: 396.1388; found: 396.1379.
OTB-505

(5R)-5-((1H-1,2,3-Triazol-1-yl)methyl)-3-(3-fluoro-4-((1R,5S)-3-oxido-3-thia-8-azabicyclo[3.2.1]octan-8-yl)phenyl)oxazolidin-2-one

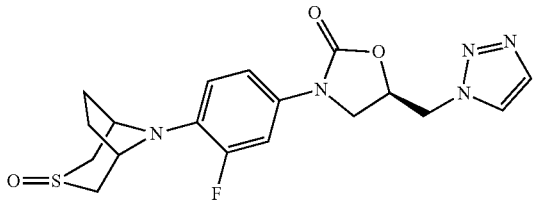 [SMILES: O=C1O[C@@H](Cn2ccnn2)CN1c1ccc(N2C3CCC2CS(=O)C3)c(F)c1]

¹H-NMR (400 MHz, CDCl₃) δ: 7.79 (s, 1H), 7.75 (s, 1H), 7.30 (dd, J=15.2, 2.0 Hz, 1H), 6.98 (d, J=8.4 Hz, 1H), 6.79 (t, J=9.2 Hz, 1H), 5.07-5.05 (m, 1H), 4.79 (s, 2H), 4.58 (s, 2H), 4.12 (t, J=9.2 Hz, 1H), 3.91-3.89 (m, 1H), 3.43 (d, J=11.6 Hz, 2H), 2.88-2.81 (m, 2H), 2.21-2.18 (m, 2H), 1.89-1.87 (m, 2H). HR-MS (ESI-TOF): m/z [M+H]⁺ calcd for C₁₈H₂₁N₅O₃FS: 406.1349; found: 406.1339.
OTB-513

N-(((5S)-3-(3,5-Difluoro-4-((1R,5S)-3-oxido-3-thia-8-azabicyclo[3.2.1]octan-8-yl)phenyl)-2-oxo-oxazolidin-5-yl)methyl)cyclobutanecarboxamide

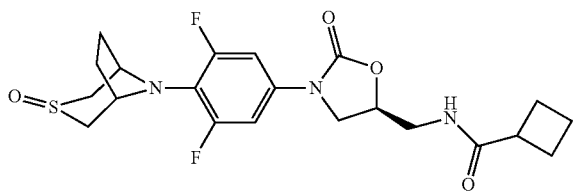 [SMILES: O=C(NC[C@H]1CN(c2cc(F)c(N3C4CCC3CS(=O)C4)c(F)c2)C(=O)O1)C1CCC1]

¹H-NMR (400 MHz, CDCl₃) δ: 7.12 (d, J=12.0 Hz, 2H), 5.97 (brs, 1H), 4.77-4.75 (m, 1H), 4.45 (s, 2H), 3.97 (t, J=8.8 Hz, 1H), 3.74 (t, J=8.4 Hz, 1H), 3.66 (t, J=5.2 Hz, 2H), 3.54 (d, J=9.2 Hz, 2H), 3.02 (m, 1H), 2.91 (d, J=12.0 Hz, 2H), 2.26-2.11 (m, 6H), 1.99-1.92 (m, 1H), 1.87-1.85 (m, 3H). HRMS (ESI): m/z [M+H]⁺ calcd for C₂₁H₂₆N₃O₄SF₂: 454.1606; found: 454.1588.
OTB-514

N-(((5S)-3-(3,5-Difluoro-4-((1R,5S)-3-oxido-3-thia-8-azabicyclo[3.2.1]octan-8-yl)phenyl)-2-oxo-oxazolidin-5-yl)methyl)acetamide

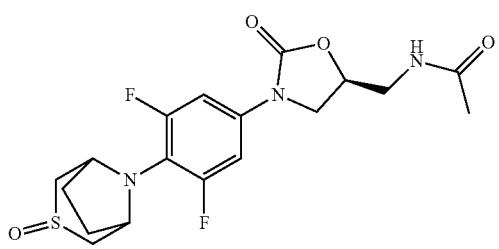 [SMILES: CC(=O)NC[C@H]1CN(c2cc(F)c(N3C4CCC3CS(=O)C4)c(F)c2)C(=O)O1]

¹H-NMR (400 MHz, CDCl₃) δ: 7.12 (d, J=12.0 Hz, 2H), 6.15 (brs, 1H), 4.81-4.75 (m, 1H), 4.45 (s, 2H), 3.98 (t, J=8.8 Hz, 1H), 3.74-3.63 (m, 3H), 3.56 (d, J=9.2 Hz, 2H), 2.92 (d, J=12.4 Hz, 2H), 2.20-2.17 (m, 2H), 2.03 (s, 3H), 1.89-1.83 (m, 2H). HRMS (ESI): m/z [M+H]⁺ calcd for C₁₈H₂₂N₃O₄SF₂: 414.1293; found: 414.1275.
OBD-017

N-(((5S)-3-(3-Fluoro-4-((1R,5S)-3-oxido-3-thia-8-azabicyclo[3.2.1]octan-8-yl)phenyl)-2-oxooxazolidin-5-yl)methyl)butyramide

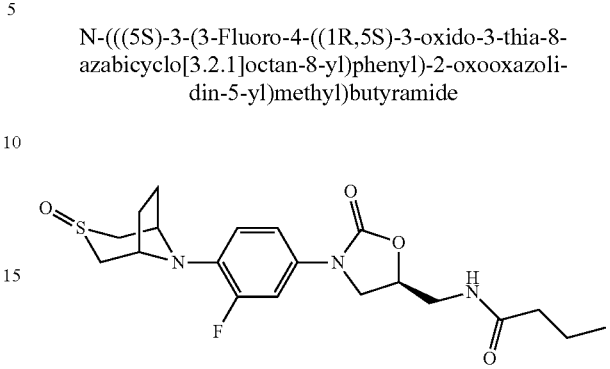

¹H-NMR (300 MHz, CDCl₃) δ: 7.39 (dd, J=15.8, 2.3 Hz, 1H), 7.03 (d, J=6.1 Hz, 2H), 6.78 (t, J=9.3 Hz, 1H), 4.72 (s, 1H), 4.55 (s, 2H), 3.94 (t, J=8.9 Hz, 1H), 3.81-3.66 (m, 1H), 3.58 (s, 2H), 3.42 (d, J=10.3 Hz, 2H), 2.77 (d, J=11.9 Hz, 2H), 2.17 (dd, J=25.1, 17.8 Hz, 4H), 1.84 (d, J=7.9 Hz, 2H), 1.56 (dd, J=14.5, 7.2 Hz, 2H), 0.83 (t, J=7.4 Hz, 3H).
LC-MS (ESI): m/z=423.8 [M+H]⁺.
OBD-018

(5R)-5-((1H-1,2,4-Triazol-1-yl)methyl)-3-(3-fluoro-4-((1R,5S)-3-oxido-3-thia-8-azabicyclo[3.2.1]octan-8-yl)phenyl)oxazolidin-2-one

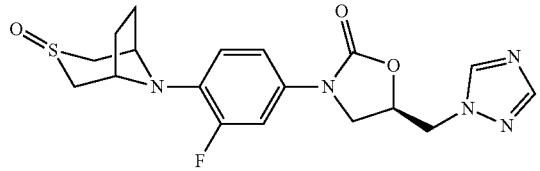 [SMILES: O=C1O[C@@H](Cn2cncn2)CN1c1ccc(N2C3CCC2CS(=O)C3)c(F)c1]

¹H-NMR (300 MHz, DMSO-d₆) δ: 12.17 (s, 1H), 8.69 (d, J=2.9 Hz, 1H), 8.20-8.03 (m, 1H), 7.44 (d, J=16.2 Hz, 1H), 7.28-7.02 (m, 2H), 5.08 (dd, J=8.5, 5.1 Hz, 1H), 4.68-4.52 (m, 4H), 4.20 (t, J=9.1 Hz, 1H), 3.91 (dd, J=8.7, 6.0 Hz, 1H), 3.56 (d, J=11.1 Hz, 2H), 2.48 (d, J=12.3 Hz, 2H), 2.06 (d, J=5.1 Hz, 2H), 1.79 (d, J=7.6 Hz, 2H).
LC-MS (ESI): m/z=405.8 [M+H]⁺.
OTB-260

(R)-3-(3-Fluoro-4-(2-thia-6-azaspiro[3.3]heptan-6-yl)phenyl)-5-(hydroxymethyl)oxazolidin-2-one

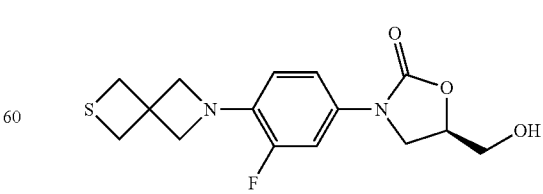

¹H-NMR (400 MHz, CDCl₃) δ:7.38 (d, J=14.0 Hz, 1H), 7.04 (d, J=8.0 Hz, 1H), 6.55 (t, J=8.8 Hz, 1H), 4.72 (brs, 1H), 4.02 (s, 4H), 3.99-3.89 (m, 3H), 3.76-3.73 (m, 1H), 3.42 (s, 4H). ¹³C-NMR (100 MHz, CDCl₃) δ: 154.8, 152.2 (d, J=240.8 Hz), 135.9 (d, J=11.7 Hz), 130.2 (d, J=9.3 Hz), 114.6 (d, J=5.2 Hz), 114.5 (d, J=3.1 Hz), 107.6 (d, J=23.8 Hz), 72.8, 66.8, 62.8, 46.7, 44.3, 36.8. HRMS (ESI): m/z [M+H]⁺ calcd for C₁₅H₁₈FN₂O₃S: 325.1022; found: 325.1010.
OTB-261

(S)—N-((3-(3-Fluoro-4-(2-thia-6-azaspiro[3.3]heptan-6-yl)phenyl)-2-oxo-oxazolidin-5-yl)methyl)acetamide

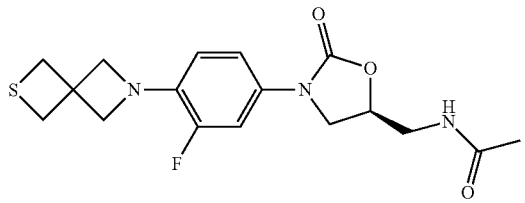 [SMILES: CC(=O)NC[C@H]1CN(c2ccc(N3CC4(CSC4)C3)c(F)c2)C(=O)O1]

¹H-NMR (400 MHz, CDCl₃) δ: 7.33 (d, J=14.0 Hz, 1H), 6.99 (d, J=8.4 Hz, 1H), 6.48 (t, J=8.8 Hz, 1H), 6.20 (brs, 1H), 4.75-4.73 (m, 1H), 3.98-3.96 (m, 5H), 3.73-3.66 (m, 2H), 3.62-3.57 (m, 1H), 3.41 (s, 4H), 2.01 (s, 3H). HRMS (ESI): m/z [M+H]⁺ calcd for C₁₇H₂₁FN₃O₃S: 366.1288; found: 366.1274.
OTB-241

(R)-5-((1H-1,2,3-Triazol-1-yl)methyl)-3-(3-fluoro-4-(2-thia-6-azaspiro[3.3]heptan-6-yl)phenyl)oxazolidin-2-one

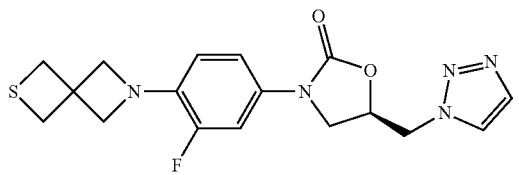 [SMILES: O=C1O[C@@H](Cn2ccnn2)CN1c1ccc(N2CC3(CSC3)C2)c(F)c1]

¹H-NMR (400 MHz, CDCl₃) δ: 7.79 (s, 1H), 7.75 (s, 1H), 7.22 (dd, J=13.6, 2.0 Hz, 1H), 6.88 (d, J=8.8 Hz, 1H), 6.51 (t, J=9.2 Hz, 1H), 5.06-5.00 (m, 1H), 4.78-4.77 (m, 2H), 4.08 (t, J=9.2 Hz, 1H), 4.01 (s, 4H), 3.89-3.85 (m, 1H), 3.40 (s, 4H). ¹³C-NMR (100 MHz, CDCl₃) δ: 153.6, 152.0 (d, J=243.1 Hz), 136.3 (d, J=11.1 Hz), 134.5, 129.1 (d, J=9.0 Hz), 125.1, 115.0 (d, J=3.2 Hz), 114.5 (d, J=5.2 Hz), 108.1 (d, J=23.6 Hz), 70.4, 66.7, 52.1, 47.7, 44.3, 36.8. HRMS (ESI): m/z [M+H]⁺ calcd for C₁₇H₁₉FN₅O₂S: 376.1244; found: 376.1231.
OTB-516

(R)-3-(3,5-Difluoro-4-(2-thia-6-azaspiro[3.3]heptan-6-yl)phenyl)-5-(hydroxymethyl)oxazolidin-2-one

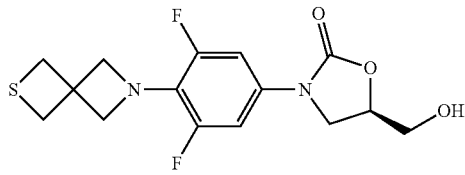 [SMILES: O=C1O[C@@H](CO)CN1c1cc(F)c(N2CC3(CSC3)C2)c(F)c1]

¹H-NMR (400 MHz, CDCl₃) δ: 7.03 (d, J=12.0 Hz, 2H), 4.74-4.70 (m, 1H), 4.18 (s, 4H), 3.98 (dd, J=12.8, 3.2 Hz, 1H), 3.93-3.85 (m, 2H), 3.75 (dd, J=12.4, 4.0 Hz, 1H), 3.41 (s, 4H). HRMS (ESI): m/z [M+H]⁺ calcd for C₁₅H₁₇N₂O₃SF₂: 343.0922; found: 343.0912.
OTB-515

(S)—N-((3-(3,5-Difluoro-4-(2-thia-6-azaspiro[3.3]heptan-6-yl)phenyl)-2-oxo-oxazolidin-5-yl)methyl)acetamide

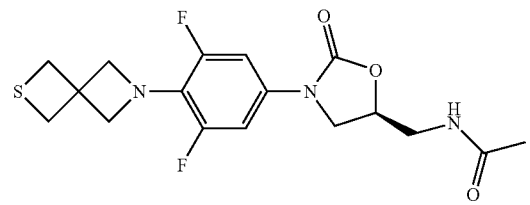 [SMILES: CC(=O)NC[C@H]1CN(c2cc(F)c(N3CC4(CSC4)C3)c(F)c2)C(=O)O1]

¹H-NMR (400 MHz, CDCl₃) δ: 6.98 (d, J=11.6 Hz, 2H), 5.99 (brs, 1H), 4.74-4.72 (m, 1H), 4.16 (s, 4H), 3.94 (t, J=8.8 Hz, 1H), 3.71-3.65 (m, 2H), 3.61-3.55 (m, 1H), 3.40 (s, 4H), 2.01 (s, 3H). ¹³C-NMR (100 MHz, CDCl₃) δ: 171.1, 154.2, 152.6 (dd, J=240.6, 11.1 Hz), 153.1, 134.5, 128.5 (t, J=12.6 Hz), 124.7 (t, J=13.3 Hz), 102.8 (dd, J=18.2, 10.7 Hz), 71.9, 68.7, 47.6, 45.2, 42.0, 36.5, 23.1. HRMS (ESI): m/z [M+H]⁺ calcd for C₁₇H₂₀N₃O₃SF₂: 384.1188; found: 384.1168.
OTB-242

Methyl (S)-((3-(3,5-difluoro-4-(2-thia-6-azaspiro[3.3]heptan-6-yl)phenyl)-2-oxo-oxazolidin-5-yl)methyl)carbamate

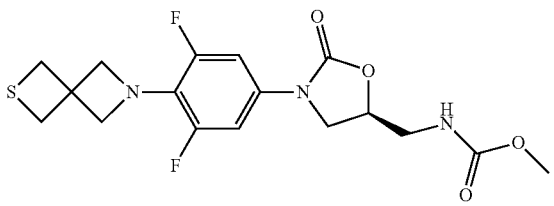 [SMILES: COC(=O)NC[C@H]1CN(c2cc(F)c(N3CC4(CSC4)C3)c(F)c2)C(=O)O1]

¹H NMR (400 MHz, CDCl₃) δ: 7.00 (d, J=11.6 Hz, 2H), 5.16 (brs, 1H), 4.81-4.67 (m, 1H), 4.16 (s, 4H), 3.94 (t, J=8.8 Hz, 1H), 3.68 (s, 3H), 3.56-3.50 (m, 3H), 3.40 (s, 4H). HRMS (ESI): m/z [M+H]⁺ calcd for C₁₇H₂₀F₂N₃O₄S: 400.1143; found: 400.1125.
OTB-245

(R)-5-((1H-1,2,3-Triazol-1-yl)methyl)-3-(3,5-difluoro-4-(2-thia-6-azaspiro[3.3]heptan-6-yl)phenyl)oxazolidin-2-one

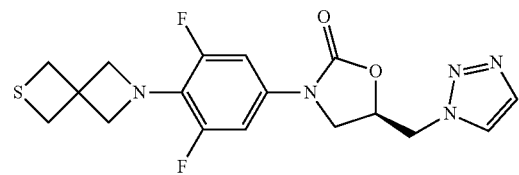 [SMILES: O=C1O[C@@H](Cn2ccnn2)CN1c1cc(F)c(N2CC3(CSC3)C2)c(F)c1]

¹H NMR (400 MHz, CDCl₃) δ: 7.77 (s, 1H), 7.74 (s, 1H), 6.87 (d, J=11.6 Hz, 2H), 5.03-5.01 (m, 1H), 4.77-4.76 (m, 2H), 4.15 (s, 4H), 4.06 (t, J=9.2 Hz, 1H), 3.86-3.82 (m, 1H), 3.41 (s, 4H). HRMS (ESI): m/z [M+H]⁺ calcd for $C_{17}H_{18}F_2N_5O_2S$: 394.1149; found: 394.1129.

OTB-243

(S)—N-((3-(3,5-Difluoro-4-(2-thia-6-azaspiro[3.3]heptan-6-yl)phenyl)-2-oxo-oxazolidin-5-yl)methyl)cyclopropanecarboxamide

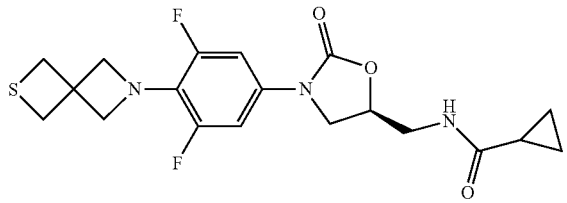 [SMILES: O=C(NC[C@H]1CN(c2cc(F)c(N3CC4(CSC4)C3)c(F)c2)C(=O)O1)C1CC1]

¹H NMR (400 MHz, CDCl₃) δ: 6.98 (d, J=11.6 Hz, 2H), 6.25-6.24 (m, 1H), 4.77-4.71 (m, 1H), 4.16 (s, 4H), 3.92 (t, J=8.8 Hz, 1H), 3.71-3.56 (m, 3H), 3.40 (s, 4H), 1.40-1.38 (m, 1H), 1.04-0.87 (m, 2H), 0.82-0.73 (m, 2H). HRMS (ESI): m/z [M+H]⁺ calcd for $C_{19}H_{22}F_2N_3O_3S$: 410.1350; found: 410.1331.

OTB-244

(S)—N-((3-(3,5-Difluoro-4-(2-thia-6-azaspiro[3.3]heptan-6-yl)phenyl)-2-oxo-oxazolidin-5-yl)methyl)cyclobutanecarboxamide

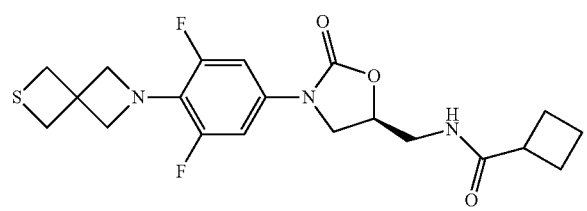 [SMILES: O=C(NC[C@H]1CN(c2cc(F)c(N3CC4(CSC4)C3)c(F)c2)C(=O)O1)C1CCC1]

¹H NMR (400 MHz, CDCl₃) δ: 6.99 (d, J=11.6 Hz, 2H), 5.83 (brs, 1H), 4.82-4.68 (m, 1H), 4.17 (s, 4H), 3.93 (t, J=8.8 Hz, 1H), 3.72-3.64 (m, 3H), 3.40 (s, 4H), 3.03-2.96 (m, 1H), 2.26-1.85 (m, 6H). HRMS (ESI): m/z [M+H]⁺ calcd for $C_{20}H_{24}F_2N_3O_3S$: 424.1506; found: 424.1483

OTB-201

(R)-3-(3-Fluoro-4-(2-oxa-6-azaspiro[3.3]heptan-6-yl)phenyl)-5-(hydroxymethyl)oxazolidin-2-one

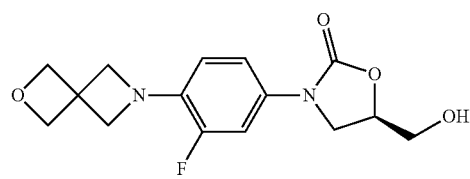 [SMILES: O=C1O[C@@H](CO)CN1c1ccc(N2CC3(COC3)C2)c(F)c1]

¹H-NMR (400 MHz, CDCl₃) δ:7.42 (dd, J=14.0, 2.0 Hz, 1H), 7.03 (dd, J=8.8, 2.0 Hz, 1H), 6.62 (t, J=8.8 Hz, 1H), 4.85 (s, 4H), 4.73 (m, 1H), 4.17 (s, 4H), 4.00-3.95 (m, 2H), 3.93-3.89 (m, 1H), 3.77-3.74 (m, 1H). ¹³C-NMR (100 MHz, CDCl₃) δ: 155.2, 152.3 (d, J=240.7 Hz), 135.9 (d, J=11.3 Hz), 130.4 (d, J=8.9 Hz), 114.7 (d, J=3.0 Hz), 114.6 (d, J=5.6 Hz), 107.8 (d, J=23.8 Hz), 81.3, 73.2, 63.1, 62.9, 46.9, 40.1. HRMS (ESI): m/z [M+H]⁺ calcd for $C_{15}H_{18}FN_2O_4$: 309.1251; found: 309.1269.

OTB-202

(S)—N-((3-(3-Fluoro-4-(2-oxa-6-azaspiro[3.3]heptan-6-yl)phenyl)-2-oxo-oxazolidin-5-yl)methyl)acetamide

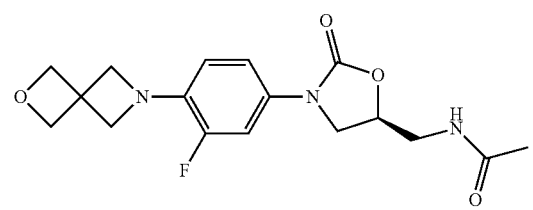 [SMILES: CC(=O)NC[C@H]1CN(c2ccc(N3CC4(COC4)C3)c(F)c2)C(=O)O1]

¹H-NMR (300 MHz, CDCl₃) δ: 7.35 (d, J=14.1 Hz, 1H), 7.00 (d, J=8.7 Hz, 1H), 6.51 (t, J=9.0 Hz, 1H), 6.03 (s, 1H), 4.84 (s, 4H), 4.74 (m, 1H), 4.12 (s, 4H), 3.99 (t, J=8.7 Hz, 1H), 3.73-3.69 (m, 2H), 3.61 (m, 1H), 2.02 (s, 3H). ¹³C-NMR (100 MHz, CDCl₃) δ: 171.4, 154.8, 152.4 (d, J=240.8 Hz), 136.1 (d, J=11.9 Hz), 130.1 (d, J=9.2 Hz), 114.7 (d, J=3.1 Hz), 114.6 (d, J=5.0 Hz), 107.9 (d, J=23.6 Hz), 81.2, 72.1, 63.1, 48.1, 42.2, 40.1, 23.4. HRMS (ESI): m/z [M+H]⁻ calcd for $C_{17}H_{21}FN_3O_4$: 350.1516; found: 350.1497.

OTB-203

(R)-5-((1H-1,2,3-Triazol-1-yl)methyl)-3-(3-fluoro-4-(2-oxa-6-azaspiro[3.3]heptan-6-yl)phenyl)oxazolidin-2-one

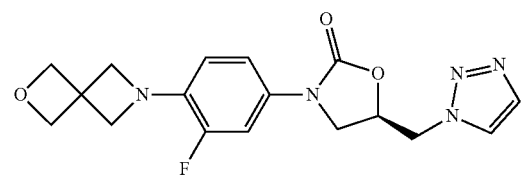 [SMILES: O=C1O[C@@H](Cn2ccnn2)CN1c1ccc(N2CC3(COC3)C2)c(F)c1]

¹H-NMR (400 MHz, CDCl₃) δ: 7.78 (s, 1H), 7.75 (s, 1H), 7.18 (d, J=13.6 Hz, 1H), 6.88 (d, J=8.8 Hz, 1H), 6.46 (t, J=9.2 Hz, 1H), 5.03 (m, 1H), 4.83 (s, 4H), 4.78 (m, 2H), 4.10-4.07 (m, 5H), 3.91-3.85 (m, 1H). ¹³C-NMR (100 MHz, CDCl₃) δ: 153.6, 152.1 (d, J=241.4 Hz), 136.1 (d, J=10.6 Hz), 134.5, 129.2 (d, J=9.3 Hz), 125.1, 115.0 (d, J=2.9 Hz), 114.5 (d, J=4.7 Hz), 108.1 (d, J=23.7 Hz), 81.0, 70.4, 62.9, 52.1, 47.7, 39.8. HRMS (ESI): m/z [M+H]⁺ calcd for $C_{17}H_{19}FN_5O_3$: 360.1472; found: 360.1451.

OTB-204

(R)-5-((2H-1,2,3-Triazol-2-yl)methyl)-3-(3-fluoro-4-(2-oxa-6-azaspiro[3.3]heptan-6-yl)phenyl)oxazolidin-2-one

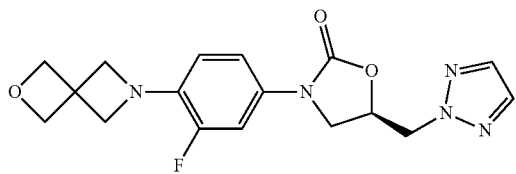

$^1$H-NMR (400 MHz, CDCl$_3$) δ: 7.65 (s, 2H), 7.31 (d, J=14.4, 2.4 Hz, 1H), 6.99 (d, J=8.4 Hz, 1H), 6.59 (t, J=9.2 Hz, 1H), 5.14-5.07 (m, 1H), 4.88-4.83 (m, 5H), 4.77-4.71 (m, 1H), 4.16 (s, 4H), 4.07-4.02 (m, 1H), 3.98-3.92 (m, 1H). $^{13}$C-NMR (100 MHz, CDCl$_3$) δ: 158.99, 154.38, 147.08, 144.53, 135.18, 115.11, 114.43, 112.30, 107.91, 107.87, 81.04, 71.85, 70.04, 62.91, 48.38, 48.02, 41.57, 39.85. HRMS (ESI): m/z [M+H]$^+$ calcd for C$_{17}$H$_{19}$FN$_5$O$_3$: 360.1472; found: 360.1451.
OTB-205

(S)—N-((3-(3-Fluoro-4-(2-oxa-6-azaspiro[3.3]heptan-6-yl)phenyl)-2-oxo-oxazolidin-5-yl)methyl)furan-2-carboxamide

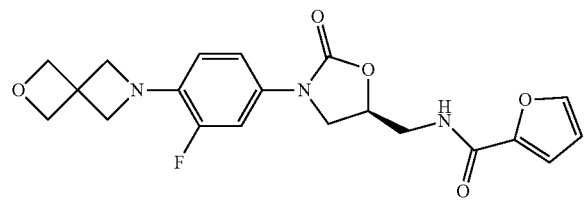 [SMILES: O=C(NC[C@H]1CN(c2ccc(N3CC4(COC4)C3)c(F)c2)C(=O)O1)c1ccco1]

$^1$H-NMR (400 MHz, CDCl$_3$) δ: 7.46 (s, 1H), 7.32 (dd, J=14.0, 2.4 Hz, 1H), 7.14 (d, J=3.2 Hz, 1H), 7.00 (d, J=8.4 Hz, 1H), 6.81 (t, J=6.4 Hz, 1H), 6.51 (d, J=3.2 Hz, 1H), 6.45 (t, J=9.2 Hz, 1H), 4.83 (brs, 5H), 4.08 (s, 4H), 4.03 (t, J=8.8 Hz, 1H), 3.92-3.85 (m, 1H), 3.79-3.73 (m, 2H). $^{13}$C-NMR (100 MHz, CDCl$_3$) δ: 159.2, 154.6, 152.4 (d, J=240.8 Hz), 147.3, 144.7, 136.5, 130.5 (d, J=9.4 Hz), 115.3, 114.7 (d, J=3.1 Hz), 112.5, 109.9, 107.9 (d, J=23.9 Hz), 81.2, 72.1, 63.1, 48.2, 41.8, 40.1. HRMS (ESI): m/z [M+H]$^+$ calcd for C$_{20}$H$_{21}$FN$_3$O$_5$: 402.1465; found: 402.1561.
OTB-206

(S)—N-((3-(3-Fluoro-4-(2-oxa-6-azaspiro[3.3]heptan-6-yl)phenyl)-2-oxo-oxazolidin-5-yl)methyl)thiophene-2-carboxamide

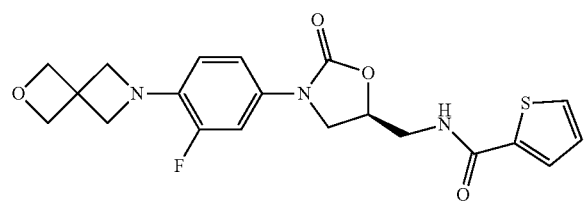

$^1$H-NMR (400 MHz, CDCl$_3$) δ: 7.53 (d, J=3.2 Hz, 1H), 7.50 (d, J=4.8 Hz, 1H), 7.32 (d, J=14.0 Hz, 1H), 7.09-6.96 (m, 2H), 6.66 (m, 1H), 6.45 (t, J=9.2 Hz, 1H), 4.82 (s, 4H), 4.09-4.01 (m, 6H), 3.81-3.79 (m, 1H), 3.78-3.73 (m, 2H). $^{13}$C-NMR (100 MHz, CDCl$_3$) δ: 162.9, 154.7, 152.5 (d, J=241.1 Hz), 150.1, 140.8, 138.1, 130.9, 128.9, 128.0, 114.9 (d, J=2.8 Hz), 114.2 (d, J=3.2 Hz), 108.1 (d, J=23.9 Hz), 81.20 72.2, 63.2, 48.3, 42.7, 40.0. HRMS (ESI): m/z [M+H]$^-$ calcd for C$_{20}$H$_{21}$FN$_3$O$_4$S: 418.1237; found: 418.1331.
OTB-222

(R)—N-((3-(3-Fluoro-4-(2-oxa-6-azaspiro[3.3]heptan-6-yl)phenyl)-2-oxo-oxazolidin-5-yl)methyl)methanesulfonamide

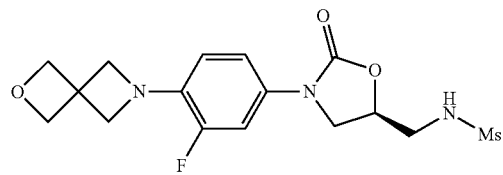 [SMILES: CS(=O)(=O)NC[C@H]1CN(c2ccc(N3CC4(COC4)C3)c(F)c2)C(=O)O1]

$^1$H-NMR (400 MHz, CDCl$_3$) δ: 7.44-7.35 (m, 1H), 7.07-6.97 (m, 1H), 6.69-6.59 (m, 1H), 4.98-4.91 (m, 1H), 4.85 (s, 4H), 4.81-4.75 (m, 1H), 4.24-4.14 (m, 4H), 4.13-4.09 (m, 1H), 4.06-3.98 (m, 1H), 3.92-3.86 (m, 1H), 3.63-3.53 (m, 1H), 3.47-3.36 (m, 1H), 3.03 (s, 3H). $^{13}$C-NMR (100 MHz, DMSO-d$_6$) δ: 154.5, 151.7 (d, J=237.7 Hz), 135.9 (d, J=11.0 Hz), 130.5 (d, J=9.4 Hz), 115.2 (d, J=5.4 Hz), 115.1 (d, J=2.8 Hz), 107.3 (d, J=23.8 Hz), 80.2, 71.7, 62.7, 47.6, 45.5. HRMS (ESI): m/z [M+H]$^+$ calcd for C$_{16}$H$_{21}$FN$_3$O$_5$S: 386.1186; found: 386.1185.
OTB-223

Methyl (S)-((3-(3-fluoro-4-(2-oxa-6-azaspiro[3.3]heptan-6-yl)phenyl)-2-oxo-oxazolidin-5-yl)methyl)carbamate

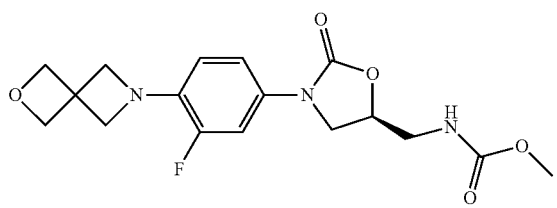 [SMILES: COC(=O)NC[C@H]1CN(c2ccc(N3CC4(COC4)C3)c(F)c2)C(=O)O1]

$^1$H-NMR (400 MHz, CDCl$_3$) δ: 7.39 (d, J=14.0 Hz, 1H), 7.01 (d, J=8.8 Hz, 1H), 6.61 (t, J=9.2 Hz, 1H), 5.11 (brs, 1H), 4.84 (s, 4H), 4.73 (brs, 1H), 4.16 (s, 4H), 3.99 (t, J=8.8 Hz, 1H), 3.77-3.75 (m, 1H), 3.68 (s, 3H), 3.64-3.60 (m, 1H), 3.55-3.50 (m, 1H). HRMS (ESI): m/z [M+H]$^+$ calcd for C$_{17}$H$_{21}$FN$_3$O$_5$: 366.1465; found: 366.1466.
OTB-238

(S)—N-((3-(3-Fluoro-4-(2-oxa-6-azaspiro[3.3]heptan-6-yl)phenyl)-2-oxo-oxazolidin-5-yl)methyl)cyclopropanecarboxamide

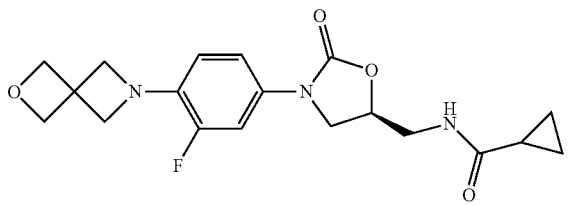 [SMILES: O=C(NC[C@H]1CN(c2ccc(N3CC4(COC4)C3)c(F)c2)C(=O)O1)C1CC1]

¹H-NMR (400 MHz, CDCl₃) δ: 7.35 (dd, J=14.0, 2.4 Hz, 1H), 7.00 (d, J=8.4 Hz, 1H), 6.51 (t, J=9.2 Hz, 1H), 6.13 (brs, 1H), 4.84 (s, 4H), 4.75-4.73 (m, 1H), 4.12 (s, 4H), 3.97 (t, J=8.8 Hz, 1H), 3.75-3.65 (m, 3H), 1.39-1.36 (m, 1H), 0.97-0.91 (m, 2H), 0.79-0.75 (m, 2H). ¹³C-NMR (100 MHz, CDCl₃) δ: 174.8, 154.6, 151.6 (d, J=240.8 Hz), 136.0 (d, J=11.3 Hz), 129.8 (d, J=9.2 Hz), 114.5 (d, J=3.1 Hz), 114.6 (d, J=3.1 Hz), 114.3 (d, J=5.2 Hz), 107.8 (d, J=23.8 Hz), 81.1, 72.1, 62.9, 47.9, 42.0, 39.9, 14.6, 7.7. HRMS (ESI): m/z [M+H]⁺ calcd for C₁₉H₂₃FN₃O₄: 376.1673; found: 376.1652.
OTB-239

(S)—N-((3-(3-Fluoro-4-(2-oxa-6-azaspiro[3.3]heptan-6-yl)phenyl)-2-oxo-oxazolidin-5-yl)methyl)cyclobutanecarboxamide

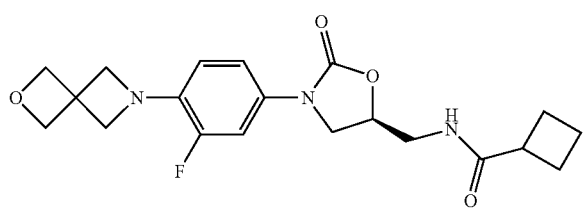 [SMILES: O=C(NC[C@H]1CN(c2ccc(N3CC4(COC4)C3)c(F)c2)C(=O)O1)C1CCC1]

¹H-NMR (400 MHz, CDCl₃) δ: 7.49 (d, J=14.4 Hz, 1H), 7.01 (d, J=8.4 Hz, 1H), 6.85 (t, J=9.2 Hz, 1H), 5.82 (brs, 1H), 4.86 (s, 4H), 4.76 (brs, 1H), 4.27 (s, 4H), 4.00 (t, J=9.2 Hz, 1H), 3.78-3.65 (m, 3H), 3.03-2.99 (m, 1H), 2.26-2.13 (m, 4H), 1.99-1.85 (m, 2H). ¹³C-NMR (100 MHz, CDCl₃) δ: 176.0, 154.5, 152.1 (d, J=240.9 Hz), 136.0 (d, J=11.2 Hz), 129.8 (d, J=9.2 Hz), 114.4 (d, J=3.1 Hz), 114.3 (d, J=5.2 Hz), 107.7 (d, J=23.9 Hz), 81.1, 71.9, 62.8, 47.9, 41.9, 39.7, 25.4, 25.3, 18.2. HRMS (ESI): m/z [M+H]⁺ calcd for C₂₀H₂₅FN₃O₄: 390.1829; found: 390.1808.
OTB-229

(R)-3-(3,5-Difluoro-4-(2-oxa-6-azaspiro[3.3]heptan-6-yl)phenyl)-5-(hydroxymethyl)oxazolidin-2-one

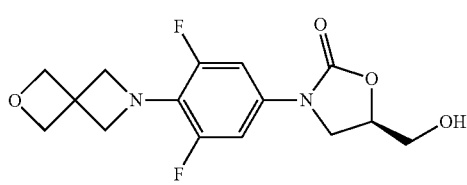 [SMILES: O=C1O[C@@H](CO)CN1c1cc(F)c(N2CC3(COC3)C2)c(F)c1]

¹H-NMR (400 MHz, CDCl₃) δ: 7.03 (d, J=10.8 Hz, 2H), 4.82 (s, 4H), 4.72 (brs, 1H), 4.28 (s, 4H), 3.99-3.85 (m, 3H), 3.75-3.72 (m, 1H). ¹³C-NMR (100 MHz, CDCl₃) δ: 154.6, 152.6 (dd, J=240.2, 10.8 Hz), 128.9 (t, J=12.8 Hz), 124.3 (t, J=13.3 Hz), 102.8 (dd, J=18.2, 10.7 Hz), 81.0, 72.9, 64.9, 62.6, 46.3, 40.8. HRMS (ESI): m/z [M+H]⁻ calcd for C₁₅H₁₇F₂N₂O₄: 327.1156; found: 327.1135.
OTB-230

(S)—N-((3-(3,5-Difluoro-4-(2-oxa-6-azaspiro[3.3]heptan-6-yl)phenyl)-2-oxo-oxazolidin-5-yl)methyl)acetamide

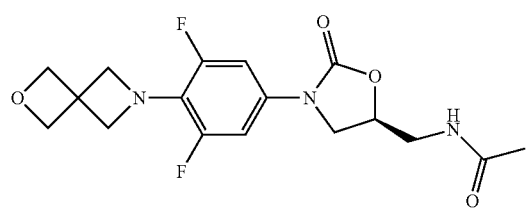 [SMILES: CC(=O)NC[C@H]1CN(c2cc(F)c(N3CC4(COC4)C3)c(F)c2)C(=O)O1]

¹H-NMR (400 MHz, CDCl₃) δ: 6.97 (d, J=10.0 Hz, 2H), 6.49 (brs, 1H), 4.81 (s, 4H), 4.75 (brs, 1H), 4.27 (s, 4H), 3.94 (t, J=8.8 Hz, 1H), 3.70-3.63 (m, 3H), 2.02 (s, 3H). ¹³C-NMR (100 MHz, CDCl₃) δ: 171.2, 154.2, 152.5 (dd, J=240.5, 10.9 Hz), 128.6 (t, J=12.6 Hz), 124.5 (t, J=13.4 Hz), 102.8 (dd, J=18.2, 10.6 Hz), 80.9, 71.9, 64.9, 47.5, 41.9, 40.8, 23.1. HRMS (ESI): m/z [M+H]⁺ calcd for C₁₇H₂₀F₂N₃O₄: 368.1422; found: 368.1418.
OTB-231

Methyl (S)-((3-(3,5-difluoro-4-(2-oxa-6-azaspiro[3.3]heptan-6-yl)phenyl)-2-oxo-oxazolidin-5-yl)methyl)carbamate

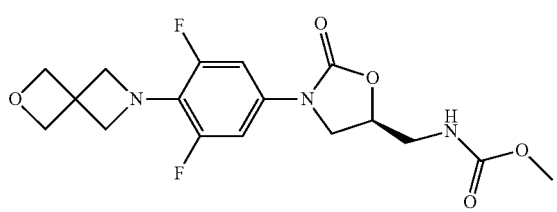 [SMILES: COC(=O)NC[C@H]1CN(c2cc(F)c(N3CC4(COC4)C3)c(F)c2)C(=O)O1]

¹H-NMR (400 MHz, CDCl₃) δ: 7.04 (d, J=10.8 Hz, 2H), 5.08 (brs, 1H), 4.83 (s, 4H), 4.74 (brs, 1H), 4.34 (s, 4H), 3.96 (t, J=9.2 Hz, 1H), 3.72-3.51 (m, 6H). ¹³C-NMR (100 MHz, CDCl₃) δ: 157.5, 154.0, 152.6 (dd, J=240.4, 10.9 Hz), 128.7 (t, J=12.8 Hz), 124.5 (t, J=13.5 Hz), 102.8 (dd, J=23.3, 15.7 Hz), 80.9, 71.7, 64.8, 52.6, 47.4, 43.6, 40.8. HRMS (ESI): m/z [M+H]⁺ calcd for C₁₇H₂₀F₂N₃O₅: 384.1371; found: 384.1367.
OTB-232

(R)—N-((3-(3,5-Difluoro-4-(2-oxa-6-azaspiro[3.3]heptan-6-yl)phenyl)-2-oxo-oxazolidin-5-yl)methyl)methanesulfonamide

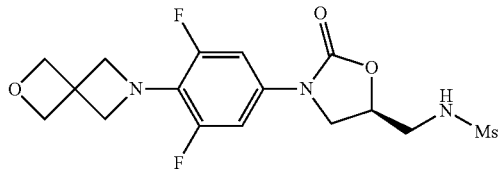 [SMILES: CS(=O)(=O)NC[C@H]1CN(c2cc(F)c(N3CC4(COC4)C3)c(F)c2)C(=O)O1]

$^1$H-NMR (400 MHz, DMSO-d$_6$) δ: 7.8 (d, J=12.4 Hz, 2H), 4.74-4.69 (m, 5H), 4.23 (s, 4H), 4.06 (t, J=8.8 Hz, 1H), 3.74-3.70 (m, 1H), 3.31-3.27 (m, 2H), 2.94 (s, 3H). $^{13}$C-NMR (100 MHz, DMSO-d$_6$) δ: 154.3, 152.2 (dd, J=237.8, 11.3 Hz), 129.5 (t, J=13.0 Hz), 124.4 (t, J=13.6 Hz), 102.9 (dd, J=18.2, 10.5 Hz), 80.0, 71.8, 64.7, 47.4, 45.5, 40.7. HRMS (ESI): m/z [M+H]$^+$ calcd for C$_{16}$H$_{20}$F$_2$N$_3$O$_5$S: 404.1092; found: 404.1087.
OTB-233

(S)—N-((3-(3,5-Difluoro-4-(2-oxa-6-azaspiro[3.3]heptan-6-yl)phenyl)-2-oxo-oxazolidin-5-yl)methyl)cyclopropanecarboxamide

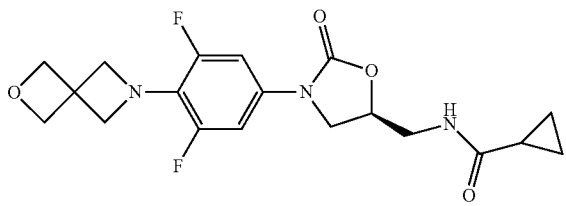

$^1$H-NMR (400 MHz, CDCl$_3$) δ: 6.98 (d, J=10.0 Hz, 2H), 6.36 (brs, 1H), 4.82 (s, 4H), 4.75 (brs, 1H), 4.28 (s, 4H), 3.93 (t, J=8.8 Hz, 1H), 3.72-3.65 (m, 3H), 1.42-1.40 (m, 1H), 0.96-0.88 (m, 2H), 0.77-0.75 (m, 2H). $^{13}$C-NMR (100 MHz, CDCl$_3$) δ: 174.9, 154.4, 152.5 (dd, J=240.4, 10.3 Hz), 128.6 (t, J=12.7 Hz), 124.4 (t, J=13.4 Hz), 102.8 (dd, J=18.2, 10.6 Hz), 80.9, 72.2, 64.8, 47.6, 41.9, 40.8, 14.5, 7.7. HRMS (ESI): m/z [M+H]$^+$ calcd for C$_{19}$H$_{22}$F$_2$N$_3$O$_4$: 394.1578; found: 394.1575.
OTB-234

(R)-5-((1H-1,2,3-Triazol-1-yl)methyl)-3-(3,5-difluoro-4-(2-oxa-6-azaspiro[3.3]heptan-6-yl)phenyl)oxazolidin-2-one

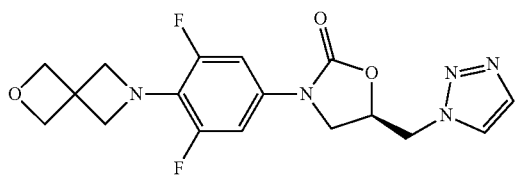 [SMILES: O=C1O[C@@H](Cn2ccnn2)CN1c1cc(F)c(N2CC3(COC3)C2)c(F)c1]

$^1$H-NMR (400 MHz, CDCl$_3$) δ: 7.77 (s, 1H), 7.75 (s, 1H), 6.86 (d, J=11.6 Hz, 2H), 5.03-5.02 (m, 1H), 4.81 (s, 4H), 4.77-4.76 (m, 2H), 4.27 (s, 4H), 4.06 (t, J=9.2 Hz, 1H), 3.86-3.82 (m, 1H). $^{13}$C-NMR (100 MHz, CDCl$_3$) δ: 153.2, 152.4 (dd, J=240.7, 11.0 Hz), 134.5, 127.8 (t, J=12.8 Hz), 125.1, 124.8 (t, J=13.3 Hz), 103.1 (dd, J=18.1, 10.7 Hz), 80.9, 70.4, 64.8, 52.0, 47.3, 40.8. HRMS (ESI): m/z [M+H]$^+$ calcd for C$_{17}$H$_{18}$F$_2$N$_5$O$_3$: 378.1378; found: 378.1365.
OTB-240

(S)—N-((3-(3,5-Difluoro-4-(2-oxa-6-azaspiro[3.3]heptan-6-yl)phenyl)-2-oxo-oxazolidin-5-yl)methyl)cyclobutanecarboxamide

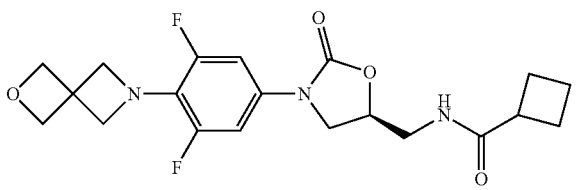 [SMILES: O=C(NC[C@H]1CN(c2cc(F)c(N3CC4(COC4)C3)c(F)c2)C(=O)O1)C1CCC1]

$^1$H-NMR (400 MHz, CDCl$_3$) δ: 7.00 (d, J=12.0 Hz, 2H), 5.87 (t, J=6.0 Hz, 1H), 4.82 (s, 4H), 4.77-4.71 (m, 1H), 4.28 (s, 4H), 3.94 (t, J=8.8 Hz, 1H), 3.72-3.64 (m, 3H), 3.03-2.99 (m, 1H), 2.26-2.13 (m, 4H), 1.99-1.82 (m, 2H). HRMS (ESI): m/z [M+H]$^+$ calcd for C$_{20}$H$_{24}$F$_2$N$_3$O$_4$: 408.1735; found: 408.1716.
OTB-701

(R)—N((3-(3-Fluoro-4-(2,6-diazaspiro[3.3]heptan-2-yl)phenyl)-2-oxo-oxazolidin-5-yl)methyl)acetamide

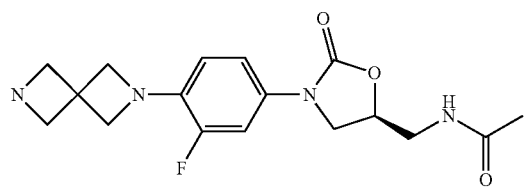 [SMILES: CC(=O)NC[C@H]1CN(c2ccc(N3CC4(CNC4)C3)c(F)c2)C(=O)O1]

$^1$H-NMR (400 MHz, CDCl$_3$) δ: 7.38 (d, J=14.4 Hz, 1H), 7.09 (d, J=8.4 Hz, 1H), 6.58 (t, J=9.2 Hz, 1H), 4.76 (m, 2H), 4.30 (s, 4H), 4.10 (s, 4H), 3.76 (m, 1H), 3.54 (m, 2H), 1.96 (s, 3H). $^{13}$C-NMR (100 MHz, CDCl$_3$) δ: 172.6, 155.4, 153.2, 150.8, 135.6, 130.5, 114.4, 107.3, 72.0, 62.2, 55.0, 48.0, 41.7, 37.2, 21.0. HRMS (ESI): m/z [M+H]$^+$ calcd for C$_{17}$H$_{22}$FN$_4$O$_3$:349.1671; found: 349.1662.
OTB-702

(R)—N-((3-(3-Fluoro-4-(6-methyl-2,6-diazaspiro[3.3]heptan-2-yl)phenyl)-2-oxo-oxazolidin-5-yl)methyl)acetamide

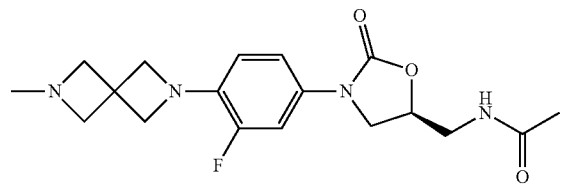 [SMILES: CC(=O)NC[C@H]1CN(c2ccc(N3CC4(CN(C)C4)C3)c(F)c2)C(=O)O1]

¹H-NMR (400 MHz, CDCl₃) δ: 7.36 (d, J=14.4 Hz, 1H), 7.08 (d, J=8.8 Hz, 1H), 6.57 (t, J=9.2 Hz, 1H), 4.75 (m, 1H), 4.10 (t, J=9.2 Hz, 1H), 4.01 (s, 4H), 3.74 (m, 1H), 3.73 (s, 4H), 3.53 (m, 2H), 2.52 (s, 3H), 1.96 (s, 3H). ¹³C NMR (100 MHz, CDCl₃) δ: 172.6, 155.4, 153.2, 150.8, 136.1, 130.3, 114.4, 107.3, 72.0, 64.9, 62.6, 48.0, 43.0, 41.7, 34.8, 21.0. HRMS (ESI): m/z [M+H]⁺ calcd for C₁₈H₂₄FN₄O₃: 363.1827, found: 363.1819.

OTB-704

(R)—N-((3-(3,5-Difluoro-4-(2,6-diazaspiro[3.3]heptan-2-yl)phenyl)-2-oxo-oxazolidin-5-yl)methyl)acetamide ¹H-NMR (400 MHz, CD₃OD) δ: 7.12 (d, J=9.6 Hz, 2H), 4.76, (m, 1H), 4.30 (s, 4H), 4.24 (s, 4H), 4.06 (m, 1H), 3.73 (m, 1H), 3.53 (m, 2H), 1.96 (s, 3H). ¹³C NMR (100 MHz, CD₃OD) δ: 172.6, 155.0, 153.7, 151.3, 129.6, 129.4, 102.7, 102.5, 72.0, 64.3, 55.0, 48.0, 41.6, 38.3, 21.0. HRMS (ESI): m/z [M+H]⁺ calcd for C₁₇H₂₁F₂N₄O₃: 367.1583, found: 367.1576.

OTB-705

(R)—N-((3-(3,5-Difluoro-4-(6-methyl-2,6-diazaspiro[3.3]heptan-2-yl)phenyl)-2-oxo-oxazolidin-5-yl)methyl)acetamide ¹H-NMR (400 MHz, CD₃OD) δ: 7.12 (d, J=10.0 Hz, 2H), 4.75 (m, 1H), 4.22 (s, 4H), 4.05 (m, 1H), 3.78 (s, 4H), 3.73 (m, 1H), 3.53 (m, 2H), 2.55 (s, 3H), 1.96 (s, 3H). ¹³C-NMR (100 MHz, CD₃OD) δ: 172.6, 155.0, 153.7, 151.3, 129.4, 102.8, 72.0, 64.7, 64.6, 48.0, 42.7, 41.7, 22.4, 21.0. HRMS (ESI): m/z [M+H]⁺ calcd for C₁₈H₂₃F₂N₄O₃: 381.1733, found: 381.1725.

Example 12

Synthesis of Additional Embodiments of the Invention

Procedures for Preparation of (6):

Experimental

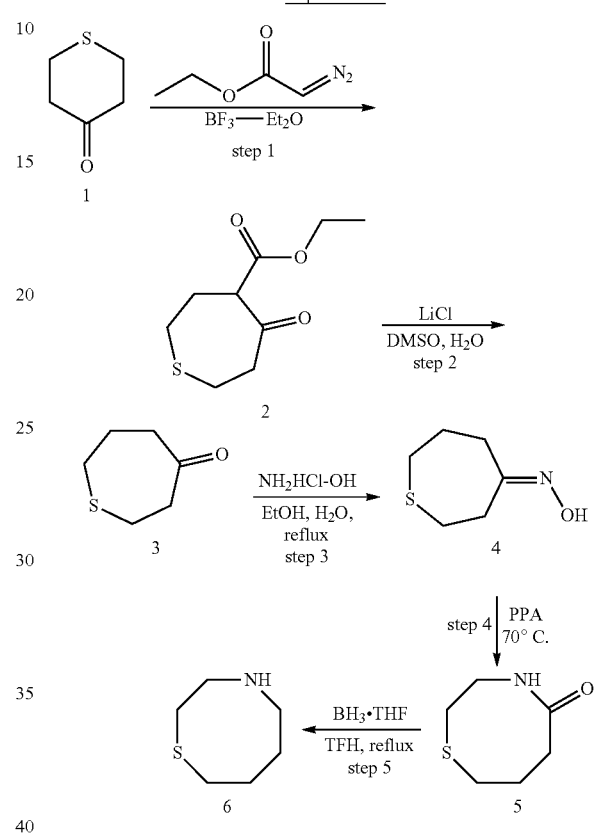

Ethyl 5-oxothiepane-4-carboxylate (2)

To a solution of tetrahydrothiopyran-4-one (100 g, 862 mmol) in Et₂O (150 mL) was added BF₃-Et₂O (120 mL, 948 mmol) at −30° C., then the reaction mixture was stirred at −30° C. for 2 h under a nitrogen gas atmosphere, after that the solution of ethyl 2-diazoacetate (147 g, 1293 mmol) in Et₂O (100 mL) was added to the mixture at −30° C., then the mixture was warmed to room temperature and stirred for overnight. Quenched with K₂CO₃, the solvent was concentrated and dried to give ethyl 5-oxothiepane-4-carboxylate (2) (80 g, 46%) as brown oil.

Thiepan-4-one (3)

A mixture of ethyl 5-oxothiepane-4-carboxylate (2) (80 g, 396 mmol) and lithium chloride (16.6 g, 396 mmol) in DMSO (100 mL) and H₂O (5 drop) was stirred at 180° C. for 2 h. The reaction mixture was cooled to room temperature and poured into ice water, extracted with EA, the organic layer was concentrated under reduced pressure to afford thiepan-4-one (3) (15.9 g crude, 31%) as brown solid.

(Z)-Thiepan-4-one oxime (4)

To a solution of thiepan-4-one (3) (15.9 g, 122 mmol) in EtOH (150 mL) and H₂O (50 mL) was added with NH$_2$OH—HCl (8.47 g, 122 mmol), then the reaction mixture was stirred at 75° C. for 4 h under a nitrogen gas atmosphere, then mixture was concentrated and dried to give (Z)-thiepan-4-one oxime (4) (9.97 g, 56%) as brown solid.

1,5-Thiazocan-4-one (5)

A mixture of (Z)-thiepan-4-one oxime (4) (9.97 g, 68.7 mmol) and polyphosphoric acid (50 g) was stirred at 70° C. for 2 h. The reaction mixture was cooled to room temperature and poured into ice water, adjusted pH=8 using potassium carbonate solution, extracted with EA, the organic layer was concentrated under reduced pressure to afford 1,5-thiazocan-4-one (5) (3 g crude, 30%) as brown solid.

1,5-Thiazocane (6)

To a solution of 1,5-thiazocan-4-one (5) (3 g, 20.7 mmol) in THF (100 mL) was added BH$_3$ (31 mL, 31.1 mmol) in THF at 0° C., followed by refluxing for 12 h. The reaction was quenched with CH$_3$OH (50 mL). The solvent was evaporated to afford 1,5-thiazocane (6) as a white oil (1.7 g, 63%), and the crude material was used for next reaction without further purification.
LC-MS (ESI) m/z=132 [M+H]$^-$.

Step 1: Preparation of 5-(2-fluoro-4-nitrophenyl)-1,5-thiazocane (8)

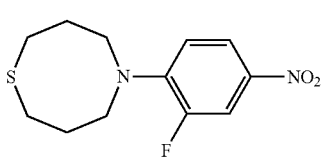

To a solution of 1,5-thiazocane (6) (1 g, 7.6 mmol) and 1,2-difluoro-4-nitrobenzene (1.2 g, 7.6 mmol) in DMF (10 mL) was added K$_2$CO$_3$ (1.05 g, 7.6 mmol) at 25° C. then the reaction mixture was stirred at 80° C. for 2 h under a nitrogen gas atmosphere, monitored by TLC. The mixture was concentrated under reduced pressure, and the crude material was purified by silica gel column chromatography (EA:PE=3:1) to afford 5-(2-fluoro-4-nitrophenyl)-1,5-thiazocane (8) (1.5 g, 74%) as a yellow solid.
LC-MS (ESI) m/z=271 [M+H]$^-$.

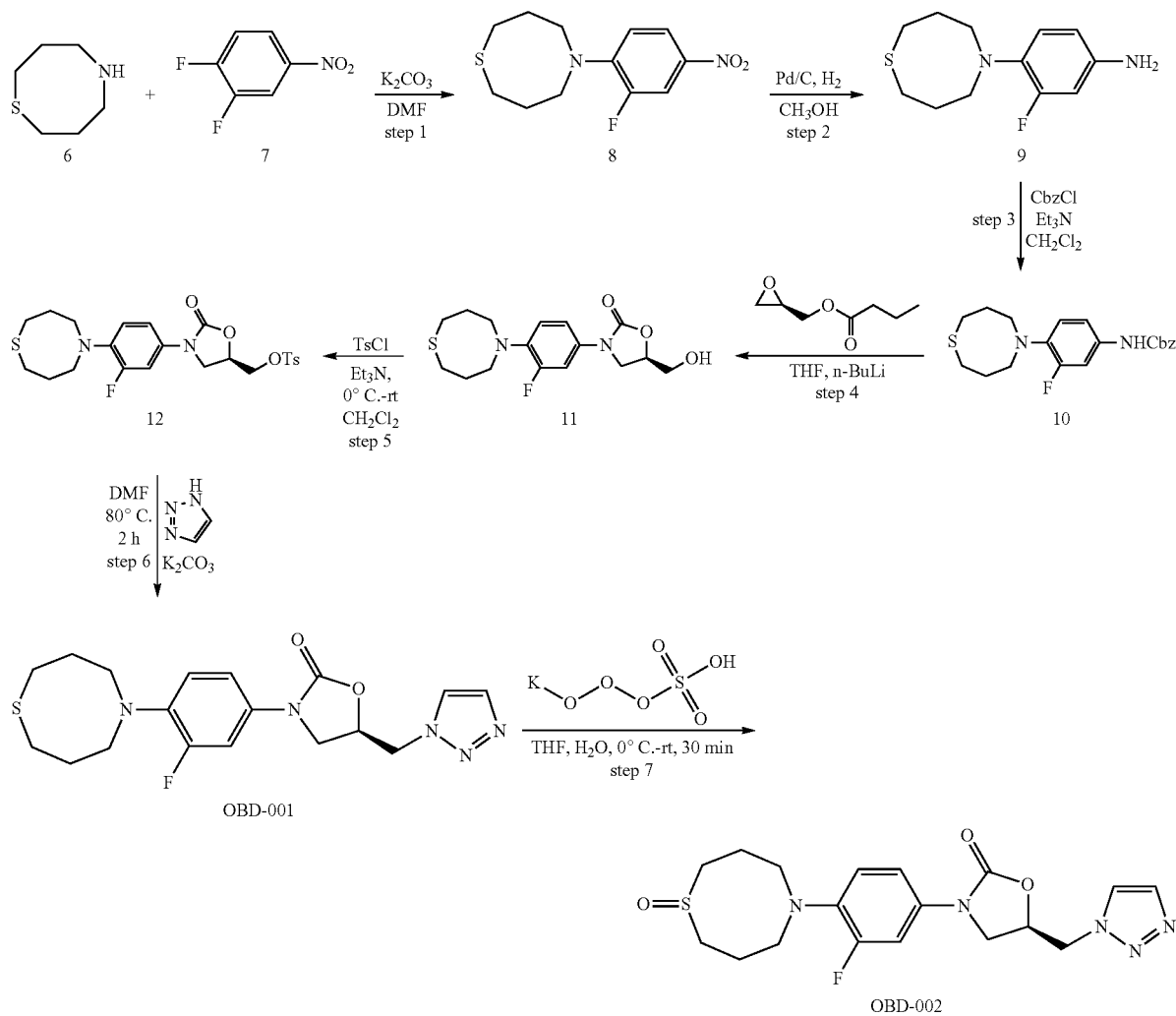

Step 2: 3-Fluoro-4-(1,5-thiazocan-5-yl)benzenamine (9)

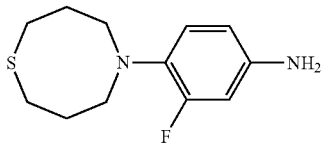

9

To a solution of 5-(2-fluoro-4-nitrophenyl)-1,5-thiazocane (8) (1.5 g, 5.7 mmol) and Palladium carbon (200 mg) in MeOH (15 mL), then under a hydrogen gas atmosphere and the reaction mixture was stirred at room temperature for overnight, monitored by TLC. The filtrate was concentrated under reduced pressure to afford 3-fluoro-4-(1,5-thiazocan-5-yl)benzenamine (9) (1.2 g, 91%) as a white oil, and the crude material was used for next reaction without further purification.
LC-MS (ESI) m/z=241 [M+H]⁻.

Step 3: Benzyl 3-fluoro-4-(1,5-thiazocan-5-yl)phenylcarbamate (10)

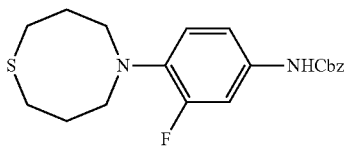

10

Benzyl carbonochloridate (1.76 g, 10.4 mmol) was added to a suspension of 3-fluoro-4-(1,5-thiazocan-5-yl)benzenamine (9) (1.2 g, 5.2 mmol) and triethylamine (1.05 g, 10.4 mmol) in DCM (200 mL) at −20° C. under a nitrogen gas atmosphere, then reaction mixture was stirred at 0° C. for 30 min, monitored by TLC. Quenched with ammonium chloride, extracted with DCM, the organic layer was concentrated under reduced pressure, and the crude material was purified by silica gel column chromatography (EA:PE=10:1) to afford benzyl 3-fluoro-4-(1,5-thiazocan-5-yl)phenylcarbamate (10) (740 mg, 38%) as a white solid.
LC-MS (ESI) m/z=375 [M+H]⁻.

Step 4

(R)-3-(3-Fluoro-4-(1,5-thiazocan-5-yl)phenyl)-5-(hydroxymethyl)oxazolidin-2-one (11)

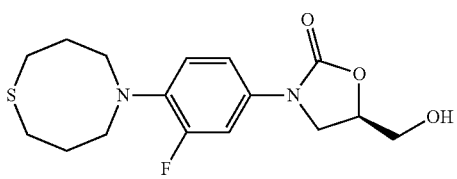

11

To a solution of benzyl 3-fluoro-4-(1,5-thiazocan-5-yl)phenylcarbamate (10) (740 mg, 1.97 mmol) in THF (10 mL) at −78° C. under a nitrogen gas atmosphere was added n-BuLi (1.3 ml, 2.96 mmol), then the mixture was stirred at −78° C. for 30 min, after that the solution of (R)-oxiran-2-ylmethyl butyrate (427 mg, 2.96 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford (R)-3-(3-fluoro-4-(1,5-thiazocan-5-yl)phenyl)-5-(hydroxymethyl)oxazolidin-2-one (11) (382 mg, 57%) as a white solid.
LC-MS (ESI) m/z=341 [M+H]⁻.

Step 5: (R)-(3-(3-fluoro-4-(1,5-thiazocan-5-yl)phenyl)-2-oxooxazolidin-5-yl)methyl 4-methylbenzenesulfonate (12)

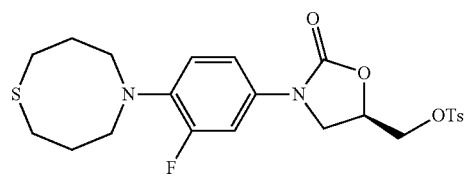

12

4-methylbenzene-1-sulfonyl chloride (418 mg, 2.2 mmol) was added to a suspension of (R)-3-(3-fluoro-4-(1,5-thiazocan-5-yl)phenyl)-5-(hydroxymethyl)oxazolidin-2-one (11) (382 mg, 1.1 mmol) and Et₃N (222 mg, 2.2 mmol) in DCM (10 mL) at 0° C. under a nitrogen gas atmosphere and the reaction mixture was stirred at room temperature for overnight, monitored by TLC. Quenched with ammonium chloride, extracted with DCM, the organic layer was concentrated under reduced pressure, and the crude material was purified by silica gel column chromatography (DCM:MeOH=50:1) to afford (R)-(3-(3-fluoro-4-(1,5-thiazocan-5-yl)phenyl)-2-oxooxazolidin-5-yl)methyl 4-methylbenzenesulfonate (12) (407 mg, 75%) as a white solid.
LC-MS (ESI) m/z=495 [M+H]⁻.

Step 6

(R)-5-((1H-1,2,3-triazol-1-yl)methyl)-3-(3-fluoro-4-(1,5-thiazocan-5-yl)phenyl)oxazolidin-2-one (OBD-001)

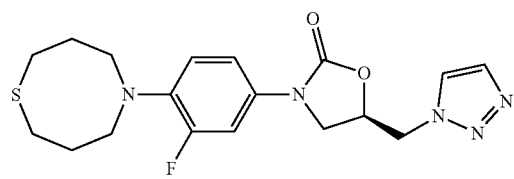

OBD-001

To a solution of (R)-(3-(3-fluoro-4-(1,5-thiazocan-5-yl)phenyl)-2-oxooxazolidin-5-yl)methyl 4-methylbenzenesulfonate (12) (200 mg, 0.4 mmol) and 1H-1,2,3-triazole (56 mg, 0.8 mmol) in DMF (5 mL) was added K₂CO₃ (110 mg, 0.8 mmol) at 25° C., then the reaction mixture was stirred at 80° C. for 2 h under a nitrogen gas atmosphere, monitored by TLC. Quenched with ammonium chloride, extracted with EA, the organic layer was concentrated under reduced pressure, and the crude material was purified by silica gel column chromatography (EA:PE=2:1) to afford (R)-5-((1H-1,2,3-triazol-1-yl)methyl)-3-(3-fluoro-4-(1,5-thiazocan-5-yl)phenyl)oxazolidin-2-one (OBD-001) (70 mg, 45%) as a white solid.

¹H NMR (301 MHz, CDCl₃) δ 7.76 (d, J=17.6 Hz, 2H), 7.41-7.09 (m, 1H), 7.11-6.73 (m, 2H), 5.04 (d, J=3.0 Hz, 1H), 4.78 (d, J=3.4 Hz, 2H), 4.12 (t, J=9.2 Hz, 1H), 3.88 (dd, J=9.2, 6.1 Hz, 1H), 3.36 (t, J=6.0 Hz, 3H), 2.92-2.59 (m, 4H), 2.01 (dd, J=27.9, 7.3 Hz, 4H).

LC-MS (ESI) m/z=391.9 [M+H]⁺.

Step 7: Preparation of (OBD-002)

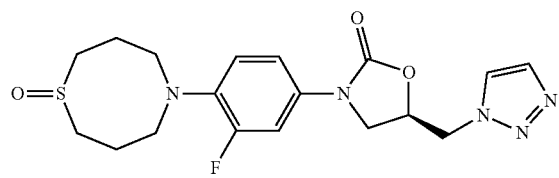

OBD-002

To a solution of (R)-5((1H-1,2,3-triazol-1-yl)methyl)-3-(3-fluoro-4-(1,5-thiazocan-5-yl)phenyl)oxazolidin-2-one (OBD-001) (50 mg, 0.13 mmol) in THF (10 mL) and 10 drops water was added potassium peroxomonosulfate (80 mg, 0.13 mmol) at 0° C., then the reaction mixture was stirred at 0° C. for 2 h, monitored by TLC. Quenched with sodium thiosulfate, and the crude material was purified by silica gel column chromatography (DCM:MeOH=80:1) to afford (OBD-002) (22 mg, 41%) as a white solid.

¹H NMR (301 MHz, CDCl₃) δ 7.92-7.67 (m, 2H), 7.32 (d, J=16.8 Hz, 1H), 7.12 (t, J=9.0 Hz, 1H), 6.96 (d, J=8.1 Hz, 1H), 5.07 (s, 1H), 4.81 (d, J=4.0 Hz, 2H), 4.15 (t, J=9.0 Hz, 1H), 4.01-3.83 (m, 1H), 3.32 (d, J=14.2 Hz, 5H), 3.11-2.87 (m, 2H), 2.59 (s, 2H), 2.19 (s, 4H).

LC-MS (ESI) m/z=407.8 [M+H]⁺.

Step 1

(R)-5-((1H-1,2,4-triazol-1-yl)methyl)-3-(3-fluoro-4-(1,5-thiazocan-5-yl)phenyl)oxazolidin-2-one (OBD-008)

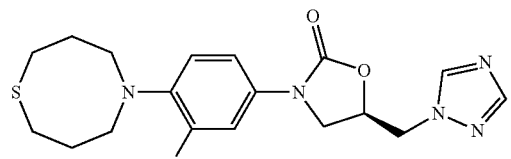

OBD-008

To a solution of (R)-(3-(3-fluoro-4-(1,5-thiazocan-5-yl)phenyl)-2-oxooxazolidin-5-yl)methyl 4-methylbenzenesulfonate (12) (200 mg, 0.4 mmol) and 1H-1,2,4-triazole (56 mg, 0.8 mmol) in DMF (5 mL) was added K₂CO₃ (110 mg, 0.8 mmol) at 25° C., then the reaction mixture was stirred at 80° C. for 2 h under a nitrogen gas atmosphere, monitored by TLC. Quenched with ammonium chloride, extracted with EA, the organic layer was concentrated under reduced pressure, and the crude material was purified by silica gel column chromatography (EA:PE=2:1) to afford (R)-5-((1H-1,2,4-triazol-1-yl)methyl)-3-(3-fluoro-4-(1,5-thiazocan-5-yl)phenyl)oxazolidin-2-one (OBD-008) (84 mg, 54%) as a white solid.

¹H NMR (301 MHz, CDCl₃) δ 8.24 (s, 1H), 7.97 (s, 1H), 7.00 (s, 2H), 5.12-4.91 (m, 1H), 4.56 (d, J=4.7 Hz, 2H), 4.24-3.83 (m, 2H), 3.38 (t, J=6.0 Hz, 4H), 2.95-2.59 (m, 4H), 1.98 (s, 5H).

LC-MS (ESI) m/z=391.9 [M+H]⁺.

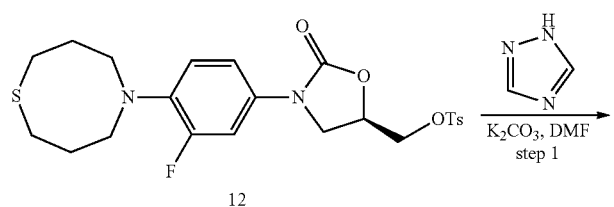

12

OBD-008

OBD-009

Step 2: Preparation of (OBD-009)

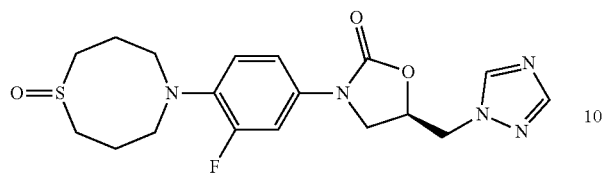

OBD-009

To a solution of (R)-5-((1H-1,2,3-triazol-1-yl)methyl)-3-(3-fluoro-4-(1,5-thiazocan-5-yl)phenyl)oxazolidin-2-one (OBD-008) (50 mg, 0.13 mmol) in THF (10 mL) and 10 drops water was added potassium peroxomonosulfate (80 mg, 0.13 mmol) at 0° C., then the reaction mixture was stirred at 0° C. for 2 h, monitored by TLC. Quenched with sodium thiosulfate, and the crude material was purified by silica gel column chromatography (DCM:MeOH=80:1) to afford (OBD-009) (22 mg, 41%) as a white solid.

$^1$H NMR (301 MHz, CDCl$_3$) δ 8.24 (s, 1H), 7.93 (s, 1H), 7.41-7.20 (m, 1H), 7.19-6.92 (m, 2H), 5.10-4.92 (m, 1H), 4.56 (d, J=4.7 Hz, 2H), 4.12 (t, J=9.0 Hz, 1H), 3.97 (dd, J=9.2, 6.2 Hz, 1H), 3.28 (dd, J=13.0, 6.9 Hz, 2H), 3.12 (dd, J=12.5, 5.9 Hz, 4H), 3.02-2.83 (m, 2H), 2.22-1.99 (m, 5H), 1.26 (d, J=9.4 Hz, 4H).

LC-MS (ESI) m/z=407.8 [M+H]$^+$.

Step 1

(R)-5-(azidomethyl)-3-(3-fluoro-4-(1,5-thiazocan-5-yl)phenyl)oxazolidin-2-one (13)

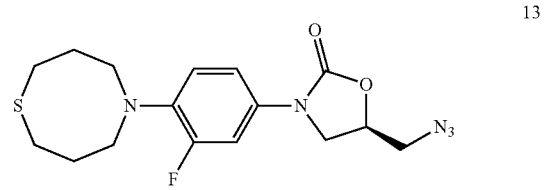 [SMILES: [N-]=[N+]=NC[C@H]1CN(c2ccc(N3CCCSCCC3)c(F)c2)C(=O)O1]

13

To a solution of (R)-(3-(3-fluoro-4-(1,5-thiazocan-5-yl)phenyl)-2-oxooxazolidin-5-yl)methyl 4-methylbenzenesulfonate (12) (800 mg, 1.62 mmol) and sodium azide (105 mg, 1.62 mmol) in DMF (10 mL) was added K$_2$CO$_3$ (447 g, 3.24 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by silica gel column chromatography (PE:EA=2:1) to afford (R)-5-(azidomethyl)-3-(3-fluoro-4-(1,5-thiazocan-5-yl)phenyl)oxazolidin-2-one (13) (470 mg, 80%) as a white solid.

LC-MS (ESI) m/z=366 [M+H]$^-$.

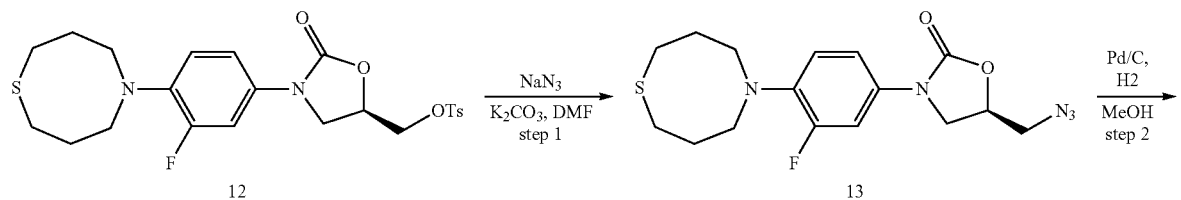

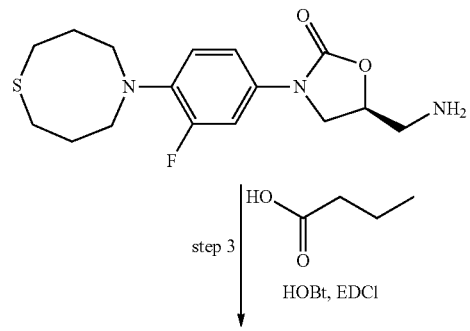

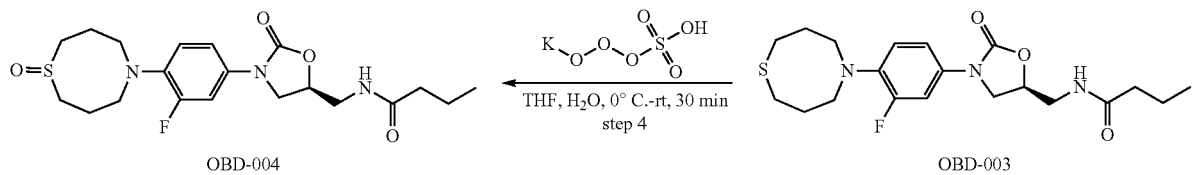

Step 2

(S)-5-(aminomethyl)-3-(3-fluoro-4-(1,5-thiazocan-5-yl)phenyl)oxazolidin-2-one (14)

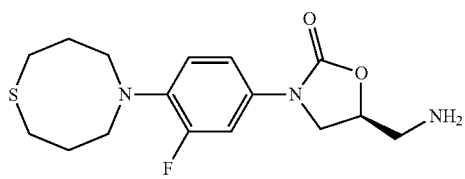

To a solution of (R)-5-(azidomethyl)-3-(3-fluoro-4-(1,5-thiazocan-5-yl)phenyl)oxazolidin-2-one (13) (470 mg, 1.3 mmol) in MeOH (10 mL) was added palladium carbon (100 mg) at 25° C., then the reaction mixture was stirred at room temperature for overnight under a hydrogen gas atmosphere, monitored by TLC. The filtrate was concentrated under reduced pressure, and the crude material was purified by silica gel column chromatography (DCM:MeOH=50:1) to afford (S)-5-(aminomethyl)-3-(3-fluoro-4-(1,5-thiazocan-5-yl)phenyl)oxazolidin-2-one (14) (374 mg, 85%) as a white solid.

LC-MS (ESI) m/z=340 [M+H]$^+$.

Step 3

(S)—N-((3-(3-fluoro-4-(1,4-thiazepan-4-yl)phenyl)-2-oxooxazolidin-5-yl)methyl)butyramide (OBD-005)

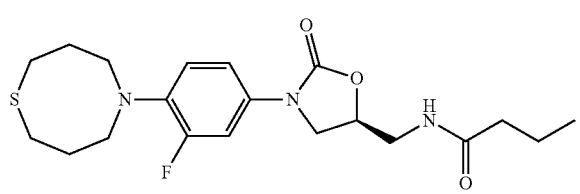

To a solution of (S)-5-(aminomethyl)-3-(3-fluoro-4-(1,5-thiazocan-5-yl)phenyl)oxazolidin-2-one (14) (374 mg, 1.1 mmol) and butyric acid (97 mg, 1.1 mmol) in DCM (10 mL) were added HOBt (223 mg, 1.65 mmol), EDCI (420 mg, 2.2 mmol) and DIPEA (284 mg, 2.2 mmol) at 25° C., then the reaction mixture was stirred at 25° C. for 2 h under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=80:1) to afford (S)—N-((3-(3-fluoro-4-(1,5-thiazocan-5-yl)phenyl)-2-oxooxazolidin-5-yl)methyl)butyramide (OBD-003) (252 mg, 56%) as a white solid.

$^1$H NMR (300 MHz, CDCl$_3$) δ 7.50 (s, 2H), 7.03 (d, J=6.1 Hz, 1H), 5.99 (s, 1H), 4.77 (d, J=5.7 Hz, 1H), 4.02 (t, J=9.0 Hz, 2H), 3.70 (ddd, J=20.7, 15.2, 7.7 Hz, 4H), 3.48 (s, 4H), 2.95-2.68 (m, 4H), 2.20 (t, J=7.2 Hz, 3H), 2.06 (d, J=6.1 Hz, 4H), 1.64 (dd, J=14.8, 7.4 Hz, 4H), 0.91 (t, J=7.4 Hz, 4H).

LC-MS (ESI) m/z=409.9 [M+H]$^+$.

Step 4: Preparation of (OBD-004)

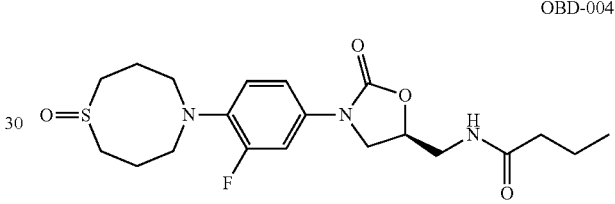

To a solution of (S)—N-((3-(3-fluoro-4-(1,5-thiazocan-5-yl)phenyl)-2-oxooxazolidin-5-yl)methyl)butyramide (OBD-003) (150 mg, 0.37 mmol) in THF (10 mL) and 10 drops water was added potassium peroxomonosulfate (225 mg, 0.37 mmol) at 0° C., then the reaction mixture was stirred at 0° C. for 2 h, monitored by TLC. Quenched with sodium thiosulfate, and the crude material was purified by prep-HPLC to afford (OBD-004) (48 mg, 31%) as a white solid.

$^1$H NMR (301 MHz, CDCl$_3$) δ 7.44 (dd, J=14.7, 2.4 Hz, 1H), 7.19-6.99 (m, 2H), 6.44 (s, 1H), 4.84-4.71 (m, 1H), 4.02 (t, J=8.9 Hz, 1H), 3.78 (dd, J=9.0, 6.6 Hz, 1H), 3.66 (t, J=4.6 Hz, 2H), 3.38-3.09 (m, 6H), 2.99 (dd, J=12.6, 6.3 Hz, 2H), 2.20 (dd, J=9.4, 5.3 Hz, 6H), 1.71-1.56 (m, 2H), 0.91 (dd, J=9.6, 5.1 Hz, 3H).

LC-MS (ESI) m/z=425.8 [M+H]$^+$.

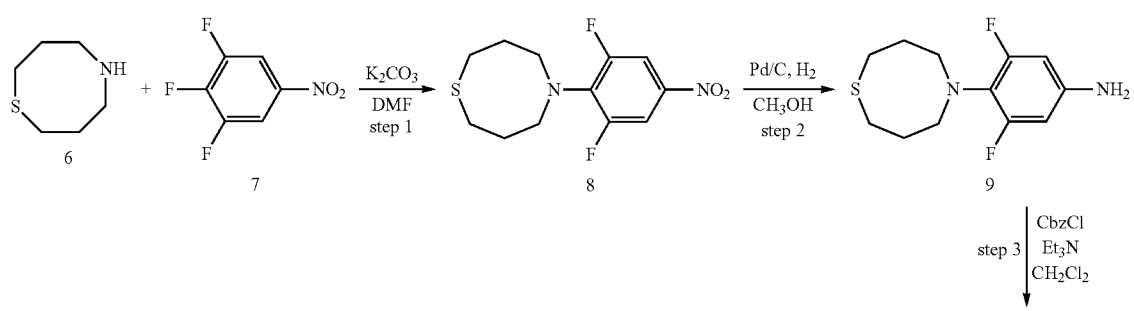

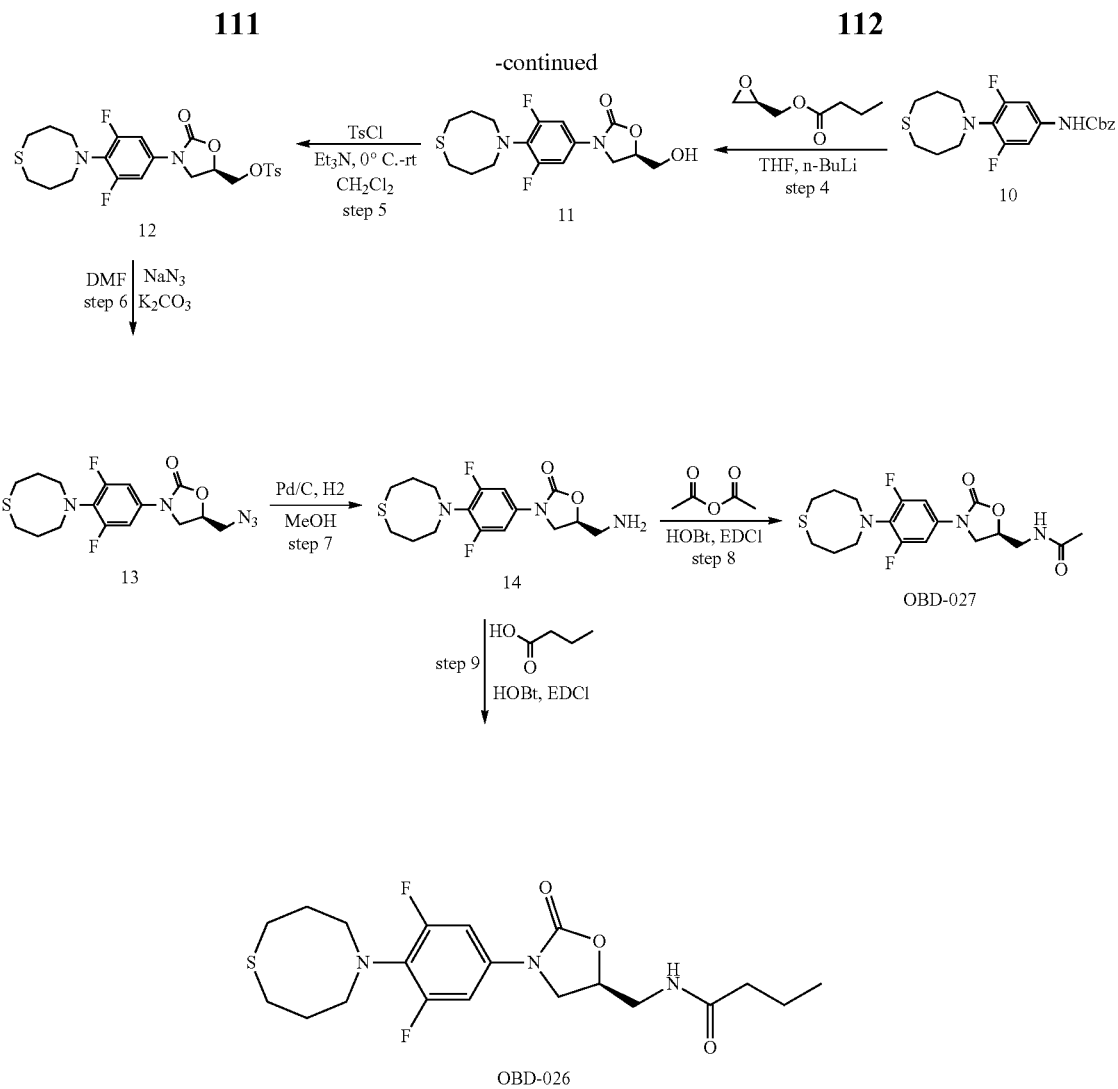

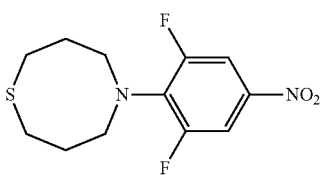

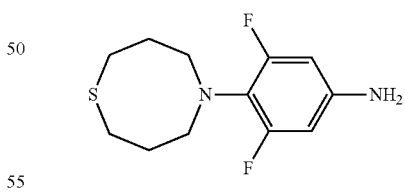

Step 1: Preparation of
5-(2,6-difluoro-4-nitrophenyl)-1,5-thiazocane (8)

Step 2:
3,5-Difluoro-4-(1,5-thiazocan-5-yl)benzenamine (9)

To a solution of 1,5-thiazocane (6) (1 g, 7.6 mmol) and 1,2,3-trifluoro-5-nitrobenzene (1.35 g, 7.6 mmol) in DMF (10 mL) was added K₂CO₃ (2.1 g, 15.2 mmol) at 25° C. then the reaction mixture was stirred at 80° C. for 2 h under a nitrogen gas atmosphere, monitored by TLC. The mixture was concentrated under reduced pressure, and the crude material was purified by silica gel column chromatography (EA:PE=3:1) to afford 5-(2,6-difluoro-4-nitrophenyl)-1,5-thiazocane (8) (1.64 g, 75%) as a yellow solid.

LC-MS (ESI) m/z=289 [M+H]⁻.

To a solution of 5-(2,6-difluoro-4-nitrophenyl)-1,5-thiazocane (8) (1.64 g, 5.7 mmol) and Palladium carbon (200 mg) in MeOH (15 mL), then under a hydrogen gas atmosphere and the reaction mixture was stirred at room temperature for overnight, monitored by TLC. The filtrate was concentrated under reduced pressure to afford 3,5-difluoro-4-(1,5-thiazocan-5-yl)benzenamine (9) (1.4 g, 94%) as a white oil, and the crude material was used for next reaction without further purification.

LC-MS (ESI) m/z=259 [M+H]⁻.

Step 3: Benzyl 3,5-difluoro-4-(1,5-thiazocan-5-yl)phenylcarbamate (10)

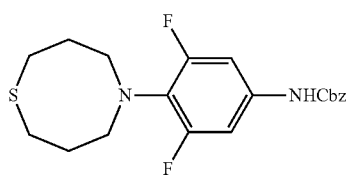

Benzyl carbonochloridate (1.87 g, 10.6 mmol) was added to a suspension of 3,5-difluoro-4-(1,5-thiazocan-5-yl)benzenamine (9) (1.4 g, 5.3 mmol) and triethylamine (1.07 g, 10.6 mmol) in DCM (200 mL) at −20° C. under a nitrogen gas atmosphere, then reaction mixture was stirred at 0° C. for 30 min, monitored by TLC. Quenched with ammonium chloride, extracted with DCM, the organic layer was concentrated under reduced pressure, and the crude material was purified by silica gel column chromatography (EA:PE=10:1) to afford benzyl 3,5-difluoro-4-(1,5-thiazocan-5-yl)phenylcarbamate (10) (872 mg, 42%) as a white solid.

LC-MS (ESI) m/z=393 [M+H]⁻.

Step 4

(R)-3-(3,5-difluoro-4-(1,5-thiazocan-5-yl)phenyl)-5-(hydroxymethyl)oxazolidin-2-one (11)

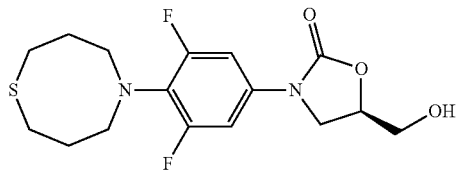

To a solution of benzyl 3,5-difluoro-4-(1,5-thiazocan-5-yl)phenylcarbamate (10) (872 mg, 2.23 mmol) in THF (10 mL) at −78° C. under a nitrogen gas atmosphere was added n-BuLi (1.4 ml, 3.34 mmol), then the mixture was stirred at −78° C. for 30 min, after that the solution of (R)-oxiran-2-ylmethyl butyrate (480 mg, 3.34 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford (R)-3-(3,5-difluoro-4-(1,5-thiazocan-5-yl)phenyl)-5-(hydroxymethyl)oxazolidin-2-one (11) (519 mg, 65%) as a white solid.

LC-MS (ESI) m/z=359 [M+H]⁻.

Step 5

(R)-(3-(3,5-difluoro-4-(1,5-thiazocan-5-yl)phenyl)-2-oxooxazolidin-5-yl)methyl 4-methylbenzenesulfonate (12)

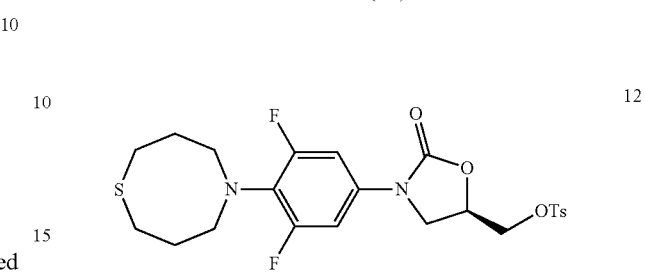

4-methylbenzene-1-sulfonyl chloride (550 mg, 2.9 mmol) was added to a suspension of (R)-3-(3,5-difluoro-4-(1,5-thiazocan-5-yl)phenyl)-5-(hydroxymethyl)oxazolidin-2-one (11) (519 mg, 1.45 mmol) and Et₃N (292 mg, 2.9 mmol) in DCM (10 mL) at 0° C. under a nitrogen gas atmosphere and the reaction mixture was stirred at room temperature for overnight, monitored by TLC. Quenched with ammonium chloride, extracted with DCM, the organic layer was concentrated under reduced pressure, and the crude material was purified by silica gel column chromatography (DCM:MeOH=50:1) to afford (R)-(3-(3,5-difluoro-4-(1,5-thiazocan-5-yl)phenyl)-2-oxooxazolidin-5-yl)methyl 4-methylbenzenesulfonate (12) (594 mg, 80%) as a white solid.

LC-MS (ESI) m/z=513 [M+H]⁻.

Step 6

(R)-5-(azidomethyl)-3-(3,5-difluoro-4-(1,5-thiazocan-5-yl)phenyl)oxazolidin-2-one (13)

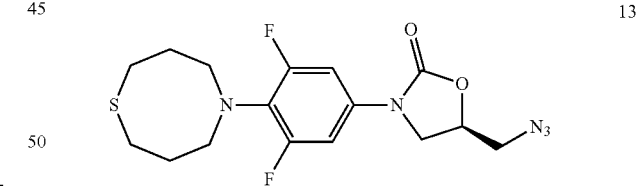

To a solution of (R)-(3-(3,5-difluoro-4-(1,5-thiazocan-5-yl)phenyl)-2-oxooxazolidin-5-yl)methyl 4-methylbenzenesulfonate (12) (594 g, 1.2 mmol) and sodium azide (75 mg, 1.2 mmol) in DMF (10 mL) was added K₂CO₃ (160 mg, 2.4 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by silica gel column chromatography (PE:EA=2:1) to afford (R)-5-(azidomethyl)-3-(3,5-difluoro-4-(1,5-thiazocan-5-yl)phenyl)oxazolidin-2-one (13) (400 mg, 87%) as a white solid.

LC-MS (ESI) m/z=384 [M+H]⁻.

Step 7

(S)-5-(aminomethyl)-3-(3,5-difluoro-4-(1,5-thiazo-can-5-yl)phenyl)oxazolidin-2-one (14)

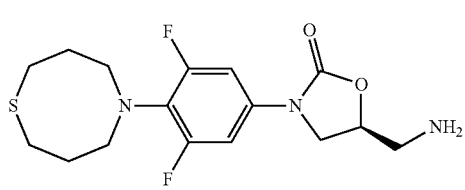

To a solution of (R)-5-(azidomethyl)-3-(3,5-difluoro-4-(1,5-thiazocan-5-yl)phenyl)oxazolidin-2-one (13) (400 g, 1.04 mmol) in MeOH (10 mL) was added palladium carbon (100 mg) at 25° C., then the reaction mixture was stirred at room temperature for overnight under a hydrogen gas atmosphere, monitored by TLC. The filtrate was concentrated under reduced pressure, and the crude material was purified by silica gel column chromatography (DCM:MeOH=50:1) to afford (S)-5-(aminomethyl)-3-(3,5-difluoro-4-(1,5-thiazocan-5-yl)phenyl)oxazolidin-2-one (14) (331 g, 89%) as a white solid.

LC-MS (ESI) m/z=358 [M+H]$^+$.

Step 8

(S)—N-((3-(3,5-difluoro-4-(1,5-thiazocan-5-yl)phenyl)-2-oxooxazolidin-5-yl)methyl)butyramide (OBD-026)

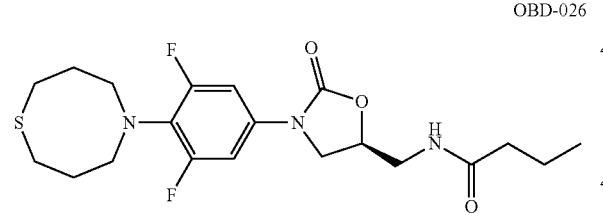

To a solution of (S)-5-(aminomethyl)-3-(3,5-difluoro-4-(1,5-thiazocan-5-yl)phenyl)oxazolidin-2-one (14) (165 mg, 0.46 mmol) and butyric acid (52 mg, 0.46 mmol) in DCM (10 mL) were added HOBt (95 mg, 0.7 mmol), EDCI (175 mg, 0.92 mmol) and DIPEA (118 mg, 0.92 mmol) at 25° C., then the reaction mixture was stirred at 25° C. for 2 h under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=80:1) to afford (S)—N-((3-(3,5-difluoro-4-(1,5-thiazocan-5-yl)phenyl)-2-oxooxazolidin-5-yl)methyl)butyramide (OBD-026) (82 mg, 42%) as a white solid.

$^1$H NMR (400 MHz, CDCl$_3$) δ 8.02 (s, 1H), 7.14 (d, J=11.1 Hz, 1H), 5.93 (s, 1H), 4.81 (s, 1H), 4.02 (t, J=8.9 Hz, 1H), 3.70 (s, 2H), 3.31 (s, 3H), 2.87 (s, 2H), 2.22 (s, 2H), 1.90 (s, 5H), 1.66 (d, J=7.3 Hz, 2H), 0.93 (t, J=7.4 Hz, 2H).
LC-MS (ESI) m/z=428 [M+H]$^+$.

Step 9

N—(((S)-3-(4-(3-thia-8-aza-bicyclo[3.2.1]octan-8-yl)-3,5-difluorophenyl)-2-oxooxazolidin-5-yl)methyl)butyramide (OBD-027)

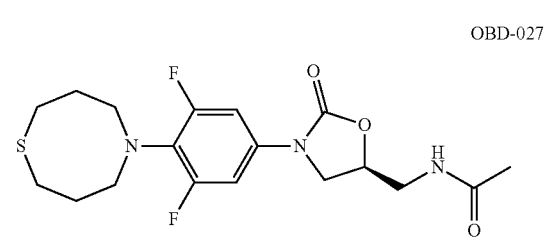 [SMILES: CC(=O)NC[C@H]1CN(c2cc(F)c(N3CCCSCCC3)c(F)c2)C(=O)O1]

To a solution of (S)-5-(aminomethyl)-3-(3,5-difluoro-4-(1,5-thiazocan-5-yl)phenyl)oxazolidin-2-one (14) (165 mg, 0.46 mmol) and butyric acid (52 mg, 0.46 mmol) in DCM (10 mL) were added HOBt (95 mg, 0.7 mmol), EDCI (175 mg, 0.92 mmol) and DIPEA (118 mg, 0.92 mmol) at 25° C., then the reaction mixture was stirred at 25° C. for 2 h under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=80:1) to afford N—(((S)-3-(4-(3-thia-8-aza-bicyclo[3.2.1]octan-8-yl)-3,5-difluorophenyl)-2-oxooxazolidin-5-yl)methyl)butyramide (OBD-027) (82 mg, 45%) as a white solid.

$^1$HNMR (301 MHz, CDCl$_3$) δ 7.23-6.85 (m, 2H), 6.00 (s, 1H), 4.90-4.66 (m, 1H), 4.17-3.86 (m, 1H), 3.71 (s, 2H), 3.28 (s, 2H), 2.84 (s, 3H), 2.04 (s, 3H), 1.88 (s, 5H).
LC-MS (ESI) m/z=400 [M+H]$^+$.

The synthesis route:

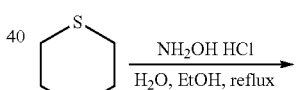

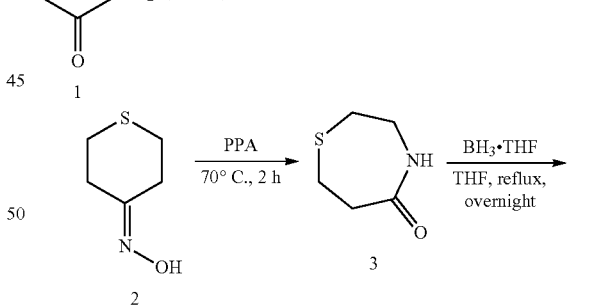

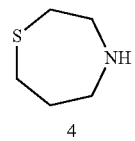

Experimental

Tetrahydrothiopyran-4-one oxime (2)

To a solution of tetrahydrothiopyran-4-one (20 g, 172 mmol) in EtOH (150 mL) and H$_2$O (50 mL) was added with NH$_2$OH—HCl (11.9 g, 172 mmol), then the reaction mixture was stirred at 75° C. for 4 h under a nitrogen gas atmosphere, then mixture was concentrated and dried to give tetrahydrothiopyran-4-one oxime (2) (14.7 g, 66%) as brown solid.

1,4-Thiazepan-5-one (3)

A mixture of tetrahydrothiopyran-4-one oxime (2) (14.7 g, 112 mmol) and polyphosphoric acid (50 g) was stirred at 70° C. for 2 h. The reaction mixture was cooled to room temperature and poured into ice water, adjusted pH=8 using potassium carbonate solution, extracted with EA, the organic layer was concentrated under reduced pressure to afford 1,4-thiazepan-5-one (3) (11.9 g crude, 81%) as brown solid. 1,4-Thiazepane (4).

To a solution of 1,4-thiazepan-5-one (3) (11.9 g, 105 mmol) in THF (100 mL) was added BH$_3$ (158 mL, 158 mol) in THF at 0° C., followed by refluxing for 12 h. The reaction was quenched with CH$_3$OH (50 mL). The solvent was evaporated to afford 1,4-thiazepane (4) as a white oil (10.7 g, 87%), and the crude material was used for next reaction without further purification.

LC-MS (ESI) m/z=118 [M+H]$^+$.

Step 1: Preparation of 4-(2-fluoro-4-nitrophenyl)-1,4-thiazepane (6)

To a solution of 1,4-thiazepane (4) (7 g, 59.8 mmol) and 1,2-difluoro-4-nitrobenzene (10.4 g, 65.8 mmol) in DMF (10 mL) was added K$_2$CO$_3$ (16.5 g, 119.6 mmol) at 25° C. and then reaction mixture was stirred at 80° C. for 2 h under a nitrogen gas atmosphere, monitored by TLC. The mixture was concentrated under reduced pressure, and the crude material was purified by silica gel column chromatography (EA:PE=3:1) to afford 4-(2-fluoro-4-nitrophenyl)-1,4-thiazepane (6) (10 g, 65%) as a yellow solid.

LC-MS (ESI) m/z=257 [M+H]$^-$.

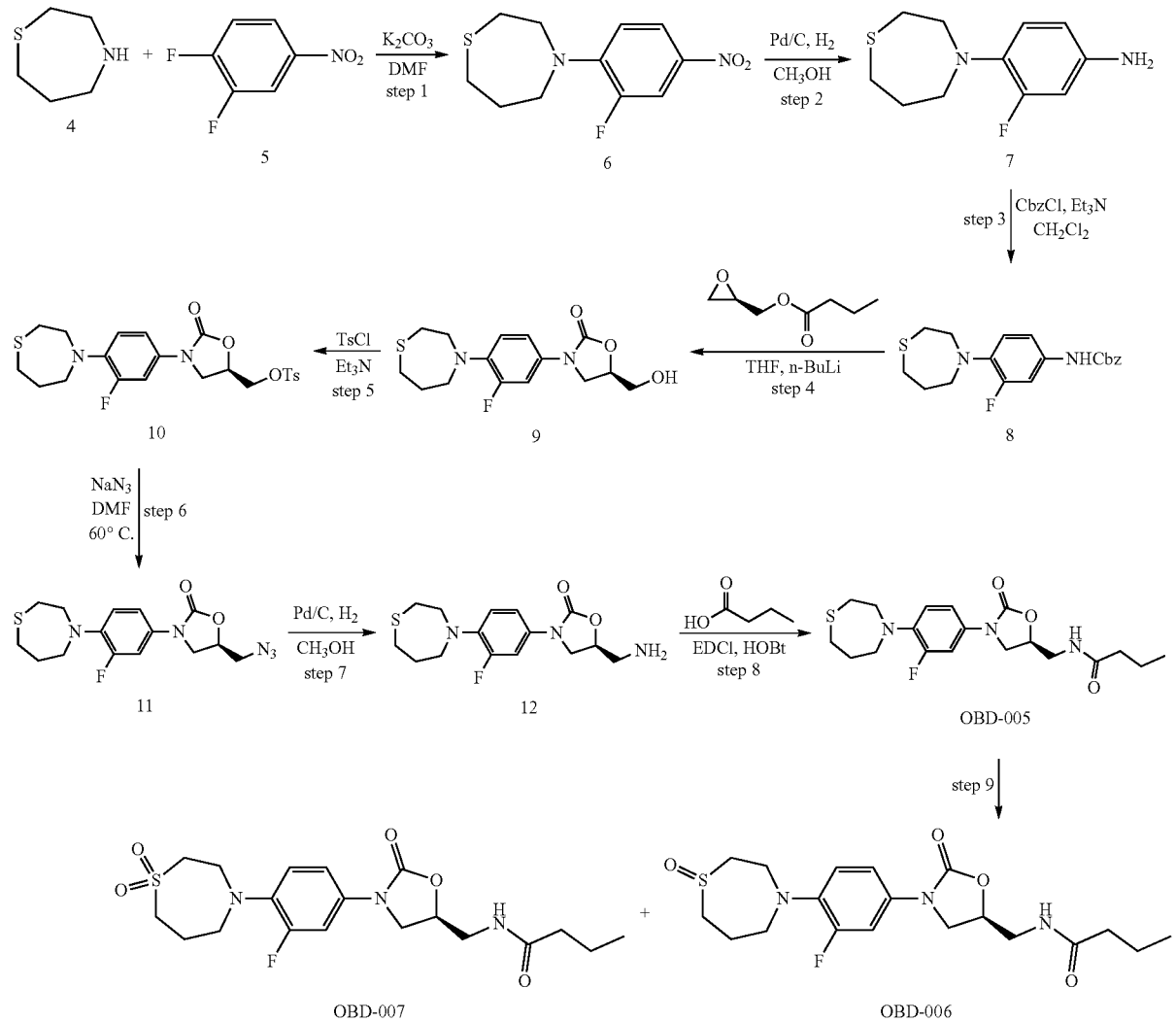

Step 2: 3-Fluoro-4-(1,4-thiazepan-4-yl)benzenamine (7)

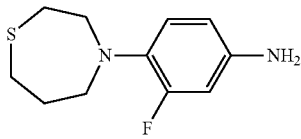

7

To a solution of 4-(2-fluoro-4-nitrophenyl)-1,4-thiazepane (6) (8 g, 31.2 mmol) and Palladium carbon (500 mg) in MeOH (15 mL), then the reaction mixture was stirred at room temperature for overnight under a hydrogen gas atmosphere, monitored by TLC. The filtrate was concentrated under reduced pressure to afford 3-fluoro-4-(1,4-thiazepan-4-yl)benzenamine (7) (6.4 g, 93%) as a white oil, and the crude material was used for next reaction without further purification.

LC-MS (ESI) m/z=227 [M+H]⁻.

Step 3: Benzyl 3-fluoro-4-(1,4-thiazepan-4-yl)phenylcarbamate (8)

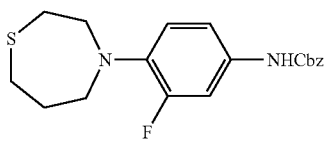

8

Benzyl carbonochloridate (9.6 g, 56.6 mmol) was added to a suspension of 3-fluoro-4-(1,4-thiazepan-4-yl)benzenamine (7) (6.4 g, 28.3 mmol) and triethylamine (5.7 g, 56.6 mmol) in DCM (200 mL) at −20° C. under a nitrogen gas atmosphere, then reaction mixture was stirred at 0° C. for 30 min, monitored by TLC. Quenched with ammonium chloride, extracted with DCM, the organic layer was concentrated under reduced pressure, and the crude material was purified by silica gel column chromatography (EA:PE=10:1) to afford benzyl 3-fluoro-4-(1,4-thiazepan-4-yl)phenylcarbamate (8) (2.34 g, 23%) as a white oil.

LC-MS (ESI) m/z=361 [M+H]⁻.

Step 4

(R)-3-(3-Fluoro-4-(1,4-thiazepan-4-yl)phenyl)-5-(hydroxymethyl)oxazolidin-2-one (9)

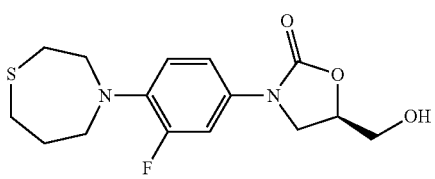

9

To a solution of benzyl 3-fluoro-4-(1,4-thiazepan-4-yl)phenylcarbamate (8) (2.34 g, 6.5 mmol) in THF (10 mL) at −78° C. under a nitrogen gas atmosphere was added n-BuLi (4 ml, 9.7 mmol), then the mixture was stirred at −78° C. for 30 min, after that the solution of (R)-oxiran-2-ylmethyl butyrate (1.4 g, 9.7 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford (R)-3-(3-fluoro-4-(1,4-thiazepan-4-yl)phenyl)-5-(hydroxymethyl)oxazolidin-2-one (9) (1.16 g, 55%) as a white solid.

LC-MS (ESI) m/z=327 [M+H]⁻.

Step 5: (R)-(3-(3-Fluoro-4-(1,4-thiazepan-4-yl)phenyl)-2-oxooxazolidin-5-yl)methyl 4-methylbenzenesulfonate (10)

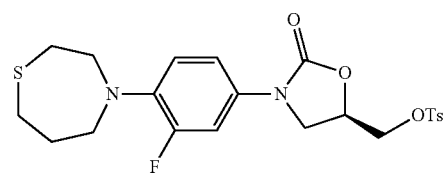

10

4-Methylbenzene-1-sulfonyl chloride (1.4 g, 7.2 mmol) was added to a suspension of (R)-3-(3-fluoro-4-(1,4-thiazepan-4-yl)phenyl)-5-(hydroxymethyl)oxazolidin-2-one (9) (1.16 g, 3.6 mmol) and Et₃N (727 mg, 7.2 mmol) in DCM (10 mL) at 0° C. under a nitrogen gas atmosphere and the reaction mixture was stirred at room temperature for overnight, monitored by TLC. Quenched with ammonium chloride, extracted with DCM, the organic layer was concentrated under reduced pressure, and the crude material was purified by silica gel column chromatography (DCM:MeOH=50:1) to afford (R)-(3-(3-fluoro-4-(1,4-thiazepan-4-yl)phenyl)-2-oxooxazolidin-5-yl)methyl 4-methylbenzenesulfonate (10) (1.41 g, 41%) as a white solid.

LC-MS (ESI) m/z=481 [M+H]⁻.

Step 1

(R)-5-(azidomethyl)-3-(3-fluoro-4-(1,4-thiazepan-4-yl)phenyl)oxazolidin-2-one (11)

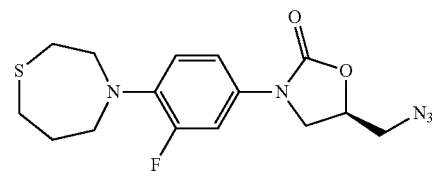

11

To a solution of (R)-(3-(3-fluoro-4-(1,4-thiazepan-4-yl)phenyl)-2-oxooxazolidin-5-yl)methyl 4-methylbenzenesulfonate (10) (1.41 g, 2.95 mmol) and sodium azide (190 mg, 2.95 mmol) in DMF (10 mL) was added K₂CO₃ (814 g, 5.9 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by silica gel column chromatography (PE:EA=2:1) to afford (R)-5-(azidomethyl)-3-(3-fluoro-4-(1,4-thiazepan-4-yl)phenyl)oxazolidin-2-one (11) (830 mg, 80%) as a white solid.

LC-MS (ESI) m/z=352 [M+H]$^+$.

Step 2

(S)-5-(aminomethyl)-3-(3-fluoro-4-(1,4-thiazepan-4-yl)phenyl)oxazolidin-2-one (12)

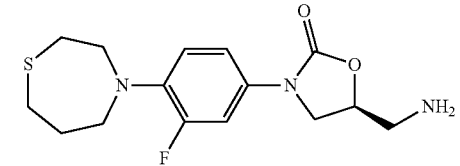

To a solution of (R)-5-(azidomethyl)-3-(3-fluoro-4-(1,4-thiazepan-4-yl)phenyl)oxazolidin-2-one (11) (830 mg, 2.4 mmol) in MeOH (10 mL) was added palladium carbon (100 mg) at 25° C., then the reaction mixture was stirred at room temperature for overnight under a hydrogen gas atmosphere, monitored by TLC. The filtrate was concentrated under reduced pressure, and the crude material was purified by silica gel column chromatography (DCM:MeOH=50:1) to afford (S)-5-(aminomethyl)-3-(3-fluoro-4-(1,4-thiazepan-4-yl)phenyl)oxazolidin-2-one (12) (654 mg, 85%) as a white solid.

LC-MS (ESI) m/z=326 [M+H]$^+$.

Step 3

(S)—N-((3-(3-fluoro-4-(1,4-thiazepan-4-yl)phenyl)-2-oxooxazolidin-5-yl)methyl)butyramide (OBD-005)

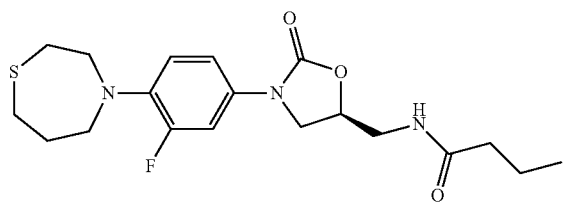

OBD-005

To a solution of (S)-5-(aminomethyl)-3-(3-fluoro-4-(1,4-thiazepan-4-yl)phenyl)oxazolidin-2-one (12) (654 mg, 2 mmol) and butyric acid (177 mg, 2 mmol) in DCM (10 mL) were added HOBt (405 mg, 3 mmol), EDCI (764 mg, 4 mmol) and DIPEA (516 mg, 4 mmol) at 25° C., then the reaction mixture was stirred at 25° C. for 2 h under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=80:1) to afford (S)—N-((3-(3-fluoro-4-(1,4-thiazepan-4-yl)phenyl)-2-oxooxazolidin-5-yl)methyl)butyramide (OBD-005) (286 mg, 34%) as a white solid.

$^1$H NMR (300 MHz, CDCl$_3$) δ 7.42-7.23 (m, 2H), 7.01 (dd, J=8.9, 2.3 Hz, 1H), 6.04 (s, 1H), 4.75 (ddd, J=9.0, 7.9, 4.6 Hz, 1H), 4.00 (t, J=9.0 Hz, 1H), 3.79-3.05 (m, 7H), 2.91 (dd, J=16.2, 10.1 Hz, 2H), 2.70 (t, J=6.3 Hz, 2H), 2.28-2.13 (m, 2H), 2.13-1.97 (m, 2H), 1.82-1.25 (m, 3H), 0.92 (t, J=7.4 Hz, 3H), 0.01 (s, 1H).

LC-MS (ESI) m/z=395.9 [M+H]$^+$.

Step 4: Preparation of (OBD-006 and OBD-007)

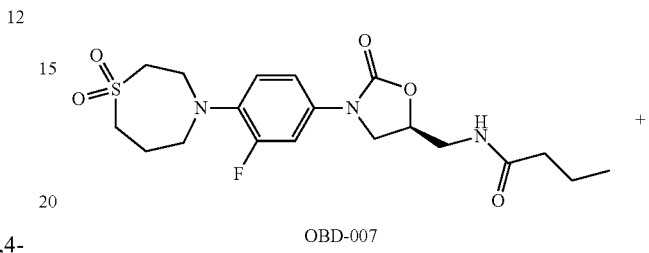

OBD-007

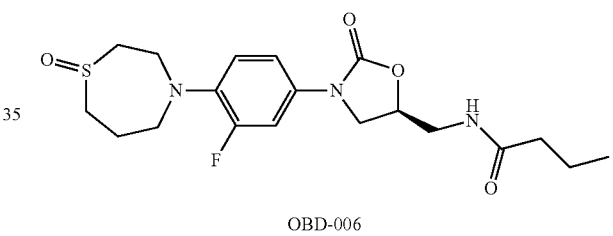

OBD-006

To a solution of (S)—N-((3-(3-fluoro-4-(1,4-thiazepan-4-yl)phenyl)-2-oxooxazolidin-5-yl)methyl)butyramide (OBD-005) (150 mg, 0.38 mmol) in THF (10 mL) and 10 drops water was added potassium peroxomonosulfate (233 mg, 0.38 mmol) at 0° C., then the reaction mixture was stirred at 0° C. for 2 h, monitored by TLC. Quenched with sodium thiosulfate, and the crude material was purified by prep-HPLC to afford (OBD-006) (50 mg, 32%) as a white solid and (OBD-007) (24 mg, 15%) as a white solid.

(OBD-006)

$^1$H NMR (301 MHz, CDCl$_3$) δ 7.52 (d, J=15.0 Hz, 1H), 7.16 (s, 1H), 7.03 (d, J=8.7 Hz, 1H), 5.99 (s, 1H), 4.78 (s, 1H), 4.02 (t, J=8.8 Hz, 2H), 3.88-3.56 (m, 3H), 3.55-2.92 (m, 7H), 2.77 (s, 1H), 2.20 (t, J=7.1 Hz, 3H), 1.64 (dd, J=14.9, 7.4 Hz, 2H), 0.91 (t, J=7.4 Hz, 3H).

LC-MS (ESI) m/z=411.8 [M+H]$^+$.

(OBD-007)

$^1$H NMR (301 MHz, CDCl$_3$) δ 7.51 (d, J=14.7 Hz, 1H), 7.10 (d, J=9.9 Hz, 2H), 5.92 (s, 1H), 4.78 (s, 1H), 4.03 (t, J=9.0 Hz, 1H), 3.87-3.39 (m, 7H), 3.27 (d, J=5.7 Hz, 2H), 2.39 (d, J=6.2 Hz, 2H), 2.20 (t, J=7.2 Hz, 2H), 1.64 (dd, J=14.8, 7.4 Hz, 2H), 0.92 (t, J=7.3 Hz, 3H).

LC-MS (ESI) m/z=427.8 [M+H]$^+$.

Procedures for preparation of R:

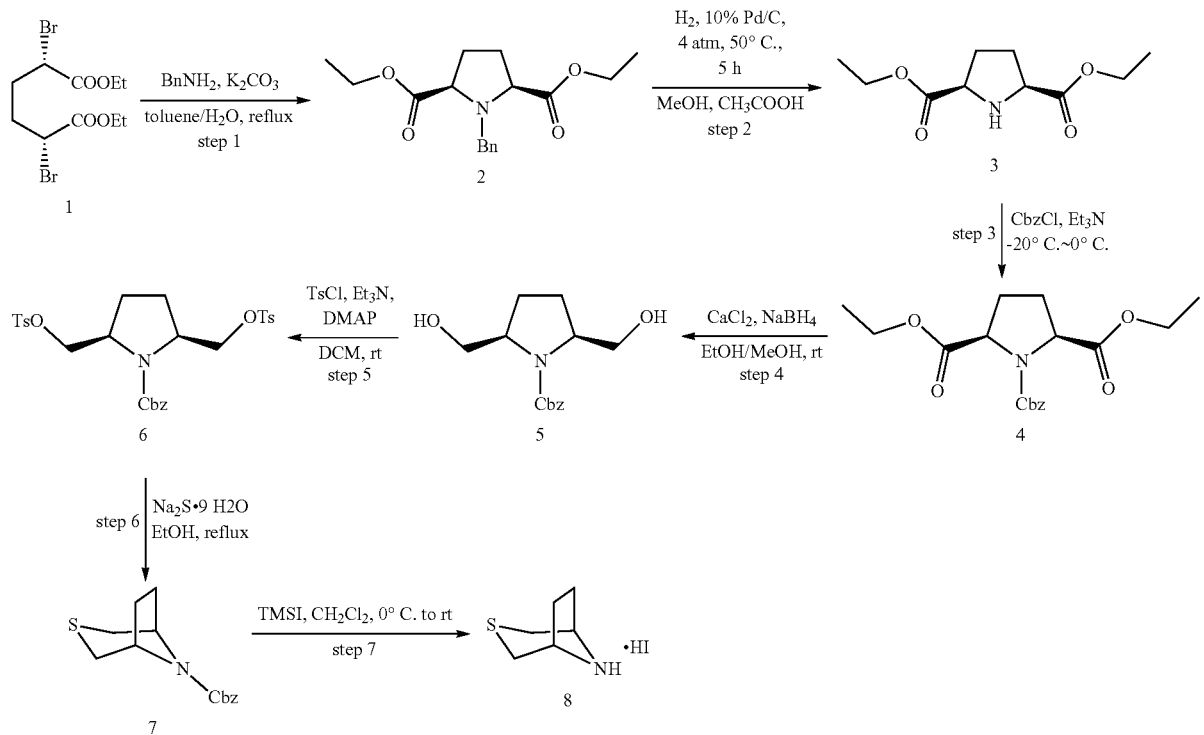

Step 1: Preparation of (2S,5R)-diethyl 1-benzylpyrrolidine-2,5-dicarboxylate (2)

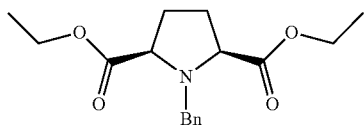

The mixture of (2R,5S)-diethyl 2,5-dibromohexanedioate (1) (100 g, 278 mmol), BnNH$_2$ (44.6 g, 416 mmol) and K$_2$CO$_3$ (76.84 g, 556 mmol) in toluene/H$_2$O was stirred at 110° C. for overnight, monitored by TLC. The mixture was extracted with EtOAc, washed with water and brine and then dried over anhydrous sodium sulfate, filtered, and concentrated under reduced pressure to afford (2S,5R)-diethyl 1-benzylpyrrolidine-2,5-dicarboxylate (2) (63.75 g, 75%) as a white oil.

LC-MS (ESI) m/z=306 [M+H]$^-$.

Step 2: (2S,5R)-diethyl pyrrolidine-2,5-dicarboxylate (3)

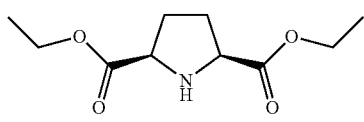

To a solution of (2S,5R)-diethyl 1-benzylpyrrolidine-2,5-dicarboxylate (2) (63.75 g, 209 mmol) and Palladium carbon (2 g) in MeOH (15 mL) was added CH$_3$COOH (5 mL), then the reaction mixture was stirred at 50° C. under a hydrogen gas atmosphere, 4 atm for 5 h, monitored by TLC. The filter was concentrated under reduced pressure, and the crude material was used for next reaction without further purification.

LC-MS (ESI) m/z=216 [M+H]$^-$.

Step 3: (2S,5R)-1-benzyl 2,5-diethyl pyrrolidine-1,2,5-tricarboxylate (4)

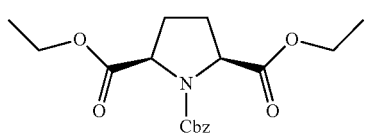

To a solution of (2S,5R)-diethyl pyrrolidine-2,5-dicarboxylate (3) (62 g, 288 mmol) and Et$_3$N (58 g, 577 mmol) in DCM (100 mL) was added benzyl carbonochloridate (98 g, 577 mmol) at −20° C. under a nitrogen gas atmosphere, then the reaction mixture was stirred at rt for 5 h, monitored by TLC. The mixture was extracted with DCM, washed with water and brine and then dried over anhydrous sodium sulfate, filtered, and concentrated under reduced pressure to afford (2S,5R)-1-benzyl 2,5-diethyl pyrrolidine-1,2,5-tricarboxylate (4) (80 g, 80%) as a white oil.

LC-MS (ESI) m/z=350 [M+H]$^-$.

Step 4: (2S,5R)-benzyl 2,5-bis(hydroxymethyl)pyrrolidine-1-carboxylate (5)

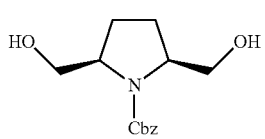

5

CaCl$_2$ (76 g, 688 mmol) and NaBH$_4$ (43 g, 1146 mmol) were added to a stirred solution of (2S,5R)-1-benzyl 2,5-diethyl pyrrolidine-1,2,5-tricarboxylate (4) (80 g, 229 mmol) in EtOH-MeOH (9:1; 200 mL) at rt under a nitrogen gas atmosphere, then the reaction mixture was stirred for 5 h, monitored by TLC. H$_2$O (5 mL) was added, and the mixture was stirred for a further 15 min. The mixture was then concentrated in vacuo. The mixture was extracted with EtOAc, then dried over anhydrous sodium sulfate, filtered, and concentrated under reduced pressure to afford (2S,5R)-benzyl 2,5-bis(hydroxymethyl)pyrrolidine-1-carboxylate (5) (32 g, 52%) as a white oil.
LC-MS (ESI) m/z=266 [M+H]$^-$.

Step 5: (2S,5R)-benzyl 2,5-bis(tosyloxymethyl)pyrrolidine-1-carboxylate (6)

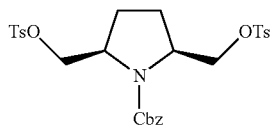

6

4-methylbenzene-1-sulfonyl chloride (92 g, 483 mmol) was added to a stirred solution of (2S,5R)-benzyl 2,5-bis(hydroxymethyl)pyrrolidine-1-carboxylate (5) (32 g, 121 mmol) and Et$_3$N in DCM (200 mL) at 0° C. under a nitrogen gas atmosphere, then the reaction mixture was allowed to warm to room temperature and stirred for 5 h, monitored by TLC. The mixture was extracted with DCM, then dried over anhydrous sodium sulfate, filtered, and concentrated under reduced pressure, and the crude material was purified by silica gel column chromatography (EA:PE=2:1) to afford (2S,5R)-benzyl 2,5-bis(tosyloxymethyl)pyrrolidine-1-carboxylate (6) (30 g, 43%) as a white solid.
LC-MS (ESI) m/z=574 [M+H]$^-$.

Step 6: 8-benzyl-3-thia-8-aza-bicyclo[3.2.1]octane-1-carboxylate (7)

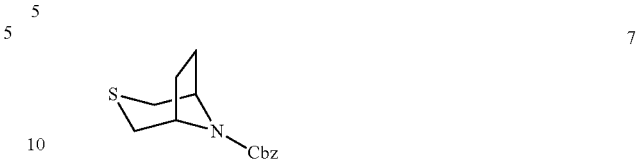

7

Sodium sulfide hydrate (38 g, 157 mmol) was added to a stirred solution of (2S,5R)-benzyl 2,5-bis(tosyloxymethyl)pyrrolidine-1-carboxylate (6) (30 g, 50 mmol) in EtOH (50 mL) and water (50 mL) at room temperature, then the reaction mixture was stirred at 90° C. for 2 h, monitored by TLC. The mixture was extracted with DCM, then dried over anhydrous sodium sulfate, filtered, and concentrated under reduced pressure, and the crude material was purified by silica gel column chromatography (EA:PE=10:1) to afford 8-benzyl-3-thia-8-aza-bicyclo[3.2.1]octane-1-carboxylate (7) (10 g, 73%) as a white solid.
LC-MS (ESI) m/z=264 [M+H]$^-$.

Step 7: 3-thia-8-aza-bicyclo[3.2.1]octane hydrogen iodide (8)

8

Iodotrimethylsilane (15 g, 75 mmol) was added to a stirred solution of 8-benzyl-3-thia-8-aza-bicyclo[3.2.1]octane-1-carboxylate (7) (10 g, 38 mmol) in DCM (200 mL) at 0° C. under a nitrogen gas atmosphere, then the reaction mixture was allowed to warm to room temperature and stirred for 30 min, monitored by TLC. The mixture was extracted with DCM, then dried over anhydrous sodium sulfate, filtered, and concentrated under reduced pressure, and the crude material was purified by silica gel column chromatography (DCM:MeOH=15:1) to afford 3-thia-8-aza-bicyclo[3.2.1]octane hydrogen iodide (8) (8.13 g, 84%) as a brown solid.
LC-MS (ESI) m/z=130 [M+H]$^-$

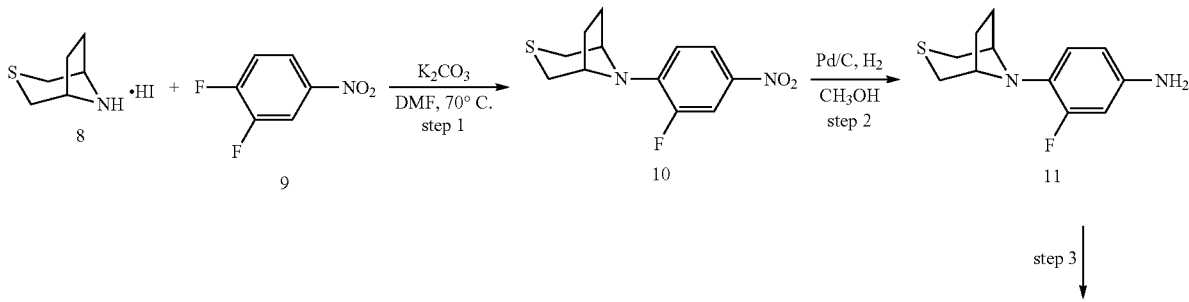

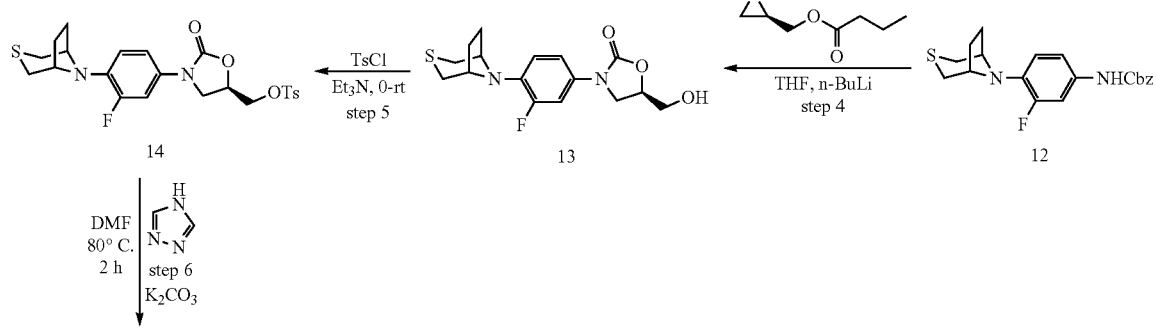

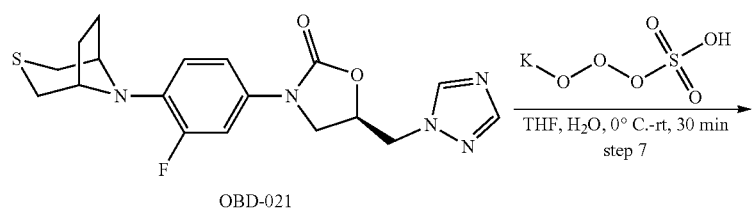

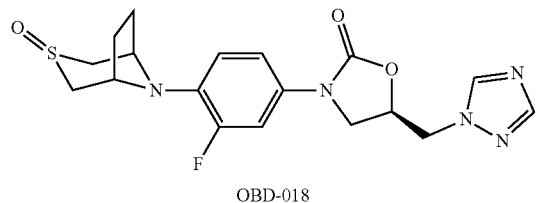

Step 1: Preparation of 8-(2-fluoro-4-nitrophenyl)-3-thia-8-aza-bicyclo[3.2.1]octane (10)

Step 2: 4-(3-thia-8-aza-bicyclo[3.2.1]octan-8-yl)-3-fluorobenzenamine (11)

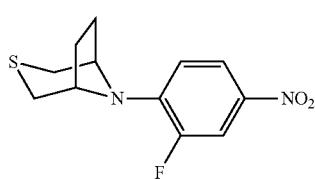

To a solution of 3-thia-8-aza-bicyclo[3.2.1]octane hydrogen iodide (8) (5.58 g, 21.7 mmol) and 1,2-difluoro-4-nitrobenzene (3.8 g, 23.8 mmol) in DMF (10 mL) was added K₂CO₃ (6 g, 43.4 mmol) at 25° C. under a nitrogen gas atmosphere and the reaction mixture was stirred at 80° C. for 2 h, monitored by TLC. The mixture was concentrated under reduced pressure, and the crude material was purified by silica gel column chromatography (EA:PE=3:1) to afford 8-(2-fluoro-4-nitrophenyl)-3-thia-8-aza-bicyclo[3.2.1]octane (10) (4.89 g, 84%) as a yellow solid.

LC-MS (ESI) m/z=269 [M+H]⁻.

To a solution of 8-(2-fluoro-4-nitrophenyl)-3-thia-8-aza-bicyclo[3.2.1]octane (10) (4.89 g, 18.2 mmol) and Palladium carbon (200 mg) in MeOH (15 mL), then under a hydrogen gas atmosphere and the reaction mixture was stirred at room temperature for overnight, monitored by TLC. The filtrate was concentrated under reduced pressure to afford 4-(3-thia-8-aza-bicyclo[3.2.1]octan-8-yl)-3-fluorobenzenamine (11) (4.08 g, 94%) as a white oil, and the crude material was used for next reaction without further purification.

LC-MS (ESI) m/z=239 [M+H]⁻.

Step 3: Benzyl 4-(3-thia-8-aza-bicyclo[3.2.1]octan-8-yl)-3-fluorophenylcarbamate (12)

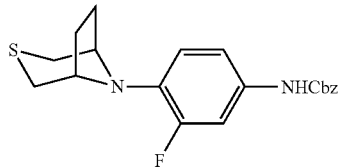

Carbonic acid, 2,5-dioxo-1-pyrrolidinyl phenylmethyl ester (6.38 g, 25.6 mmol) was added to a suspension of 4-(3-thia-8-aza-bicyclo[3.2.1]octan-8-yl)-3-fluorobenzenamine (11) (4.08 g, 17.1 mmol) in THF (30 mL) at 0° C. under a nitrogen gas atmosphere and the reaction mixture was stirred at 50° C. for 5 h, monitored by TLC. The mixture was concentrated under reduced pressure, and the crude material was purified by silica gel column chromatography (EA:PE=10:1) to afford benzyl 4-(3-thia-8-aza-bicyclo[3.2.1]octan-8-yl)-3-fluorophenylcarbamate (12) (4.34 g, 68%) as a white solid.

LC-MS (ESI) m/z=373 [M+H]$^-$.

Step 4: (5R)-3-(4-(3-thia-8-aza-bicyclo[3.2.1]octan-8-yl)-3-fluorophenyl)-5-(hydroxymethyl)oxazolidin-2-one (13)

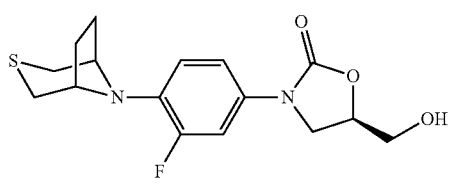

To a solution of benzyl 4-(3-thia-8-aza-bicyclo[3.2.1]octan-8-yl)-3-fluorophenylcarbamate (12) (4.34 g, 11.6 mmol) in THF (10 mL) at −78° C. under a nitrogen gas atmosphere was added n-BuLi (7.3 ml, 17.5 mmol), then the mixture was stirred at −78° C. for 30 min, after that the solution of (R)-oxiran-2-ylmethyl butyrate (2.5 g, 17.4 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford (5R)-3-(4-(3-thia-8-aza-bicyclo[3.2.1]Octan-8-yl)-3-fluorophenyl)-5-(hydroxymethyl)oxazolidin-2-one (13) (3.03 g, 77%) as a white solid.

LC-MS (ESI) m/z=339 [M+H]$^-$.

Step 5

((R)-3-(4-(3-thia-8-aza-bicyclo[3.2.1]octan-8-yl)-3-fluorophenyl)-2-oxooxazolidin-5-yl)methyl 4-methylbenzenesulfonate (14)

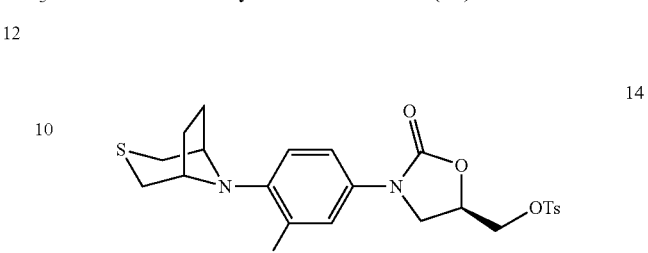

4-methylbenzene-1-sulfonyl chloride (3.41 g, 17.9 mmol) was added to a suspension of (5R)-3-(4-(3-thia-8-aza-bicyclo[3.2.1]octan-8-yl)-3-fluorophenyl)-5-(hydroxymethyl)oxazolidin-2-one (13) (3.03 g, 8.9 mmol) and Et$_3$N (1.8 g, 17.9 mmol) in DCM (10 mL) at 0° C. under a nitrogen gas atmosphere and the reaction mixture was stirred at room temperature for overnight, monitored by TLC. Quenched with ammonium chloride, extracted with DCM, the organic layer was concentrated under reduced pressure, and the crude material was purified by silica gel column chromatography (DCM:MeOH=50:1) to afford ((R)-3-(4-(3-thia-8-aza-bicyclo[3.2.1]octan-8-yl)-3-fluorophenyl)-2-oxooxazolidin-5-yl)methyl 4-methylbenzenesulfonate (14) (3.74 g, 85%) as a white solid.

LC-MS (ESI) m/z=493 [M+H]$^-$.

Step 6

(5R)-5-((1H-1,2,4-triazol-1-yl)methyl)-3-(4-(3-thia-8-aza-bicyclo[3.2.1]octan-8-yl)-3-fluorophenyl)oxazolidin-2-one (OBD-021)

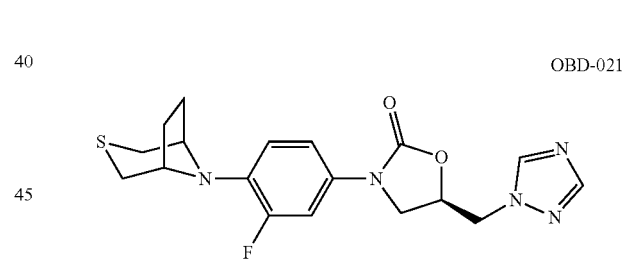

To a solution of ((R)-3-(4-(3-thia-8-aza-bicyclo[3.2.1]octan-8-yl)-3-fluorophenyl)-2-oxooxazolidin-5-yl)methyl 4-methylbenzenesulfonate (14) (500 mg, 1 mmol) and 1H-1,2,4-triazole (140 mg, 2 mmol) in DMF (10 mL) was added K$_2$CO$_3$ (280 mg, 2 mmol) at 25° C., then the reaction mixture was stirred at 80° C. for 2 h under a nitrogen gas atmosphere, monitored by TLC. Quenched with ammonium chloride, extracted with EA, the organic layer was concentrated under reduced pressure, and the crude material was purified by silica gel column chromatography (EA:PE=2:1) to afford (5R)-5-((1H-1,2,4-triazol-1-yl)methyl)-3-(4-(3-thia-8-aza-bicyclo[3.2.1]octan-8-yl)-3-fluorophenyl)oxazolidin-2-one (OBD-021) (177 mg, 45%) as a white solid.

$^1$H NMR (300 MHz, DMSO-d$_6$) δ 8.57 (s, 1H), 8.01 (s, 1H), 7.36 (dd, J=15.8, 2.1 Hz, 1H), 7.18-6.92 (m, 2H), 5.06 (dd, J=8.9, 4.8 Hz, 1H), 4.72-4.52 (m, 2H), 4.36 (s, 2H), 4.17 (t, J=9.1 Hz, 1H), 3.84 (dt, J=49.3, 24.7 Hz, 1H), 3.12 (d, J=12.8 Hz, 2H), 2.16 (s, 1H), 2.11 (s, 1H), 2.04 (s, 4H).

LC-MS (ESI) m/z=390 [M+H]$^-$.

Step 7: Preparation of (OBD-018)

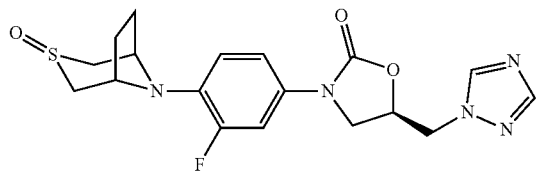

To a solution of (5R)-5-((1H-1,2,4-triazol-1-yl)methyl)-3-(4-(3-thia-8-aza-bicyclo[3.2.1]octan-8-yl)-3-fluorophenyl)oxazolidin-2-one (OBD-021) (100 mg, 0.26 mmol) in THF (10 mL) and 10 drops water was added potassium peroxomonosulfate (157 mg, 0.26 mmol) at 0° C., then the reaction mixture was stirred at 0° C. for 2 h, monitored by TLC. Quenched with sodium thiosulfate, and the crude material was purified by silica gel column chromatography (DCM:MeOH=80:1) to afford (OBD-018) (52 mg, 50%) as a white solid.

$^1$H NMR (300 MHz, DMSO-$d_6$) δ 12.17 (s, 1H), 8.69 (d, J=2.9 Hz, 1H), 8.20-8.03 (m, 1H), 7.44 (d, J=16.2 Hz, 1H), 7.28-7.02 (m, 2H), 5.08 (dd, J=8.5, 5.1 Hz, 1H), 4.68-4.52 (m, 4H), 4.20 (t, J=9.1 Hz, 1H), 3.91 (dd, J=8.7, 6.0 Hz, 1H), 3.56 (d, J=11.1 Hz, 2H), 2.48 (d, J=12.3 Hz, 2H), 2.06 (d, J=5.1 Hz, 2H), 1.79 (d, J=7.6 Hz, 2H).

LC-MS (ESI) m/z=405.8 [M+H]$^+$.

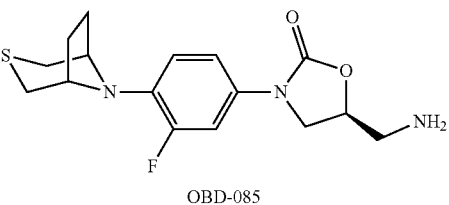

OBD-085

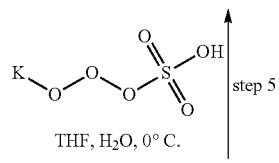

step 5

THF, H$_2$O, 0° C.

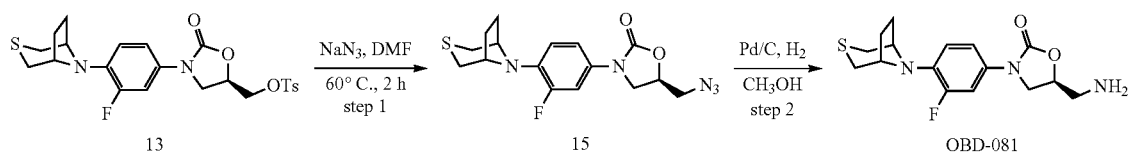

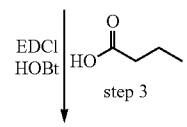

step 3

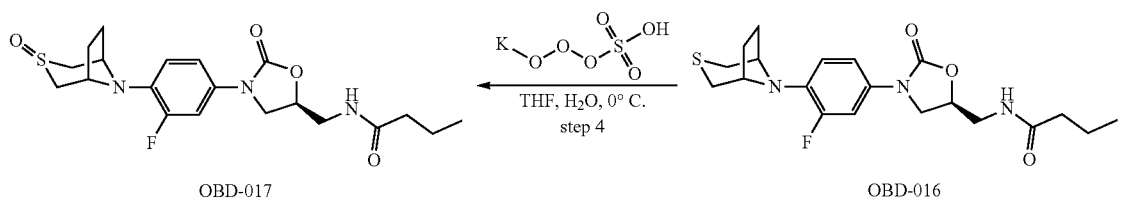

OBD-017     OBD-016

Step 1

(5R)-3-(4-(3-thia-8-aza-bicyclo[3.2.1]octan-8-yl)-3-fluorophenyl)-5-(azidomethyl)oxazolidin-2-one (15)

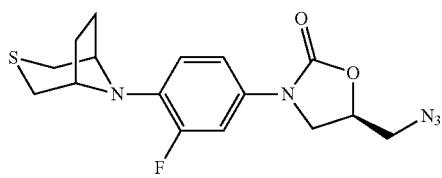

To a solution of ((R)-3-(4-(3-thia-8-aza-bicyclo[3.2.1]octan-8-yl)-3-fluorophenyl)-2-oxooxazolidin-5-yl)methyl 4-methylbenzenesulfonate (14) (2 g, 4 mmol) and sodium azide (265 mg, 4 mmol) in DMF (10 mL) was added $K_2CO_3$ (1.1 g, 8 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by silica gel column chromatography (PE:EA=2:1) to afford (5R)-3-(4(3-thia-8-aza-bicyclo[3.2.1]octan-8-yl)-3-fluorophenyl)-5-(azidomethyl)oxazolidin-2-one (15) (1.01 g, 70%) as a white solid.

LC-MS (ESI) m/z=364 [M+H]$^+$.

Step 2

(5S)-3-(4-(3-thia-8-aza-bicyclo[3.2.1]octan-8-yl)-3-fluorophenyl)-5-(aminomethyl)oxazolidin-2-one (OBD-081)

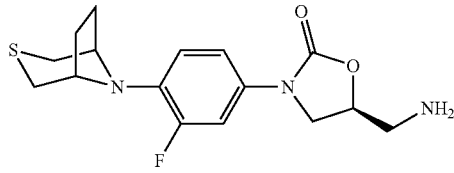

To a solution of (5R)-3-(4-(3-thia-8-aza-bicyclo[3.2.1]octan-8-yl)-3-fluorophenyl)-5-(azidomethyl)oxazolidin-2-one (15) (1.01 g, 2.8 mmol) in MeOH (10 mL) was added palladium carbon (100 mg) at 25° C., then the reaction mixture was stirred at room temperature for overnight under a hydrogen gas atmosphere, monitored by TLC. The filtrate was concentrated under reduced pressure, and the crude material was purified by silica gel column chromatography (DCM:MeOH=50:1) to afford (5S)-3-(4-(3-thia-8-aza-bicyclo[3.2.1]octan-8-yl)-3-fluorophenyl)-5-(aminomethyl)oxazolidin-2-one (OBD-081) (800 mg, 85%) as a white solid.

LC-MS (ESI) m/z=338 [M+H]$^+$.

Step 3

N—(((S)-3-(4-(3-thia-8-aza-bicyclo[3.2.1]octan-8-yl)-3-fluorophenyl)-2-oxooxazolidin-5-yl)methyl)butyramide (OBD-016)

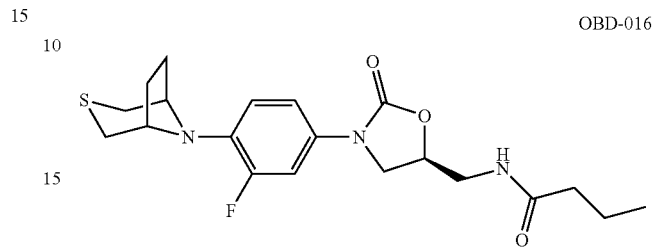

To a solution of (5S)-3-(4-(3-thia-8-aza-bicyclo[3.2.1]octan-8-yl)-3-fluorophenyl)-5-(aminomethyl)oxazolidin-2-one (OBD-081) (200 mg, 0.59 mmol) and butyric acid (52 mg, 0.59 mmol) in DCM (10 mL) were added HOBt (95 mg, 0.7 mmol), EDCI (170 mg, 0.88 mmol) and DIPEA (115 mg, 0.88 mmol) at 25° C., then the reaction mixture was stirred at 25° C. for 2 h under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=80:1) to afford N—(((S)-3-(4-(3-thia-8-aza-bicyclo[3.2.1]octan-8-yl)-3-fluorophenyl)-2-oxooxazolidin-5-yl)methyl)butyramide (OBD-016) (156 mg, 65%) as a white solid.

$^1$H NMR (300 MHz, DMSO-d$_6$) δ 8.18 (s, 1H), 7.42 (d, J=16.0 Hz, 1H), 7.35-6.88 (m, 2H), 4.71 (s, 1H), 4.35 (s, 2H), 4.07 (t, J=8.7 Hz, 1H), 3.77-3.57 (m, 1H), 3.51-3.27 (m, 2H), 3.12 (d, J=12.4 Hz, 2H), 2.09 (dd, J=20.9, 12.2 Hz, 8H), 1.47 (dd, J=14.0, 7.1 Hz, 2H), 0.80 (dd, J=8.0, 6.7 Hz, 3H).

LC-MS (ESI) m/z=407.9 [M+H]$^+$.

Step 4 Preparation of (OBD-017)

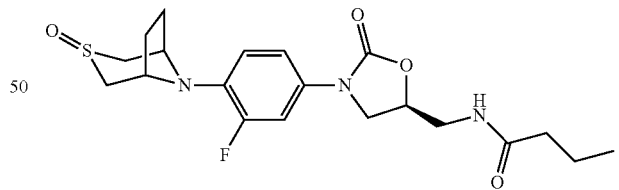

To a solution of N—(((S)-3-(4-(3-thia-8-aza-bicyclo[3.2.1]octan-8-yl)-3-fluorophenyl)-2-oxooxazolidin-5-yl)methyl)butyramide (OBD-016) (100 mg, 0.25 mmol) in THF (10 mL) and 10 drops water was added potassium peroxomonosulfate (157 mg, 0.26 mmol) at 0° C., then the reaction mixture was stirred at 0° C. for 2 h, monitored by TLC. Quenched with sodium thiosulfate, and the crude material was purified by prep-HPLC to afford (OBD-017) (16 mg, 15%) as a white solid.

$^1$H-NMR (301 MHz, CDCl$_3$) δ 7.39 (dd, J=15.8, 2.3 Hz, 1H), 7.03 (d, J=6.1 Hz, 2H), 6.78 (t, J=9.3 Hz, 1H), 4.72 (s, 1H), 4.55 (s, 2H), 3.94 (t, J=8.9 Hz, 1H), 3.81-3.66 (m, 1H), 3.58 (s, 2H), 3.42 (d, J=10.3 Hz, 2H), 2.77 (d, J=11.9 Hz, 2H), 2.17 (dd, J=25.1, 17.8 Hz, 4H), 1.84 (d, J=7.9 Hz, 2H), 1.56 (dq, J=14.5, 7.2 Hz, 2H), 0.83 (t, J=7.4 Hz, 3H).

LC-MS (ESI) m/z=423.8 [M+H]⁺.

Step 4: Preparation of (OBD-085)

To a solution of (5S)-3-(4-(3-thia-8-aza-bicyclo[3.2.1]octan-8-yl)-3-fluorophenyl)-5-(aminomethyl)oxazolidin-2-one (OBD-081) (100 mg, 0.29 mmol) in THF (10 mL) and 10 drops water was added potassium peroxomonosulfate (182 mg, 0.29 mmol) at 0° C., then the reaction mixture was stirred at 0° C. for 2 h, monitored by TLC. Quenched with sodium thiosulfate, and the crude material was purified by prep-HPLC to afford (OBD-085) (28 mg, 28%) as a white solid.

¹H NMR (400 MHz, DMSO-d₆) δ 7.52 (dd, J=16.4, 2.2 Hz, 1H), 7.24 (dd, J=8.9, 2.0 Hz, 1H), 7.13 (t, J=9.6 Hz, 1H), 4.58 (dd, J=14.1, 4.9 Hz, 3H), 4.04 (t, J=8.9 Hz, 1H), 3.84 (dd, J=8.7, 6.5 Hz, 1H), 3.56 (d, J=10.0 Hz, 2H), 2.81 (dd, J=9.3, 4.9 Hz, 2H), 2.46 (s, 2H), 2.17-1.99 (m, 2H), 1.79 (dd, J=17.3, 9.5 Hz, 4H).

LC-MS (ESI) m/z=354 [M+H]⁺.

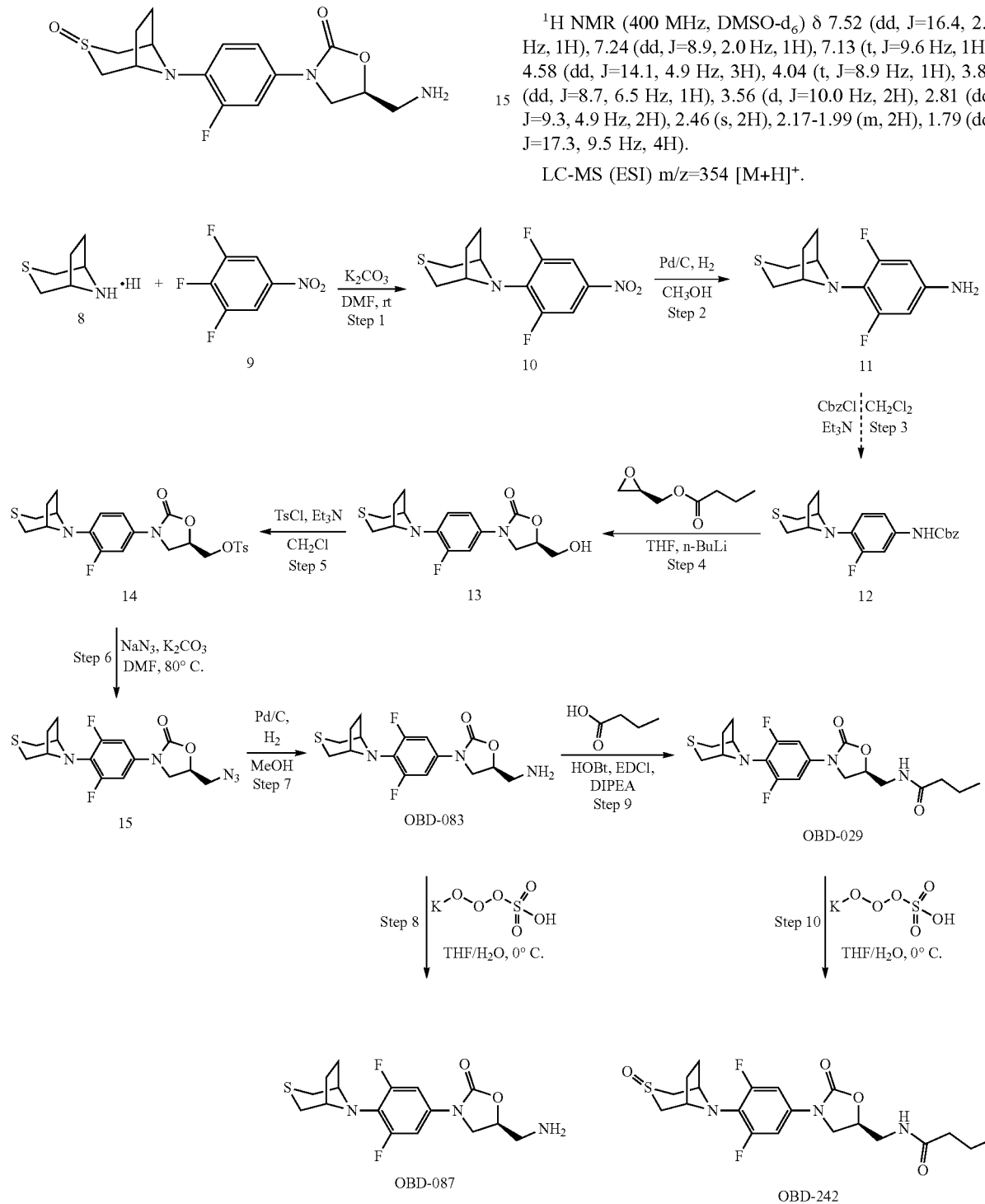

Step 1: Preparation of 8-(2,6-difluoro-4-nitrophenyl)-3-thia-8-aza-bicyclo[3.2.1]octane (10)

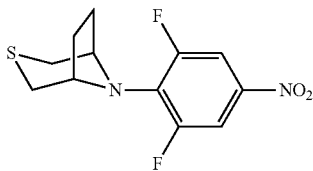

To a solution of 3-thia-8-aza-bicyclo[3.2.1]octane hydrogen iodide (8) (5.0 g, 19.4 mmol) and 1,2,3-trifluoro-5-nitrobenzene (4.13 g, 23.3 mmol) in DMF (10 mL) was added $K_2CO_3$ (5.35 g, 38.8 mmol) at 25° C. then the reaction mixture was stirred at 80° C. for 2 h under a nitrogen gas atmosphere, monitored by TLC. The mixture was concentrated under reduced pressure, and the crude material was purified by silica gel column chromatography (EA:PE=3:1) to afford 8-(2,6-difluoro-4-nitrophenyl)-3-thia-8-aza-bicyclo[3.2.1]octane (10) (3.6 g, 65%) as a yellow solid.

LC-MS (ESI) m/z=287 [M+H]⁻.

Step 2: 4-(3-thia-8-aza-bicyclo[3.2.1]octan-8-yl)-3,5-difluorobenzenamine (11)

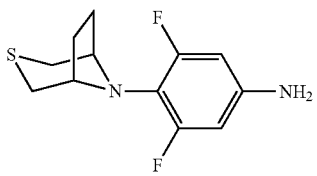

To a solution of 8-(2-fluoro-4-nitrophenyl)-3-thia-8-aza-bicyclo[3.2.1]octane (10) (3.6 g, 12.5 mmol) and Palladium carbon (200 mg) in MeOH (15 mL), then under a hydrogen gas atmosphere and the reaction mixture was stirred at room temperature for overnight, monitored by TLC. The filtrate was concentrated under reduced pressure to afford 4-(3-thia-8-aza-bicyclo[3.2.1]octan-8-yl)-3,5-difluorobenzenamine (11) (2.9 g, 90%) as a white oil, and the crude material was used for next reaction without further purification.

LC-MS (ESI) m/z=257 [M+H]⁻.

Step 3: benzyl 4-(3-thia-8-aza-bicyclo[3.2.1]octan-8-yl)-3,5-difluorophenylcarbamate (12)

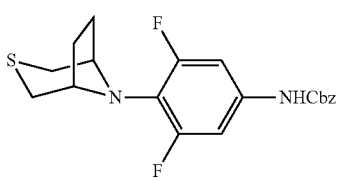

Carbonic acid, 2,5-dioxo-1-pyrrolidinyl phenylmethyl ester (5.57 g, 22.4 mmol) was added to a suspension of 4-(3-thia-8-aza-bicyclo[3.2.1]octan-8-yl)-3,5-difluorobenzenamine (11) (2.9 g, 11.2 mmol) in THF (30 mL) at 0° C. under a nitrogen gas atmosphere and the reaction mixture was stirred at 50° C. for 5 h, monitored by TLC. The mixture was concentrated under reduced pressure, and the crude material was purified by silica gel column chromatography (EA:PE=10:1) to afford benzyl 4-(3-thia-8-aza-bicyclo[3.2.1]octan-8-yl)-3,5-difluorophenylcarbamate (12) (3.0 g, 68%) as a white solid.

LC-MS (ESI) m/z=391 [M+H]⁻.

Step 4

(5R)-3-(4-(3-thia-8-aza-bicyclo[3.2.1]octan-8-yl)-3,5-difluorophenyl)-5-(hydroxymethyl)oxazolidin-2-one (13)

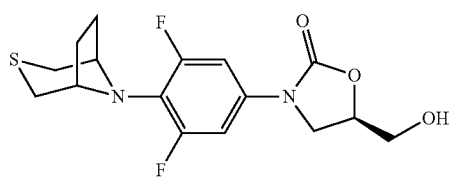

To a solution of benzyl 4-(3-thia-8-aza-bicyclo[3.2.1]octan-8-yl)-3,5-difluorophenylcarbamate (12) (3.0 g, 7.7 mmol) in THF (10 mL) at −78° C. under a nitrogen gas atmosphere was added n-BuLi (4.8 ml, 11.5 mmol), then the mixture was stirred at −78° C. for 30 min, after that the solution of (R)-oxiran-2-ylmethyl butyrate (1.66 g, 11.5 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford (5R)-3-(4-(3-thia-8-aza-bicyclo[3.2.1]octan-8-yl)-3,5-difluorophenyl)-5-(hydroxymethyl)oxazolidin-2-one (13) (2.3 g, 84%) as a white solid.

LC-MS (ESI) m/z=357 [M+H]⁻.

Step 5

((R)-3-(4-(3-thia-8-aza-bicyclo[3.2.1]octan-8-yl)-3,5-difluorophenyl)-2-oxooxazolidin-5-yl)methyl 4-methylbenzenesulfonate (14)

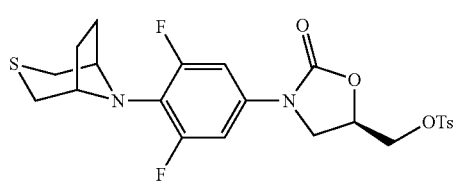

4-methylbenzene-1-sulfonyl chloride (2.45 g, 13 mmol) was added to a suspension of (5R)-3-(4-(3-thia-8-aza-bicyclo[3.2.1]octan-8-yl)-3,5-difluorophenyl)-5-(hydroxymethyl)oxazolidin-2-one (13) (2.3 g, 6.5 mmol) and $Et_3N$ (1.3 g, 13 mmol) in DCM (10 mL) at 0° C. under a nitrogen gas atmosphere and the reaction mixture was stirred at room temperature for overnight, monitored by TLC. Quenched with ammonium chloride, extracted with DCM, the organic layer was concentrated under reduced pressure, and the crude material was purified by silica gel column chromatography (DCM:MeOH=50:1) to afford ((R)-3-(4-(3-thia-8-aza-bicyclo[3.2.1]octan-8-yl)-3,5-difluorophenyl)-2-oxooxazolidin-5-yl)methyl 4-methylbenzenesulfonate (14) (2.81 g, 85%) as a white solid.

LC-MS (ESI) m/z=511 [M+H]⁺.

Step 6

(5R)-3-(4-(3-thia-8-aza-bicyclo[3.2.1]octan-8-yl)-3,5-difluorophenyl)-5-(azidomethyl)oxazolidin-2-one (15)

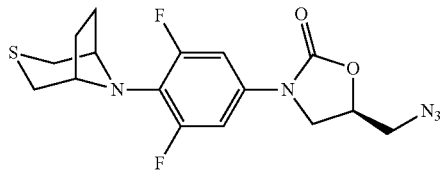

To a solution of ((R)-3-(4-(3-thia-8-aza-bicyclo[3.2.1]octan-8-yl)-3,5-difluorophenyl)-2-oxooxazolidin-5-yl)methyl 4-methylbenzenesulfonate (14) (2.81 g, 5.52 mmol) and sodium azide (360 mg, 5.52 mmol) in DMF (10 mL) was added K₂CO₃ (1.52 mg, 11.04 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by silica gel column chromatography (PE:EA=2:1) to afford (5R)-3-(4-(3-thia-8-aza-bicyclo[3.2.1]octan-8-yl)-3,5-difluorophenyl)-5-(azidomethyl)oxazolidin-2-one (15) (1.85 g, 88%) as a white solid.

LC-MS (ESI) m/z=382 [M+H]⁻.

Step 7

(5S)-3-(4-(3-thia-8-aza-bicyclo[3.2.1]octan-8-yl)-3,5-difluorophenyl)-5-(aminomethyl)oxazolidin-2-one (OBD-083)

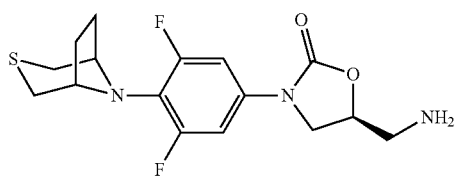

To a solution of (5R)-3-(4-(3-thia-8-aza-bicyclo[3.2.1]octan-8-yl)-3,5-difluorophenyl)-5-(azidomethyl)oxazolidin-2-one (15) (1.85 g, 4.87 mmol) in MeOH (10 mL) was added palladium carbon (100 mg) at 25° C., then the reaction mixture was stirred at room temperature for overnight under a hydrogen gas atmosphere, monitored by TLC. The filtrate was concentrated under reduced pressure, and the crude material was purified by silica gel column chromatography (DCM:MeOH=50:1) to afford (5S)-3-(4-(3-thia-8-aza-bicyclo[3.2.1]octan-8-yl)-3,5-difluorophenyl)-5-(aminomethyl)oxazolidin-2-one (OBD-083) (1.6 g, 90%) as a white solid.

¹H NMR (400 MHz, DMSO) δ 7.34-7.15 (m, 2H), 4.59 (td, J=11.0, 5.0 Hz, 1H), 4.10 (s, 2H), 3.99 (t, J=8.9 Hz, 1H), 3.79 (dd, J=8.9, 6.4 Hz, 1H), 3.11 (dd, J=12.6, 1.6 Hz, 2H), 2.79 (qd, J=13.7, 4.9 Hz, 2H), 2.26 (dd, J=12.4, 3.3 Hz, 2H), 2.01 (s, 4H), 1.72 (d, J=59.8 Hz, 2H).

LC-MS (ESI) m/z=356 [M+H]⁺.

Step 8: Preparation of (OBD-087)

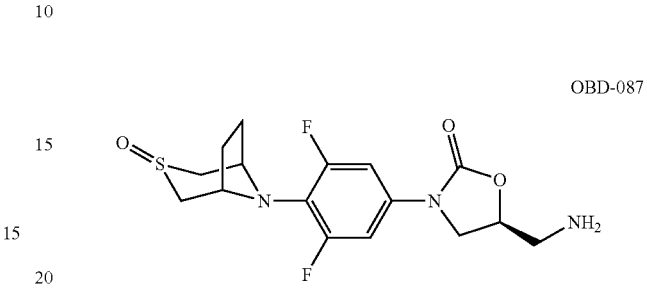

To a solution of (5S)-3-(4-(3-thia-8-aza-bicyclo[3.2.1]octan-8-yl)-3,5-difluorophenyl)-5-(aminomethyl)oxazolidin-2-one (OBD-083) (100 mg, 0.28 mmol) in THF (10 mL) and 10 drops water was added potassium peroxomonosulfate (173 mg, 0.28 mmol) at 0° C., then the reaction mixture was stirred at 0° C. for 2 h, monitored by TLC. Quenched with sodium thiosulfate, and the crude material was purified by prep-HPLC to afford (OBD-087) (31 mg, 30%) as a white solid.

¹H NMR (400 MHz, DMSO) δ 7.32 (t, J=9.4 Hz, 2H), 4.61 (dd, J=8.8, 6.0 Hz, 0H), 4.34 (s, 1H), 4.02 (t, J=8.9 Hz, 1H), 3.82 (dd, J=8.9, 6.4 Hz, 1H), 3.68 (dd, J=12.4, 3.7 Hz, 1H), 2.81 (qd, J=13.7, 4.9 Hz, 1H), 2.58 (d, J=11.6 Hz, 1H), 2.12-1.98 (m, 1H), 1.78 (q, J=6.9 Hz, 2H).

LC-MS (ESI) m/z=372 [M+H]⁺.

Step 9

N—(((S)-3-(4-(3-thia-8-aza-bicyclo[3.2.1]octan-8-yl)-3,5-difluorophenyl)-2-oxooxazolidin-5-yl)methyl)butyramide (OBD-029)

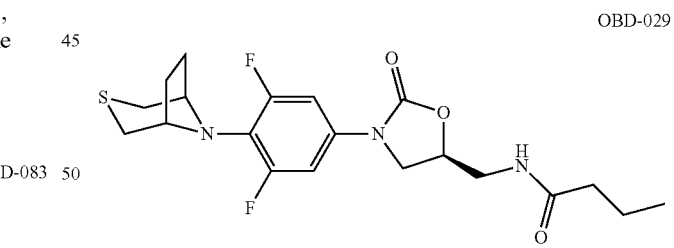

To a solution of (5S)-3-(4-(3-thia-8-aza-bicyclo[3.2.1]octan-8-yl)-3,5-difluorophenyl)-5-(aminomethyl)oxazolidin-2-one (OBD-083) (200 mg, 0.56 mmol) and butyric acid (52 mg, 0.59 mmol) in DCM (10 mL) were added HOBt (95 mg, 0.7 mmol), EDCI (170 mg, 0.88 mmol) and DIPEA (115 mg, 0.88 mmol) at 25° C., then the reaction mixture was stirred at 25° C. for 2 h under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=80:1) to afford N—(((S)-3-(4-(3-thia-8-aza-bicyclo[3.2.1]octan-8-yl)-3,5-difluorophenyl)-2-oxooxazolidin-5-yl)methyl)butyramide (OBD-029) (119 mg, 50%) as a white solid.

¹H NMR (400 MHz, DMSO-d₆) δ 8.18 (s, 1H), 7.22 (d, J=12.2 Hz, 2H), 4.73 (d, J=3.6 Hz, 1H), 4.07 (dd, J=19.1, 10.0 Hz, 3H), 3.68 (dd, J=9.1, 6.2 Hz, 1H), 3.41 (s, 2H), 3.12 (d, J=11.3 Hz, 2H), 2.26 (dd, J=12.4, 3.0 Hz, 2H), 2.05 (dd, J=16.8, 9.5 Hz, 6H), 1.47 (dd, J=14.7, 7.3 Hz, 2H), 0.79 (t, J=7.4 Hz, 3H).

LC-MS (ESI) m/z=426 [M+H]⁺.

Step 10: Preparation of (OBD-242)

OBD-242

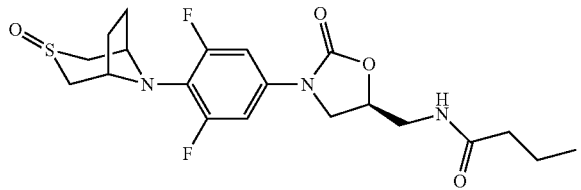

To a solution of N—(((S)-3-(4-(3-thia-8-aza-bicyclo[3.2.1]octan-8-yl)-3,5-difluorophenyl)-2-oxooxazolidin-5-yl)methyl)butyramide (OBD-029) (100 mg, 0.23 mmol) in THF (10 mL) and 10 drops water was added potassium peroxomonosulfate (144 mg, 0.23 mmol) at 0° C., then the reaction mixture was stirred at 0° C. for 2 h, monitored by TLC. Quenched with sodium thiosulfate, and the crude material was purified by prep-HPLC to afford (OBD-242) (30 mg, 15%) as a white solid.

¹H NMR (400 MHz, DMSO-d₆) δ 8.19 (d, J=5.6 Hz, 1H), 7.28 (d, J=12.7 Hz, 3H), 4.77-4.69 (m, 1H), 4.34 (s, 2H), 4.07 (t, J=9.0 Hz, 1H), 3.67 (d, J=9.0 Hz, 3H), 3.40 (dd, J=11.0, 5.5 Hz, 1H), 2.56 (d, J=11.9 Hz, 1H), 2.06 (t, J=7.3 Hz, 4H), 1.82-1.72 (m, 2H), 1.51-1.40 (m, 2H), 0.78 (t, J=7.4 Hz, 3H).

LC-MS (ESI) m/z=442 [M+H]⁺.

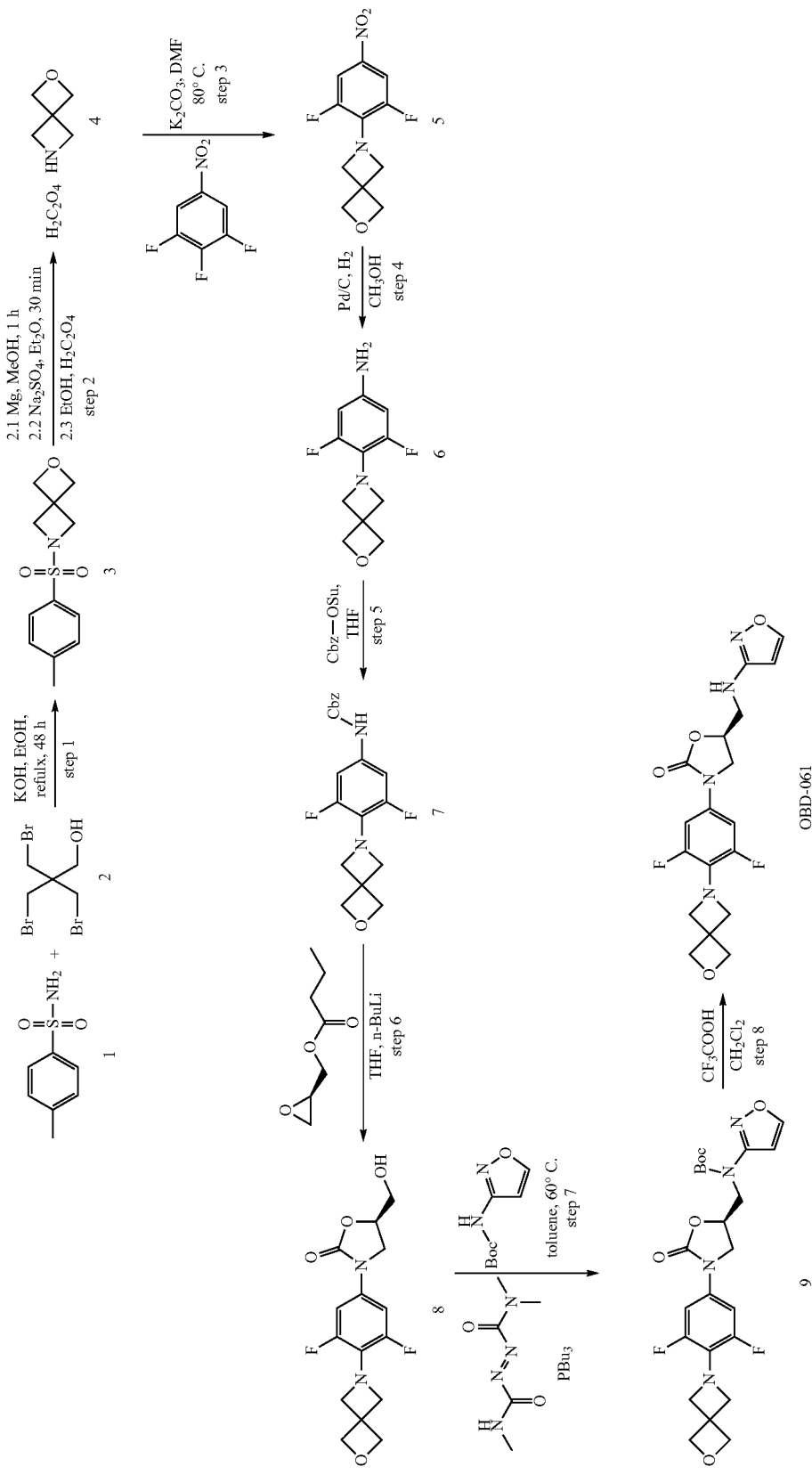

Step 1: Preparation of (3)

To a solution of p-toluenesulfonamide (57 g, 330 mmol) and potassium hydroxide (49.8 g, 890 mmol) in ethanol (1000 mL) was added 3-bromo-2,2-bis(bromomethyl)propan-1-ol (90 g, 270 mmol) at 25° C. then the reaction mixture was stirred at 100° C. for 48 h. The mixture was concentrated under reduced pressure, and the crude material was poured into solution of potassium hydroxide (75 mL) and stirred for 2 h, to afford filter cake (3) (10 g, 59%) as a white solid.

LC-MS (ESI) m/z=254 [M+H]$^-$.

Step 2: Preparation of (4)

A mixture of (3) (10 g, 39.5 mmol) and magnesium (6.7 g) in methanol (15 mL) was sonicated for 1 h at 40° C., after that the solvent was removed under reduced pressure to afford a viscous grey residue, Et2O and sodium sulfate were added and the resulting grey mixture was stirred vigorously for 30 min before filtration. A solution of oxalic acid in ethanol was added to the filtrate. A think white precipitate formed instantly, which was target product (4) (3.7 g, 50%), and the crude material was used for next reaction without further purification.

Step 3: Preparation of (5)

To a solution of (4) (3.7 g, 19.5 mmol) and 1,2,3-trifluoro-5-nitrobenzene (3.81 g, 21.5 mmol) in DMF (10 mL) was added K$_2$CO$_3$ (5.38 g, 39 mmol) at 25° C. then the reaction mixture was stirred at 80° C. for 2 h under a nitrogen gas atmosphere, monitored by TLC. The mixture was concentrated under reduced pressure, and the crude material was purified by silica gel column chromatography (EA:PE=3:1) to afford (5) (1.9 g, 38%) as a yellow solid.

LC-MS (ESI) m/z=257 [M+H]$^-$.

Step 4: Preparation of (6)

To a solution of (5) (1.9 g, 7.4 mmol) and Palladium carbon (200 mg) in methanol (15 mL), then under a hydrogen gas atmosphere and the reaction mixture was stirred at room temperature for overnight, monitored by TLC. The filtrate was concentrated under reduced pressure to afford (6) (1.5 g, 90%) as a white oil, and the crude material was used for next reaction without further purification.

LC-MS (ESI) m/z=227 [M+H]$^-$.

Step 5: Preparation of (7)

Carbonic acid, 2,5-dioxo-1-pyrrolidinyl phenylmethyl ester (3.3 g, 13.3 mmol) was added to a suspension of (6) (1.5 g, 6.7 mmol) in THF (30 mL) at 0° C. under a nitrogen gas atmosphere and the reaction mixture was stirred at 50° C. for 5 h, monitored by TLC. The mixture was concentrated under reduced pressure, and the crude material was purified by silica gel column chromatography (EA:PE=10:1) to afford (7) (1.6 g, 68%) as a white solid.

LC-MS (ESI) m/z=361 [M+H]$^-$.

Step 6: Preparation of (8)

To a solution of (7) (1.6 g, 4.6 mmol) in THF (10 mL) at −78° C. under a nitrogen gas atmosphere was added n-BuLi (2.8 ml, 6.8 mmol), then the mixture was stirred at −78° C. for 30 min, after that the solution of (R)-oxiran-2-ylmethyl butyrate (980 mg, 6.8 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford (8) (1.2 g, 84%) as a white solid.

LC-MS (ESI) m/z=327 [M+H]$^-$.

Step 7: Preparation of (9)

(E)-N1,N1,N2-trimethyldiazene-1,2-dicarboxamide (443 mg, 2.6 mmol) was added to a suspension of (8) (560 mg, 1.7 mmol), tert-butyl isoxazol-3-ylcarbamate (380 mg, 2.1 mmol) and tributylphosphine (521 mg, 2.6 mmol) in toluene (30 mL) at 0° C. under a nitrogen gas atmosphere and then the reaction mixture was stirred at 60° C. for overnight, monitored by TLC. The mixture was concentrated under reduced pressure, and the crude material was purified by silica gel column chromatography (EA:PE=10:1) to afford (9) (309 mg, 37%) as a white solid.

LC-MS (ESI) m/z=493 [M+H]$^-$.

Step 8: Preparation of (OBD-061)

To a solution of (9) (309 g, 0.6 mmol) in CH$_2$Cl$_2$ (10 mL) at 0° C. was added trifluoroacetic acid (1 ml), then the mixture was stirred at 0° C. for 30 min, monitored by TLC. Quenched with ammonium chloride, extracted with CH$_2$Cl$_2$, the organic layer was concentrated under reduced pressure, and the crude material was purified by prep-HPLC to afford (OBD-061) (93 mg, 38%) as a white solid.

$^1$H NMR (300 MHz, CDCl$_3$) δ 8.07 (s, 1H), 7.01 (d, J=12.1 Hz, 2H), 5.85 (d, J=1.7 Hz, 1H), 4.92 (s, 1H), 4.82 (s, 4H), 4.29 (s, 4H), 3.99 (s, 2H), 3.75 (s, 2H), 3.60 (s, 2H)

LC-MS (ESI) m/z=392.9 [M+H]$^+$.

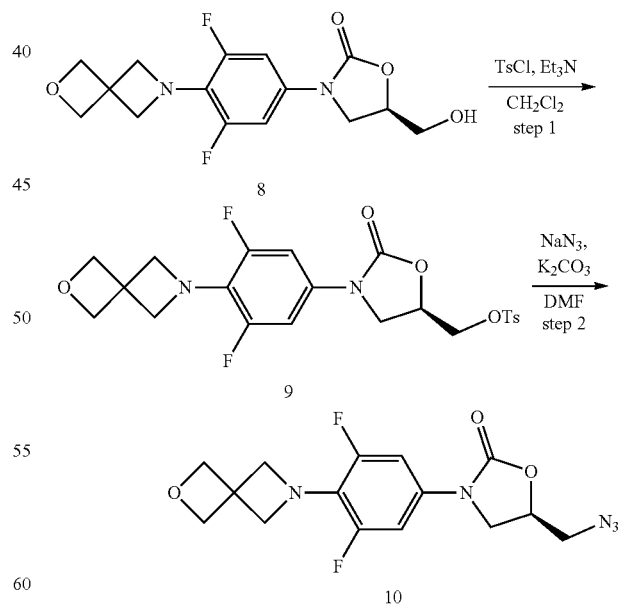

-continued

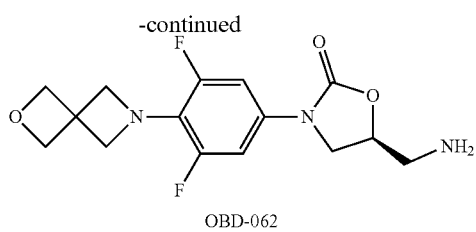
OBD-062

Step 1: Preparation of (9)

4-methylbenzene-1-sulfonyl chloride (2.45 g, 13 mmol) was added to a suspension of (8) (2.3 g, 6.5 mmol) and Et$_3$N (1.3 g, 13 mmol) in DCM (10 mL) at 0° C. and then the reaction mixture was stirred at room temperature for overnight under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=50:1) to afford (9) (2.65 g, 85%) as a white solid.

LC-MS (ESI) m/z=481 [M+H]⁻.

Step 2: Preparation of (10)

To a solution of (9) (2.65 g, 5.52 mmol) and sodium azide (360 mg, 5.52 mmol) in DMF (10 mL) was added K$_2$CO$_3$ (1.52 mg, 11.04 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by silica gel column chromatography (PE:EA=2:1) to afford (10) (1.7 g, 88%) as a white solid.

LC-MS (ESI) m/z=352 [M+H]⁻.

Step 3: Preparation of (OBD-062)

To a solution of (10) (1.7 g, 4.86 mmol) in MeOH (10 mL) was added palladium carbon (100 mg) at 25° C., then the reaction mixture was stirred at room temperature for overnight under a hydrogen gas atmosphere, monitored by TLC. The filtrate was concentrated under reduced pressure, and the crude material was purified by silica gel column chromatography (DCM:MeOH=50:1) to afford (OBD-062) (1.3 g, 85%) as a white solid.

$^1$H NMR (400 MHz, DMSO-d$_6$) δ 7.34-6.98 (m, 2H), 4.70 (s, 4H), 4.59 (dt, J=11.3, 5.1 Hz, 1H), 4.23 (d, J=2.2 Hz, 4H), 3.99 (dd, J=20.9, 12.0 Hz, 1H), 3.78 (dd, J=8.9, 6.4 Hz, 1H), 2.80 (ddd, J=24.5, 13.6, 4.9 Hz, 2H), 1.99 (s, 2H).

LC-MS (ESI) m/z=326.1 [M+H]⁺.

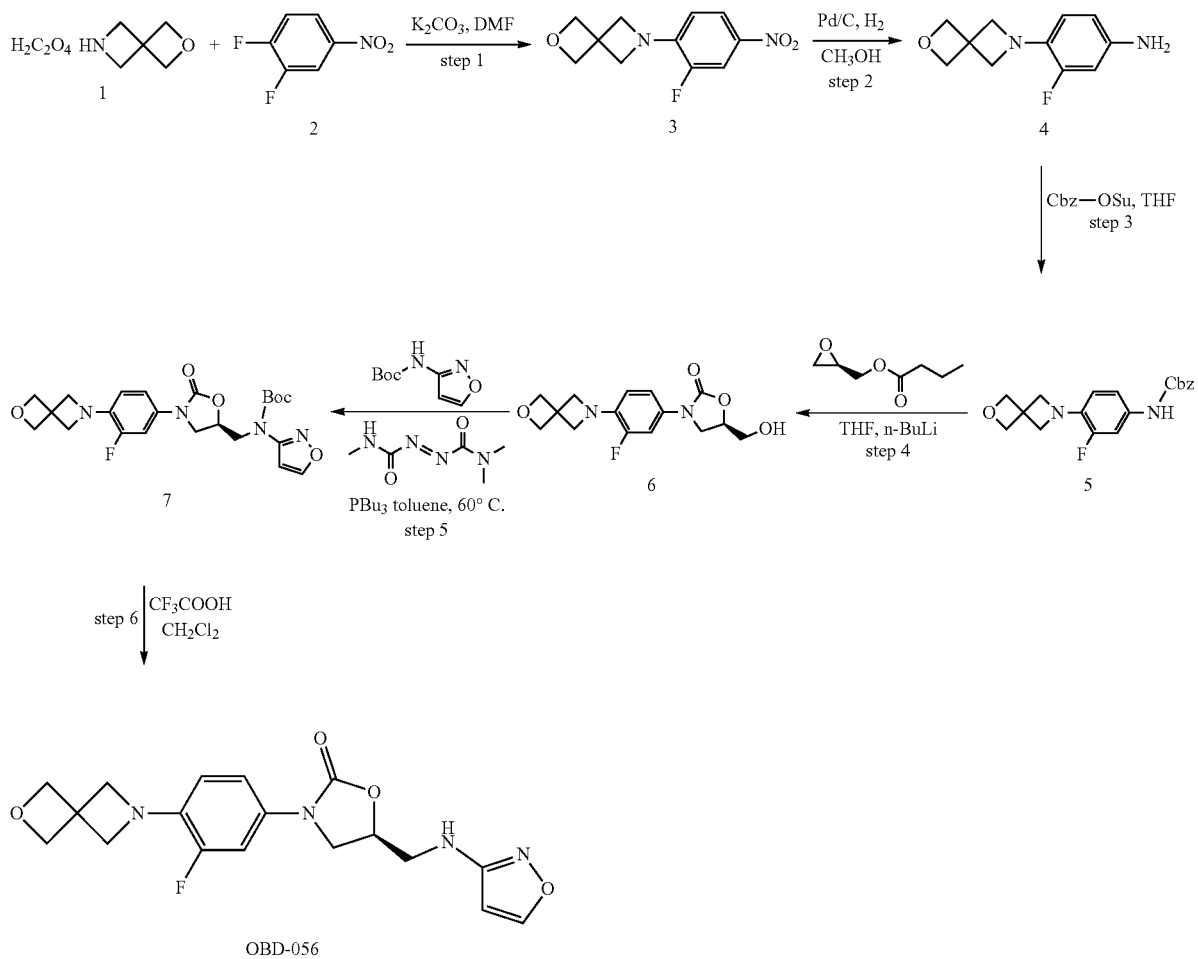
OBD-056

Step 1: Preparation of (3)

To a solution of (1) (3.7 g, 19.5 mmol) and 1,2-difluoro-4-nitrobenzene (3.41 g, 21.5 mmol) in DMF (10 mL) was added $K_2CO_3$ (5.38 g, 39 mmol) at 25° C. then the reaction mixture was stirred at 80° C. for 2 h under a nitrogen gas atmosphere, monitored by TLC. The mixture was concentrated under reduced pressure, and the crude material was purified by silica gel column chromatography (EA:PE=3:1) to afford (3) (1.7 g, 38%) as a yellow solid.

LC-MS (ESI) m/z=239 $[M+H]^-$.

Step 2: Preparation of (4)

To a solution of (3) (1.7 g, 7.4 mmol) and Palladium carbon (200 mg) in methanol (15 mL), then under a hydrogen gas atmosphere and the reaction mixture was stirred at room temperature for overnight, monitored by TLC. The filtrate was concentrated under reduced pressure to afford (4) (1.4 g, 90%) as a white oil, and the crude material was used for next reaction without further purification.

LC-MS (ESI) m/z=209 $[M+H]^-$.

Step 3: Preparation of (7)

Carbonic acid, 2,5-dioxo-1-pyrrolidinyl phenylmethyl ester (3.3 g, 13.3 mmol) was added to a suspension of (6) (1.4 g, 6.7 mmol) in THF (30 mL) at 0° C. under a nitrogen gas atmosphere and the reaction mixture was stirred at 50° C. for 5 h, monitored by TLC. The mixture was concentrated under reduced pressure, and the crude material was purified by silica gel column chromatography (EA:PE=10:1) to afford (7) (1.6 g, 70%) as a white solid.

LC-MS (ESI) m/z=343 $[M+H]^-$.

Step 4: Preparation of (8)

To a solution of (7) (1.6 g, 4.7 mmol) in THF (10 mL) at −78° C. under a nitrogen gas atmosphere was added n-BuLi (2.9 ml, 7.0 mmol), then the mixture was stirred at −78° C. for 30 min, after that the solution of (R)-oxiran-2-ylmethyl butyrate (1 g, 7.0 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford (8) (1.2 g, 84%) as a white solid.

LC-MS (ESI) m/z=309 $[M+H]^-$.

Step 5: Preparation of (9)

(E)-$N_1,N_1,N_2$-trimethyldiazene-1,2-dicarboxamide (443 mg, 2.6 mmol) was added to a suspension of (8) (523 mg, 1.7 mmol), tert-butyl isoxazol-3-ylcarbamate (380 mg, 2.1 mmol) and tributylphosphine (521 mg, 2.6 mmol) in toluene (30 mL) at 0° C. under a nitrogen gas atmosphere and then the reaction mixture was stirred at 60° C. for overnight, monitored by TLC. The mixture was concentrated under reduced pressure, and the crude material was purified by silica gel column chromatography (EA:PE=10:1) to afford (9) (298 mg, 37%) as a white solid.

LC-MS (ESI) m/z=475 $[M+H]^-$.

Step 6: Preparation of (OBD-056)

To a solution of (9) (298 mg, 0.6 mmol) in $CH_2Cl_2$ (10 mL) at 0° C. was added trifluoroacetic acid (1 ml), then the mixture was stirred at 0° C. for 30 min, monitored by TLC. Quenched with ammonium chloride, extracted with $CH_2Cl_2$, the organic layer was concentrated under reduced pressure, and the crude material was purified by prep-HPLC to afford (OBD-056) (84 mg, 38%) as a white solid.

$^1$H NMR (301 MHz, $CDCl_3$) δ 7.39 (d, J=14.4 Hz, 1H), 7.25 (s, 1H), 7.04 (d, J=8.6 Hz, 1H), 6.83 (t, J=8.9 Hz, 1H), 5.14 (s, 1H), 4.73 (s, 1H), 4.39 (s, 2H), 4.00 (t, J=8.8 Hz, 1H), 3.84-3.42 (m, 8H), 3.05 (dd, J=23.2, 11.2 Hz, 5H), 2.13-1.88 (m, 5H).

LC-MS (ESI) m/z=375 $[M+H]^+$.

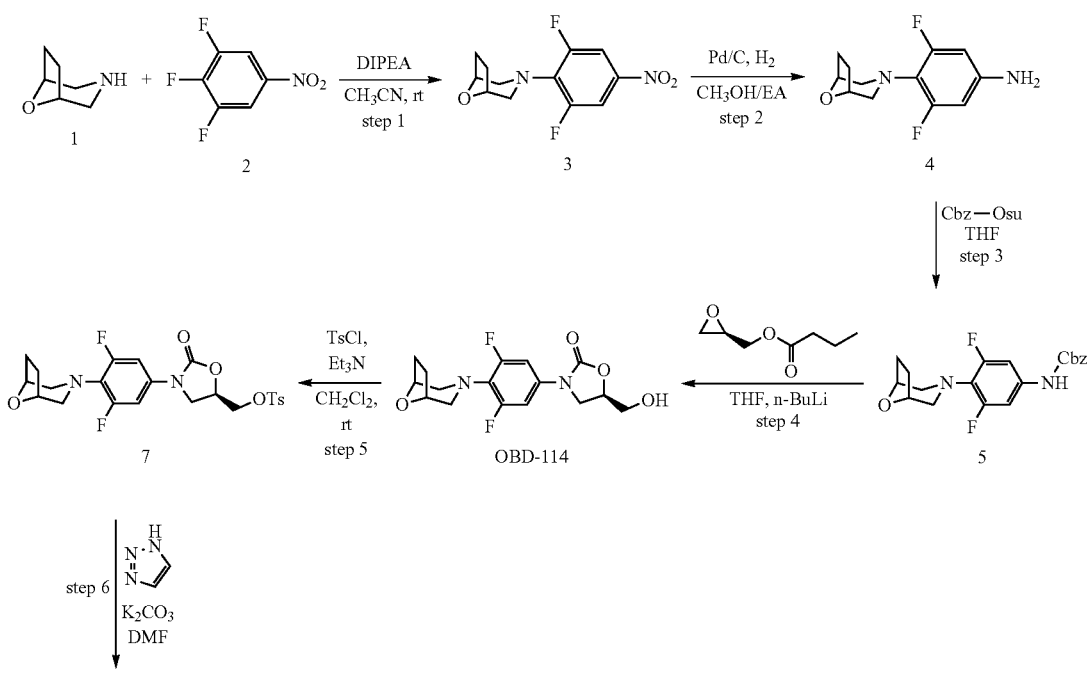

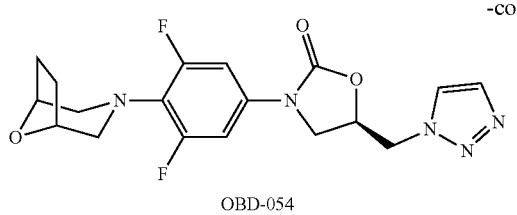

OBD-054

Step 1: Preparation of 3-(2,6-difluoro-4-nitrophenyl)-8-oxa-3-aza-bicyclo[3.2.1]octane (3)

To a solution of 8-oxa-3-aza-bicyclo[3.2.1]octane (1) (5.0 g, 44.2 mmol) and 1,2,3-trifluoro-5-nitrobenzene (8.6 g, 48.6 mmol) in DMF (10 mL) was added $K_2CO_3$ (12.2 g, 88.4 mmol) at 25° C. then the reaction mixture was stirred at 80° C. for 2 h under a nitrogen gas atmosphere, monitored by TLC. The mixture was concentrated under reduced pressure, and the crude material was purified by silica gel column chromatography (EA:PE=3:1) to afford 3-(2,6-difluoro-4-nitrophenyl)-8-oxa-3-aza-bicyclo[3.2.1]octane (3) (9.3 g, 78%) as a yellow solid.
LC-MS (ESI) m/z=271 [M+H]⁻.

Step 2: Preparation of 4-(8-oxa-3-aza-bicyclo[3.2.1]octan-3-yl)-3,5-difluorobenzenamine (4)

To a solution of 3-(2,6-difluoro-4-nitrophenyl)-8-oxa-3-aza-bicyclo[3.2.1]octane (3) (9.3 g, 34.4 mmol) and Palladium carbon (1 g) in MeOH (15 mL), then under a hydrogen gas atmosphere and the reaction mixture was stirred at room temperature for overnight, monitored by TLC. The filtrate was concentrated under reduced pressure to afford 4-(8-oxa-3-aza-bicyclo[3.2.1]octan-3-yl)-3,5-difluorobenzenamine (4) (7.8 g, 95%) as a white oil, and the crude material was used for next reaction without further purification.
LC-MS (ESI) m/z=241 [M+H]⁻.

Step 3: Preparation of benzyl 4-(8-oxa-3-aza-bicyclo[3.2.1]octan-3-yl)-3,5-difluorophenylcarbamate (5)

Carbonic acid, 2,5-dioxo-1-pyrrolidinyl phenylmethyl ester (12 g, 48.7 mmol) was added to a suspension of 4-(8-oxa-3-aza-bicyclo[3.2.1]octan-3-yl)-3,5-difluorobenzenamine (4) (7.8 g, 32.5 mmol) in THF (100 mL) at 0° C. under a nitrogen gas atmosphere and the reaction mixture was stirred at 50° C. for 5 h, monitored by TLC. The mixture was concentrated under reduced pressure, and the crude material was purified by silica gel column chromatography (EA:PE=10:1) to afford benzyl 4-(8-oxa-3-aza-bicyclo[3.2.1]octan-3-yl)-3,5-difluorophenylcarbamate (5) (8.2 g, 68%) as a white solid.
LC-MS (ESI) m/z=375 [M+H]⁻.

Step 4: Preparation of 3-(4-(8-oxa-3-aza-bicyclo[3.2.1]octan-3-yl)-3,5-difluorophenyl)-5-(hydroxymethyl)oxazolidin-2-one (OBD-114)

To a solution of benzyl 4-(8-oxa-3-aza-bicyclo[3.2.1]octan-3-yl)-3,5-difluorophenylcarbamate (5) (8.2 g, 22.1 mmol) in THF (10 mL) at −78° C. under a nitrogen gas atmosphere was added n-BuLi (13.8 ml, 33.1 mmol), then the mixture was stirred at −78° C. for 30 min, after that the solution of (R)-oxiran-2-ylmethyl butyrate (4.7 g, 33.1 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford 3-(4-(8-oxa-3-aza-bicyclo[3.2.1]octan-3-yl)-3,5-difluorophenyl)-5-(hydroxymethyl)oxazolidin-2-one (OBD-114) (4.5 g, 60%) as a white solid.
LC-MS (ESI) m/z=341 [M+H]⁻.

Step 5: Preparation of (3-(4-(8-oxa-3-aza-bicyclo[3.2.1]octan-3-yl)-3,5-difluorophenyl)-2-oxooxazolidin-5-yl)methyl 4-methylbenzenesulfonate (7)

4-methylbenzene-1-sulfonyl chloride (5 g, 26.6 mmol) was added to a suspension of 3-(4-(8-oxa-3-aza-bicyclo[3.2.1]octan-3-yl)-3,5-difluorophenyl)-5-(hydroxymethyl)oxazolidin-2-one (OBD-114) (4.5 g, 13.3 mmol) and $Et_3N$ (2.7 g, 26.6 mmol) in DCM (10 mL) at 0° C. under a nitrogen gas atmosphere and the reaction mixture was stirred at room temperature for overnight, monitored by TLC. Quenched with ammonium chloride, extracted with DCM, the organic layer was concentrated under reduced pressure, and the crude material was purified by silica gel column chromatography (DCM:MeOH=50:1) to afford (3-(4-(8-oxa-3-aza-bicyclo[3.2.1]octan-3-yl)-3,5-difluorophenyl)-2-oxooxazolidin-5-yl)methyl 4-methylbenzenesulfonate (7) (5.58 g, 85%) as a white solid.
LC-MS (ESI) m/z=495 [M+H]⁻.

Step 6: Preparation of 5-((1H-1,2,3-triazol-1-yl)methyl)-3-(4-(8-oxa-3-aza-bicyclo[3.2.1]octan-3-yl)-3,5-difluorophenyl)oxazolidin-2-one (OBD-054)

To a solution of (3-(4-(8-oxa-3-aza-bicyclo[3.2.1]octan-3-yl)-3,5-difluorophenyl)-2-oxooxazolidin-5-yl)methyl 4-methylbenzenesulfonate (7) (300 mg, 0.6 mmol) and 1H-1,2,3-triazole (42 mg, 0.6 mmol) in DMF (10 mL) was added $K_2CO_3$ (166 mg, 1.2 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by prep-HPLC to afford 5-((1H-1,2,3-triazol-1-yl)methyl)-3-(4-(8-oxa-3-aza-bicyclo[3.2.1]octan-3-yl)-3,5-difluorophenyl)oxazolidin-2-one (OBD-054) (82 mg, 35%) as a white solid.
¹H NMR (300 MHz, DMSO-$d_6$) δ 8.14 (d, J=1.0 Hz, 1H), 7.73 (d, J=1.0 Hz, 1H), 7.17 (d, J=11.7 Hz, 2H), 5.11 (d, J=3.5 Hz, 1H), 4.79 (d, J=5.0 Hz, 2H), 4.18 (dd, J=23.1, 13.7 Hz, 3H), 3.91-3.70 (m, 1H), 3.23 (d, J=10.9 Hz, 3H), 2.72 (d, J=10.7 Hz, 3H), 2.07-1.61 (m, 7H).
LC-MS (ESI) m/z=392 [M+H]⁻.

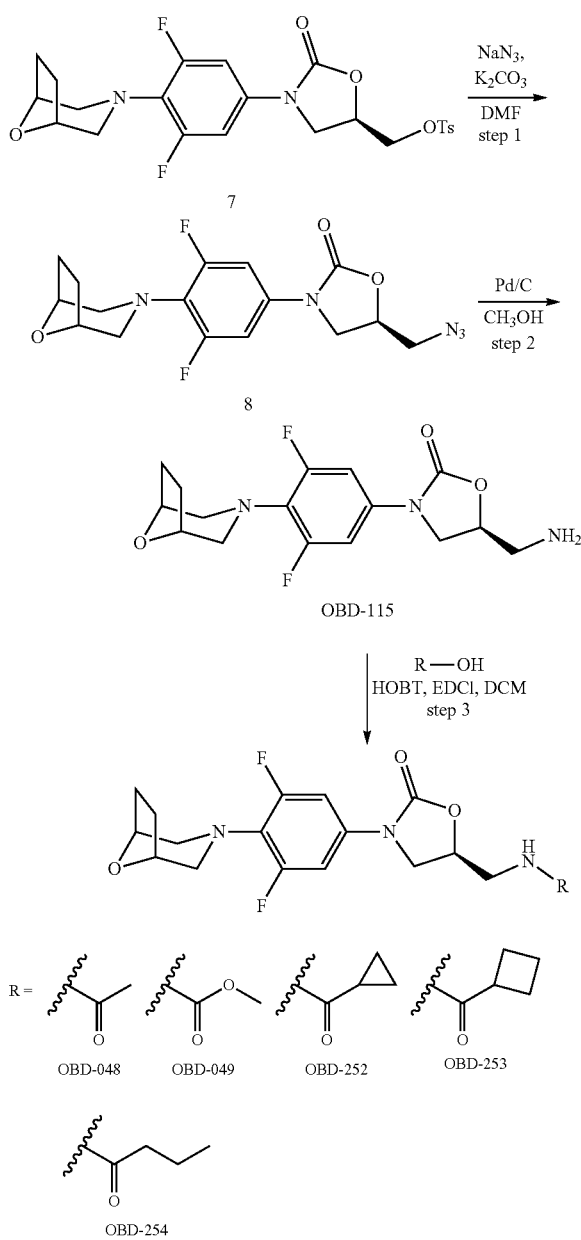

Step 1: Preparation of 3-(4-(8-oxa-3-aza-bicyclo [3.2.1]octan-3-yl)-3,5-difluorophenyl)-5-(azidomethyl)oxazolidin-2-one (8)

To a solution of (3-(4-(8-oxa-3-aza-bicyclo[3.2.1]octan-3-yl)-3,5-difluorophenyl)-2-oxooxazolidin-5-yl)methyl 4-methylbenzenesulfonate (7) (4 g, 8 mmol) and sodium azide (526 mg, 8 mmol) in DMF (10 mL) was added $K_2CO_3$ (2.2 mg, 16 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by silica gel column chromatography (PE:EA=2:1) to afford 3-(4-(8-oxa-3-aza-bicyclo[3.2.1]octan-3-yl)-3,5-difluorophenyl)-5-(azidomethyl)oxazolidin-2-one (8) (2.57 g, 88%) as a white solid.
LC-MS (ESI) m/z=366 [M+H]⁻.

Step 2: Preparation of 3-(4-(8-oxa-3-aza-bicyclo [3.2.1]octan-3-yl)-3,5-difluorophenyl)-5-(aminomethyl)oxazolidin-2-one (OBD-115)

To a solution of 3-(4-(8-oxa-3-aza-bicyclo[3.2.1]octan-3-yl)-3,5-difluorophenyl)-5-(azidomethyl)oxazolidin-2-one (8) (2.57 g, 7 mmol) in MeOH (10 mL) was added palladium carbon (300 mg) at 25° C., then the reaction mixture was stirred at room temperature for overnight under a hydrogen gas atmosphere, monitored by TLC. The filtrate was concentrated under reduced pressure, and the crude material was purified by silica gel column chromatography (DCM:MeOH=50:1) to afford 3-(4-(8-oxa-3-aza-bicyclo[3.2.1]octan-3-yl)-3,5-difluorophenyl)-5-(aminomethyl)oxazolidin-2-one (OBD-115) (2.1 g, 85%) as a white solid.
¹H NMR (400 MHz, CDCl₃) δ 7.40-7.20 (m, 2H), 4.62 (td, J=10.9, 4.9 Hz, 1H), 4.28 (s, 2H), 4.02 (t, J=8.9 Hz, 1H), 3.81 (dd, J=8.9, 6.3 Hz, 1H), 3.27 (d, J=10.4 Hz, 2H), 2.81 (ddd, J=28.3, 18.6, 7.7 Hz, 4H), 2.21 (s, 2H), 2.04-1.94 (m, 2H), 1.88-1.71 (m, 2H).
LC-MS (ESI) m/z=340 [M+H]⁻.

Step 3: Preparation of (OBD-048, 049, 252, 253, 254)

To a solution of 3-(4-(8-oxa-3-aza-bicyclo[3.2.1]octan-3-yl)-3,5-difluorophenyl)-5-(aminomethyl)oxazolidin-2-one (OBD-115) (200 mg, 0.59 mmol) and R—OH (0.59 mmol) in DCM (10 mL) were added HOBt (119 mg, 0.88 mmol), EDCI (225 mg, 1.18 mmol) and DIPEA (152 mg, 1.18 mmol) at 25° C., then the reaction mixture was stirred at 25° C. for 2 h under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=80:1) to afford (OBD-048, 049, 252, 253, 254) as a white solid.

OBD-048
¹H NMR (300 MHz, CDCl₃) δ 7.06 (d, J=10.9 Hz, 2H), 5.98 (s, 1H), 4.75 (s, 1H), 4.33 (s, 2H), 3.98 (t, J=8.8 Hz, 1H), 3.68 (dd, J=19.8, 11.0 Hz, 3H), 3.45 (d, J=10.9 Hz, 3H), 2.78 (d, J=11.1 Hz, 2H), 2.11 (d, J=6.6 Hz, 3H), 1.98 (d, J=24.1 Hz, 6H).
LC-MS (ESI) m/z=426 [M+H]⁺.

OBD-049
¹H NMR (301 MHz, CDCl₃) δ 7.06 (d, J=11.0 Hz, 2H), 5.15 (s, 1H), 4.75 (s, 1H), 4.32 (s, 2H), 3.97 (t, J=9.0 Hz, 2H), 3.80-3.70 (m, 4H), 3.56 (d, J=5.9 Hz, 2H), 3.42 (s, 2H), 2.77 (d, J=11.1 Hz, 2H), 2.10 (d, J=6.4 Hz, 2H), 1.92 (d, J=5.0 Hz, 2H).
LC-MS (ESI) m/z=397.7 [M+H]⁺.

OBD-252
¹H NMR (301 MHz, CDCl₃) δ 7.07 (d, J=11.0 Hz, 2H), 6.19 (s, 1H), 4.77 (s, 1H), 4.35 (s, 2H), 3.97 (t, J=8.9 Hz, 1H), 3.78-3.62 (m, 3H), 3.46 (d, J=10.1 Hz, 2H), 2.79 (d, J=11.1 Hz, 2H), 2.12 (d, J=6.5 Hz, 2H), 1.94 (d, J=4.5 Hz, 2H), 1.43-1.33 (m, 1H), 0.95 (dd, J=9.5, 4.4 Hz, 2H), 0.78 (d, J=6.4 Hz, 2H).
LC-MS (ESI) m/z=408.1 [M+H]⁺.

OBD-253
¹H NMR (301 MHz, CDCl₃) δ 7.07 (d, J=11.0 Hz, 2H), 5.88 (s, 1H), 4.76 (s, 1H), 4.34 (s, 2H), 3.98 (t, J=9.0 Hz, 1H), 3.79-3.59 (m, 3H), 3.45 (d, J=10.8 Hz, 2H), 3.12-2.97 (m, 1H), 2.79 (d, J=11.3 Hz, 2H), 2.38-2.10 (m, 6H), 2.00-1.79 (m, 4H).
LC-MS (ESI) m/z=422.1 [M+H]⁺.

OBD-254

¹H NMR (301 MHz, CDCl₃) δ 7.17-6.96 (m, 2H), 6.07 (s, 1H), 4.78 (s, 1H), 4.34 (s, 2H), 3.98 (t, J=8.9 Hz, 1H), 3.82-3.64 (m, 3H), 3.45 (d, J=10.0 Hz, 2H), 2.79 (d, J=11.2 Hz, 2H), 2.38-2.06 (m, 4H), 1.98-1.78 (m, 2H), 1.63 (dq, J=14.7, 7.3 Hz, 2H), 1.26 (s, 1H), 0.90 (t, J=7.4 Hz, 3H).
LC-MS (ESI) m/z=410.1 [M+H]⁺.

temperature for overnight, monitored by TLC. The filtrate was concentrated under reduced pressure to afford 4-(8-oxa-3-aza-bicyclo[3.2.1]octan-3-yl)-3-fluorobenzenamine (4) (7.3 g, 91%) as a white oil, and the crude material was used for next reaction without further purification.
LC-MS (ESI) m/z=223 [M+H]⁻.

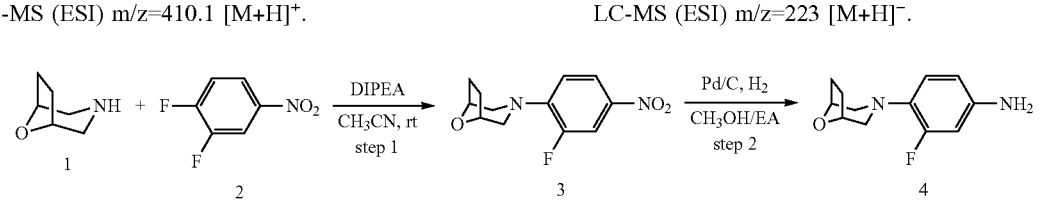

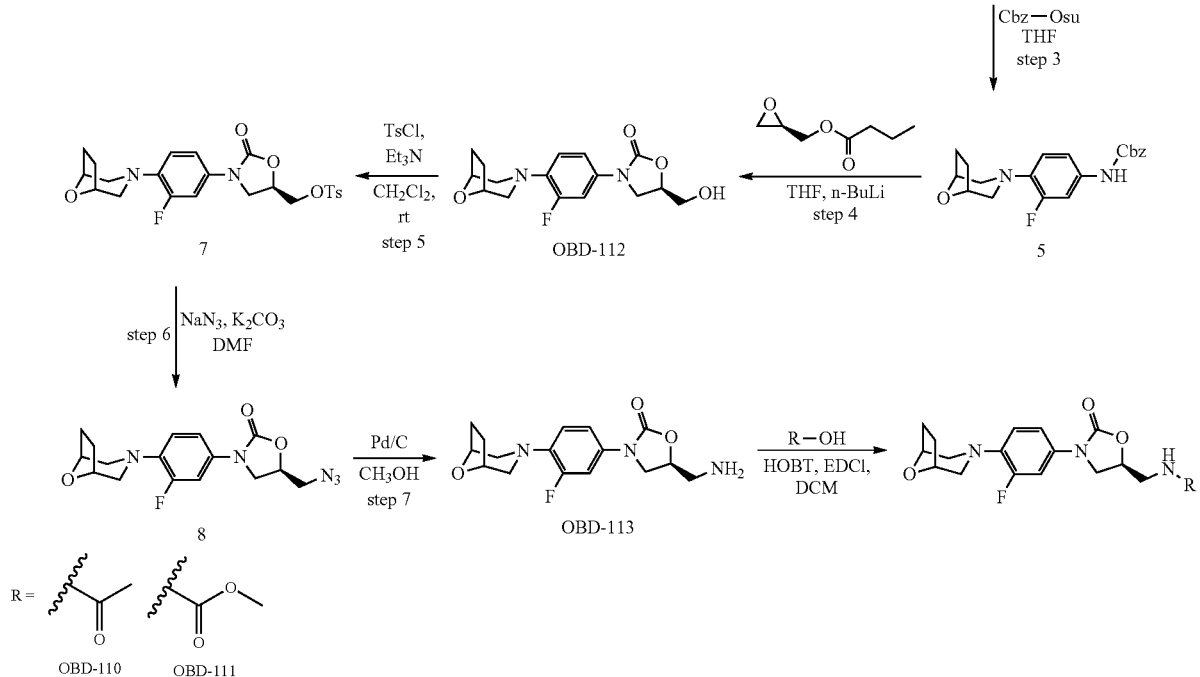

Step 1: Preparation of 3-(2-fluoro-4-nitrophenyl)-8-oxa-3-aza-bicyclo[3.2.1]octane (3)

To a solution of 8-oxa-3-aza-bicyclo[3.2.1]octane (1) (5.0 g, 44.2 mmol) and 1,2-difluoro-4-nitrobenzene (7.7 g, 48.6 mmol) in DMF (10 mL) was added K₂CO₃ (12.2 g, 88.4 mmol) at 25° C. then the reaction mixture was stirred at 80° C. for 2 h under a nitrogen gas atmosphere, monitored by TLC. The mixture was concentrated under reduced pressure, and the crude material was purified by silica gel column chromatography (EA:PE=5:1) to afford 3-(2-fluoro-4-nitrophenyl)-8-oxa-3-aza-bicyclo[3.2.1]octane (3) (9.1 g, 82%) as a yellow solid.
LC-MS (ESI) m/z=253 [M+H]⁻.

Step 2: Preparation of 4-(8-oxa-3-aza-bicyclo[3.2.1]octan-3-yl)-3-fluorobenzenamine (4)

To a solution of 3-(2-fluoro-4-nitrophenyl)-8-oxa-3-aza-bicyclo[3.2.1]octane (3) (3) (9.1 g, 36.2 mmol) and Palladium carbon (1 g) in MeOH (15 mL), then under a hydrogen gas atmosphere and the reaction mixture was stirred at room

Step 3: Preparation of benzyl 4-(8-oxa-3-aza-bicyclo[3.2.1]octan-3-yl)-3-fluorophenylcarbamate (5)

Carbonic acid, 2,5-dioxo-1-pyrrolidinyl phenylmethyl ester (16.4 g, 65.88 mmol) was added to a suspension of 4-(8-oxa-3-aza-bicyclo[3.2.1]octan-3-yl)-3-fluorobenzenamine (4) (7.3 g, 32.9 mmol) in THF (100 mL) at 0° C. under a nitrogen gas atmosphere and the reaction mixture was stirred at 50° C. for 5 h, monitored by TLC. The mixture was concentrated under reduced pressure, and the crude material was purified by silica gel column chromatography (PE:EA=10:1) to afford benzyl 4-(8-oxa-3-aza-bicyclo[3.2.1]octan-3-yl)-3-fluorophenylcarbamate (5) (7.1 g, 61%) as a white solid.
LC-MS (ESI) m/z=357 [M+H]⁻.

Step 4: Preparation of 3-(4-(8-oxa-3-aza-bicyclo[3.2.1]octan-3-yl)-3-fluorophenyl)-5-(hydroxymethyl)oxazolidin-2-one (OBD-112)

To a solution of benzyl 4-(8-oxa-3-aza-bicyclo[3.2.1]octan-3-yl)-3-fluorophenylcarbamate (5) (7.1 g, 20.1 mmol) in THF (10 mL) at −78° C. under a nitrogen gas atmosphere was added n-BuLi (12.5 ml, 30.1 mmol), then the mixture was stirred at −78° C. for 30 min, after that the solution of (R)-oxiran-2-ylmethyl butyrate (4.3 g, 30.1 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford 3-(4-(8-oxa-3-aza-bicyclo[3.2.1]octan-3-yl)-3-fluorophenyl)-5-(hydroxymethyl)oxazolidin-2-one (OBD-112) (3.9 g, 60%) as a white solid.

$^1$H NMR (301 MHz, DMSO-$d_6$) δ 7.46 (dd, J=15.4, 2.5 Hz, 1H), 7.14 (d, J=6.5 Hz, 1H), 7.03-6.84 (m, 1H), 5.18 (s, 1H), 4.64 (d, J=3.3 Hz, 1H), 4.31 (s, 2H), 4.00 (t, J=9.0 Hz, 1H), 3.81-3.72 (m, 1H), 3.57 (d, J=24.9 Hz, 2H), 3.00 (d, J=11.2 Hz, 3H), 2.85 (d, J=10.9 Hz, 2H), 2.08-1.63 (m, 5H).

LC-MS (ESI) m/z=323 [M+H]$^-$.

Step 5: Preparation of (3-(4-(8-oxa-3-aza-bicyclo[3.2.1]octan-3-yl)-3-fluorophenyl)-2-oxooxazolidin-5-yl) methyl 4-methylbenzenesulfonate (7)

4-methylbenzene-1-sulfonyl chloride (2.3 g, 24 mmol) was added to a suspension of 3-(4-(8-oxa-3-aza-bicyclo[3.2.1]octan-3-yl)-3-fluorophenyl)-5-(hydroxymethyl)oxazolidin-2-one (OBD-112) (3.9 g, 12 mmol) and Et$_3$N (1.2 g, 24 mmol) in DCM (10 mL) at 0° C. under a nitrogen gas atmosphere and the reaction mixture was stirred at room temperature for overnight, monitored by TLC. Quenched with ammonium chloride, extracted with DCM, the organic layer was concentrated under reduced pressure, and the crude material was purified by silica gel column chromatography (DCM:MeOH=50:1) to afford (3-(4-(8-oxa-3-aza-bicyclo[3.2.1]octan-3-yl)-3-fluorophenyl)-2-oxooxazolidin-5-yl)methyl 4-methylbenzenesulfonate (7) (4.86 g, 85%) as a white solid.

LC-MS (ESI) m/z=477 [M+H]$^-$.

Step 6: Preparation of 3-(4-(8-oxa-3-aza-bicyclo[3.2.1]octan-3-yl)-3-fluorophenyl)-5-(azidomethyl)oxazolidin-2-one (8)

To a solution of (3-(4-(8-oxa-3-aza-bicyclo[3.2.1]octan-3-yl)-3-fluorophenyl)-2-oxooxazolidin-5-yl)methyl 4-methylbenzenesulfonate (7) (4.86 g, 10.2 mmol) and sodium azide (663 mg, 10.2 mmol) in DMF (10 mL) was added K$_2$CO$_3$ (1.4 g, 20.4 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by silica gel column chromatography (PE:EA=2:1) to afford 3-(4-(8-oxa-3-aza-bicyclo[3.2.1]octan-3-yl)-3-fluorophenyl)-5-(azidomethyl)oxazolidin-2-one (8) (2.97 g, 84%) as a white solid.

LC-MS (ESI) m/z=348 [M+H]$^-$.

Step 7: Preparation of 3-(4-(8-oxa-3-aza-bicyclo[3.2.1]octan-3-yl)-3-fluorophenyl)-5-(aminomethyl)oxazolidin-2-one (OBD-113)

To a solution of 3-(4-(8-oxa-3-aza-bicyclo[3.2.1]octan-3-yl)-3-fluorophenyl)-5-(azidomethyl)oxazolidin-2-one (8) (2.97 g, 8.5 mmol) in MeOH (10 mL) was added palladium carbon (300 mg) at 25° C., then the reaction mixture was stirred at room temperature for overnight under a hydrogen gas atmosphere, monitored by TLC. The filtrate was concentrated under reduced pressure, and the crude material was purified by silica gel column chromatography (DCM:MeOH=50:1) to afford 3-(4-(8-oxa-3-aza-bicyclo[3.2.1]octan-3-yl)-3-fluorophenyl)-5-(aminomethyl)oxazolidin-2-one (OBD-113) (2.2 g, 81%) as a white solid.

$^1$H NMR (301 MHz, CDCl$_3$) δ 7.53-7.35 (m, 1H), 7.09 (d, J=8.9 Hz, 1H), 6.96-6.73 (m, 1H), 4.66 (s, 1H), 4.40 (s, 1H), 4.00 (t, J=8.7 Hz, 1H), 3.89-3.74 (m, 1H), 3.06 (dd, J=21.9, 11.0 Hz, 6H), 2.27-1.85 (m, 4H).

LC-MS (ESI) m/z=322 [M+H]$^-$.

Step 8: Preparation of (OBD-110, 111)

To a solution of 3-(4-(8-oxa-3-aza-bicyclo[3.2.1]octan-3-yl)-3-fluorophenyl)-5-(aminomethyl)oxazolidin-2-one (OBD-113) (200 mg, 0.62 mmol) and R—OH (0.62 mmol) in DCM (10 mL) were added HOBt (126 mg, 0.96 mmol), EDCI (237 mg, 1.24 mmol) and DIPEA (160 mg, 1.24 mmol) at 25° C., then the reaction mixture was stirred at 25° C. for 2 h under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=80:1) to afford (OBD-110, 111) as a white solid.

OBD-110

$^1$H NMR (301 MHz, CDCl$_3$) δ 7.51-7.32 (m, 1H), 7.02 (d, J=8.5 Hz, 1H), 6.83 (t, J=9.1 Hz, 1H), 6.07 (s, 1H), 4.74 (s, 1H), 4.39 (s, 2H), 4.00 (t, J=8.9 Hz, 1H), 3.85-3.49 (m, 3H), 3.05 (dd, J=23.2, 10.6 Hz, 4H), 2.32-1.67 (m, 8H).

LC-MS (ESI) m/z=426 [M+H]$^+$.

OBD-111

$^1$H NMR (301 MHz, CDCl$_3$) δ 7.41 (s, 1H), 7.03 (s, 1H), 6.17 (s, OH), 5.20-5.02 (m, 1H), 4.85-4.62 (m, 1H), 4.41 (s, 1H), 4.01 (s, 1H), 3.68 (s, 3H), 3.09 (d, J=7.9 Hz, 2H), 2.05 (d, J=42.7 Hz, 3H), 1.83-1.35 (m, 3H).

LC-MS (ESI) m/z=397.7 [M+H]$^+$.

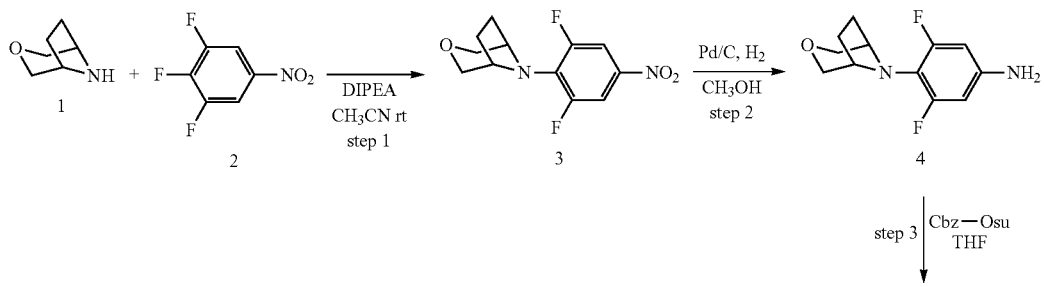

-continued

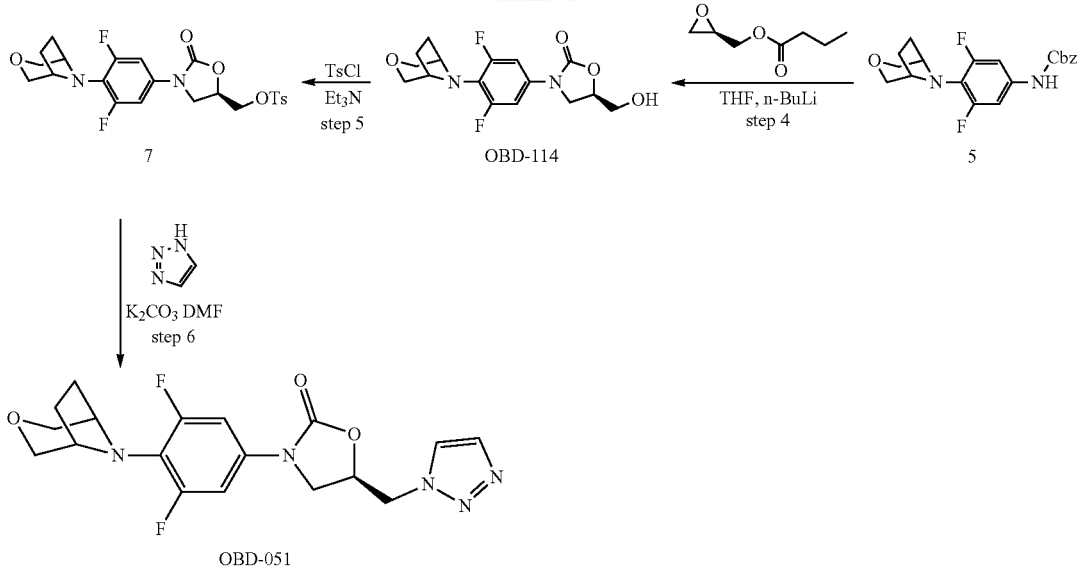

Step 1: Preparation of 8-(2,6-difluoro-4-nitrophenyl)-3-oxa-8-aza-bicyclo[3.2.1]octane (3)

To a solution of 3-oxa-8-aza-bicyclo[3.2.1]octane (1) (5.0 g, 44.2 mmol) and 1,2,3-trifluoro-5-nitrobenzene (8.6 g, 48.6 mmol) in DMF (10 mL) was added $K_2CO_3$ (12.2 g, 88.4 mmol) at 25° C. then the reaction mixture was stirred at 80° C. for 2 h under a nitrogen gas atmosphere, monitored by TLC. The mixture was concentrated under reduced pressure, and the crude material was purified by silica gel column chromatography (EA:PE=3:1) to afford 8-(2,6-difluoro-4-nitrophenyl)-3-oxa-8-aza-bicyclo[3.2.1]octane (3) (9.3 g, 78%) as a yellow solid.

LC-MS (ESI) m/z=271 [M+H]⁻.

Step 2: Preparation of 4-(3-oxa-8-aza-bicyclo[3.2.1]octan-8-yl)-3,5-difluorobenzenamine (4)

To a solution of 3-(2,6-difluoro-4-nitrophenyl)-8-oxa-3-aza-bicyclo[3.2.1]octane (3) (9.3 g, 34.4 mmol) and Palladium carbon (1 g) in MeOH (15 mL), then under a hydrogen gas atmosphere and the reaction mixture was stirred at room temperature for overnight, monitored by TLC. The filtrate was concentrated under reduced pressure to afford 4-(3-oxa-8-aza-bicyclo[3.2.1]octan-8-yl)-3,5-difluorobenzenamine (4) (7.8 g, 95%) as a white oil, and the crude material was used for next reaction without further purification.

LC-MS (ESI) m/z=241 [M+H]⁺.

Step 3: Preparation of benzyl 4-(3-oxa-8-aza-bicyclo[3.2.1]octan-8-yl)-3,5-difluorophenylcarbamate (5)

Carbonic acid, 2,5-dioxo-1-pyrrolidinyl phenylmethyl ester (12 g, 48.7 mmol) was added to a suspension of 4-(3-oxa-8-aza-bicyclo[3.2.1]octan-3-yl)-3,5-difluorobenzenamine (4) (7.8 g, 32.5 mmol) in THF (100 mL) at 0° C. under a nitrogen gas atmosphere and the reaction mixture was stirred at 50° C. for 5 h, monitored by TLC. The mixture was concentrated under reduced pressure, and the crude material was purified by silica gel column chromatography (PE:EA=10:1) to afford benzyl 4-(3-oxa-8-aza-bicyclo[3.2.1]octan-8-yl)-3,5-difluorophenylcarbamate (5) (8.2 g, 68%) as a white solid.

LC-MS (ESI) m/z=375 [M+H]⁻.

Step 4: Preparation of (5R)-3-(4-(3-oxa-8-aza-bicyclo[3.2.1]octan-8-yl)-3,5-difluorophenyl)-5-(hydroxymethyl)oxazolidin-2-one (6)

To a solution of benzyl 4-(3-oxa-8-aza-bicyclo[3.2.1]octan-8-yl)-3,5-difluorophenylcarbamate (5) (8.2 g, 22.1 mmol) in THF (10 mL) at −78° C. under a nitrogen gas atmosphere was added n-BuLi (13.8 ml, 33.1 mmol), then the mixture was stirred at −78° C. for 30 min, after that the solution of (R)-oxiran-2-ylmethyl butyrate (4.7 g, 33.1 mmol) in THF was added to the mixture at −78° C., then warmed to room temperature and stirred for overnight, monitored by TLC. Quenched with ammonium chloride, extracted with EA, the organic layer was concentrated under reduced pressure, and the crude material was purified by silica gel column chromatography (DCM:MeOH=70:1) to afford (5R)-3-(4-(3-oxa-8-aza-bicyclo[3.2.1]octan-8-yl)-3,5-difluorophenyl)-5-(hydroxymethyl)oxazolidin-2-one (6) (4.5 g, 60%) as a white solid.

LC-MS (ESI) m/z=341 [M+H]⁻.

Step 5: Preparation of ((R)-3-(4-(3-oxa-8-aza-bicyclo[3.2.1]octan-8-yl)-3,5-difluorophenyl)-2-oxooxazolidin-5-yl)methyl 4-methylbenzenesulfonate (7)

4-methylbenzene-1-sulfonyl chloride (5 g, 26.6 mmol) was added to a suspension of (5R)-3-(4-(3-oxa-8-aza-bicyclo[3.2.1]octan-8-yl)-3,5-difluorophenyl)-5-(hydroxymethyl)oxazolidin-2-one (6) (4.5 g, 13.3 mmol) and $Et_3N$ (2.7 g, 26.6 mmol) in DCM (10 mL) at 0° C. under a nitrogen gas atmosphere and the reaction mixture was stirred at room temperature for overnight, monitored by TLC. Quenched with ammonium chloride, extracted with DCM, the organic layer was concentrated under reduced pressure, and the crude material was purified by silica gel column chromatography (DCM:MeOH=50:1) to afford ((R)-3-(4-(3-oxa-8- aza-bicyclo[3.2.1]octan-8-yl)-3,5-difluorophenyl)-2-oxoox-azolidin-5-yl)methyl 4-methylbenzenesulfonate (7) (5.58 g, 85%) as a white solid.

LC-MS (ESI) m/z=495 [M+H]⁻.

Step 6: Preparation of (5R)-5-((1H-1,2,3-triazol-1-yl)methyl)-3-(4-(3-oxa-8-aza-bicyclo[3.2.1]octan-8-yl)-3,5-difluorophenyl)oxazolidin-2-one (OBD-055)

To a solution of ((R)-3-(4-(3-oxa-8-aza-bicyclo[3.2.1]octan-8-yl)-3,5-difluorophenyl)-2-oxooxazolidin-5-yl)methyl 4-methylbenzenesulfonate (7) (300 mg, 0.6 mmol) and 1H-1,2,3-triazole (42 mg, 0.6 mmol) in DMF (10 mL) was added K₂CO₃ (166 mg, 1.2 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by prep-HPLC to afford (5R)-5-((1H-1,2,3-triazol-1-yl)methyl)-3-(4-(3-oxa-8-aza-bicyclo[3.2.1]octan-8-yl)-3,5-difluorophenyl)oxazolidin-2-one (OBD-055) (82 mg, 35%) as a white solid.

¹H NMR (301 MHz, CDCl₃) δ 7.76 (d, J=5.7 Hz, 2H), 6.94 (d, J=12.1 Hz, 2H), 5.06 (s, 1H), 4.78 (d, J=4.1 Hz, 1H), 4.08 (t, J=9.0 Hz, 1H), 3.90 (t, J=8.9 Hz, 4H), 3.58 (d, J=10.4 Hz, 2H), 2.04 (t, J=8.0 Hz, 4H), 1.76 (s, 2H).

LC-MS (ESI) m/z=391.8 [M+H]⁺.

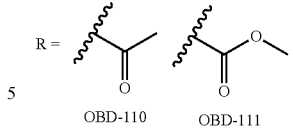

-continued

OBD-110    OBD-111

Step 1: Preparation of (5R)-3-(4-(3-oxa-8-aza-bicyclo[3.2.1]octan-8-yl)-3,5-difluorophenyl)-5-(azidomethyl)oxazolidin-2-one (8)

To a solution of ((R)-3-(4-(3-oxa-8-aza-bicyclo[3.2.1]octan-8-yl)-3,5-difluorophenyl)-2-oxooxazolidin-5-yl)methyl 4-methylbenzenesulfonate (7) (4 g, 8 mmol) and sodium azide (526 mg, 8 mmol) in DMF (10 mL) was added K₂CO₃ (2.2 g, 16 mmol) at 25° C., then the reaction mixture was stirred at 80° C. for 1 h under a nitrogen gas atmosphere, monitored by TLC. Quenched with ammonium chloride, extracted with EA, the organic layer was concentrated under reduced pressure, and the crude material was purified by silica gel column chromatography (PE:EA=2:1) to afford (5R)-3-(4-(3-oxa-8-aza-bicyclo[3.2.1]octan-8-yl)-3,5-difluorophenyl)-5-(azidomethyl)oxazolidin-2-one (8) (2.4 g, 82%) as a white solid.

LC-MS (ESI) m/z=366 [M+H]⁻.

Step 2: Preparation of (5S)-3-(4-(3-oxa-8-aza-bicyclo[3.2.1]octan-8-yl)-3,5-difluorophenyl)-5-(aminomethyl)oxazolidin-2-one (9)

To a solution of (5R)-3-(4-(3-oxa-8-aza-bicyclo[3.2.1]octan-8-yl)-3,5-difluorophenyl)-5-(azidomethyl)oxazolidin-2-one (8) (2.4 g, 6.5 mmol) in MeOH (10 mL) was added palladium carbon (300 mg) at 25° C., then the reaction mixture was stirred at room temperature for overnight under a hydrogen gas atmosphere, monitored by TLC. The filtrate was concentrated under reduced pressure, and the crude material was purified by silica gel column chromatography (DCM:MeOH=50:1) to afford (5S)-3-(4-(3-oxa-8-aza-bicyclo[3.2.1]octan-8-yl)-3,5-difluorophenyl)-5-(aminomethyl)oxazolidin-2-one (9) (1.9 g, 86%) as a white solid.

LC-MS (ESI) m/z=340 [M+H]⁻.

Step 3: Preparation of (OBD-051, 052)

To a solution of (5S)-3-(4-(3-oxa-8-aza-bicyclo[3.2.1]octan-8-yl)-3,5-difluorophenyl)-5-(aminomethyl)oxazolidin-2-one (9) (200 mg, 0.59 mmol) and R—OH (0.59 mmol) in DCM (10 mL) were added HOBt (119 mg, 0.88 mmol), EDCI (224 mg, 1.18 mmol) and DIPEA (152 mg, 1.18 mmol) at 25° C., then the reaction mixture was stirred at 25° C. for 2 h under a nitrogen gas atmosphere, monitored by TLC. Quenched with ammonium chloride, extracted with DCM, the organic layer was concentrated under reduced pressure, and the crude material was purified by silica gel column chromatography (DCM:MeOH=80:1) to afford (OBD-051, 052) as a white solid.

OBD-051

¹H NMR (301 MHz, CDCl₃) δ 6.99 (t, J=9.3 Hz, 2H), 5.38 (s, 1H), 4.84-4.69 (m, 1H), 3.98-3.86 (m, 4H), 3.75-3.60 (m, 4H), 2.24-1.97 (m, 8H).

LC-MS (ESI) m/z=381.9 [M+H]⁺.

OBD-052

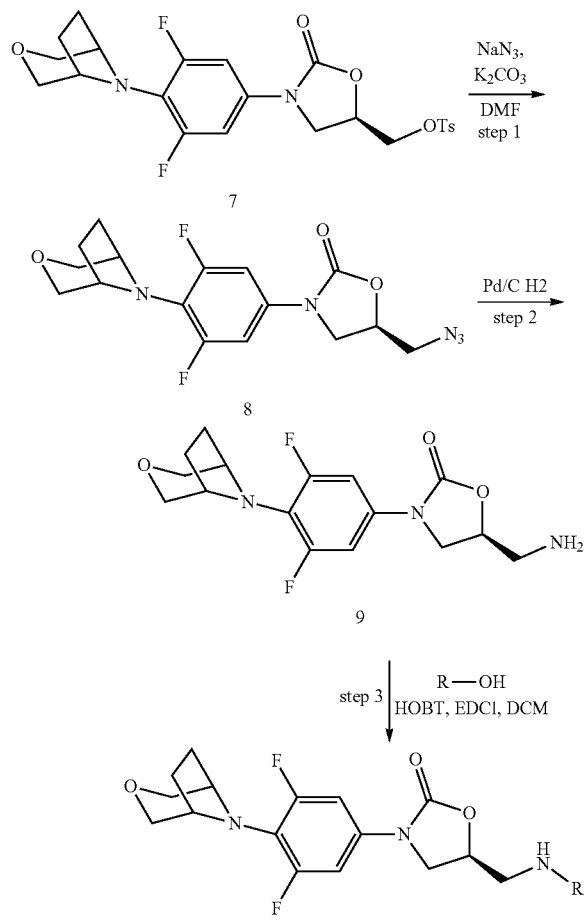

¹H NMR (301 MHz, CDCl₃) δ 7.06 (d, J=12.4 Hz, 2H), 5.10 (s, 1H), 4.75 (s, 1H), 4.02-3.86 (m, 4H), 3.68 (s, 2H), 3.58 (d, J=9.6 Hz, 2H), 2.02 (d, J=7.7 Hz, 2H), 1.80 (s, 4H), 0.98 (d, J=6.7 Hz, 3H).

LC-MS (ESI) m/z=398.0 [M+H]⁺.

Example 13

Synthesis of Additional Embodiments of the Invention

In a manner similar to those disclosed in Examples 8 and 12 above, the following compounds were made:

OTB-518

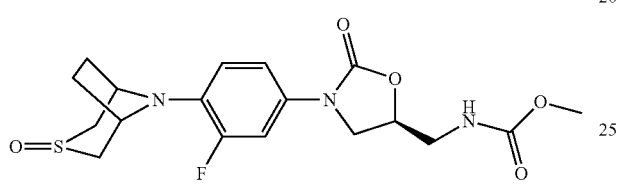

Methyl (((5S)-3-(3-fluoro-4-((1R,5S)-3-oxido-3-thia-8-azabicyclo[3.2.1]octan-8-yl)phenyl)-2-oxooxazolidin-5-yl)methyl)carbamate 1H-NMR (400 MHz, CDCl3) δ: 7.45 (d, J=16.4 Hz, 1H), 7.12 (d, J=7.6 Hz, 1H), 6.83 (t, J=9.2 Hz, 1H), 5.17-5.12 (m, 1H), 4.80-4.74 (m, 1H), 4.62 (brs, 2H), 4.02 (t, J=8.4 Hz, 1H), 3.77 (t, J=8.0 Hz, 1H), 3.69-3.53 (m, 4H), 3.45 (d, J=10.4 Hz, 2H), 2.86 (d, J=12.0 Hz, 2H), 2.22 (m, 2H), 1.90-1.88 (m, 2H).

HRMS (ESI): m/z [M+H]+ calcd for C₁₈H₂₃FN₃O₅S: 412.1344; found: 412.1359

OTB-519

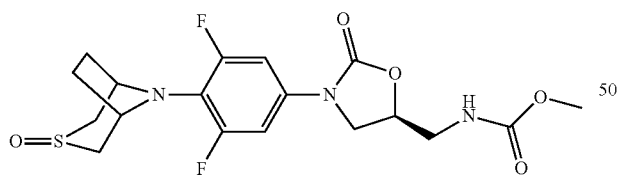

Methyl (((5S)-3-(3,5-difluoro-4-((1R,5S)-3-oxido-3-thia-8-azabicyclo[3.2.1]octan-8-yl)phenyl)-2-oxooxazolidin-5-yl)methyl)carbamate 1H-NMR (400 MHz, CDCl3) δ: 7.13 (d, J=12.4 Hz, 2H), 5.10 (m, 1H), 4.80-4.74 (m, 1H), 4.46 (brs, 2H), 3.98 (t, J=8.8 Hz, 1H), 3.76-3.69 (m, 4H), 3.60-3.49 (m, 3H), 2.94 (d, J=12.0 Hz, 2H), 2.20-2.18 (m, 2H), 1.87-1.85 (m, 2H).

HRMS (ESI): m/z [M+H]+ calcd for C₁₈H₂₂F₂N₃O₅S: 430.1248; found: 430.1259

OTB-517

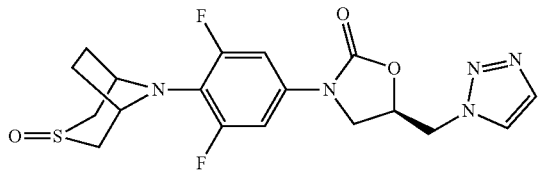

(5R)-5-((1H-1,2,3-Triazol-1-yl)methyl)-3-(3,5-difluoro-4-((1R,5S)-3-oxido-3-thia-8-azabicyclo[3.2.1]octan-8-yl)phenyl)oxazolidin-2-one 1H-NMR (400 MHz, CDCl3) δ: 7.79 (s, 1H), 7.77 (s, 1H), 6.98 (d, J=12.0 Hz, 2H), 5.10-5.04 (m, 1H), 4.79 (d, J=4.0 Hz, 2H), 4.43 (brs, 2H), 4.10 (t, J=9.2 Hz, 1H), 3.91-3.87 (m, 1H), 3.55 (d, J=12.4 Hz, 2H), 2.92 (d, J=10.4 Hz, 2H), 2.19-2.16 (m, 2H), 1.88-1.83 (m, 2H).

HRMS (ESI): m/z [M+H]+ calcd for C₁₈H₂₀F₂N₅O₃S: 424.1249; found: 424.1271

OTB-523

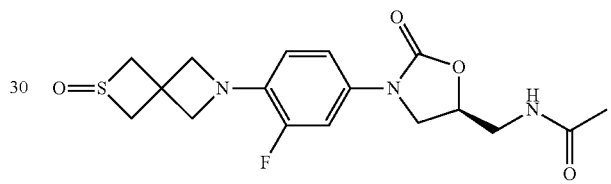

(S)—N-((3-(3-Fluoro-4-(2-oxido-2-thia-6-azaspiro[3.3]heptan-6-yl)phenyl)-2-oxooxazolidin-5-yl)methyl)acetamide 1H-NMR (400 MHz, CDCl3) δ: 7.34 (d, J=14.0 Hz, 1H), 7.01 (d, J=8.8 Hz, 1H), 6.41 (t, J=8.8 Hz, 1H), 6.12 (t, J=6.0 Hz, 1H), 4.76-4.73 (m, 1H), 4.01-3.90 (m, 7H), 3.74-3.66 (m, 2H), 3.62-3.56 (m, 1H), 3.45-3.40 (m, 2H), 2.02 (s, 3H).

HRMS (ESI): m/z [M+H]+ calcd for C17H21FN3O4S: 382.1237; found: 382.1217

OTB-515

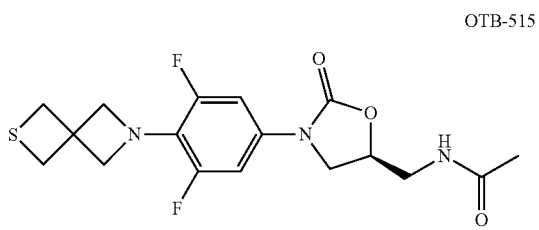 [SMILES: CC(=O)NC[C@H]1CN(c2cc(F)c(N3CC4(CSC4)C3)c(F)c2)C(=O)O1]

(S)—N-((3-(3,5-Difluoro-4-(2-thia-6-azaspiro[3.3]heptan-6-yl)phenyl)-2-oxooxazolidin-5-yl)methyl)acetamide HNMR (400 MHz, CDCl3) δ: 7.03-6.94 (m, 2H), 6.09 (t, J=5.6 Hz, 1H), 4.75 (q, J=3.2 Hz, J=2.8 Hz, 1H), 4.16 (s, 4H), 3.95 (t, J=8.8 Hz, 1H), 3.72-3.61 (m, 3H), 3.40 (s, 4H), 2.03 (s, 3H).

m/z [M+Na]+ calcd for C$_{17}$H$_{19}$F$_2$N$_3$O$_3$S:383.1115; found: 384.0

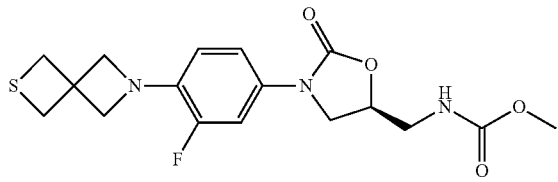

OTB-248

(S)-Methyl ((3-(3-fluoro-4-(2-thia-6-azaspiro[3.3]
heptan-6-yl)phenyl)-2-oxooxazolidin-5-yl)methyl)
carbamate HNMR (400 MHz, CDCl3) δ: 7.33 (q, J=2.0 Hz, J=11.6 Hz, 2H), 7.01 (d, J=2.0 Hz, 1H), 6.44 (t, J=9.2 Hz, 1H), 5.15 (bs, 1H), 4.77-4.73 (m, 1H), 4.01-3.97 (m, 4H), 3.76-3.52 (m, 6H), 3.42 (s, 4H).
m/z [M+Na]+ calcd for C$_{17}$H$_{20}$FN$_3$O$_4$S:381.1159; found: 404.1

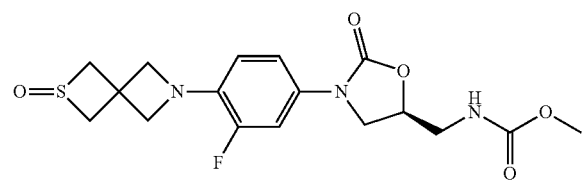

OTB-256

(S)-Methyl ((3-(3-fluoro-4-(2-oxido-2-thia-6-
azaspiro[3.3]heptan-6-yl)phenyl)-2-oxooxazolidin-5-
yl)methyl)carbamate 1H-NMR (400 MHz, CDCl3) δ: 7.51 (d, J=14.4 Hz, 1H), 7.04 (d, J=8.4 Hz, 1H), 6.80 (t, J=8.8 Hz, 1H), 5.09 (brs, 1H), 4.76 (brs, 1H), 4.16 (d, J=13.2 Hz, 4H), 4.01-3.98 (m, 3H), 3.77-3.75 (m, 1H), 3.69 (s, 3H), 3.61-3.55 (m, 2H), 3.46-3.44 (m, 2H).
HRMS (ESI): m/z [M+H]+ calcd for C$_{17}$H$_{21}$FN$_3$O$_5$S: 398.1186; found: 398.1166

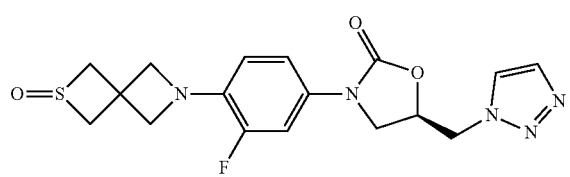

OTB-247

(R)-5-((1H-1,2,3-Triazol-1-yl)methyl)-3-(3-fluoro-4-
(2-oxido-2-thia-6-azaspiro[3.3]heptan-6-yl)phenyl)
oxazolidin-2-one HNMR (400 MHz, CDCl3) δ: 7.78 (d, J=0.8 Hz, 1H), 7.74 (d, J=0.8 Hz, 1H), 7.18 (dd, J=13.6, 2.4 Hz, 1H), 6.87 (dd, J=8.8, 1.6 Hz, 1H), 6.37 (t, J=9.2 Hz, 1H), 5.04-5.00 (m, 1H), 4.77 (d, J=3.6 Hz, 2H), 4.08 (t, J=9.2 Hz, 1H), 3.96 (dd, J=10.4, 1.6 Hz, 4H), 3.92-3.89 (m, 3H), 3.42-3.39 (m, 2H).
m/z [M+H]+ calcd for C$_{17}$H$_{18}$FN$_5$O$_3$S: 391.1114; found: 392.0

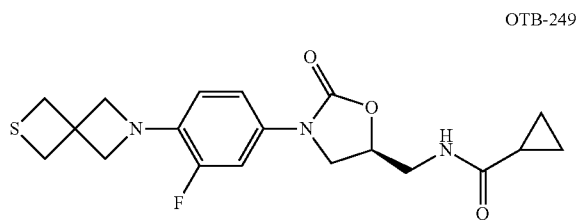 [SMILES: O=C(NC[C@H]1CN(c2ccc(N3CC4(CSC4)C3)c(F)c2)C(=O)O1)C1CC1]

OTB-249

(S)—N-((3-(3-Fluoro-4-(2-thia-6-azaspiro[3.3]hep-
tan-6-yl)phenyl)-2-oxooxazolidin-5-yl)methyl)cyclo-
propanecarboxamide 1H-NMR (400 MHz, CDCl3) δ: 7.33 (d, J=14.0 Hz, 1H), 6.99 (d, J=8.8 Hz, 1H), 6.47 (t, J=9.2 Hz, 1H), 6.13 (brs, 1H), 4.73 (m, 1H), 3.98-3.95 (m, 5H), 3.73-3.66 (m, 3H), 3.42 (s, 4H), 1.39-1.37 (m, 1H), 0.97-0.91 (m, 2H), 0.78-0.76 (m, 2H).
HRMS (ESI): m/z [M+H]+ calcd for C$_{19}$H$_{23}$FN$_3$O$_3$S: 392.1444; found: 392.1426

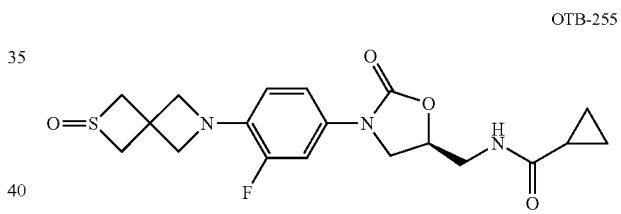

OTB-255

(S)—N-((3-(3-Fluoro-4-(2-oxido-2-thia-6-azaspiro
[3.3]heptan-6-yl)phenyl)-2-oxooxazolidin-5-yl)
methyl)cyclopropanecarboxamide 1H-NMR (400 MHz, CDCl3) δ: 7.35 (d, J=14.0 Hz, 1H), 7.01 (d, J=8.4 Hz, 1H), 6.44 (t, J=9.2 Hz, 1H), 6.13 (brs, 1H), 4.74 (m, 1H), 4.00-3.91 (m, 7H), 3.75-3.62 (m, 3H), 3.47-3.41 (m, 2H), 1.38-1.37 (m, 1H), 0.97-0.92 (m, 2H), 0.78-0.76 (m, 2H).
HRMS (ESI): m/z [M+H]+ calcd for C19H23FN3O4S: 408.1393; found: 408.1378

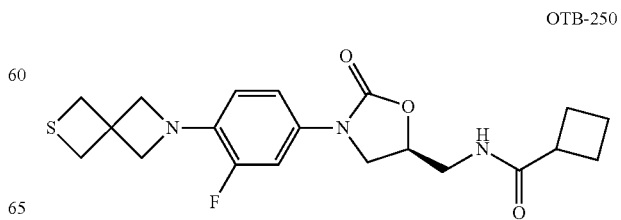

OTB-250

(S)—N-((3-(3-Fluoro-4-(2-thia-6-azaspiro[3.3]heptan-6-yl)phenyl)-2-oxooxazolidin-5-yl)methyl)cyclobutanecarboxamide HNMR (400 MHz, CDCl3) δ: 7.76 (d, J=8.8 Hz, 2H), 6.92-6.83 (m, 2H), 5.04 (m, 1H), 4.78 (q, J=0.8 Hz, J=3.2 Hz 2H), 4.15 (t, J=2.4 Hz, 4H), 3.85 (t, J=6.0 Hz, 1H), 3.72-3.63 (m, 3H), 3.40 (s, 4H), 3.05-2.99 (m, 1H), 2.24-2.13 (m, 4H), 1.97-1.60 (m, 2H).
m/z [M+Na]+ calcd for $C_{20}H_{24}FN_3O_3S$: 405.1522; found: 428.2

(R)—N-((3-(3-Fluoro-4-(2-oxido-2-thia-6-azaspiro[3.3]heptan-6-yl)phenyl)-2-oxooxazolidin-5-yl)methyl)methanesulfonamide HNMR (400 MHz, CDCl$_3$) δ: 7.32 (dd, J=14.0, 2.4 Hz, 1H), 7.04-7.02 (m, 1H), 6.41 (t, J=9.6 Hz, 1H), 4.86-4.77 (m, 2H), 4.04-3.95 (m, 8H), 3.93 (dd, J=9.6, 3.2 Hz, 1H), 3.43-3.40 (m, 3H), 3.02 (s, 3H).
m/z [M+H]+ calcd for $C_{16}H_{20}FN_3O_5S_2$: 417.0828; found: 418.0

OTB-254

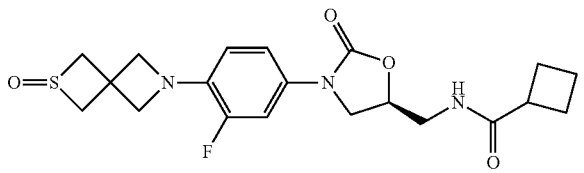

OTB-260-5A

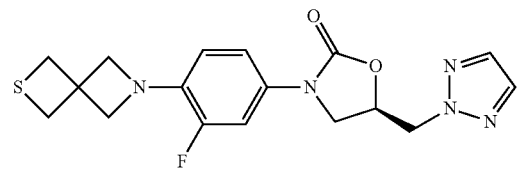

(S)-N-((3-(3-fluoro-4-(2-oxido-2-thia-6-azaspiro[3.3]heptan-6-yl)phenyl)-2-oxooxazolidin-5-yl)methyl)cyclobutanecarboxamide 1H-NMR (400 MHz, CDCl3) δ: 7.36 (d, J=14.4 Hz, 1H), 7.00 (d, J=8.0 Hz, 1H), 6.47 (t, J=9.2 Hz, 1H), 5.80 (brs, 1H), 4.73 (brs, 1H), 4.00 (d, J=12.0 Hz, 4H), 3.95-3.92 (m, 3H), 3.76-3.72 (m, 1H), 3.65-3.62 (m, 2H), 3.47-3.41 (m, 2H), 3.02-2.96 (m, 1H), 2.26-2.13 (m, 4H), 1.98-1.84 (m, 2H).
HRMS (ESI): m/z [M+H]+ calcd for $C_{20}H_{25}FN_3O_4S$: 422.1549; found: 422.1531

(R)-5-((2H-1,2,3-Triazol-2-yl)methyl)-3-(3-fluoro-4-(2-thia-6-azaspiro[3.3]heptan-6-yl)phenyl)oxazolidin-2-one HNMR (400 MHz, CDCl$_3$) δ: 7.64 (s, 2H), 7.24-7.21 (m, 1H), 6.99 (dd, J=8.8, 1.6 Hz, 1H), 6.41 (t, J=9.6 Hz, 1H), 5.12-5.06 (m, 1H), 4.87-4.82 (m, 1H), 4.75-4.72 (m, 1H), 4.05-4.01 (m, 1H), 3.96-3.93 (m, 5H), 3.40 (s, 4H).
m/z [M+H]+ calcd for $C_{17}H_{18}FN_5O_2S$: 375.1165; found: 376.1

OTB-260-2A

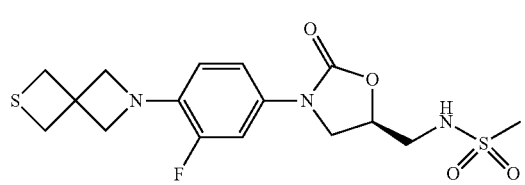

OTB-260-5B

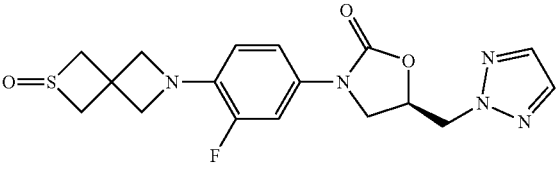

(R)—N-((3-(3-Fluoro-4-(2-thia-6-azaspiro[3.3]heptan-6-yl)phenyl)-2-oxooxazolidin-5-yl)methyl)methanesulfonamide HNMR (400 MHz, CDCl3) δ: 7.04-6.95 (m, 2H), 5.05 (s, 1H), 4.80-4.77 (m, 1H), 4.15 (t, J=2.4 Hz, 4H), 3.97 (t, J=8.8 Hz, 1H), 3.86 (dd, J=6.4, 8.8 Hz, 1H), 3.56 (dd, J=3.6, 14.4 Hz, 1H), 3.43-3.39 (m, 5H), 3.01 (s, 3H).
m/z [M+H]+ calcd for $C_{16}H_{20}FN_3O_4S_2$: 401.0879; found: 402.1

(R)-5-((2H-1,2,3-Triazol-2-yl)methyl)-3-(3-fluoro-4-(2-oxido-2-thia-6-azaspiro[3.3]heptan-6-yl)phenyl)oxazolidin-2-one HNMR (400 MHz, CDCl$_3$) δ: 7.64 (s, 2H), 7.27-7.23 (m, 1H), 6.99 (dd, J=8.8, 2.0 Hz, 1H), 6.39 (t, J=9.2 Hz, 1H), 5.11-5.06 (m, 1H), 4.87-4.82 (m, 1H), 4.76-4.70 (m, 1H), 4.06-4.03 (m, 1H), 3.98-3.90 (m, 7H), 3.43-3.40 (m, 2H).
m/z [M+H]+ calcd for $C_{17}H_{18}FN_5O_3S$: 391.1114; found: 392.1

OTB-260-2B

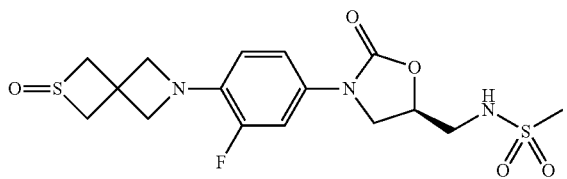

OTB-260-4A

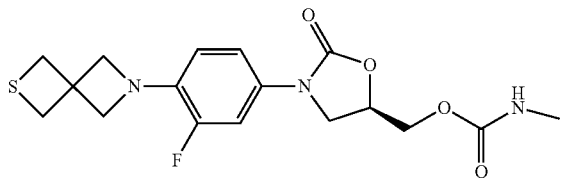

(R)-(3-(3-Fluoro-4-(2-thia-6-azaspiro[3.3]heptan-6-yl)phenyl)-2-oxooxazolidin-5-yl)methyl methylcarbamate HNMR (400 MHz, CDCl₃) δ: 7.33 (dd, J=2.4, 13.6 Hz, 1H), 7.04 (dd, J=1.6, 8.4 Hz, 1H), 6.44 (t, J=9.2 Hz, 1H), 4.88-4.72 (m, 2H), 4.33 (t, J=4.0 Hz, 2H), 4.02 (t, J=9.2 Hz, 1H), 3.97 (d, J=1.6 Hz, 4H), 3.77 (dd, J=6.4, 8.8 Hz, 1H), 3.42 (s, 4H), 2.80 (d, J=4.8 Hz, 3H).

m/z [M+H]+ calcd for $C_{17}H_{20}FN_3O_4S$: 381.1159; found: 382.0

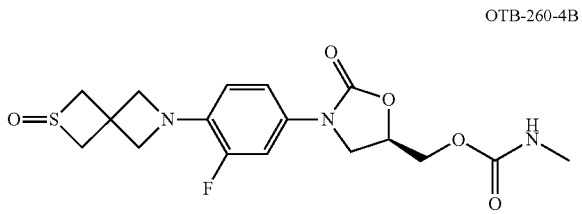 [SMILES: CNC(=O)OC[C@H]1CN(c2ccc(N3CC4(C3)CS(=O)C4)c(F)c2)C(=O)O1]

OTB-260-4B

(R)-(3-(3-Fluoro-4-(2-oxido-2-thia-6-azaspiro[3.3]heptan-6-yl)phenyl)-2-oxooxazolidin-5-yl)methyl methylcarbamate HNMR (400 MHz, CDCl₃) δ: 7.35 (dd, J=2.0, 11.6 Hz, 1H), 7.06 (d, J=8.4 Hz, 1H), 6.42 (t, J=9.2 Hz, 1H), 4.89-4.70 (m, 2H), 4.42-4.26 (m, 2H), 4.08-3.88 (m, 7H), 3.84-3.71 (m, 1H), 3.47-3.37 (m, 2H), 2.81 (m, 3H).

m/z [M+H]+ calcd for $C_{17}H_{20}FN_3O_5S$: 397.1108; found: 398.0

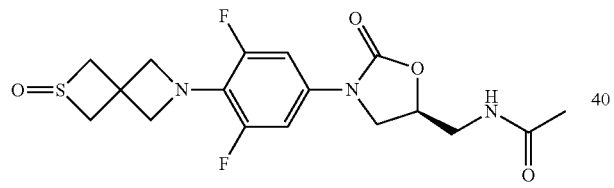

OTB-520

(S)-N-((3-(3,5-Difluoro-4-(2-oxido-2-thia-6-azaspiro[3.3]heptan-6-yl)phenyl)-2-oxooxazolidin-5-yl)methyl)acetamide 1H-NMR (400 MHz, CDCl3) δ: 7.02 (d, J=12.0 Hz, 2H), 5.92 (brs, 1H), 4.75-4.74 (m, 1H), 4.16 (d, J=12.0 Hz, 4H), 3.97-3.90 (m, 2H), 3.72-3.65 (m, 4H), 3.41-3.37 (m, 2H), 2.02 (s, 3H).

HRMS (ESI): m/z [M+H]+ calcd for $C_{17}H_{20}F_2N_3O_4S$: 400.1143; found: 400.1158

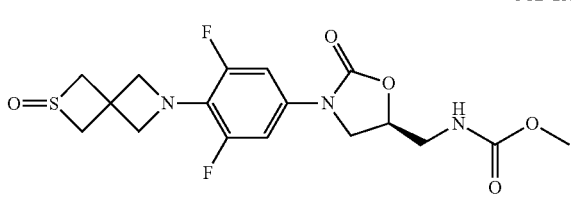

OTB-253

(S)-Methyl ((3-(3,5-difluoro-4-(2-oxido-2-thia-6-azaspiro[3.3]heptan-6-yl)phenyl)-2-oxooxazolidin-5-yl)methyl)carbamate 1H-NMR (400 MHz, CDCl3) δ: 7.00 (d, J=10.8 Hz, 2H), 5.36 (m, 1H), 4.72 (m, 1H), 4.14 (d, J=12.0 Hz, 4H), 3.92 (m, 3H), 3.69 (m, 1H), 3.67 (s, 3H), 3.52 (m, 2H), 3.39 (d, J=12.4 Hz, 2H).

HRMS (ESI) calcd for $C_{17}H_{20}F_2N_3O_5S$ [M+H]+ 416.1086, found: 416.1073

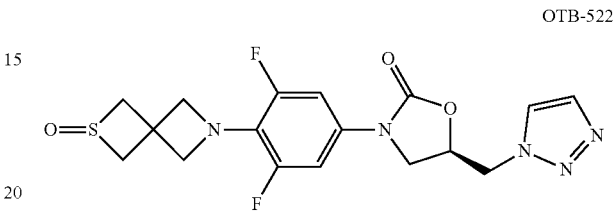

OTB-522

HNMR (400 MHz, CDCl₃) δ: 7.75 (d, J=8.0 Hz, 2H), 6.92-6.83 (m, 2H), 5.05-5.01 (m, 1H), 4.77 (d, J=4.0 Hz, 2H), 4.15 (dt, J=11.6, 2.4 Hz, 4H), 4.05 (t, J=9.2 Hz, 1H), 3.92-3.89 (m, 3H), 3.40-3.37 (m, 2H).

m/z [M+H]+ calcd for $C_{17}H_{17}F_2N_5O_3S$: 409.1020; found: 410.1

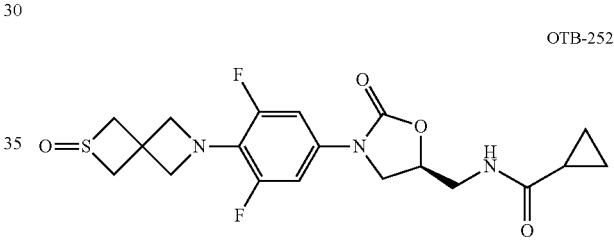

OTB-252

(S)-N-((3-(3,5-Difluoro-4-(2-oxido-2-thia-6-azaspiro[3.3]heptan-6-yl)phenyl)-2-oxooxazolidin-5-yl)methyl)cyclopropanecarboxamide 1H-NMR (400 MHz, CDCl3) δ: 6.98 (d, J=11.6 Hz, 2H), 6.60 (m, 1H), 4.73 (m, 1H), 4.13 (d, J=12.4 Hz, 4H), 3.91 (m, 3H), 3.70 (m, 1H), 3.64 (m, 2H), 3.79 (d, J=10.4 Hz, 2H), 1.41 (m, 1H), 0.94 (m, 1H), 0.87 (m, 1H), 0.74 (m, 2H)

HRMS (ESI) calcd for $C_{19}H_{22}F_2N_3O_4S$ [M+H]+ 426.1294, found: 426.1278

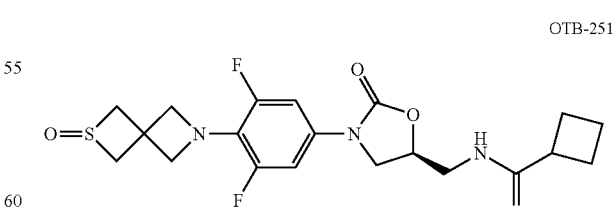

OTB-251

(S)-N-((3-(3,5-Difluoro-4-(2-oxido-2-thia-6-azaspiro[3.3]heptan-6-yl)phenyl)-2-oxooxazolidin-5-yl)methyl)cyclobutanecarboxamide 1H-NMR (400 MHz, CDCl3) δ: 6.99 (d, J=10.4 Hz, 2H), 6.06 (m, 1H), 4.74 (m, 1H), 4.14 (d, J=12.4 Hz, 4H), 3.93

(m, 3H), 3.70 (m, 1H), 3.62 (m, 2H), 3.38 (d, J=12.4 Hz, 2H), 3.00 (m, 1H), 2.21 (m, 1H), 2.11 (m, 3H), 1.92 (m, 1H), 1.83 (m, 1H)

HRMS (ESI) calcd for $C_{20}H_{24}F_2N_3O_4S$ [M+H]+ 440.1450, found: 440.1441

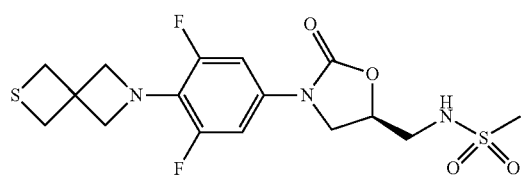

OTB-516-2A (R)—N-((3-(3,5-Difluoro-4-(2-thia-6-azaspiro[3.3]heptan-6-yl)phenyl)-2-oxooxazolidin-5-yl)methyl)methanesulfonamide HNMR (400 MHz, CDCl3) δ: 7.04-6.95 (m, 2H), 5.05 (s, 1H), 4.80-4.77 (m, 1H), 4.15 (t, J=2.4 Hz, 4H), 3.97 (t, J=8.8 Hz, 1H), 3.86 (dd, J=6.4, 8.8 Hz, 1H), 3.56 (dd, J=3.6, 14.4 Hz, 1H), 3.43-3.39 (m, 5H), 3.01 (s, 3H).

m/z [M+H]+ calcd for $C_{16}H_{19}F_2N_3O_4S_2$: 419.0785; found: 420.1

OTB-516-2B (R)—N-((3-(3,5-Difluoro-4-(2-oxido-2-thia-6-azaspiro[3.3]heptan-6-yl)phenyl)-2-oxooxazolidin-5-yl)methyl)methanesulfonamide HNMR (400 MHz, CDCl3) δ: 7.03-7.00 (m, 2H), 4.81-4.78 (m, 2H), 4.18-4.14 (m, 4H), 3.98-3.93 (m, 1H), 3.91-3.85 (m, 3H), 3.60-3.41 (m, 4H), 3.40-3.37 (m, 3H), 3.02 (s, 3H).

m/z [M+H]+ calcd for $C_{16}H_{19}F_2N_3O_5S_2$: 435.0734; found: 436.0

OTB-516-4A (R)-(3-(3,5-Difluoro-4-(2-thia-6-azaspiro[3.3]heptan-6-yl)phenyl)-2-oxooxazolidin-5-yl)methyl methylcarbamate HNMR (400 MHz, CDCl$_3$) δ: 7.08-6.91 (m, 2H), 4.91-4.70 (m, 2H), 4.38-4.28 (m, 2H), 4.16 (t, J=2.4 Hz, 4H), 3.98 (t, J=9.2 Hz, 1H), 3.74 (dd, J=6.4, 8.8 Hz, 1H), 3.43-3.37 (m, 4H), 2.81 (d, J=4.8 Hz, 3H).

m/z [M+H]+ calcd for $C_{17}H_{19}F_2N_3O_4S$: 399.1064; found: 400.1

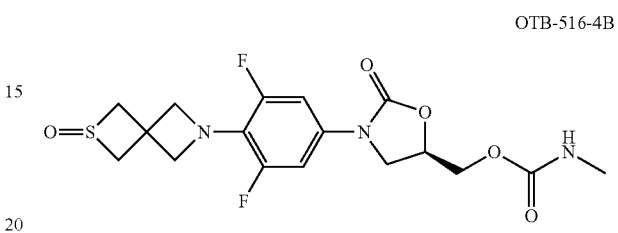

OTB-516-4B (R)-(3-(3,5-Difluoro-4-(2-oxido-2-thia-6-azaspiro[3.3]heptan-6-yl)phenyl)-2-oxooxazolidin-5-yl) methyl methylcarbamate HNMR (400 MHz, CDCl$_3$) δ: 7.10-6.95 (m, 2H), 4.89-4.69 (m, 2H), 4.30-4.36 (m, 2H), 4.17 (d, J=11.6 Hz, 4H), 4.02-3.89 (m, 3H), 3.74 (dd, J=6.4, 8.6 Hz, 1H), 3.44-3.33 (m, 2H), 2.81 (d, J=4.8 Hz, 3H).

m/z [M+H]+ calcd for $C_{17}H_{19}F_2N_3O_5S$: 415.1013; found: 416.0

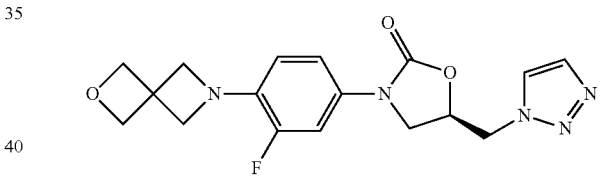

OTB-204

(R)-5-((1H-1,2,3-tTriazol-1-yl)methyl)-3-(3-fluoro-4-(2-oxa-6-azaspiro[3.3]heptan-6-yl)phenyl)oxazolidin-2-one 1H-NMR (400 MHz, CDCl3) δ: 7.65 (s, 2H), 7.31 (d, J=14.4, 2.4 Hz, 1H), 6.99 (d, J=8.4 Hz, 1H), 6.59 (t, J=9.2 Hz, 1H), 5.14-5.07 (m, 1H), 4.88-4.83 (m, 5H), 4.77-4.71 (m, 1H), 4.16 (s, 4H), 4.07-4.02 (m, 1H), 3.98-3.92 (m, 1H)

HRMS (ESI): m/z [M+H]+ calcd for $C_{17}H_{19}FN_5O_3$: 360.1472; found: 360.1451

The invention will be further described, without limitation, by the following numbered paragraphs:

1. A compound of Formula I, or a pharmaceutically acceptable salt, hydrate, or solvate of:

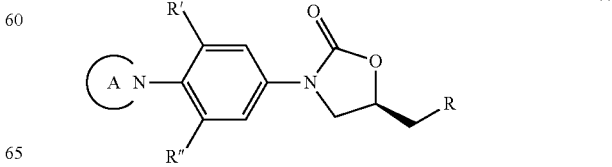

(I)

wherein:

R is independently $OR_1$, $OC(O)R_2$, $OC(O)NHR_2$, $OS(O_2)R_2$, $NHS(O)_2R_2$, $NR_3R_4$, $NHC(O)R_5$;

R' and R" are independently H, F, Cl or OMe;

each $R_1$ is independently H, $C_1$-$C_6$ alkyl, $C_3$-$C_8$ cycloalkyl, wherein said alkyl, cycloalkyl are optionally substituted with 1 to 4 groups selected from halo, hydroxy, $C_1$-$C_6$ alkyl, $C_1$-$C_6$ alkyloxy;

each $R_2$ is independently $C_1$-$C_6$ alkyl, $C_3$-$C_8$ cycloalkyl, heterocyclyl, heteroaryl or aryl, wherein said alkyl, cycloalkyl, heterocyclyl, heteroaryl, or aryl are optionally substituted with 1 to 4 groups selected from halo, hydroxyl, $C_1$-$C_6$ alkyl, $C_1$-$C_6$ alkoxy, $C_1$-$C_6$ acyloxy, $CF_3$, $NO_2$, CN and $NH_2$;

each $R_3$ and $R_4$ is independently H, $C_1$-$C_6$ alkyl, $C_3$-$C_8$ cycloalkyl, heterocyclyl heteroaryl, aryl; or $R_3$ and $R_4$ taken together with the nitrogen to which they are attached, form a 4- to 8-membered heterocyclyl or heteroaryl with 1 to 3 additional heteroatoms selected from O, S, or N, wherein said alkyl, cycloalkyl, heterocyclyl, heteroaryl, or aryl are optionally substituted with 1 to 4 groups selected from halo, $C_1$-$C_6$ alkyl, $C_1$-$C_6$ alkoxy, $CF_3$, $NO_2$, CN;

each $R_5$ is independently $C_1$-$C_6$ alkyl, $C_3$-$C_8$ cycloalkyl, $C_1$-$C_6$ alkoxy, heteroaryl, aryl, wherein said alkyl, cycloalkyl, heterocyclyl, heteroaryl, or aryl are optionally substituted with 1 to 4 groups selected from halo, hydroxyl, $C_1$-$C_6$ alkyl, $C_1$-$C_6$ alkoxy, $C_1$-$C_6$ acyloxy, $CF_3$, $NO_2$, CN and $NH_2$;

Ring A is selected from:

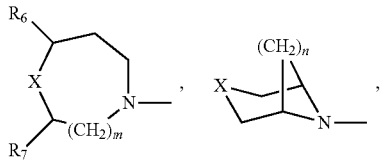

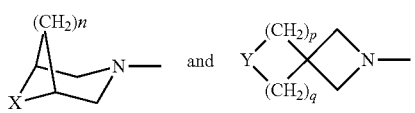

wherein, each $R_6$ and $R_7$ is independently H, F, $CH_3$, $CH_2CH_3$, $CF_3$, phenyl;

X=O, S, SO, $SO_2$;

Y=O, S, SO, $SO_2$, and $NR_8$;

m is 1, or 2;

n is 1, or 2;

p is 1, or 2;

q is 1, or 2;

$R_8$ in independently H, $C_1$-$C_4$ alkyl, $C_3$-$C_6$ cycloalkyl, $COCH_3$, and p-toluenesulfonyl, wherein said alkyl, cycloalkyl are optionally substituted with 1 to 4 groups selected from halo, hydroxyl, $C_1$-$C_6$ alkyl, $C_1$-$C_6$ alkoxy, $C_1$-$C_6$ acyloxy, $CF_3$, $NO_2$, CN and $NH_2$.

2. The compound of paragraph 1, wherein the compound is represented by Formula II:

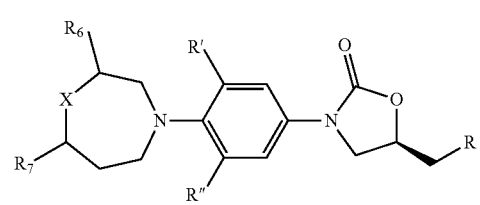

wherein,

R is independently $OR_1$, $OC(O)R_2$, $NR_3R_4$, $NHS(O)_2R_2$, $NHC(O)R_5$;

R' and R" are independently H, or F;

$R_1$ is independently H, $C_1$-$C_6$ alkyl, $C_3$-$C_6$ cycloalkyl;

$R_2$ is independently $C_1$-$C_6$ alkyl, $C_3$-$C_6$ cycloalkyl;

$R_3$ and $R_4$ is independently H, $C_1$-$C_6$ alkyl, $C_3$-$C_6$ cycloalkyl, phenyl; or $R_3$ and $R_4$ taken together with the nitrogen to which they are attached to form morpholine, thiamorpholine, piperazine and triazole;

$R_5$ is independently $C_1$-$C_6$ alkyl, $C_3$-$C_6$ cycloalkyl, $C_1$-$C_6$ alkoxy, 5- or 6-membered heteroaryl or phenyl;

$R_6$ and $R_7$ is independently H, F, $CH_3$, $CH_2CH_3$, $CF_3$;

X=O, S, SO, $SO_2$; when X=S, SO, $SO_2$, R'=H, R"=F, $R_5$ can not be $CH_3$;

3. The compound of paragraph 1, wherein the compound is represented by Formula III:

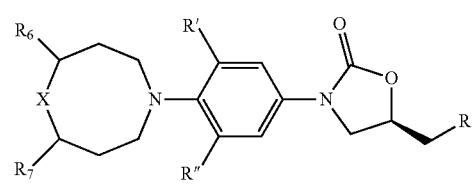

wherein,

R is independently $OR_1$, $OC(O)R_2$, $NR_3R_4$, $NHS(O)_2R_2$, $NHC(O)R_5$;

R' and R" are independently H, or F;

$R_1$ is independently H, $C_1$-$C_6$ alkyl, $C_3$-$C_6$ cycloalkyl;

$R_2$ is independently $C_1$-$C_6$ alkyl, $C_3$-$C_6$ cycloalkyl;

$R_3$ and $R_4$ is independently H, $C_1$-$C_6$ alkyl, $C_3$-$C_6$ cycloalkyl, or phenyl; or $R_3$ and $R_4$ taken together with the nitrogen to which they are attached to form morpholine, thiamorpholine, piperazine and triazole;

$R_5$ is independently $C_1$-$C_6$ alkyl, $C_3$-$C_6$ cycloalkyl, $C_1$-$C_6$ alkoxy, 5- or 6-membered heteroaryl or phenyl;

$R_6$ and $R_7$ is independently H, F, $CH_3$, $CH_2CH_3$, $CF_3$;

X=O, S, SO, $SO_2$;

4. The compound of paragraph 1, wherein the compound is represented by Formula IV:

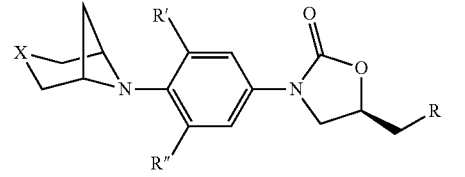

wherein,

R is independently $OR_1$, $OC(O)R_2$, $NR_3R_4$, $NHS(O)_2R_2$, $NHC(O)R_5$;

R' and R" are independently H, or F;

$R_1$ is independently H, $C_1$-$C_6$ alkyl, $C_3$-$C_6$ cycloalkyl;

$R_2$ is independently $C_1$-$C_6$ alkyl, $C_3$-$C_6$ cycloalkyl;

$R_3$ and $R_4$ is independently H, $C_1$-$C_6$ alkyl, $C_3$-$C_6$ cycloalkyl, 5- or 6-membered heteroaryl or phenyl; or $R_3$ and $R_4$ taken together with the nitrogen to which they are attached, to form morpholine, thiamorpholine, piperazine and triazole;

$R_5$ is independently $C_1$-$C_6$ alkyl, $C_3$-$C_6$ cycloalkyl, $C_1$-$C_6$ alkoxy, 5- or 6-membered heteroaryl or phenyl; and $X=O$, S, SO, $SO_2$.

5. The compound of paragraph 1, wherein the compound is represented by Formula V:

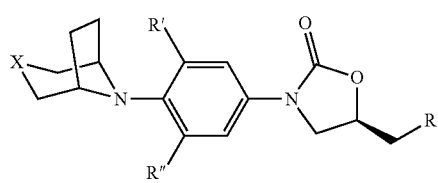

V wherein,

R is independently $OR_1$, $OC(O)R_2$, $NR_3R_4$, $NHS(O)_2R_2$, $NHC(O)R_5$;

R' and R" are independently H, or F;

$R_1$ is independently H, $C_1$-$C_6$ alkyl, $C_3$-$C_6$ cycloalkyl;

$R_2$ is independently $C_1$-$C_6$ alkyl, $C_3$-$C_6$ cycloalkyl;

$R_3$ and $R_4$ is independently H, $C_1$-$C_6$ alkyl, $C_3$-$C_6$ cycloalkyl, 5- or 6-membered heteroaryl or phenyl; or $R_3$ and $R_4$ taken together with the nitrogen to which they are attached, to form morpholine, thiamorpholine, piperazine and triazole;

$R_5$ is independently $C_1$-$C_6$ alkyl, $C_3$-$C_6$ cycloalkyl, $C_1$-$C_6$ alkoxy, 5- or 6-membered heteroaryl or phenyl; and $X=O$, S, SO, $SO_2$.

6. The compound of paragraph 1, wherein the compound is represented by Formula VI:

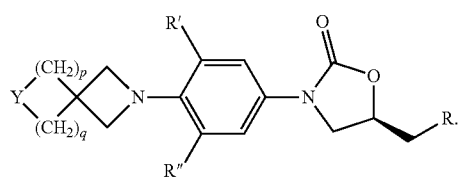

VI

7. The compound of paragraph 6, wherein the compound is represented by Formula VII, Formula VIII, or Formula IX:

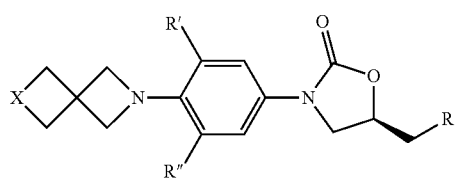

VII

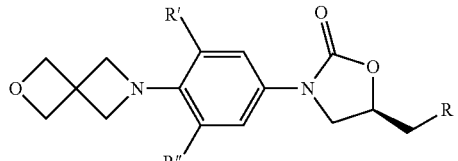

VIII

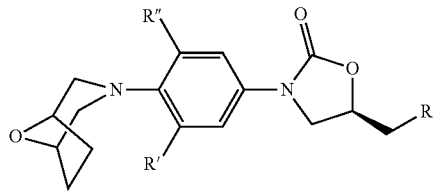

IX wherein,

R is independently $OR_1$, $OC(O)R_2$, $NR_3R_4$, $NHS(O)_2R_2$, $NHC(O)R_5$;

R' and R" are independently H, or F;

$R_1$ is independently H, $C_1$-$C_6$ alkyl, $C_3$-$C_6$ cycloalkyl;

$R_2$ is independently $C_1$-$C_6$ alkyl, $C_3$-$C_6$ cycloalkyl;

$R_3$ and $R_4$ is independently H, $C_1$-$C_6$ alkyl, $C_3$-$C_6$ cycloalkyl, 5- or 6-membered heteroaryl or phenyl; or $R_3$ and $R_4$ taken together with the nitrogen to which they are attached, to form morpholine, thiamorpholine, piperazine and triazole;

$R_5$ is independently $C_1$-$C_6$ alkyl, $C_3$-$C_6$ cycloalkyl, $C_1$-$C_6$ alkoxy, 5- or 6-membered heteroaryl or phenyl; and $X=O$, S, SO, $SO_2$.

8. The compound of paragraph 1, the compound is represented by Formula IIa, IIb, IIIa, IIIb, IVa, IVb, Va, Vb, VIIa, VIIb, VIIIa, VIIIb, IXa, or IXb:

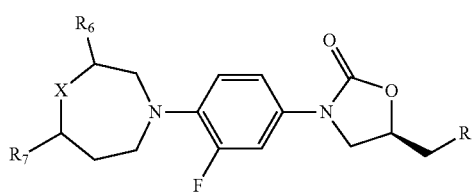

IIa

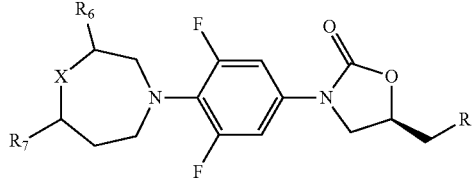

IIb

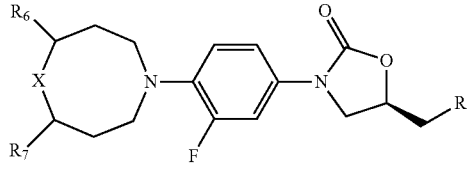

IIIa

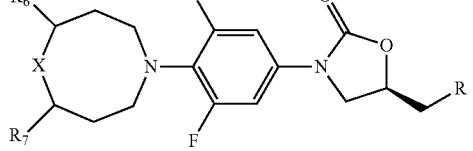

IIIb

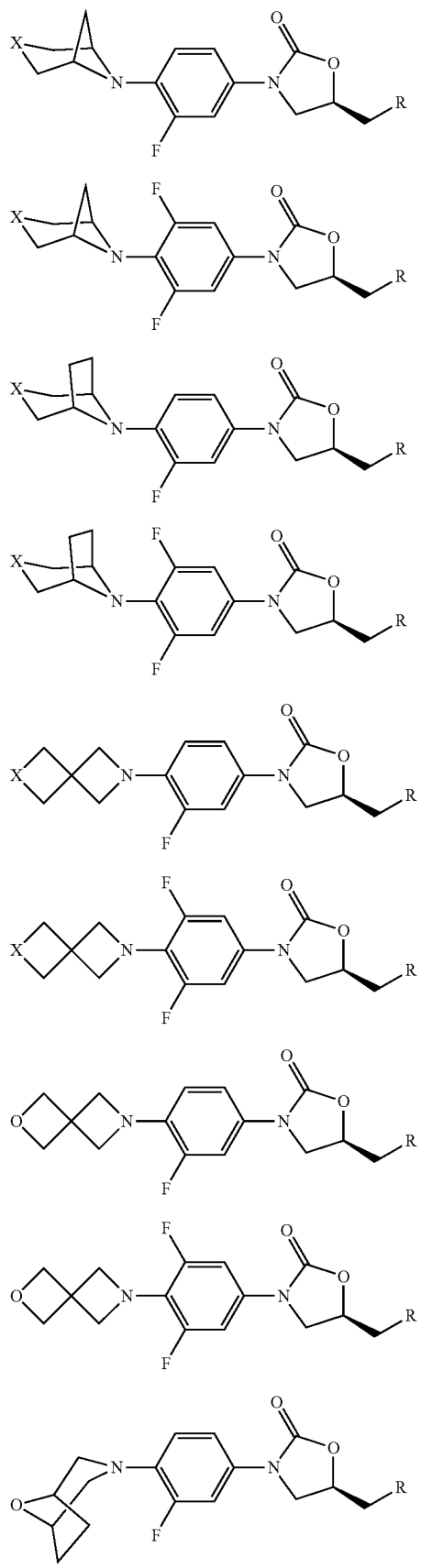
wherein,
R is independently OH, OCH₃, OCH₂CH₃, OC(O)CH₃, NH₂, NHCH₃, NHC₆H₅, 1,2,3-triazole, 1,2,4-triazole, 1,2,5-triazole, NHS(O)₂R₂, NHC(O)R₅;
R₂ is independently C₁-C₆ alkyl;
R₅ is independently C₁-C₆ alkyl, C₃-C₆ cycloalkyl, C₁-C₆ alkoxy, furan, thiophene or phenyl; in Formula IIa, R₅ can not be CH₃; and
X═O, S, SO, SO₂.
9. The compound of paragraph 1, wherein the compound is:

-continued
OTB-112
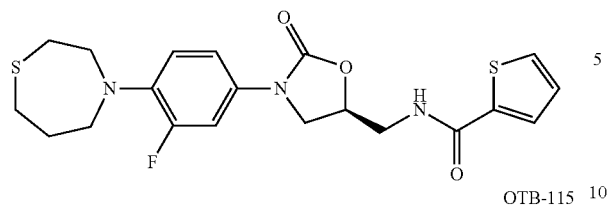
OTB-115
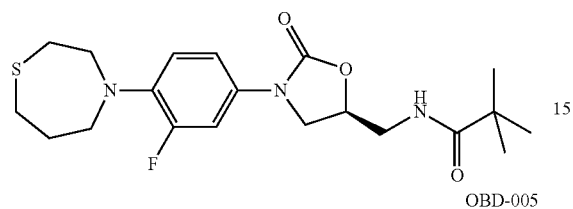
OBD-005
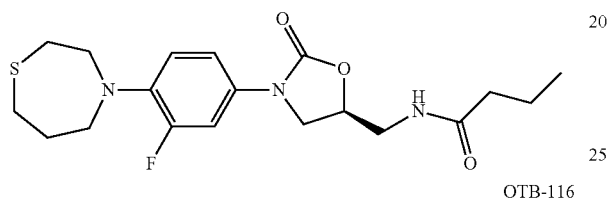
OTB-116
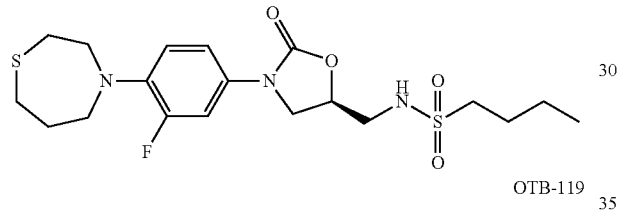
OTB-119
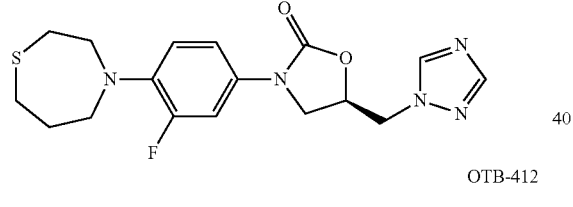
OTB-412
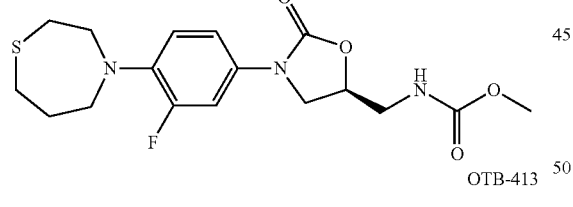
OTB-413
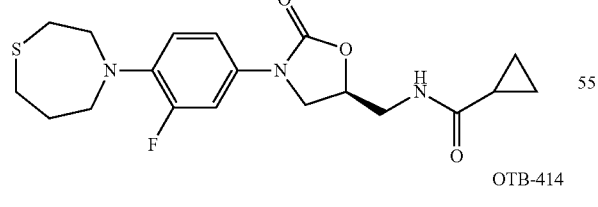
OTB-414
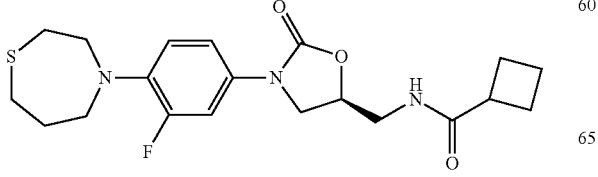
-continued
OTB-407
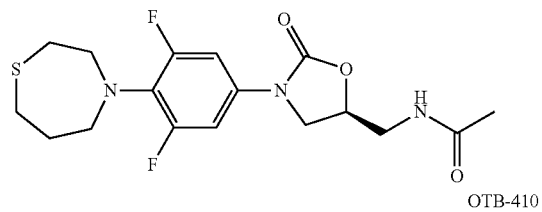
OTB-410
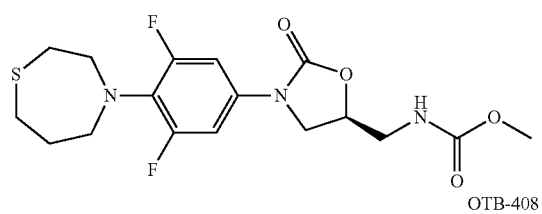
OTB-408
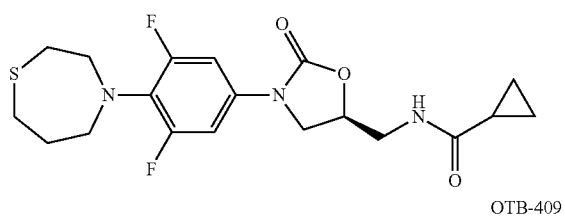
OTB-409
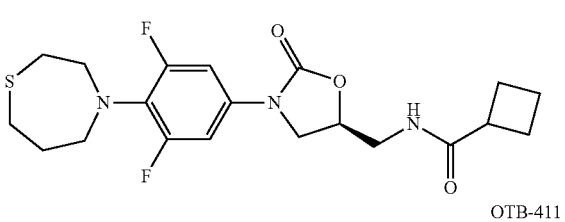
OTB-411
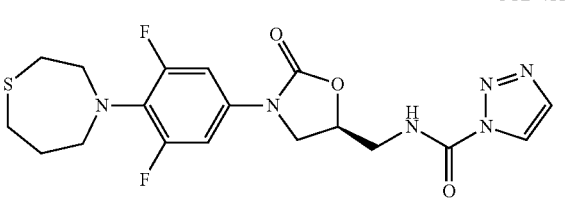
OTB-126
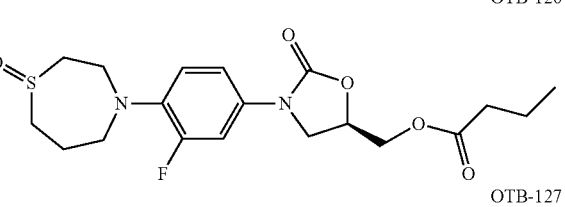
OTB-127
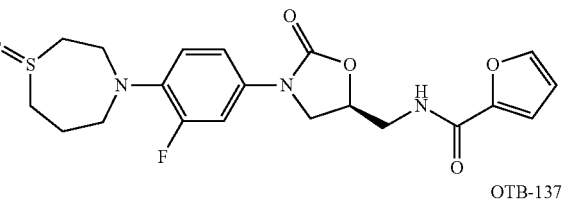
OTB-137
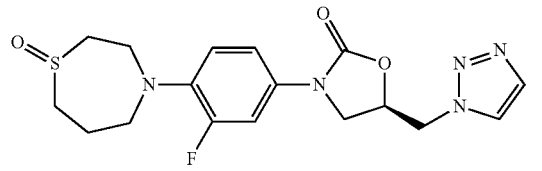

OTB-138
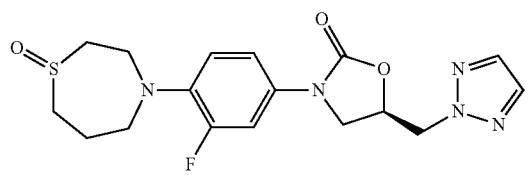
OTB-140
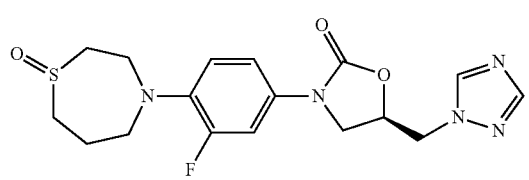
OBD-006
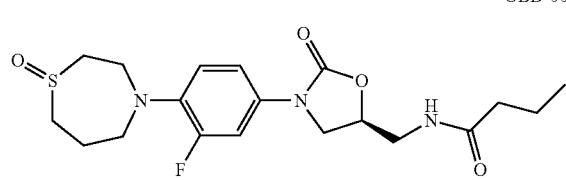
OBD-007
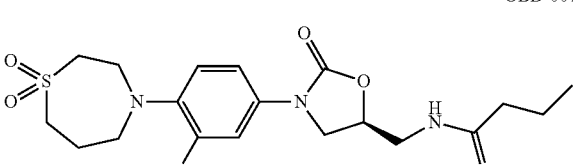
OTB-110
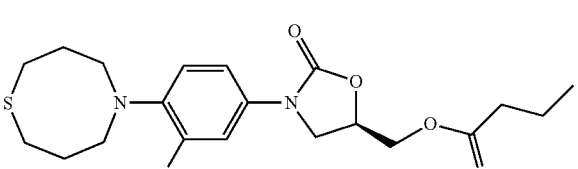
OTB-113
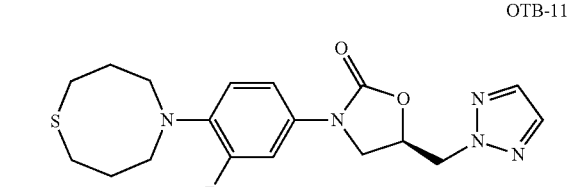
OTB-114
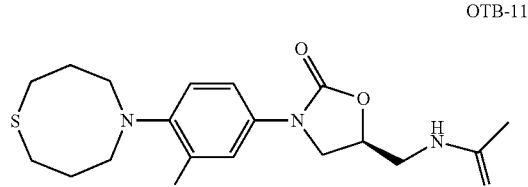
OTB-124
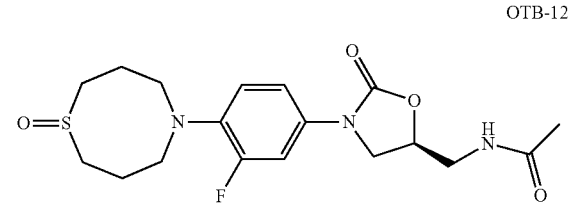
OTB-117
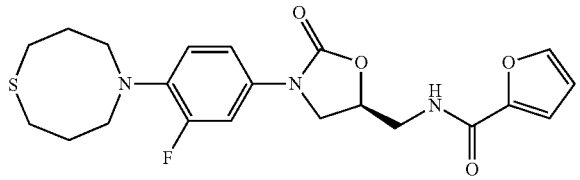
OTB-118
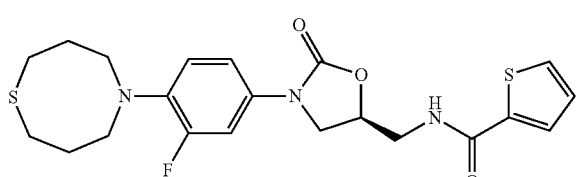
OTB-120
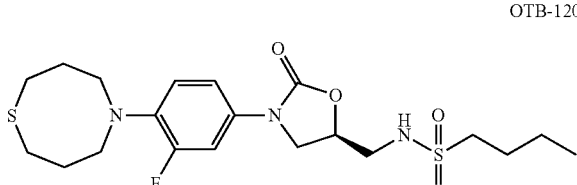
OTB-121
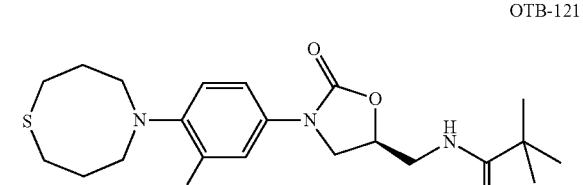
OBD-001
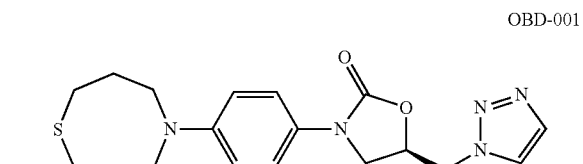
OBD-002
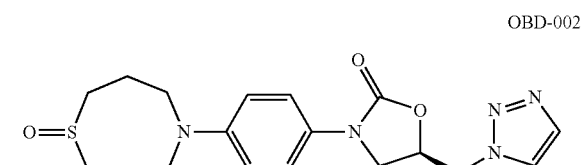
OBD-003
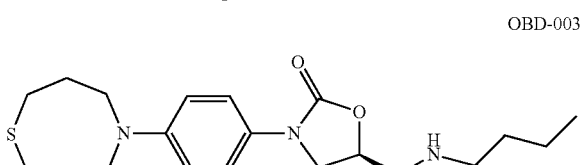
OBD-004
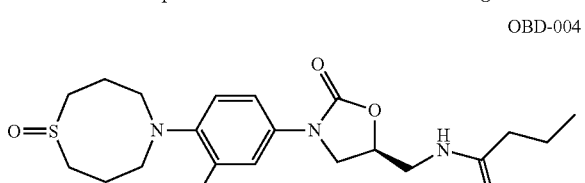

OBD-008
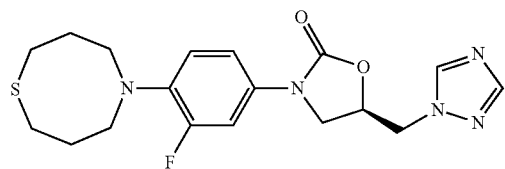
OBD-009
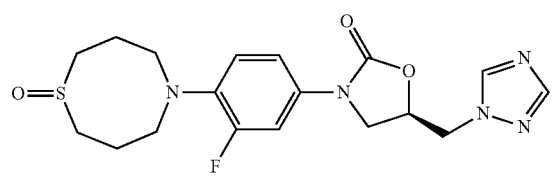
OBD-027
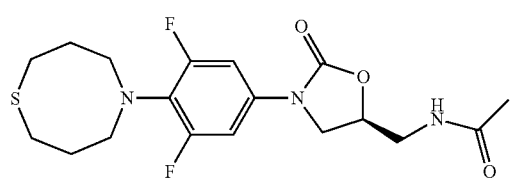
OBD-240
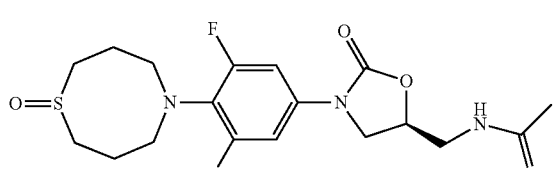
OBD-026
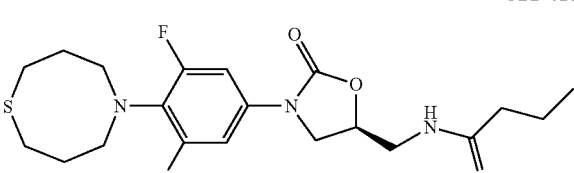
OBD-241
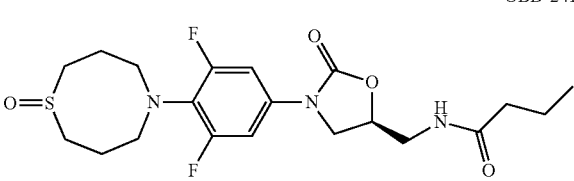
OTB-227
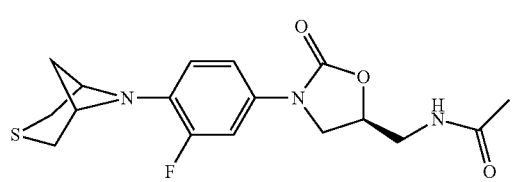
OTB-501
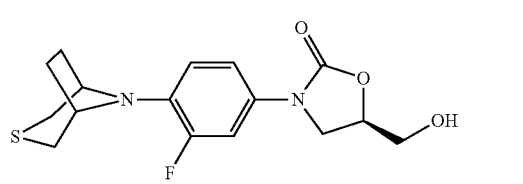
OBD-081
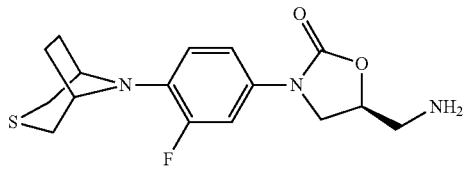
OBD-085
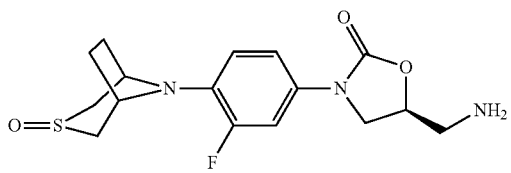
OTB-502
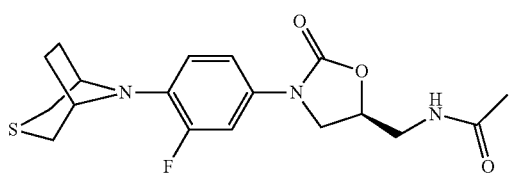
OTB-503
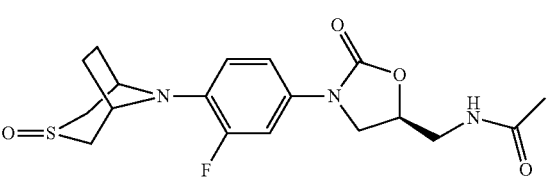
OTB-504
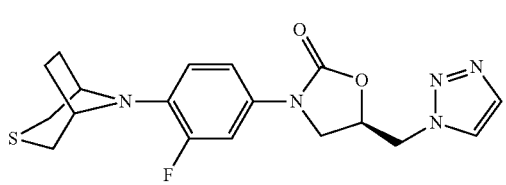
OTB-505
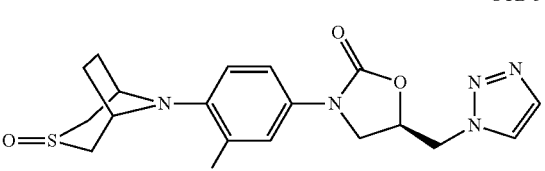
OTB-236
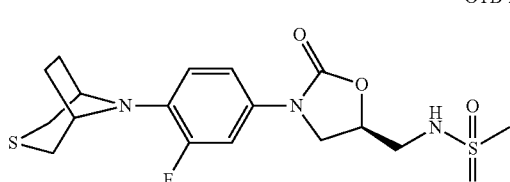
OTB-237
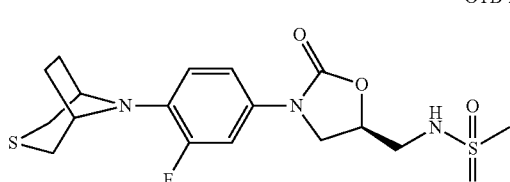

OTB-518
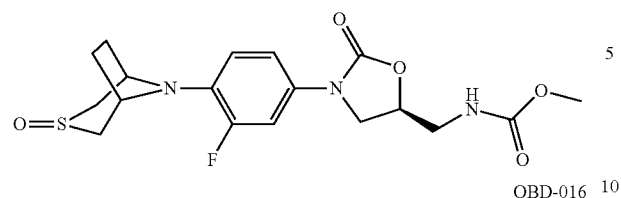
OBD-016
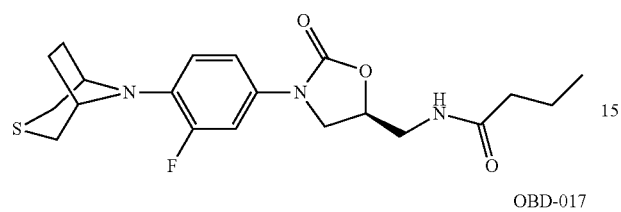
OBD-017
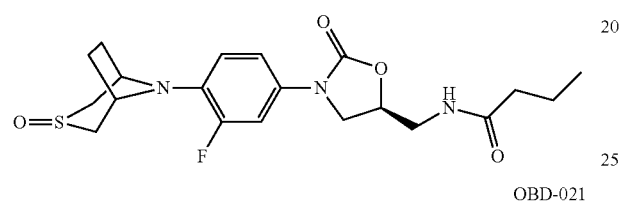
OBD-021
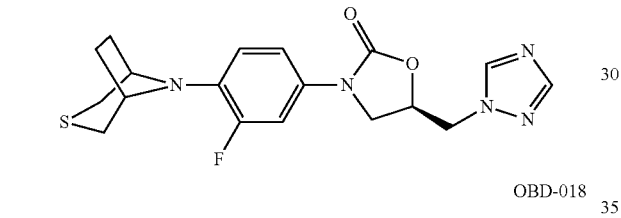
OBD-018
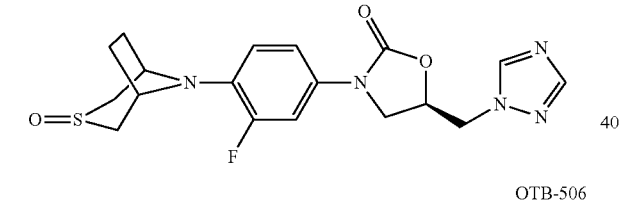
OTB-506
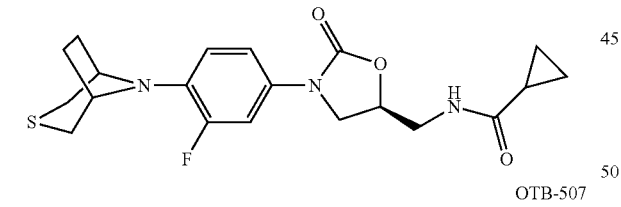
OTB-507
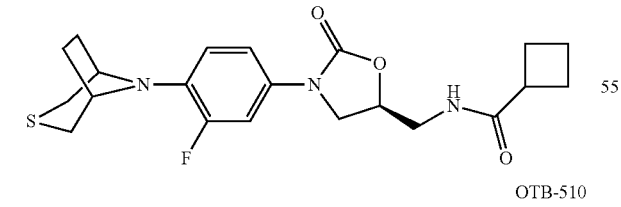
OTB-510
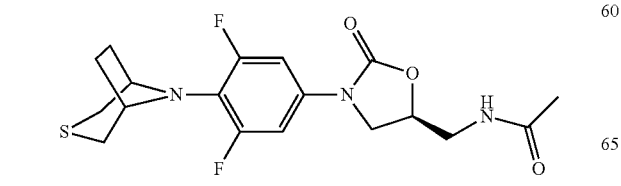
OTB-514
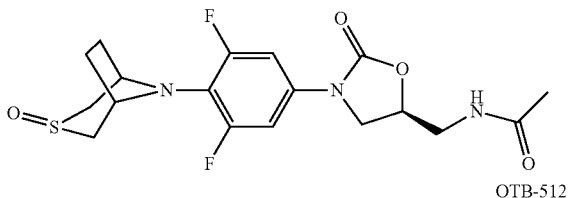
OTB-512
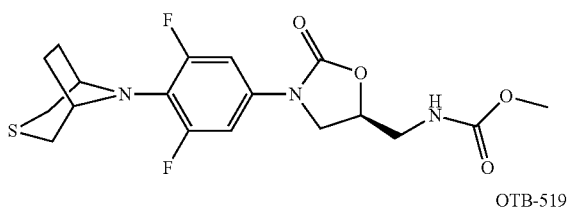
OTB-519
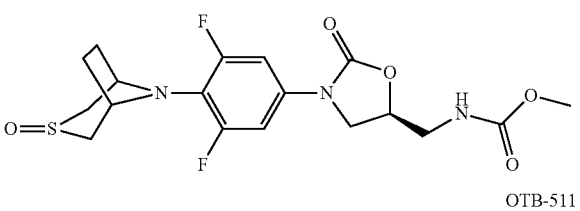
OTB-511
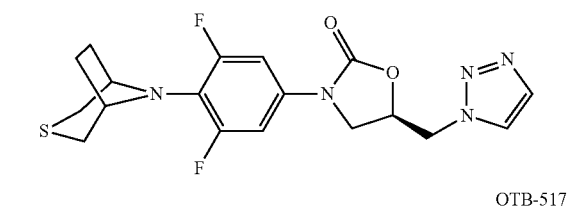
OTB-517
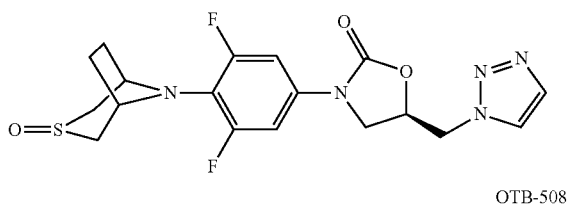
OTB-508
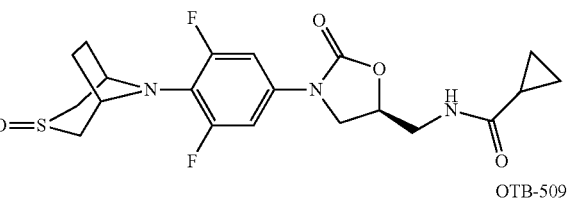
OTB-509
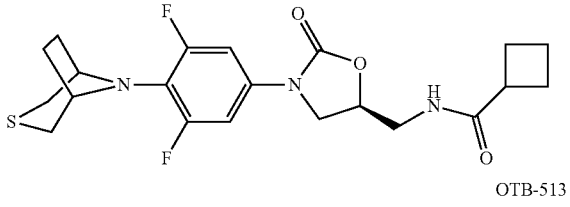
OTB-513
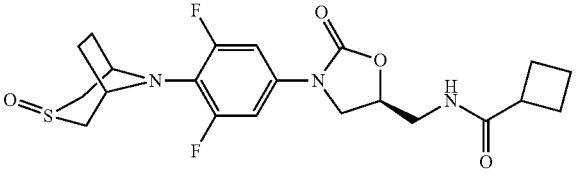

-continued
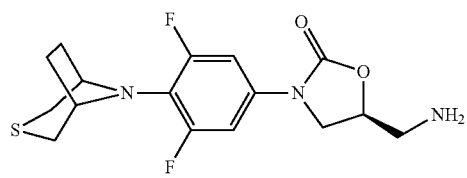
OBD-083
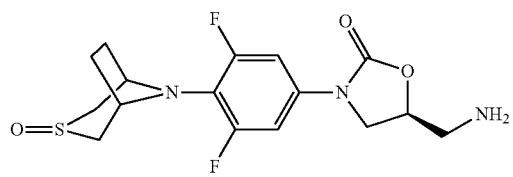
OBD-087
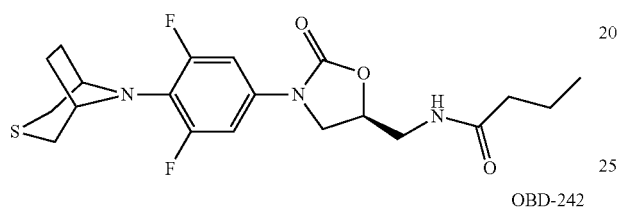
OBD-029
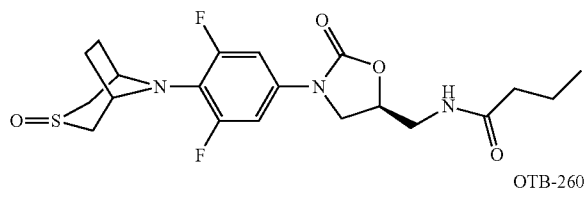
OBD-242
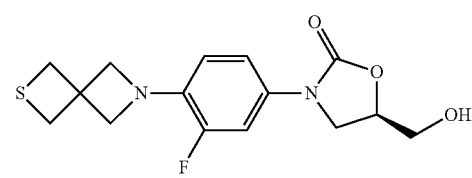
OTB-260
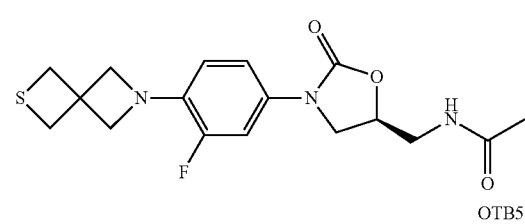
OTB-261
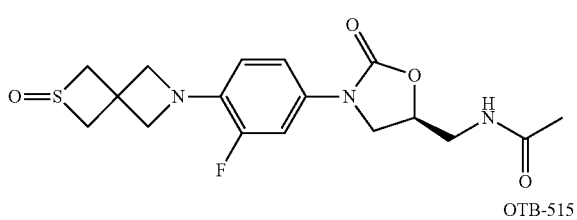
OTB523
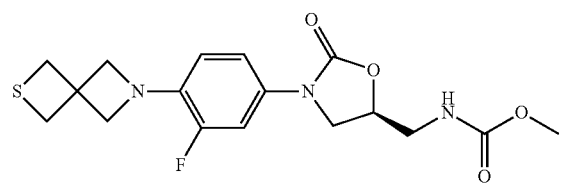
OTB-515
-continued
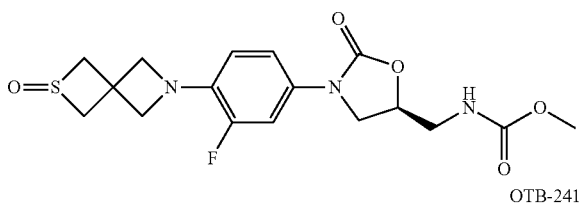
OTB-256
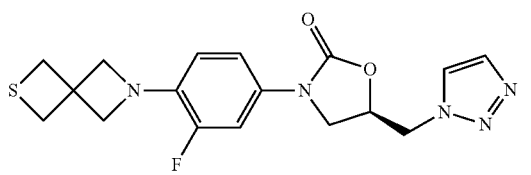
OTB-241
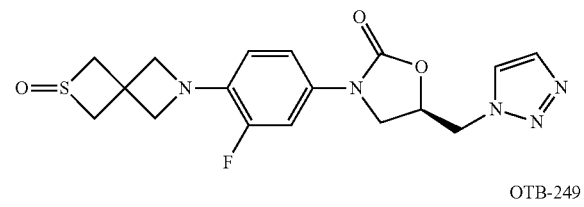
OTB-247
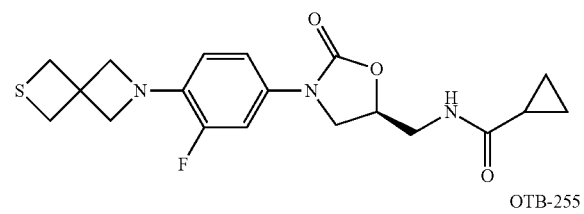
OTB-249
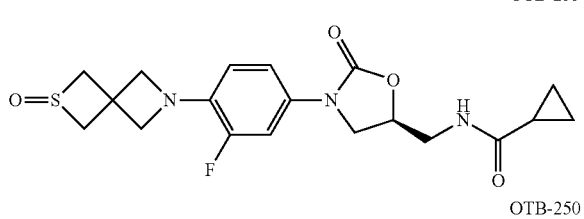
OTB-255
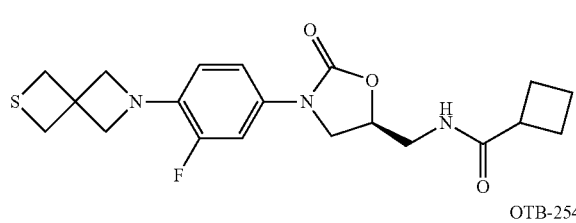
OTB-250
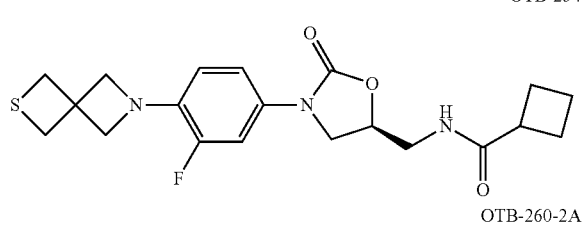
OTB-254
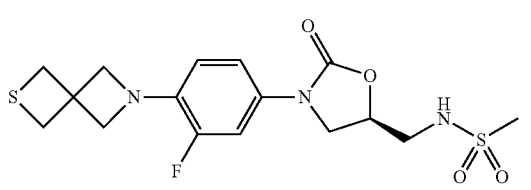
OTB-260-2A -continued
OTB-260-2B
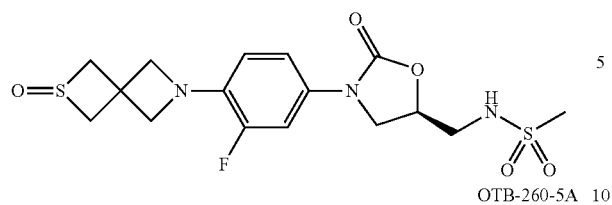
OTB-260-5A
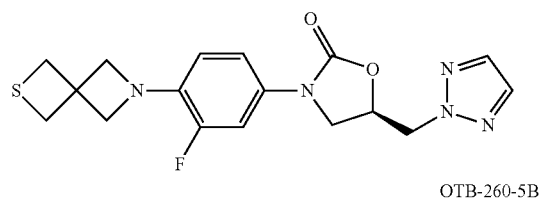
OTB-260-5B
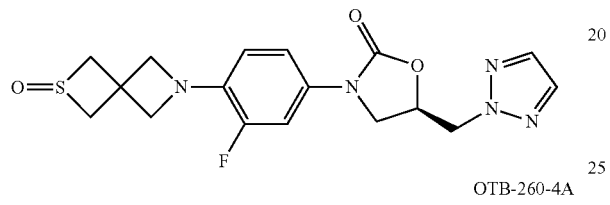
OTB-260-4A
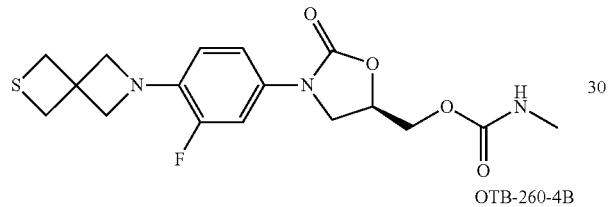
OTB-260-4B
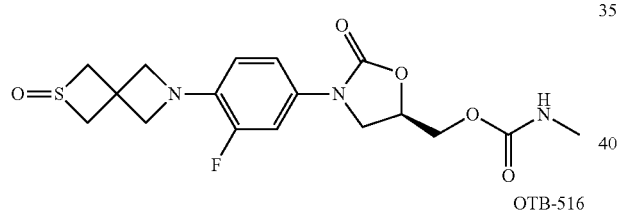
OTB-516
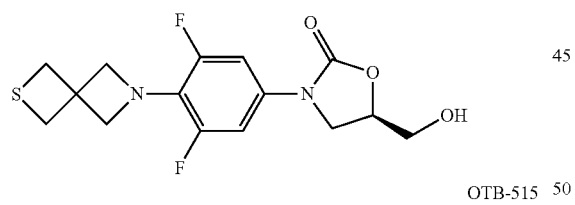
OTB-515
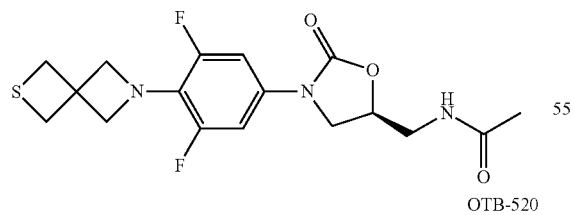
OTB-520
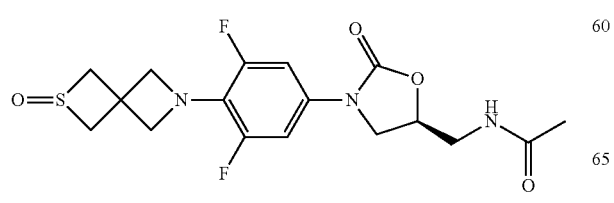
-continued
OTB-242
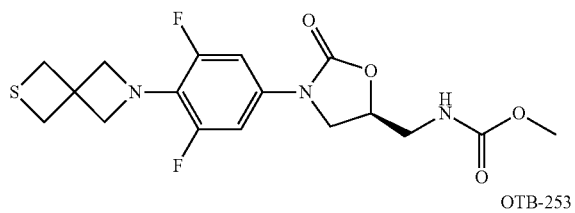
OTB-253
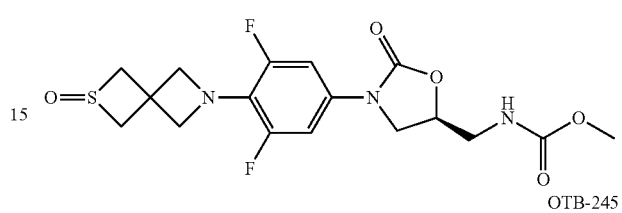
OTB-245
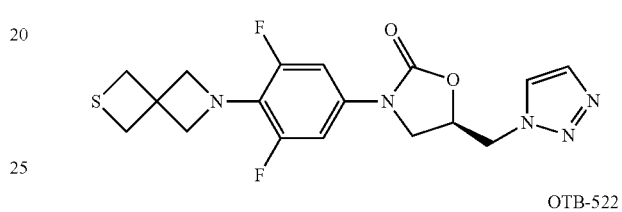
OTB-522
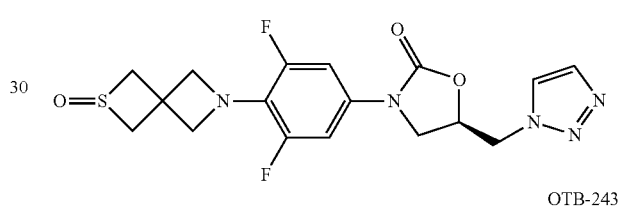
OTB-243
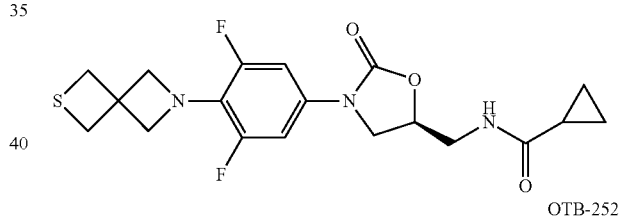
OTB-252
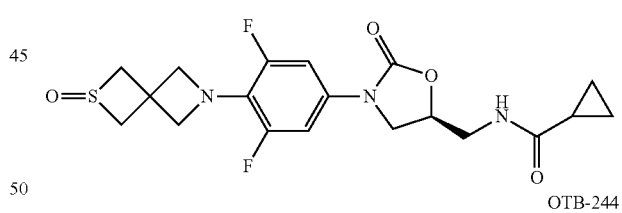
OTB-244
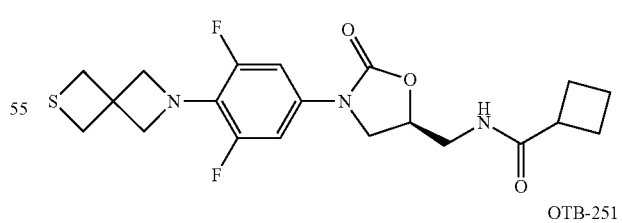
OTB-251
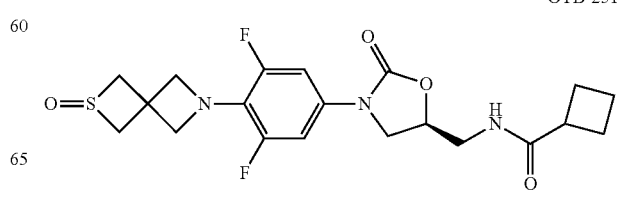

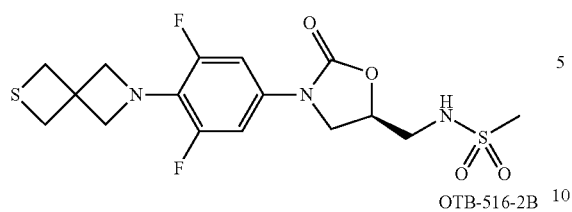
OTB-516-2A
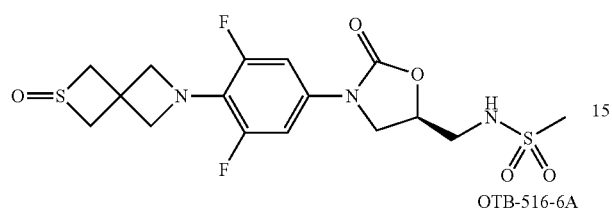
OTB-516-2B
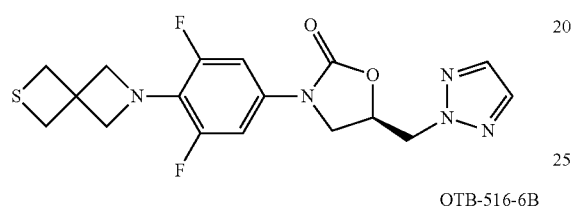
OTB-516-6A
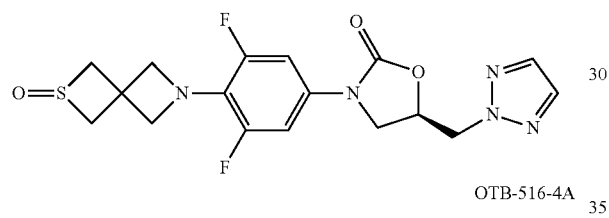
OTB-516-6B
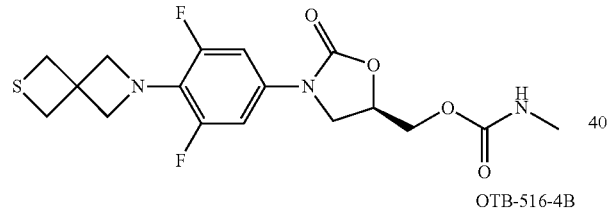
OTB-516-4A
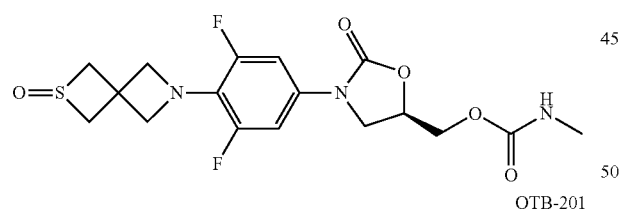
OTB-516-4B
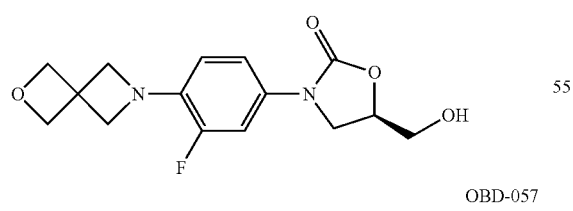
OBD-057
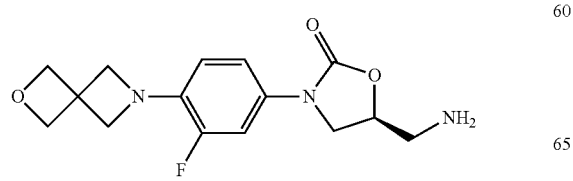
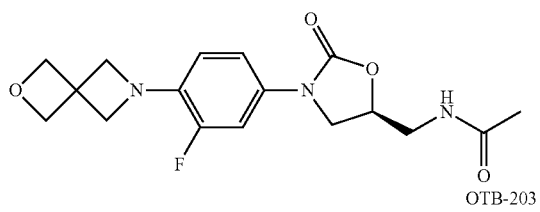
OTB-201
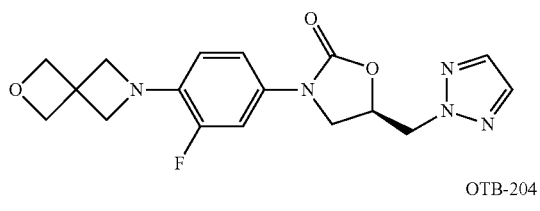
OTB-202
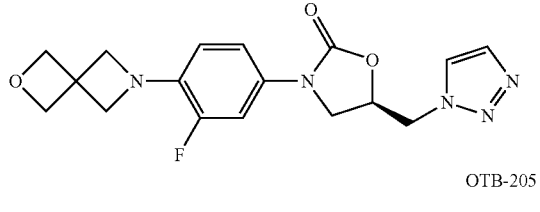
OTB-203
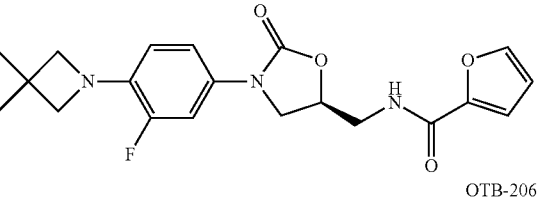
OTB-204
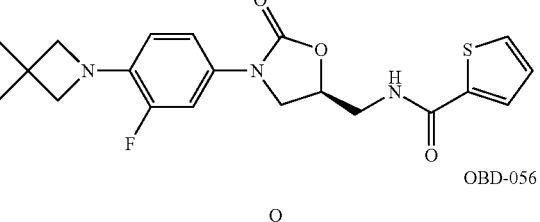
OTB-205
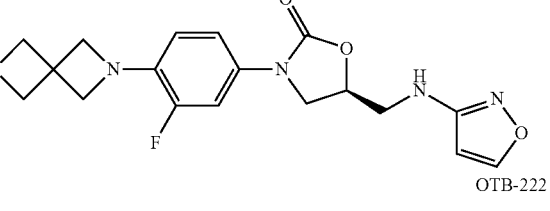
OBD-056
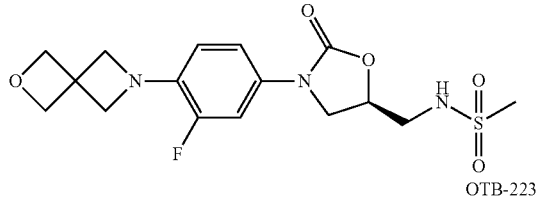
OTB-222
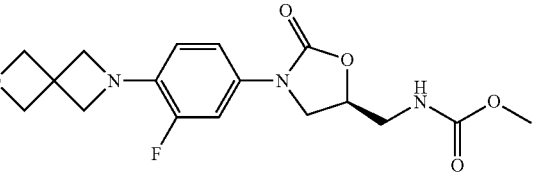
OTB-223

-continued
OTB-238
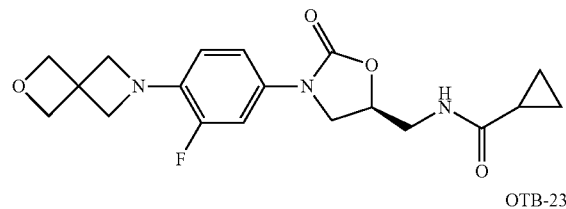
OTB-239
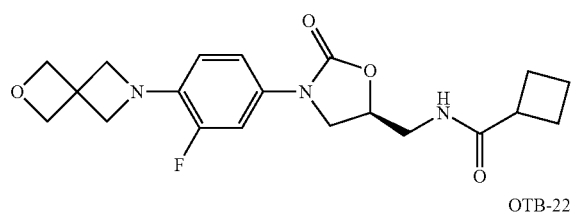
OBD-062
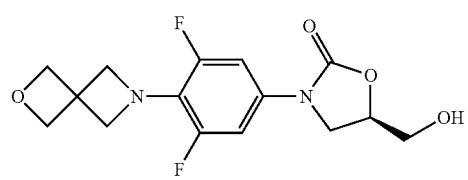
OTB-230
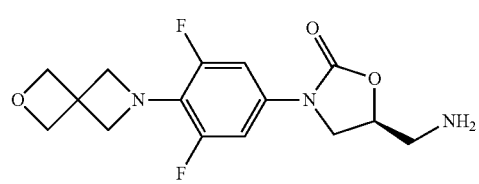
OTB-231
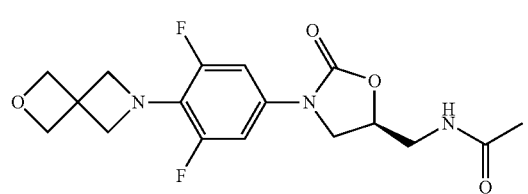
OTB-232
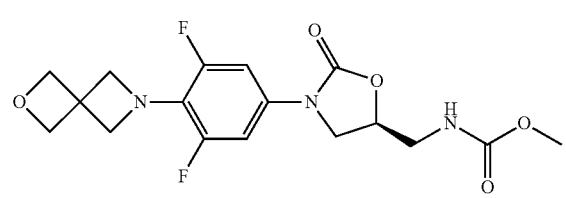
-continued
OTB-233
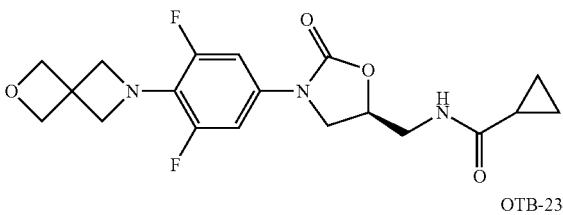
OTB-234
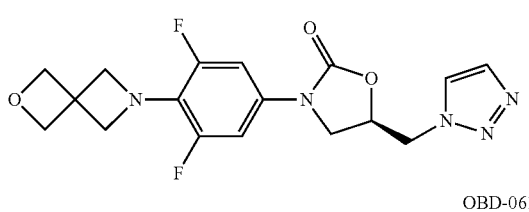
OTB-229
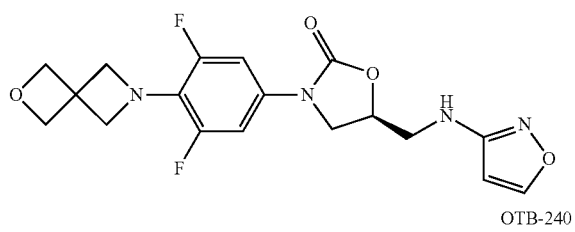
OTB-240
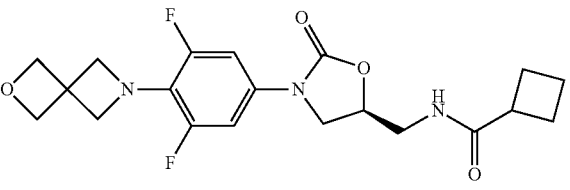
OBD-051
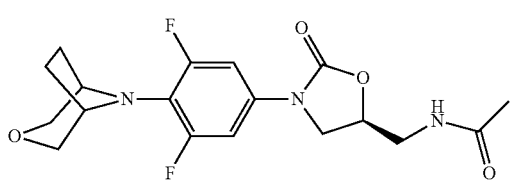
OBD-052
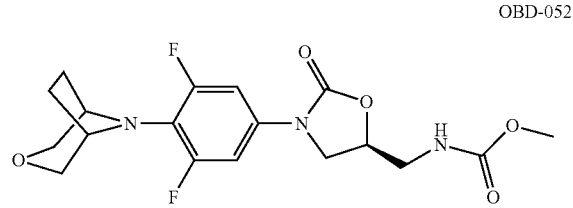
OBD-055
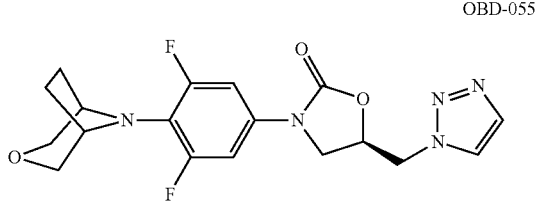

OBD-112

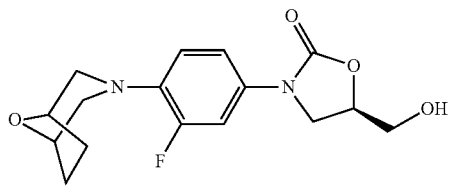

OBD-113

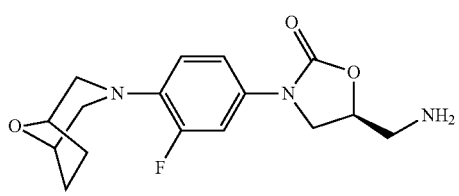

OBD-110

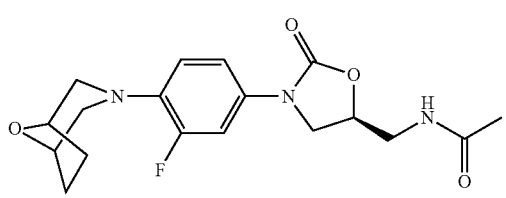

OBD-111

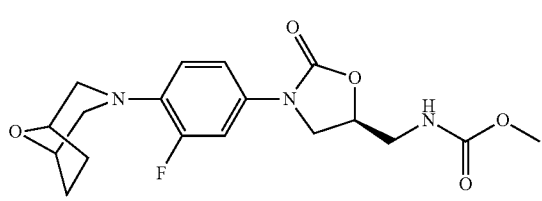

OBD-114

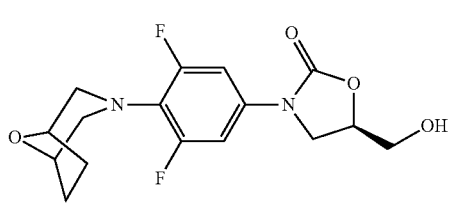

OBD-115

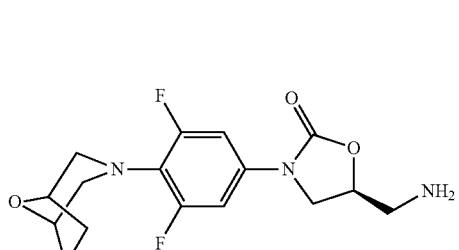

OBD-048

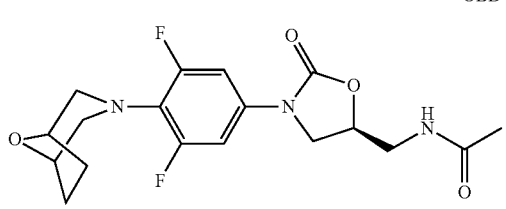

OBD-049

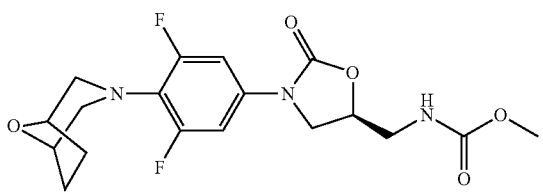

OBD-252

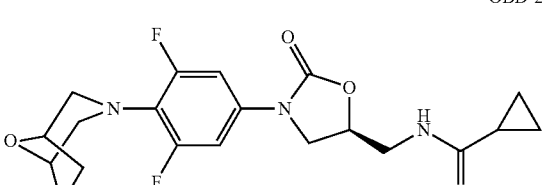

OBD-253

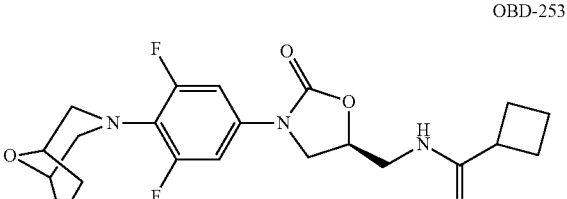

OBD-054

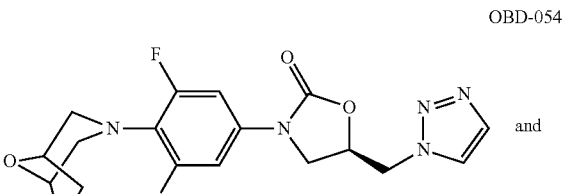

and

OBD-254

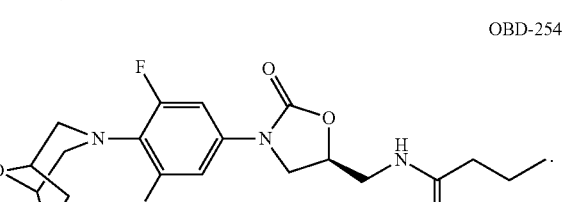

10. A pharmaceutical composition comprising at least one compound of Formula I, or a salt, hydrate, or solvate thereof, and one or more pharmaceutically acceptable carriers and/or additives.

11. The pharmaceutical compositions Formula I, or a salt, hydrate, or solvate thereof, further comprising one or more additional anti-infective treatments.

12. A method of preventing and treating microbial infections in humans by administering a therapeutically effective amount of a compound of Formula I, or a salt, hydrate, or solvate thereof to a patient in need thereof.

13. The method of paragraph 12, wherein the microbial infection is caused by *Mycobacterium tuberculosis*.

It is to be understood that the invention is not limited to the particular embodiments of the invention described above, as variations of the particular embodiments may be made and still fall within the scope of the appended claims.

What is claimed is:

1. A compound of Formula I, or a pharmaceutically acceptable salt, hydrate, or solvate of:

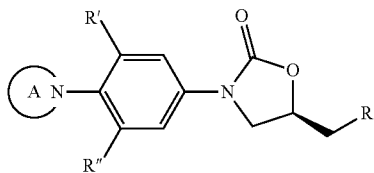

(I)

wherein:

R is independently $OR_1$, $OC(O)R_2$, $OC(O)NHR_2$, $OS(O_2)R_2$, $NHS(O)_2R_2$, $NR_3R_4$, $NHC(O)R_5$:

R' and R" are independently H, F, Cl or OMe;

each $R_1$ is independently H, $C_1$-$C_6$ alkyl, $C_3$-$C_8$ cycloalkyl, wherein said alkyl, cycloalkyl are optionally substituted with 1 to 4 groups selected from halo, hydroxy, $C_1$-$C_6$ alkyl, $C_1$-$C_6$ alkyloxy;

each $R_2$ is independently $C_1$-$C_6$ alkyl, $C_3$-$C_8$ cycloalkyl, heterocyclyl, heteroaryl or aryl, wherein said alkyl, cycloalkyl, heterocyclyl, heteroaryl, or aryl are optionally substituted with 1 to 4 groups selected from halo, hydroxyl, $C_1$-$C_6$ alkyl, $C_1$-$C_6$ alkoxy, $C_1$-$C_6$ acyloxy, $CF_3$, $NO_2$, CN and $NH_2$;

each $R_3$ and $R_4$ is independently H, $C_1$-$C_6$ alkyl, $C_3$-$C_8$ cycloalkyl, heterocyclyl heteroaryl, aryl;

or $R_3$ and $R_4$ taken together with the nitrogen to which they are attached, form a 4- to 8-membered heterocyclyl or heteroaryl with 1 to 3 additional heteroatoms selected from O, S, or N, wherein said alkyl, cycloalkyl, heterocyclyl, heteroaryl, or aryl are optionally substituted with 1 to 4 groups selected from halo, $C_1$-$C_6$ alkyl, $C_1$-$C_6$ alkoxy, $CF_3$, $NO_2$, CN;

each $R_5$ is independently $C_1$-$C_6$ alkyl, $C_3$-$C_8$ cycloalkyl, $C_1$-$C_6$ alkoxy, heteroaryl, aryl, wherein said alkyl, cycloalkyl, heterocyclyl, heteroaryl, or aryl are optionally substituted with 1 to 4 groups selected from halo, hydroxyl, $C_1$-$C_6$ alkyl, $C_1$-$C_6$ alkoxy, $C_1$-$C_6$ acyloxy, $CF_3$, $NO_2$, CN and $NH_2$;

Ring A is selected from:

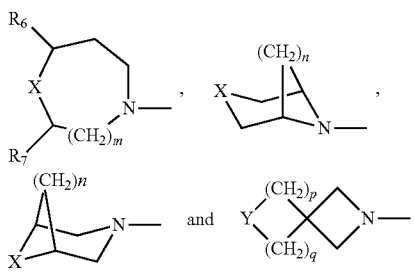

wherein, each $R_6$ and $R_7$ is independently H, F, $CH_3$, $CH_2CH_3$, $CF_3$, phenyl;

X=O, S, SO, $SO_2$;

Y=O, S, SO, $SO_2$, and $NR_8$;

m is 2;

n is 1, or 2;

p is 1, or 2;

q is 1, or 2;

$R_8$ in independently H, $C_1$-$C_4$ alkyl, $C_3$-$C_6$ cycloalkyl, $COCH_3$, and p-toluenesulfonyl, wherein said alkyl, cycloalkyl are optionally substituted with 1 to 4 groups selected from halo, hydroxyl, $C_1$-$C_6$ alkyl, $C_1$-$C_6$ alkoxy, $C_1$-$C_6$ acyloxy, $CF_3$, $NO_2$, CN and $NH_2$.

2. The compound of claim 1, wherein the compound is represented by Formula III:

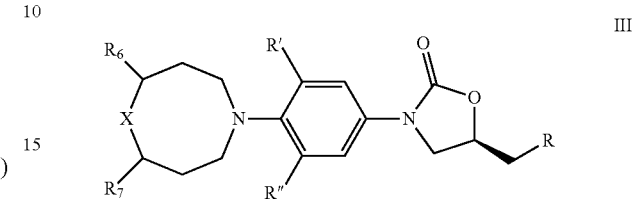

III wherein,

R is independently $OR_1$, $OC(O)R_2$, $NR_3R_4$, $NHS(O)_2R_2$, $NHC(O)R_5$;

R' and R" are independently H, or F;

$R_1$ is independently H, $C_1$-$C_6$ alkyl, $C_3$-$C_6$ cycloalkyl;

$R_2$ is independently $C_1$-$C_6$ alkyl, $C_3$-$C_6$ cycloalkyl;

$R_3$ and $R_4$ is independently H, $C_1$-$C_6$ alkyl, $C_3$-$C_6$ cycloalkyl, or phenyl; or $R_3$ and $R_4$ taken together with the nitrogen to which they are attached to form morpholine, thiamorpholine, piperazine and triazole;

$R_5$ is independently $C_1$-$C_6$ alkyl, $C_3$-$C_6$ cycloalkyl, $C_1$-$C_6$ alkoxy, 5- or 6-membered heteroaryl or phenyl;

$R_6$ and $R_7$ is independently H, F, $CH_3$, $CH_2CH_3$, $CF_3$; and

X=O, S, SO, $SO_2$.

3. The compound of claim 1, wherein the compound is represented by Formula IV:

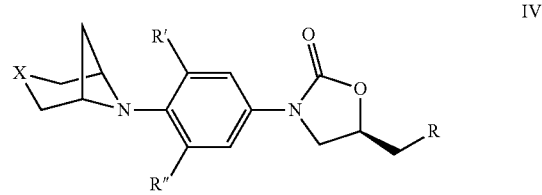

IV wherein,

R is independently $OR_1$, $OC(O)R_2$, $NR_3R_4$, $NHS(O)_2R_2$, $NHC(O)R_5$;

R' and R" are independently H, or F;

$R_1$ is independently H, $C_1$-$C_6$ alkyl, $C_3$-$C_6$ cycloalkyl;

R is independently $C_1$-$C_6$ alkyl, $C_3$-$C_6$ cycloalkyl;

$R_3$ and $R_4$ is independently H, $C_1$-$C_6$ alkyl, $C_3$-$C_6$ cycloalkyl, 5- or 6-membered heteroaryl or phenyl; or $R_3$ and $R_4$ taken together with the nitrogen to which they are attached, to form morpholine, thiamorpholine, piperazine and triazole;

$R_5$ is independently $C_1$-$C_6$ alkyl, $C_3$-$C_6$ cycloalkyl, $C_1$-$C_6$ alkoxy, 5- or 6-membered heteroaryl or phenyl; and

X=O, S, SO, $SO_2$.

4. The compound of claim 1, wherein the compound is represented by Formula V:

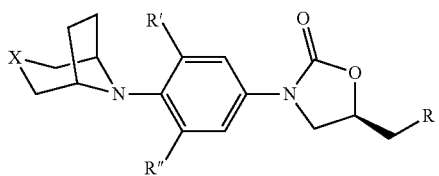

wherein,
R is independently $OR_1$, $OC(O)R_2$, $NR_3R_4$, $NHS(O)_2R_2$, $NHC(O)R_5$;
R' and R" are independently H, or F;
$R_1$ is independently H, $C_1$-$C_6$ alkyl, $C_3$-$C_6$ cycloalkyl;
$R_2$ is independently $C_1$-$C_6$ alkyl, $C_3$-$C_6$ cycloalkyl;
$R_3$ and $R_4$ is independently H, $C_1$-$C_6$ alkyl, $C_3$-$C_6$ cycloalkyl, 5- or 6-membered heteroaryl or phenyl; or $R_3$ and $R_4$ taken together with the nitrogen to which they are attached, to form morpholine, thiamorpholine, piperazine and triazole;
$R_5$ is independently $C_1$-$C_6$ alkyl, $C_3$-$C_6$ cycloalkyl, $C_1$-$C_6$ alkoxy, 5- or 6-membered heteroaryl or phenyl; and
X=O, S, SO, $SO_2$.

5. The compound of claim 1, wherein the compound is represented by Formula VI:

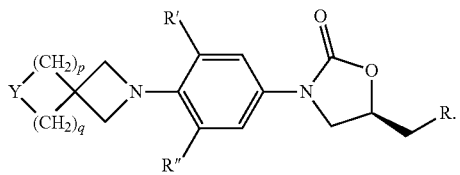

6. The compound of claim 5, wherein the compound is represented by Formula VII, Formula VIII, or Formula IX:

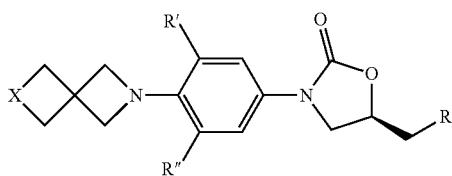

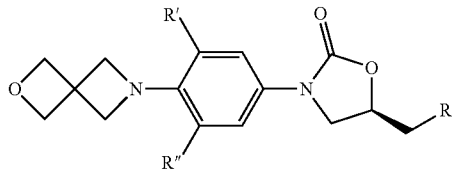

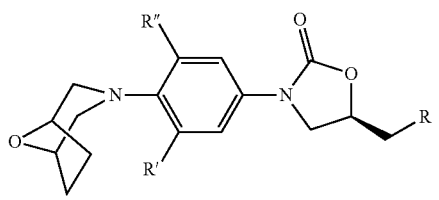

wherein,
R is independently $OR_1$, $OC(O)R_2$, $NR_3R_4$, $NHS(O)_2R_2$, $NHC(O)R_5$;
R' and R" are independently H, or F;
$R_1$ is independently H, $C_1$-$C_6$ alkyl, $C_3$-$C_6$ cycloalkyl;
$R_2$ is independently $C_1$-$C_6$ alkyl, $C_3$-$C_6$ cycloalkyl;
$R_3$ and $R_4$ is independently H, $C_1$-$C_6$ alkyl, $C_3$-$C_6$ cycloalkyl, 5- or 6-membered heteroaryl or phenyl; or $R_3$ and $R_4$ taken together with the nitrogen to which they are attached, to form morpholine, thiamorpholine, piperazine and triazole;
$R_5$ is independently $C_1$-$C_6$ alkyl, $C_3$-$C_6$ cycloalkyl, $C_1$-$C_6$ alkoxy, 5- or 6-membered heteroaryl or phenyl; and
X=O, S, SO, $SO_2$.

7. The compound of claim 1, wherein the compound is represented by Formula IIIa, IIIb, IVa, IVb, Va, Vb, VIIa, VIIb, VIIIa, VIIIb, IXa, or IXb:

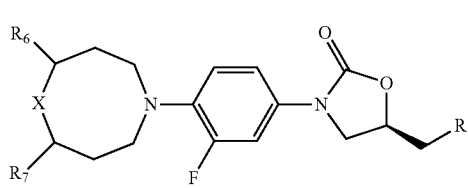

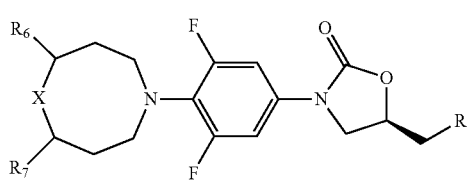

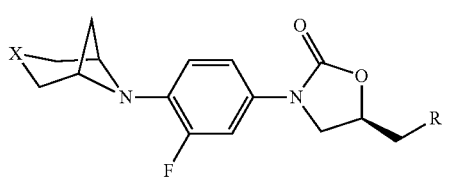

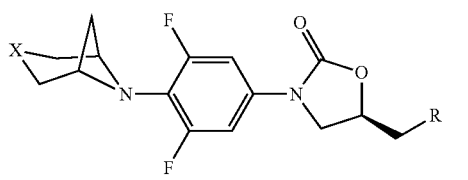

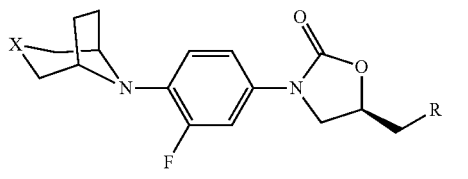

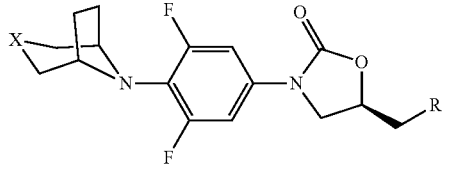

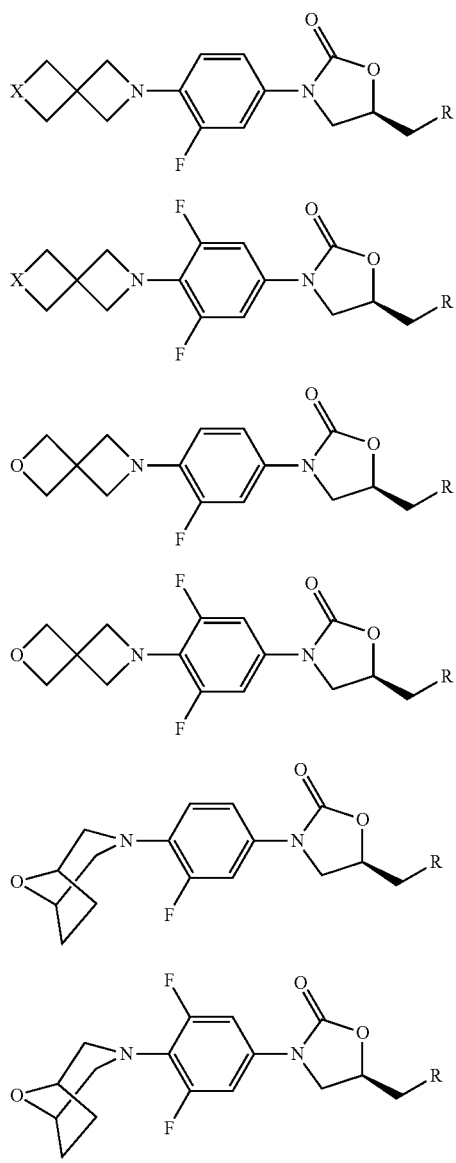
wherein,
R is independently OH, OCH₃, OCH₂CH₃, OC(O)CH₃, NH₂, NHCH₃, NHC₆H₅, 1,2,3-triazole, 1,2,4-triazole, 1,2,5-triazole, NHS(O)₂R₂, NHC(O)R₅;
R₂ is independently $C_1$-$C_6$ alkyl;
R₅ is independently $C_1$-$C_6$ alkyl, $C_3$-$C_6$ cycloalkyl, $C_1$-$C_6$ alkoxy, furan, thiophene or phenyl; in Formula IIa, R₅ can not be CH₃; and
X=O, S, SO, SO₂.
8. A compound, wherein the compound is:
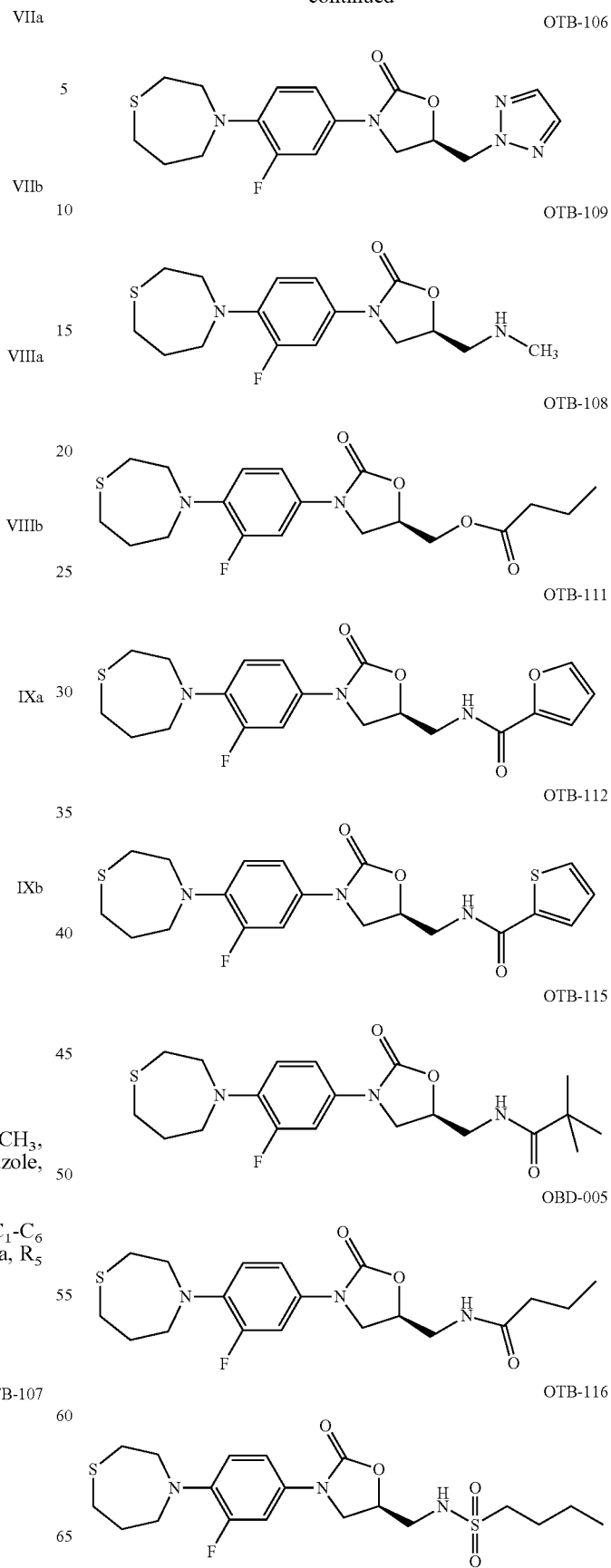

OTB-119
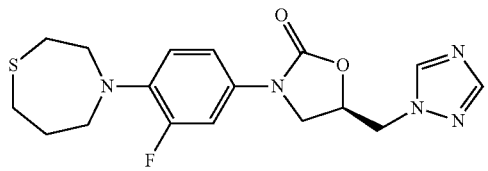
OTB-412
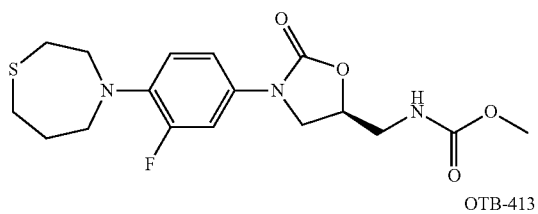
OTB-413
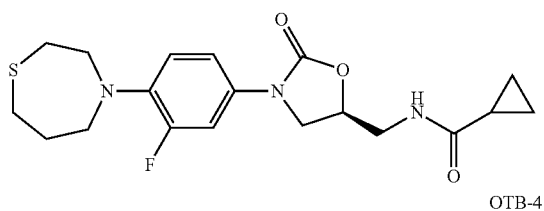
OTB-414
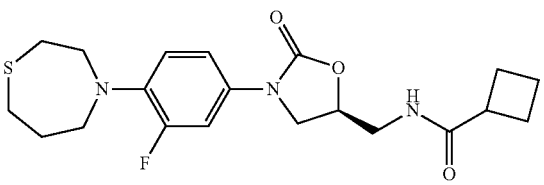
OTB-407
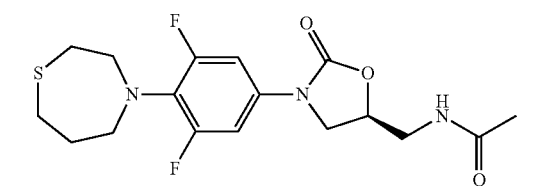
OTB-410
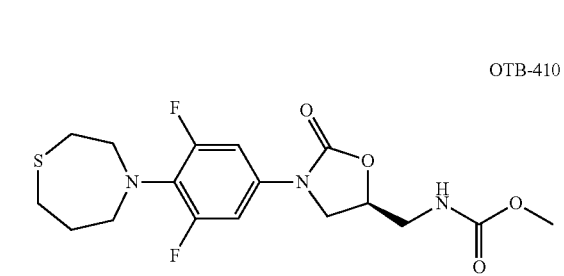
OTB-408
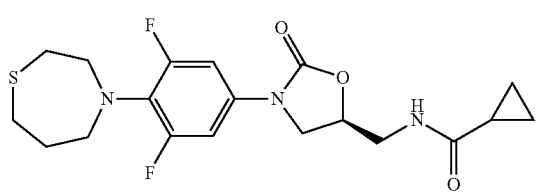
OTB-409
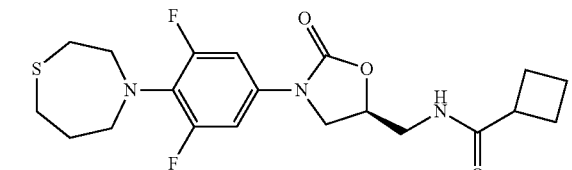
OTB-411
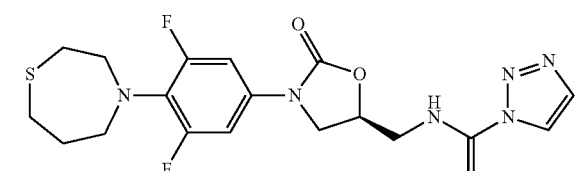
OTB-126
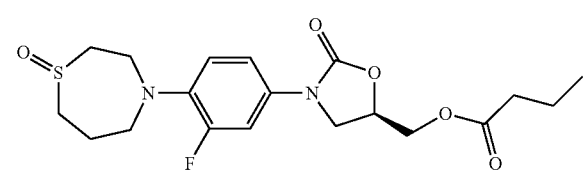
OTB-127
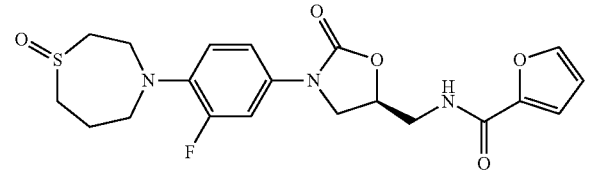
OTB-137
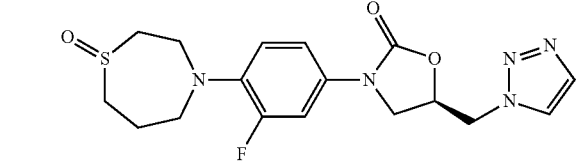
OTB-138
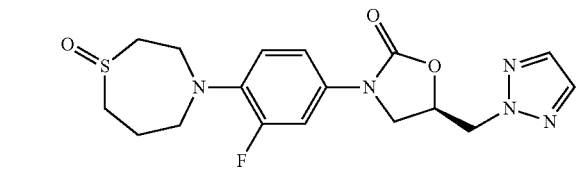
OTB-140
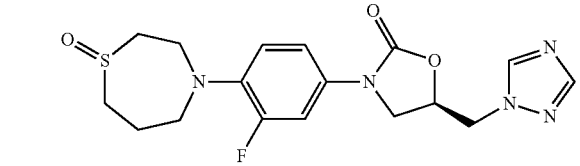
OBD-006
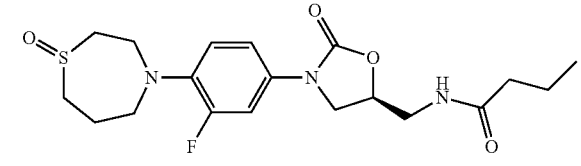

OBD-007
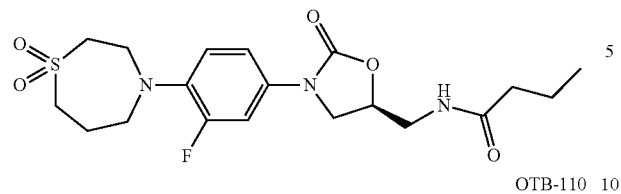
OTB-110
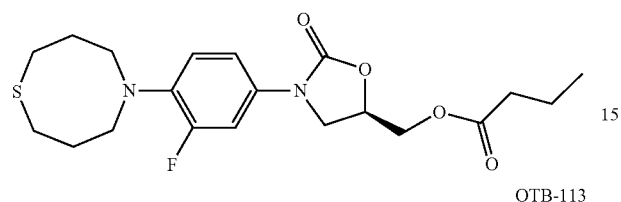
OTB-113
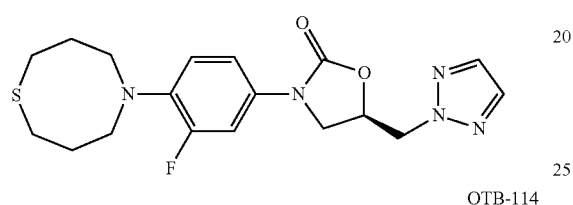
OTB-114
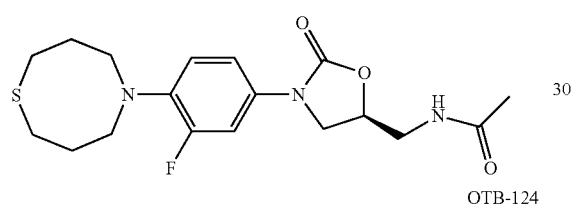
OTB-117
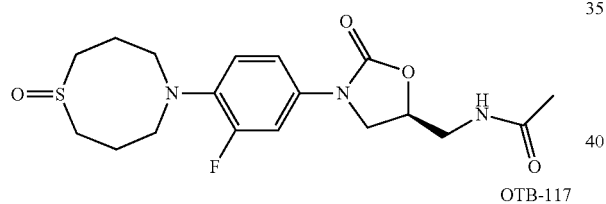
OTB-118
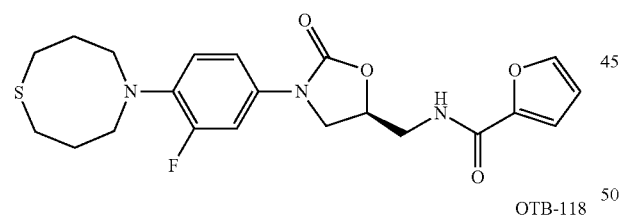
OTB-120
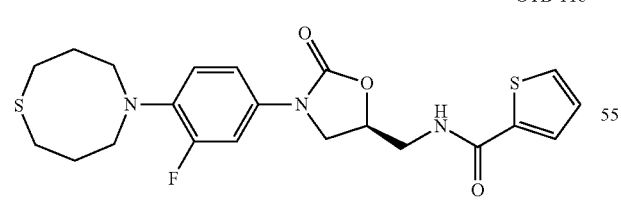
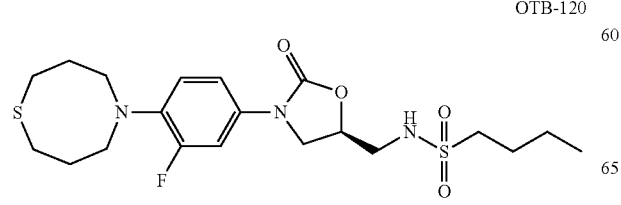
OTB-121
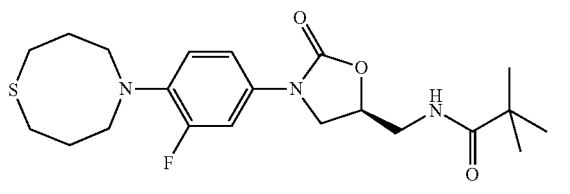
OBD-001
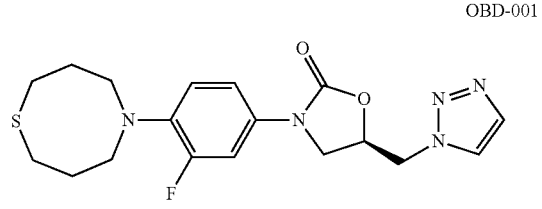
OBD-002
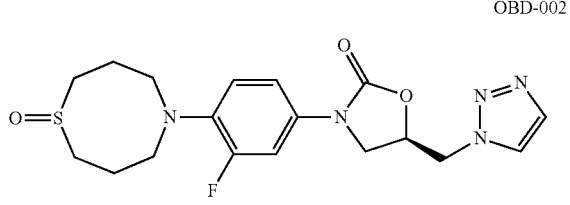
OBD-003
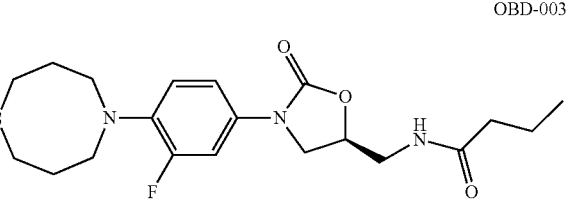
OBD-004
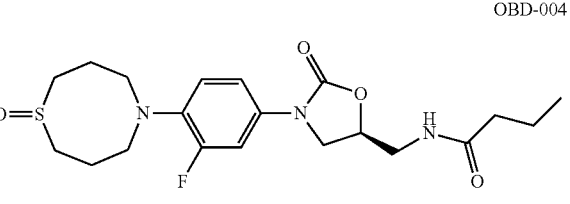
OBD-008
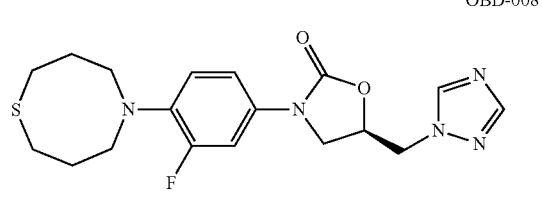
OBD-009
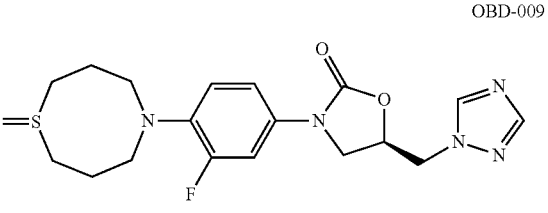
OBD-027
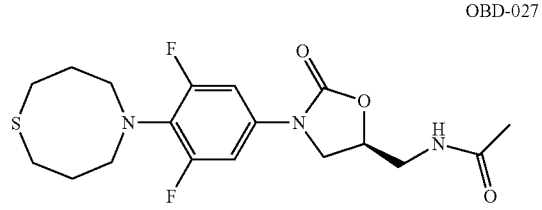

OBD-240
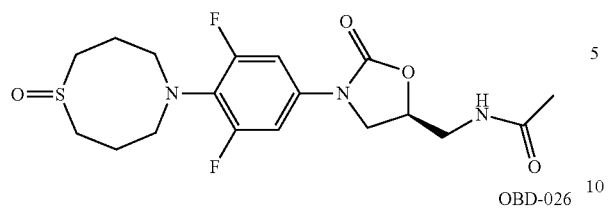
OBD-026
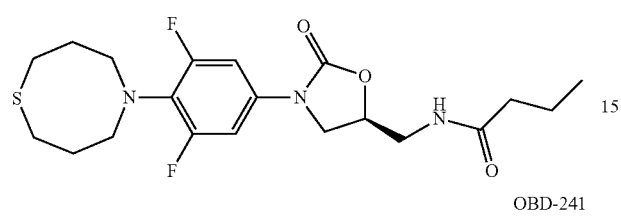
OBD-241
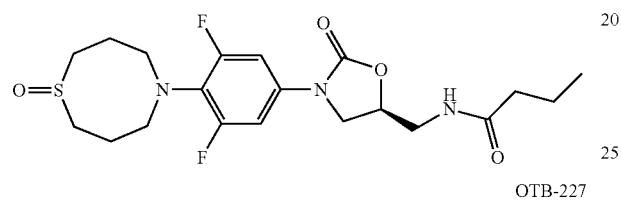
OTB-227
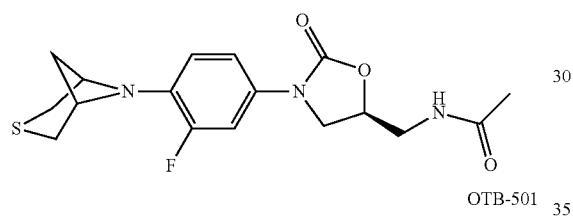
OTB-501
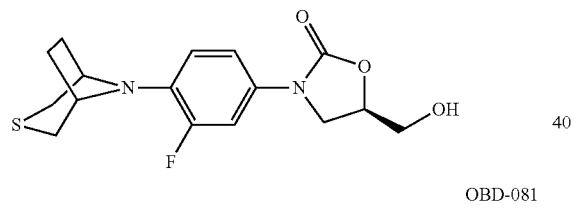
OBD-081
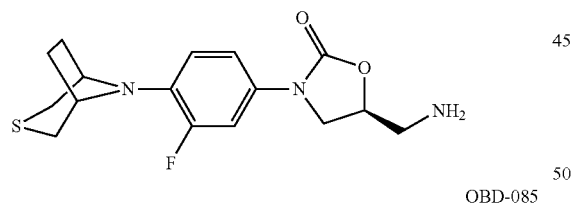
OBD-085
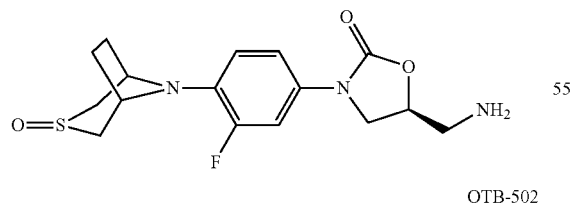
OTB-502
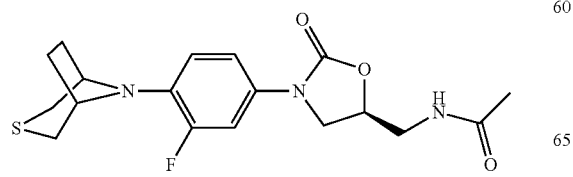
OTB-503
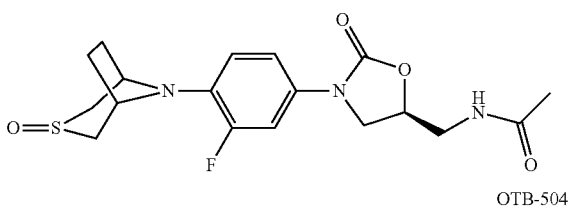
OTB-504
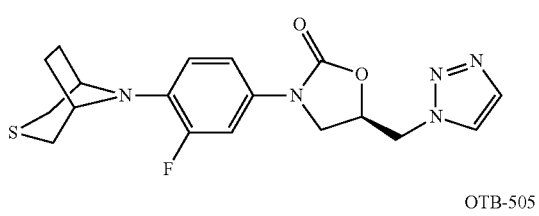
OTB-505
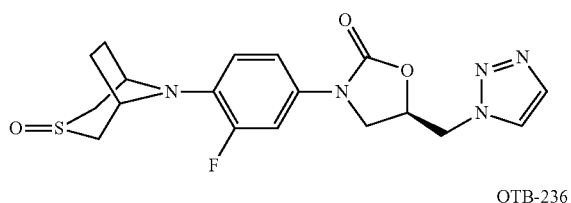
OTB-236
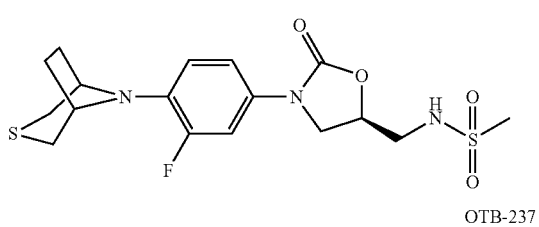
OTB-237
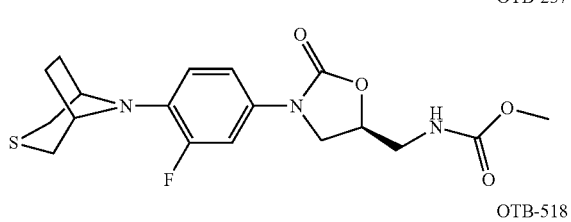
OTB-518
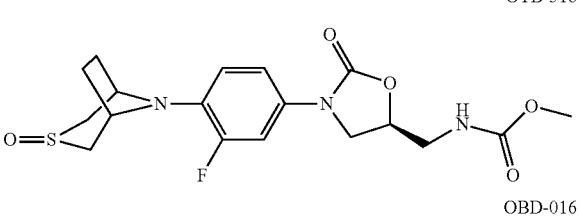
OBD-016
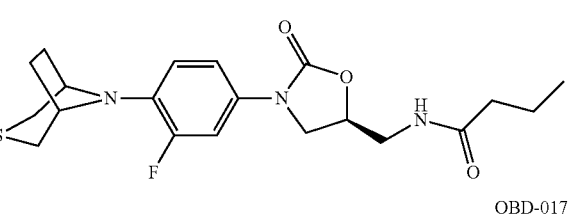
OBD-017
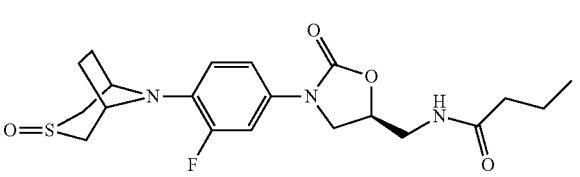

OBD-021
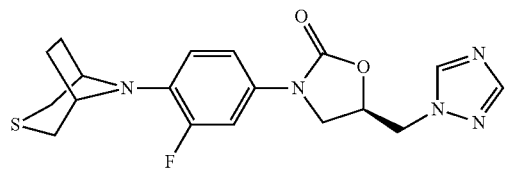
OBD-018
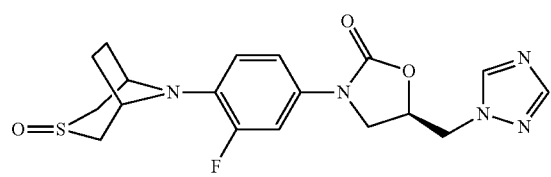
OTB-506
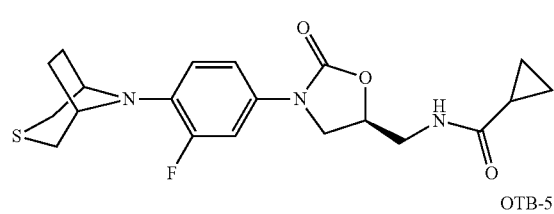
OTB-507
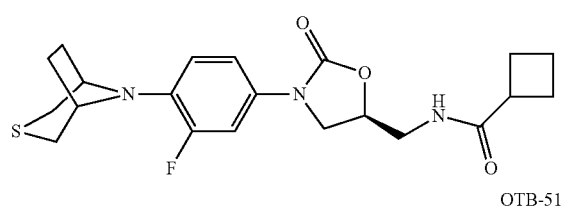
OTB-510
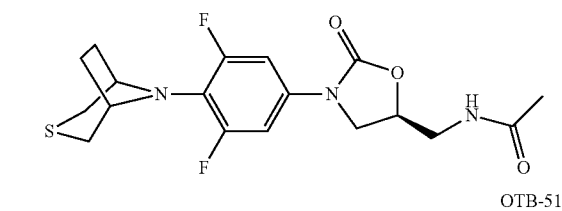
OTB-514
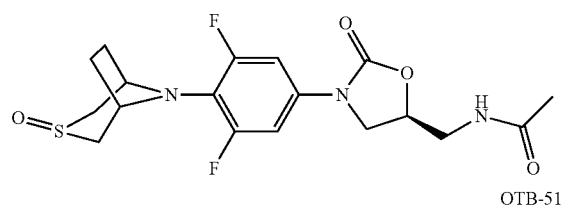
OTB-512
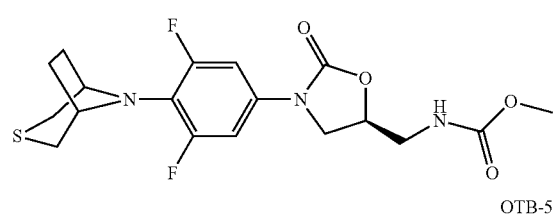
OTB-519
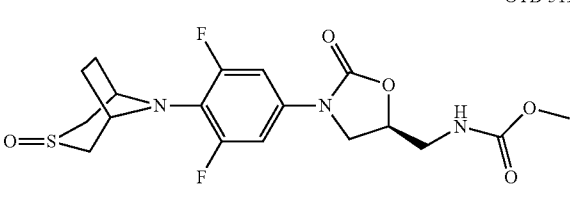
OTB-511
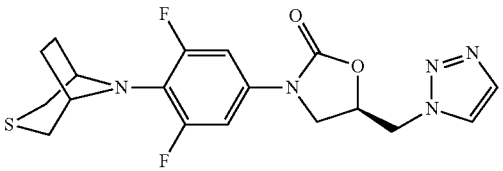
OTB-517
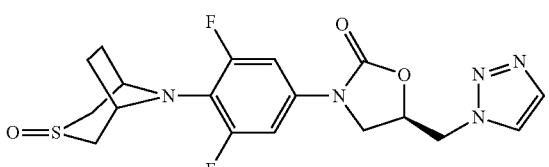
OTB-508
OTB-509
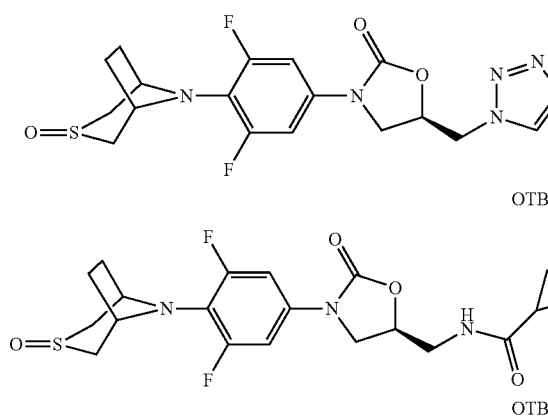
OTB-513
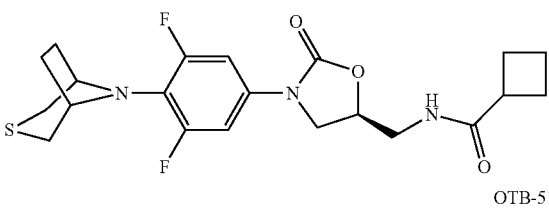
OBD-083
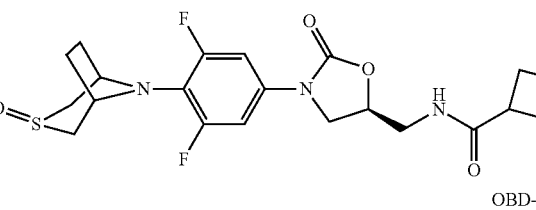
OBD-087
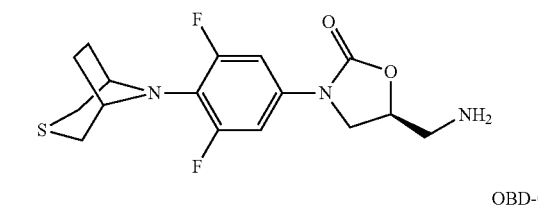
OBD-029
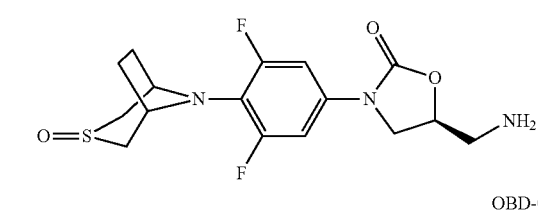
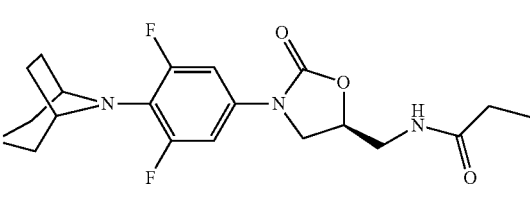

-continued
OBD-242
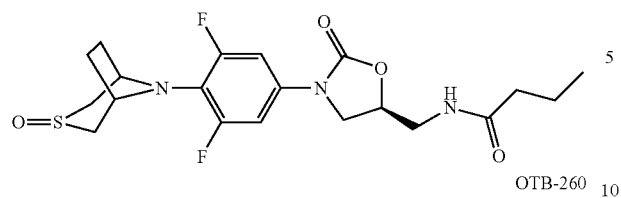
OTB-260
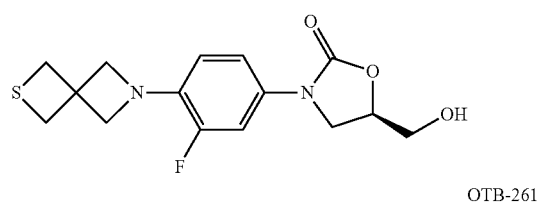
OTB-261
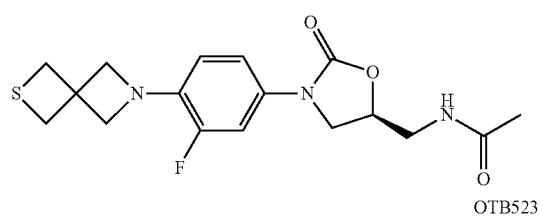
OTB523
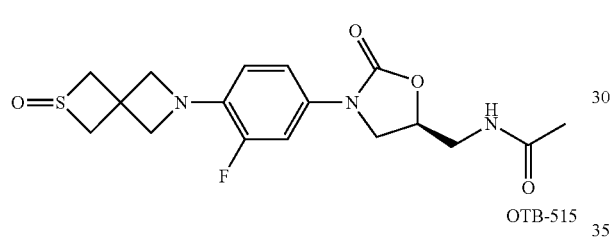
OTB-515
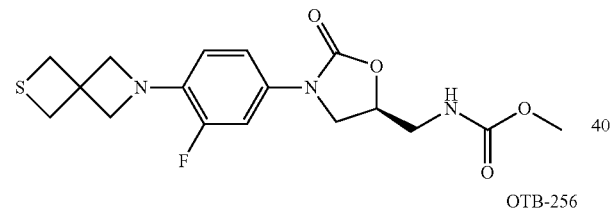
OTB-256
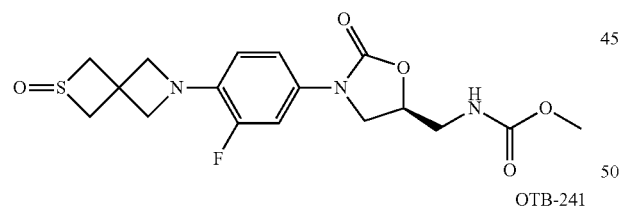
OTB-241
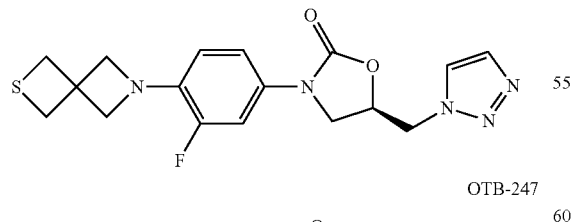
OTB-247
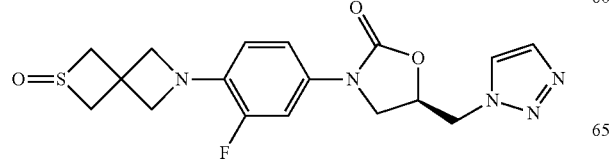
-continued
OTB-249
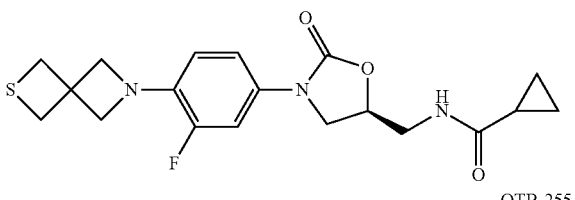
OTB-255
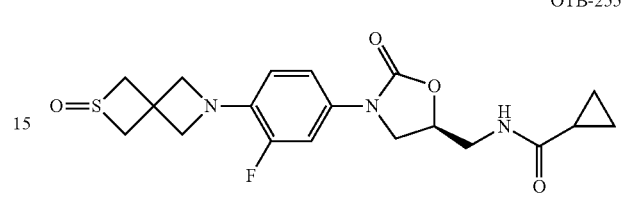
OTB-250
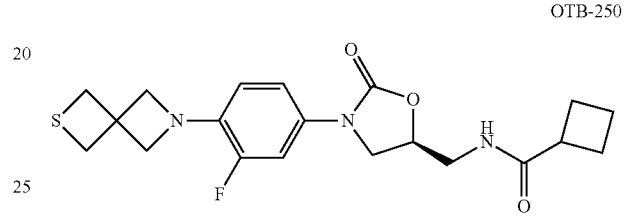
OTB-254
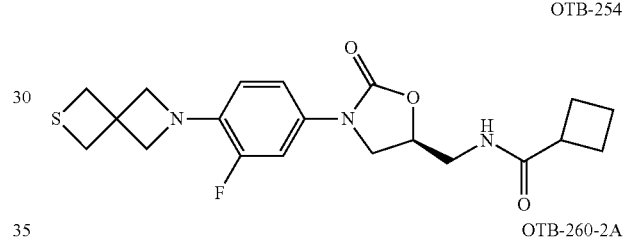
OTB-260-2A
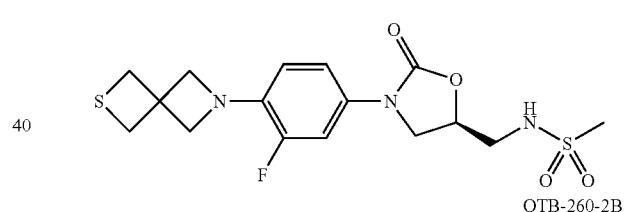
OTB-260-2B
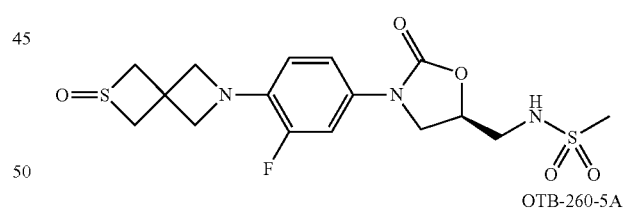
OTB-260-5A
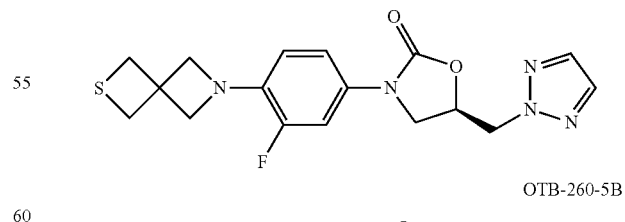
OTB-260-5B
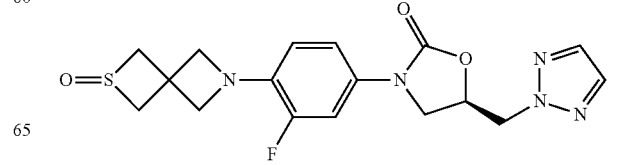

OTB-260-4A
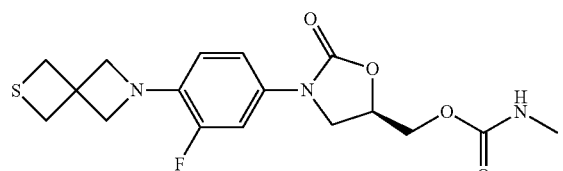
OTB-260-4B
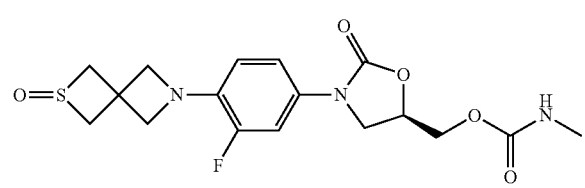
OTB-516
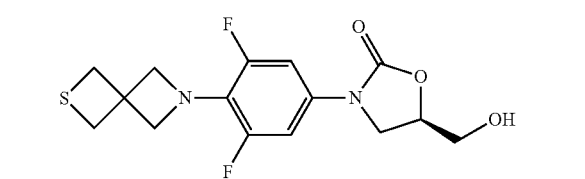
OTB-515
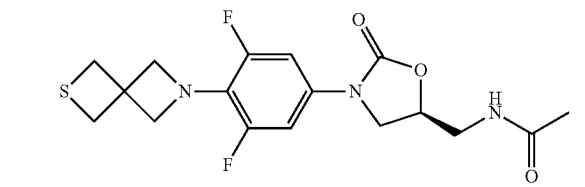
OTB-520
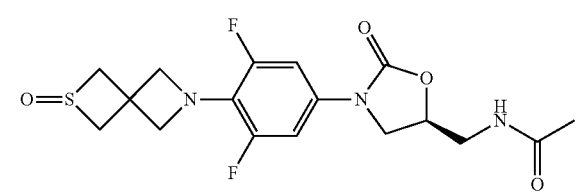
OTB-242
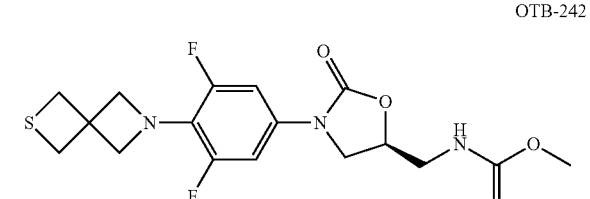
OTB-253
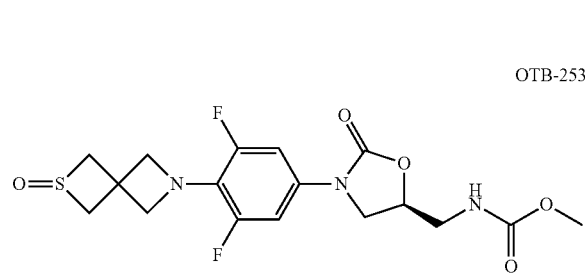
OTB-245
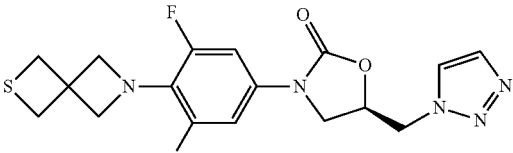
OTB-522
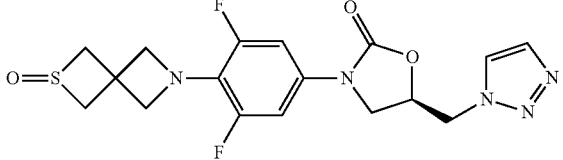
OTB-243
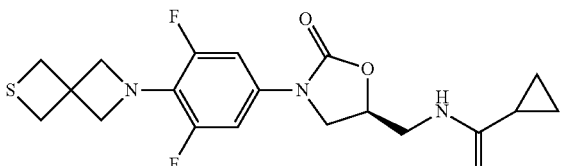
OTB-252
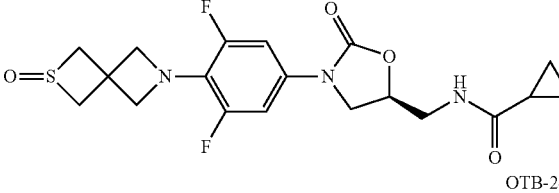
OTB-244
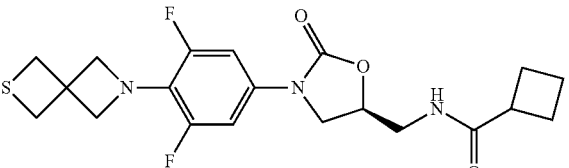
OTB-251
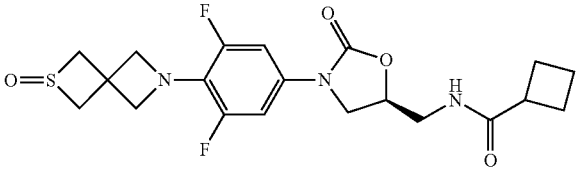
OTB-516-2A
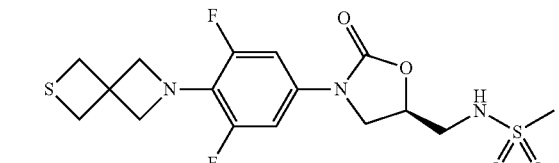
OTB-516-2B OTB-516-6A
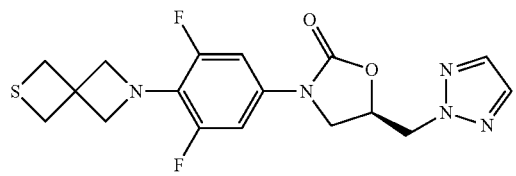
OTB-516-6B
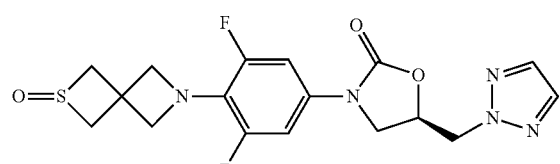
OTB-516-4A
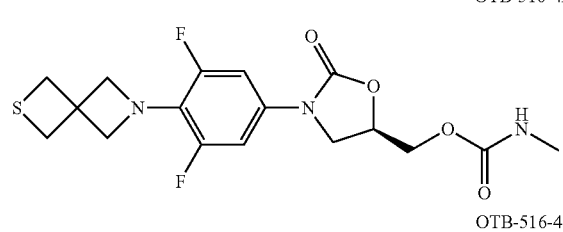
OTB-516-4B
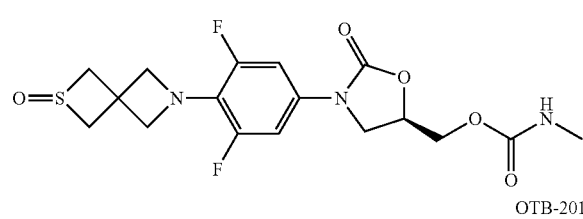
OTB-201
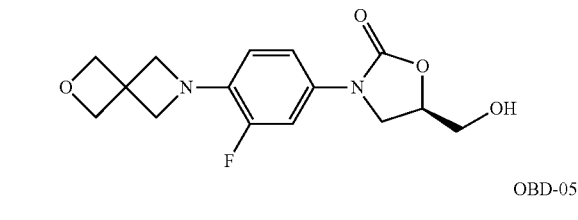
OTB-202
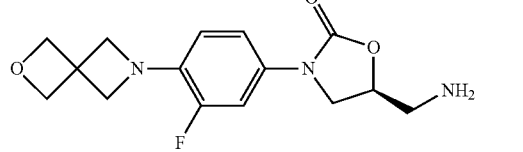
OTB-203
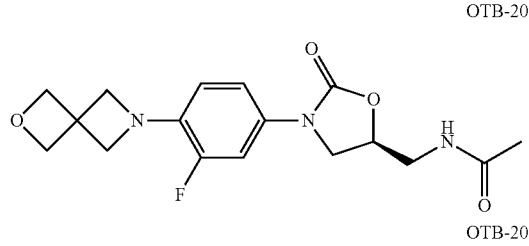
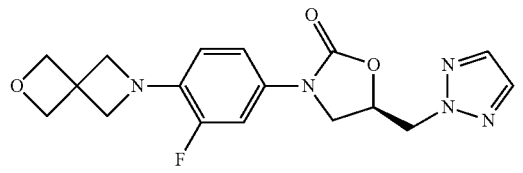
OTB-204
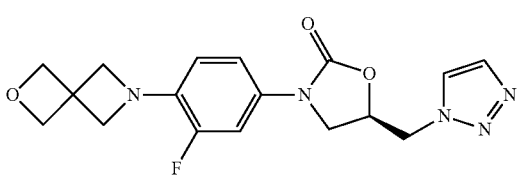
OTB-205
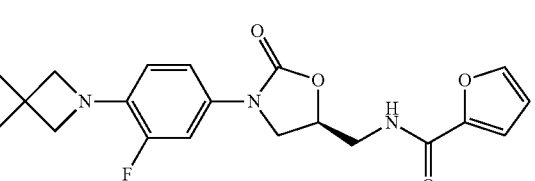
OTB-206
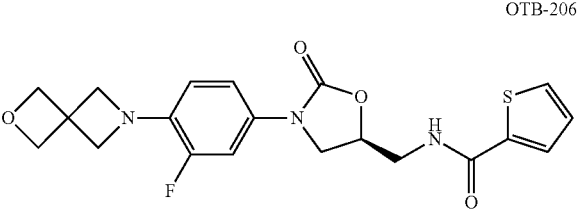
OBD-056
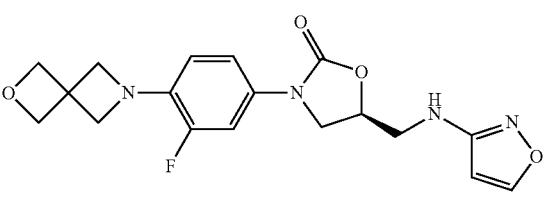
OTB-222
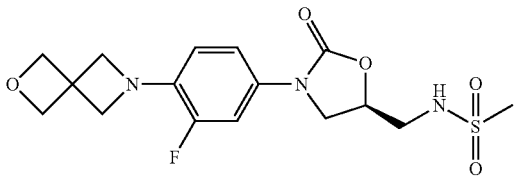
OTB-223
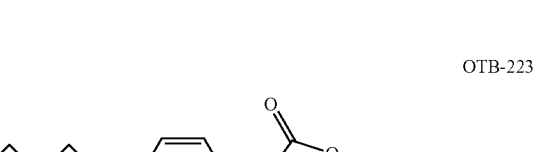
OTB-238
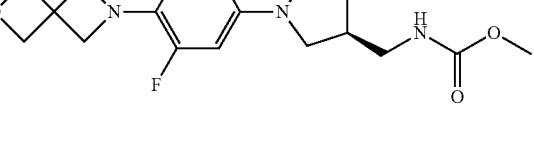
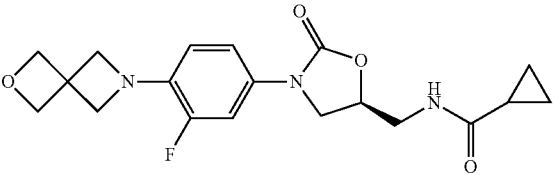

OTB-239
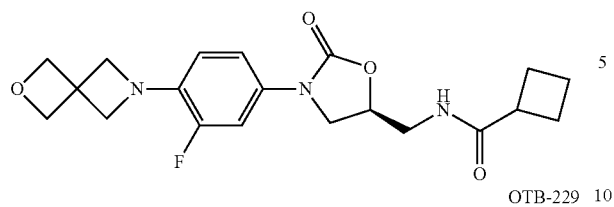
OTB-229
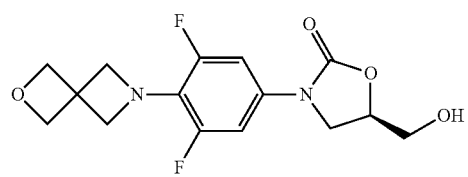
OBD-062
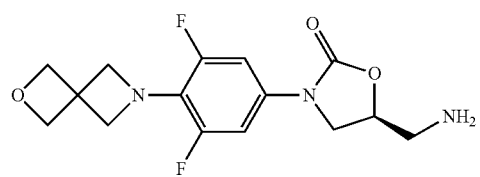
OTB-230
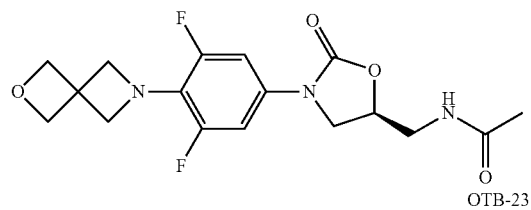
OTB-231
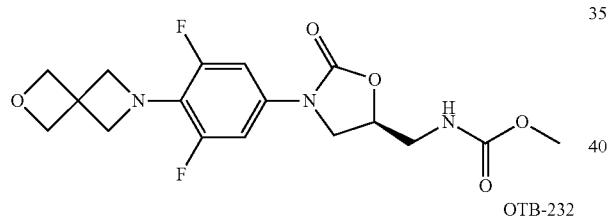
OTB-232
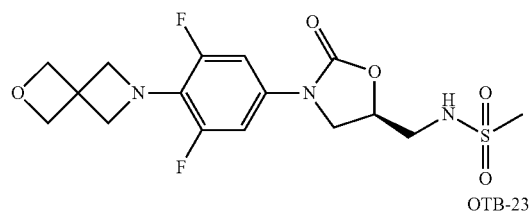
OTB-233
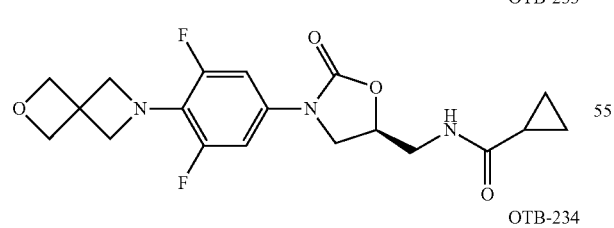
OTB-234
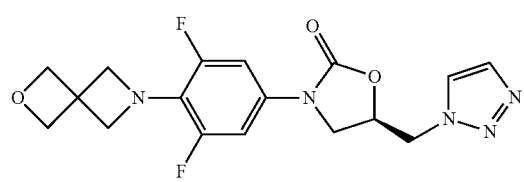
OBD-061
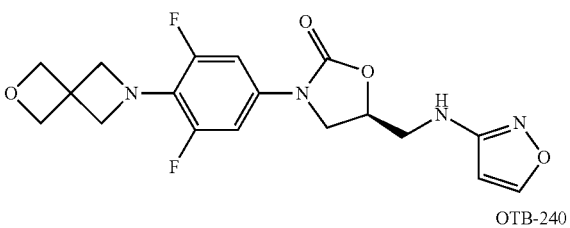
OTB-240
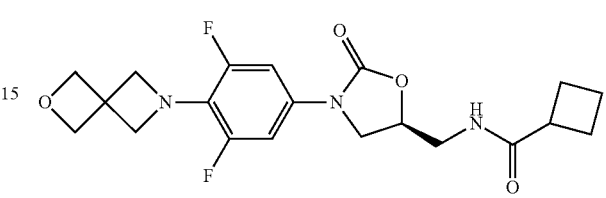
OBD-051
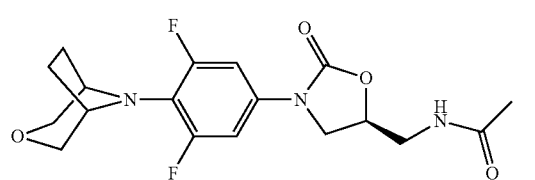
OBD-052
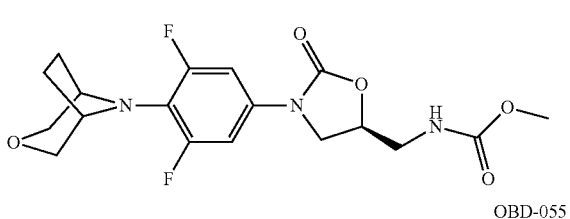
OBD-055
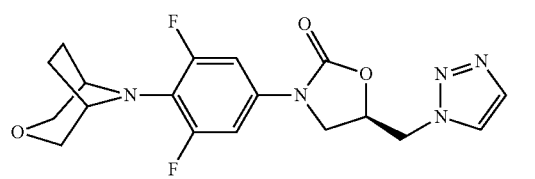
OBD-112
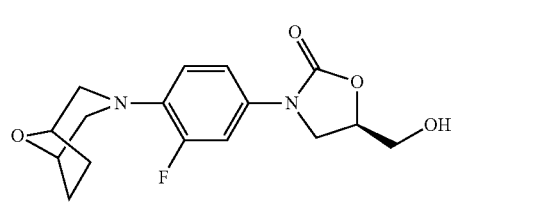
OBD-113
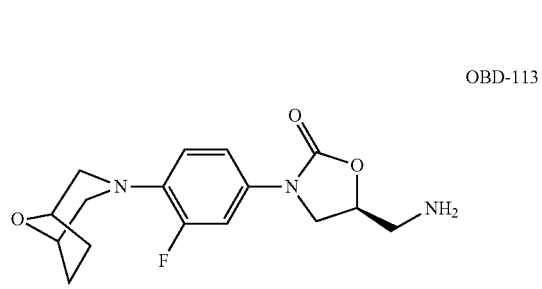

OBD-110
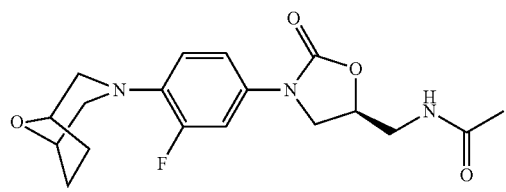

OBD-111
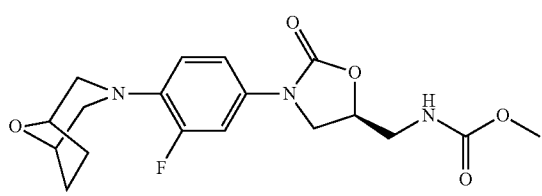

OBD-114
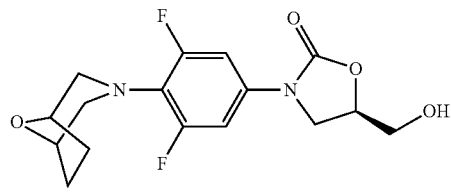

OBD-115
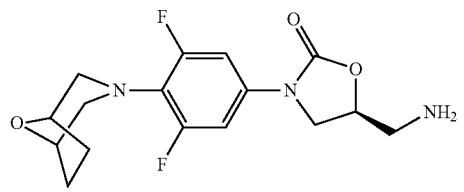

OBD-048
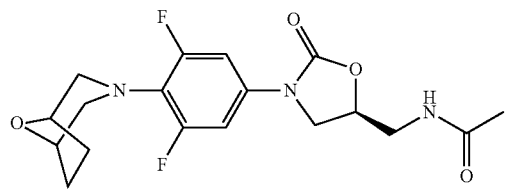

OBD-049
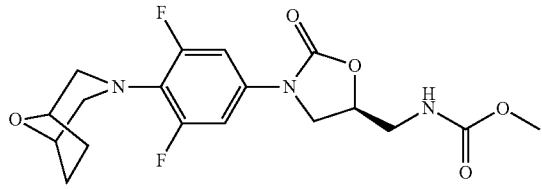

OBD-252
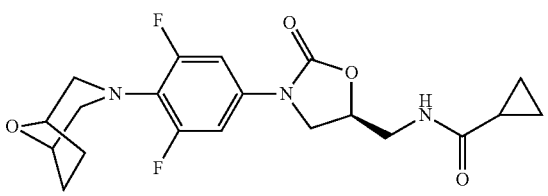

OBD-253
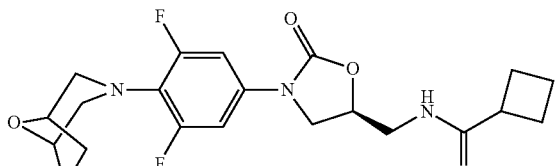

OBD-054
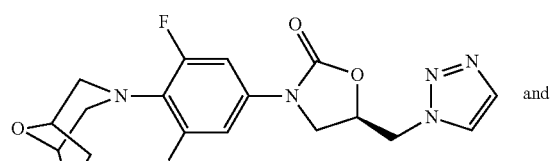

OBD-254
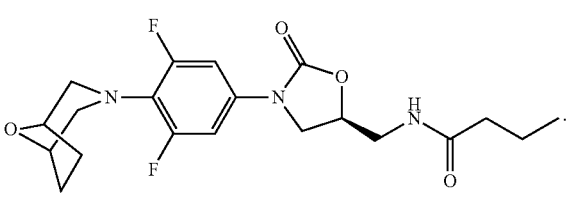

and or a pharmaceutically acceptable salt, hydrate, or solvate thereof.

9. A pharmaceutical composition, comprising at least one compound of Formula I according to claim 1, or a salt, hydrate, or solvate thereof, and one or more pharmaceutically acceptable carriers and/or additives.

10. The pharmaceutical composition according to claim 9, further comprising one or more additional anti-infective treatments.

11. A method of treating microbial infections in a human comprising the step of administering a therapeutically effective amount of a compound of Formula I according to claim 1, or a salt, hydrate, or solvate thereof, to a said human in need thereof.

12. The method of claim 11, wherein the microbial infection is caused by *Mycobacterium tuberculosis*.

13. A compound, wherein said compound is:

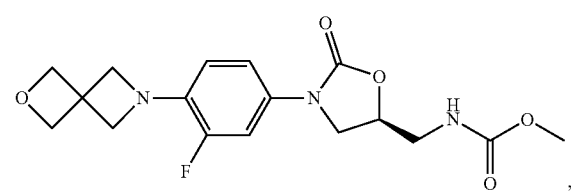 [SMILES: COC(=O)NC[C@H]1CN(c2ccc(N3CC4(COC4)C3)c(F)c2)C(=O)O1]

or a pharmaceutically acceptable salt, hydrate, or solvate thereof.

14. A pharmaceutical composition, comprising the compound according to claim 13, or a salt, hydrate, or solvate thereof, and one or more pharmaceutically acceptable carriers and/or additives.

15. The pharmaceutical composition according to claim 14, further comprising one or more additional anti-infective treatments.

16. A method of treating microbial infections in a human, comprising the step of administering a therapeutically effective amount of a compound according to claim 14, or a salt, hydrate, or solvate thereof, to said human in need thereof.

17. The method of claim 16, wherein the microbial infection is caused by *Mycobacterium tuberculosis*.

\* \* \* \* \*